United States Patent
Nie et al.

(10) Patent No.: US 12,048,240 B2
(45) Date of Patent: Jul. 23, 2024

(54) ORGANIC COMPOUND, ELECTRONIC COMPONENT AND ELECTRONIC APPARATUS COMPRISING THE SAME

(71) Applicant: SHAANXI LIGHTE OPTOELECTRONICS MATERIAL CO., LTD., Shaanxi (CN)

(72) Inventors: Qiqi Nie, Shaanxi (CN); Youngkook Kim, Shaanxi (CN); Yun Liu, Shaanxi (CN)

(73) Assignee: SHAANXI LIGHTE OPTOELECTRONICS MATERIAL CO., LTD., Shaanxi (CN)

( * ) Notice: Subject to any disclaimer, the term of this patent is extended or adjusted under 35 U.S.C. 154(b) by 0 days.

(21) Appl. No.: 18/552,412

(22) PCT Filed: Dec. 9, 2022

(86) PCT No.: PCT/CN2022/138052
§ 371 (c)(1),
(2) Date: Sep. 25, 2023

(87) PCT Pub. No.: WO2023/160121
PCT Pub. Date: Aug. 31, 2023

(65) Prior Publication Data
US 2024/0206326 A1 Jun. 20, 2024

(30) Foreign Application Priority Data
Feb. 25, 2022 (CN) .......................... 202210182946.9

(51) Int. Cl.
*H10K 85/60* (2023.01)
*C07C 211/58* (2006.01)
(Continued)

(52) U.S. Cl.
CPC .......... *H10K 85/633* (2023.02); *C07C 211/58* (2013.01); *C07C 211/61* (2013.01);
(Continued)

(58) Field of Classification Search
CPC ... C07C 211/54; C07C 211/57; C07C 211/60; C07C 211/61; H10K 85/633; H10K 85/636
See application file for complete search history.

(56) References Cited

U.S. PATENT DOCUMENTS

2017/0301861 A1* 10/2017 Wang ................... C07C 211/54
2019/0378980 A1* 12/2019 Kim ........................ C09K 11/06
2020/0044161 A1* 2/2020 Han ....................... C07D 307/91

FOREIGN PATENT DOCUMENTS

CN 102600921 A 7/2012
CN 106810456 A 6/2017
(Continued)

OTHER PUBLICATIONS

Office Action and English translation for corresponding Chinese application No. 202210182946.9, dated May 19, 2023.
(Continued)

*Primary Examiner* — Vu A Nguyen
(74) *Attorney, Agent, or Firm* — Leason Ellis LLP

(57) ABSTRACT

The present application relates to the technical field of organic materials and provides an organic compound, an electronic component and an electronic apparatus containing the organic compound. The organic compound has a structure shown in Formula 1. The organic compound, when used in an organic electroluminescent device, can improve the performance of the device.

(Continued)

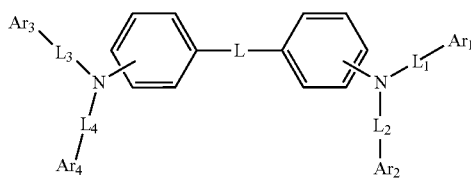

Formula 1

8 Claims, 2 Drawing Sheets

(51) Int. Cl.
*C07C 211/61* (2006.01)
*C07D 307/91* (2006.01)
*C07D 333/76* (2006.01)
*C09K 11/06* (2006.01)
*H10K 50/15* (2023.01)

(52) U.S. Cl.
CPC ......... *C07D 307/91* (2013.01); *C07D 333/76* (2013.01); *C09K 11/06* (2013.01); *H10K 85/636* (2023.02); *C07B 2200/05* (2013.01); *C07C 2602/08* (2017.05); *C07C 2602/10* (2017.05); *C07C 2602/18* (2017.05); *C09K 2211/1014* (2013.01); *H10K 50/15* (2023.02); *H10K 85/626* (2023.02); *H10K 85/6574* (2023.02); *H10K 85/6576* (2023.02)

(56) References Cited

FOREIGN PATENT DOCUMENTS

| CN | 109400488 | A | * | 3/2019 | |
|---|---|---|---|---|---|
| CN | 109400488 | A | | 3/2019 | |
| CN | 109438258 | A | | 3/2019 | |
| CN | 113567213 | A | | 10/2021 | |
| CN | 113735759 | A | | 12/2021 | |
| CN | 113773207 | A | * | 12/2021 | ........... C07C 211/54 |
| CN | 114354312 | A | | 4/2022 | |
| CN | 114394949 | A | | 4/2022 | |
| CN | 114394949 | A | * | 4/2022 | ........... C07D 307/91 |
| CN | 114805179 | A | * | 7/2022 | ........... C07B 59/002 |
| CN | 115521214 | A | | 12/2022 | |
| EP | 0826420 | A1 | | 3/1998 | |
| JP | 2002014478 | A | | 1/2002 | |
| JP | 2012220727 | A | | 11/2012 | |
| JP | 2013124271 | A | | 6/2013 | |
| KR | 20210067843 | A | | 6/2021 | |
| KR | 20220049358 | A | * | 4/2022 | |
| WO | WO-2022108258 | A1 | * | 5/2022 | |
| WO | 2023160121 | A1 | | 8/2023 | |

OTHER PUBLICATIONS

International Search Report and English Translation for corresponding International application No. PCT/CN2022/129052, dated Dec. 15, 2022.

Notification of Grant and English translation for corresponding Chinese application No. 202210182946.9, dated Jun. 27, 2023.

* cited by examiner

ORGANIC COMPOUND, ELECTRONIC COMPONENT AND ELECTRONIC APPARATUS COMPRISING THE SAME

CROSS-REFERENCE TO RELATED APPLICATIONS

This application is a U.S. National Stage of International Application No. PCT/CN2022/138052, filed on Dec. 9, 2022 claims the priority of Chinese patent application No. 202210182946.9 filed on Feb. 25, 2022, both of which are incorporated herein by reference in their enteritis as a part of the present application.

FIELD OF THE INVENTION

The present application relates to the technical field of organic luminescent materials, and in particular to an organic compound, an electronic component and an electronic apparatus comprising the organic compound.

BACKGROUND OF THE INVENTION

In recent years, organic electroluminescent devices (OLED), as a new generation of display technology, have been widely used in the field of mobile phone display, vehicle display, and the like. A common organic electroluminescent device consists of an anode, a cathode, and more than one organic layers disposed between the cathode and the anode. When a voltage is applied to the cathode and the anode, an electric field is formed between the two electrodes. Under the influence of the electric field, electrons on the cathode side migrate to an organic light emitting layer, and holes on the anode side also migrate to the organic light emitting layer. The electrons and the holes recombine in the organic light emitting layer, forming excitons which, in excited state, release energy. During the process that the excitons change from the excited state to the ground state by releasing energy, light is emitted. Therefore, it is very important to improve the recombination of electrons and holes in OLED devices.

In order to improve the brightness, efficiency, and service life of an organic electroluminescent device, a multi-layer structure is often used in the device. The multi-layer structure includes a hole injection layer, a hole transport layer, an organic light emitting layer, an electron transport layer, and the like. These organic layers can improve the injection efficiency of carriers (holes and electrons) between the layers, balance the transporting of the carriers between the layers, and thus improve the brightness and the efficiency of the device.

Bis-triarylamine-based hole transport layers have been disclosed in many documents, such as JP1997316038A. Bis-triarylamine-based hole transport materials, including NPB, have also been widely used in mass production due to their excellent hole transport properties.

Although NPB has an excellent hole transport property, its glass-transition temperature (Tg) is only 96° C., which makes the organic electroluminescent device prone to crystallize at high temperatures and thus leads to reduced performance of the device.

SUMMARY OF THE INVENTION

Directed against the above problems with the existing technology, the present application aims at providing an organic compound, an electronic component and an electronic apparatus comprising the organic compound. The organic compound, when used in an organic electroluminescent device, can improve the performance of the device.

A first aspect of the present application provides an organic compound having a structure shown in Formula 1:

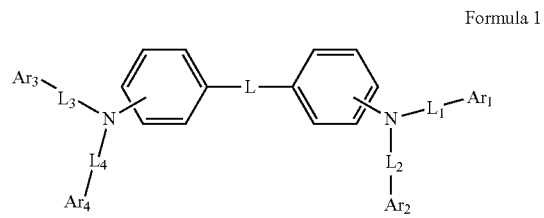

Formula 1 wherein L, $L_1$, $L_2$, $L_3$, and $L_4$ are identical or different, and are each independently selected from a single bond, or a substituted or unsubstituted arylene having 6 to 30 carbon atoms;

substituents of L, $L_1$, $L_2$, $L_3$, and $L_4$ are identical or different, and are each independently selected from deuterium, a halogen, a cyano, a trialkylsiyl having 3 to 12 carbon atoms, an alkyl having 1 to 10 carbon atoms, an aryl having 6 to 20 carbon atoms, or a heteroaryl having 3 to 20 carbon atoms;

$Ar_1$, $Ar_2$, $Ar_3$, and $Ar_4$ are identical or different, and are each independently selected from a substituted or unsubstituted aryl having 6 to 14 ring carbon atoms, a substituted or unsubstituted heteroaryl having 5 to 15 ring carbon atoms, or a group shown in Formula 2; and at least one of $Ar_1$ and $Ar_3$ is selected from the group shown in Formula 2;

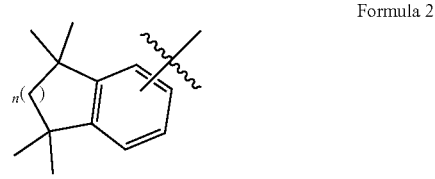

Formula 2 wherein n is 1 or 2;

substituents of $Ar_1$, $Ar_2$, $Ar_3$, and $Ar_4$ are identical or different, and are each independently selected from deuterium, a halogen, a cyano, a trialkylsiyl having 3 to 12 carbon atoms, an alkyl having 1 to 10 carbon atoms, a haloalkyl having 1 to 10 carbon atoms, a deuterated alkyl having 1 to 10 carbon atoms, an aryl having 6 to 12 carbon atoms, or a heteroaryl having 5 to 12 carbon atoms.

A second aspect of the present application provides an electronic component including an anode and a cathode disposed opposite each other, and an organic functional layer disposed between the anode and the cathode, the functional layer comprises the above described organic compound.

A third aspect of the present application provides an electronic apparatus including the electronic component described in the second aspect of the present application.

In the organic compound of the present application, two arylamines are linked by a linking group containing at least two benzene rings. The formed compound exhibits an appropriate degree of torque in space. Further, a benzo 5-/6-membered ring with a particular spatial configuration is introduced on at least one of the arylamines, and meanwhile the aromatic group on the arylamine is controlled to be a smaller group. This can avoid intermolecular stacking of the compound, and thus make the compound not prone to crystallization during evaporation, thereby improving the film-forming property of the material. The organic compound, when used in an organic luminescent device, can prolong the service life of the device. In addition, the particular structure of the organic compound of the present application exhibits better hole mobility, which can improve the matching between the hole transport layer and the organic layer, and can effectively improve the luminescence efficiency of the device.

BRIEF DESCRIPTION OF THE DRAWINGS

The accompanying drawings are intended to provide a further understanding of the present application and form a part of the specification. The accompanying drawings, together with the following specific embodiments, are used to illustrate the present application, but do not constitute any limitation to the present application.

LIST OF REFERENCE SIGNS

Figure 1:
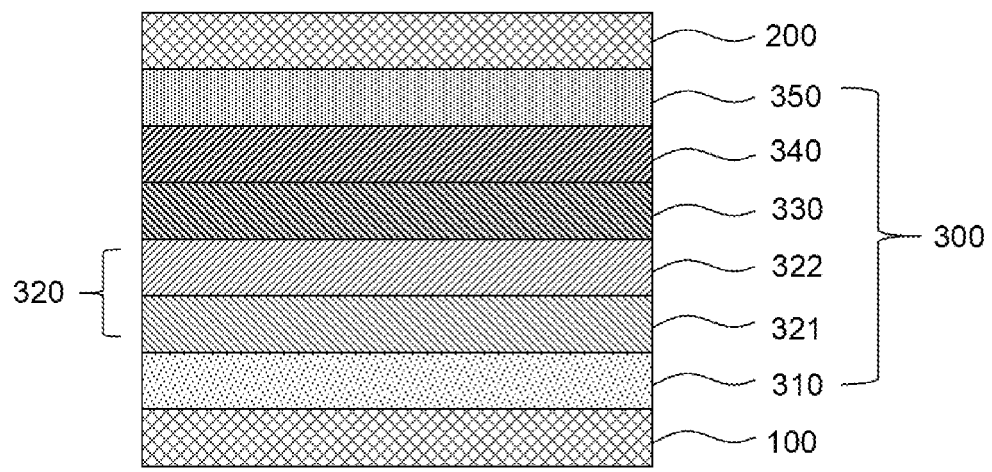
FIG. 1 is a schematic structural diagram of an organic electroluminescent device according to an embodiment of the present application.

100: anode; 200: cathode; 300: functional layer; 310: hole injection layer; 320: hole transport layer; 321: first hole transport layer; 322: second hole transport layer; 330: organic light emitting layer; 340: electron transport layer; 350: electron injection layer; 360: photoelectric conversion layer; 400: first electronic apparatus; 500: second electronic apparatus

DETAILED DESCRIPTION OF THE EMBODIMENTS

Exemplary embodiments will now be described more comprehensively with reference to the accompanying drawings. The exemplary embodiments, however, can be implemented in a variety of forms and should not be interpreted as being limited to the examples set forth herein. On the contrary, these embodiments are provided to make the present application more comprehensive and complete, and to communicate the concepts of these exemplary embodiments fully to those skilled in the art. Features, structures, or characteristics described can be combined in one or more embodiments in any suitable manner. In the following description, many specific details are provided to give a full understanding of the embodiments of the present application.

In a first aspect, the present application provides an organic compound having a structure shown in Formula 1:

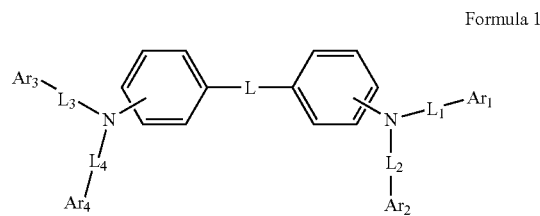

Formula 1 wherein L, $L_1$, $L_2$, $L_3$, and $L_4$ are identical or different, and are each independently selected from a single bond, or a substituted or unsubstituted arylene having 6 to 30 carbon atoms;

substituents of L, $L_1$, $L_2$, $L_3$, and $L_4$ are identical or different, and are each independently selected from deuterium, a halogen, a cyano, a trialkylsiyl having 3 to 12 carbon atoms, an alkyl having 1 to 10 carbon atoms, an aryl having 6 to 20 carbon atoms, or a heteroaryl having 3 to 20 carbon atoms;

$Ar_1$, $Ar_2$, $Ar_3$, and $Ar_4$ are identical or different, and are each independently selected from a substituted or unsubstituted aryl having 6 to 14 ring carbon atoms, a substituted or unsubstituted heteroaryl having 5 to 15 ring carbon atoms, or a group shown in Formula 2; and at least one of $Ar_1$ and $Ar_3$ is selected from the group shown in Formula 2;

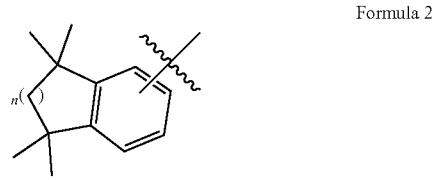

Formula 2 wherein n is 1 or 2 substituents of $Ar_1$, $Ar_2$, $Ar_3$, and $Ar_4$ are identical or different, and are each independently selected from deuterium, a halogen, a cyano, a trialkylsiyl having 3 to 12 carbon atoms, an alkyl having 1 to 10 carbon atoms, a haloalkyl having 1 to 10 carbon atoms, a deuterated alkyl having 1 to 10 carbon atoms, an aryl having 6 to 12 carbon atoms, or a heteroaryl having 5 to 12 carbon atoms.

In the present application, the expression "at least one of $Ar_1$ and $Ar_3$ is selected from the group shown in Formula 2" means that one of $Ar_1$ and $Ar_3$ is selected from the group shown in Formula 2, i.e., $Ar_1$ is selected from the group shown in Formula 2 or $Ar_3$ is selected from the group shown in Formula 2; optionally, both $Ar_1$ and $Ar_3$ are selected from the group shown in Formula 2.

In an embodiment, $Ar_1$ and $Ar_3$ are identical or different, and are each independently selected from a substituted or unsubstituted aryl having 6 to 14 ring carbon atoms, a substituted or unsubstituted heteroaryl having 5 to 15 ring carbon atoms, or a group shown in Formula 2, and at least one of $Ar_1$ and $Ar_3$ is selected from the group shown in Formula 2; $Ar_2$ and $Ar_4$ are identical or different, and are each independently selected from a substituted or unsubstituted aryl having 6 to 14 ring carbon atoms, or a substituted or unsubstituted heteroaryl having 5 to 15 ring carbon atoms.

In the present application, the number of ring carbon atoms is the number of carbon atoms on the ring of "aryl", "heteroaryl" in "a substituted or unsubstituted aryl having 6 to 14 ring carbon atoms, a substituted or unsubstituted heteroaryl having 5 to 15 ring carbon atoms". It should be noted that, the number of carbon atoms of substituents of "a substituted or unsubstituted aryl having 6 to 14 ring carbon atoms, or a substituted or unsubstituted heteroaryl having 5 to 15 ring carbon atoms" is not counted in the number of ring carbon atoms. For example, 9,9-dimethylfluorenyl is methyl-substituted aryl having 13 ring carbon atoms, diphenylfluorenyl is a phenyl-substituted aryl having 13 ring carbon atoms, and phenyl-substituted dibenzofuranyl is a phenyl-substituted heteroaryl having 12 ring carbon atoms; in diphenylfluorenyl and phenyl-substituted diphenylfluorenyl, the number of carbon atoms of phenyl as the substituent is not counted in the number of ring carbon atoms of "a substituted or unsubstituted aryl having 6 to 14 ring carbon atoms, or a substituted or unsubstituted heteroaryl having 5 to 15 ring carbon atoms".

In the present application, the expression " . . . each independently" may be used interchangeably with the expressions " . . . respectively and independently", and " . . . independently selected from", and all these expressions should be interpreted in a broad sense. They can not only mean that, in different groups, specific options expressed between the same symbols do not affect each other, but also mean that in a same group, specific options expressed between the same symbols do not affect each other. For example, the meaning of "

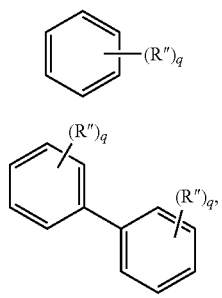

where each q is independently 0, 1, 2 or 3, and each R" is independently selected from hydrogen, deuterium, fluorine and chlorine" is as follows: formula Q-1 represents that q substituent R"s exist on a benzene ring, each R" can be the identical or different, and options of each R" do not affect each other; and formula Q-2 represents that each benzene ring of biphenyl has q substituent R"s, the number q of the substituent R"s on the two benzene rings can be the identical or different, each R" can be the identical or different, and options of each R" do not affect each other.

In the present application, the term "substituted or unsubstituted" means that the functional group defined by the term may or may not have a substituent (hereinafter referred to as Rc for ease of description). For example, "a substituted or unsubstituted aryl" is an aryl having a substituent Rc or is an unsubstituted aryl. The foregoing substituent, namely Rc, may be, for example, deuterium, halogen, cyano, trialkylsilyl, alkyl, heteroaryl, aryl, or the like.

In the present application, the number of carbon atoms of a substituted or unsubstituted functional group is the number of all carbon atoms. For example, if L is a substituted arylene having 12 carbon atoms, then the number of all carbon atoms of the arylene group and substituents thereof is 12.

In the present application, aryl refers to any functional group or substituent derived from an aromatic carbon ring. An aryl group may be a monocyclic aryl group (e.g., phenyl) or a polycyclic aryl group. In other words, an aryl group may be a monocyclic aryl group, a fused aryl group, two or more monocyclic aryl groups connected by a carbon-carbon conjugate linkage, a monocyclic aryl group and a fused aryl group connected by a carbon-carbon conjugate linkage, or two or more fused aryl groups connected by a carbon-carbon conjugate linkage. That is, unless otherwise specified, two or more aromatic groups connected by a carbon-carbon conjugate linkage may also be regarded as an aryl group in the present application. Among them, fused aryl groups may include, for example, bicyclic fused aryl groups (e.g., naphthyl), tricyclic fused aryl groups (e.g., phenanthryl, fluorenyl, anthryl), and the like. An aryl group does not contain heteroatoms such as B, N, O, S, P, Se, Si, or the like. For example, in the present application, biphenyl and terphenyl

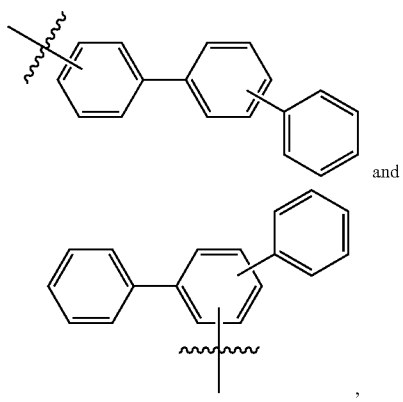

and the like are aryl groups. Examples of aryl may include, but are not limited to, phenyl, naphthyl, fluorenyl, anthryl, phenanthryl, biphenyl, terphenyl, benzo[9,10]phenanthryl, pyrenyl, benzofluoranthenyl, chrysenyl, and the like. In the present application, arylene refers to a divalent group formed by further removing one hydrogen atom from an aryl group.

In the present application, a substituted aryl may mean that one or more hydrogen atoms of the aryl group are replaced by a group such as deuterium, halogen, cyano, trialkylsilyl, alkyl, haloalkyl, deuterated alkyl, heteroaryl, aryl, or the like. It should be appreciated that the number of carbon atoms of substituted arylene is the number of all carbon atoms of the arylene group and substituents thereof. For example, substituted arylene having 18 carbon atoms means that the number of all carbon atoms of the arylene group and substituents thereof is 18.

In the present application, heteroaryl refers to a monovalent aromatic ring containing at least one heteroatom or a derivative thereof. The heteroatom may be one or more selected from B, O, N, P, Si, Se, or S. A heteroaryl group may be a monocyclic heteroaryl group or polycyclic heteroaryl group. In other words, a heteroaryl group may be a single aromatic ring system, or a plurality of aromatic ring systems connected by a carbon-carbon conjugate linkage, with any of the aromatic ring systems being an aromatic monocyclic ring or a fused aromatic ring. For example, heteroaryl groups may include, but are not limited to, thiophenyl, furyl, pyrryl, imidazolyl, thiazolyl, oxazolyl, oxadiazolyl, triazolyl, pyridyl, bipyridyl, pyrimidyl, triazinyl, acridinyl, pyridazinyl, pyrazinyl, quinolyl, quinazolinyl, quinoxalinyl, phenoxazinyl, phthalazinyl, pyridopyrimidinyl, pyridopyrazinyl, pyrazinopyrazinyl, isoquinolyl, indolyl, carbazolyl, benzoxazolyl, benzimidazolyl, benzothiazolyl, benzocarbazolyl, benzothiophenyl, dibenzothiophenyl, thienothiophenyl, benzofuranyl, phenanthrolinyl, isoxazolyl, thiadiazolyl, benzothiazolyl, phenothiazinyl, silafluorenyl, dibenzofuranyl, N-phenylcarbazolyl, N-pyridylcarbazolyl, N-methylcarbazolyl, and the like. Among these, thiophenyl, furyl, phenanthrolinyl, and the like are heteroaryl group of a single aromatic ring system, and N-phenylcarbazolyl and N-pyridylcarbazolyl are each a heteroaryl group of polycyclic systems connected by a carbon-carbon conjugate linkage. In the present application, heteroarylene involved is a divalent group formed by further removing one hydrogen atom from a heteroaryl group.

In the present application, substituted heteroaryl may mean that one or more hydrogen atoms in the heteroaryl group are replaced by group such as deuterium atom, halogen, cyano, aryl, heteroaryl, trialkylsilyl, alkyl, cycloalkyl, haloalkyl, and the like. It should be understood that the number of carbon atoms of a substituted heteroarylene is the number of all carbon atoms of the heteroarylene group and substituents of the heteroarylene group.

In the present application, the number of carbon atoms of aryl as a substituent may be 6 to 20. For example, the number of carbon atoms may be 6, 7, 8, 9, 10, 11, 12, 13, 14, 15, 16, 17, 18, 19, or 20. Specific Examples of aryl as a substituent include, but are not limited to, phenyl, biphenyl, naphthyl, fluorenyl, phenanthryl, anthryl, and chrysenyl.

In the present application, the number of carbon atoms of heteroaryl as a substituent may be 3 to 20. For example, the number of carbon atoms may be 3, 4, 5, 6, 7, 8, 9, 10, 11, 12, 13, 14, 15, 16, 17, 18, 19, or 20. Specific examples of heteroaryl as a substituent include, but are not limited to, triazinyl, pyridyl, pyrimidyl, carbazolyl, dibenzofuranyl, dibenzothiophenyl, quinolyl, quinazolinyl, quinoxalinyl, and isoquinolyl.

In the present application, alkyl having 1 to 10 carbon atoms may include straight-chain alkyl having 1 to 10 carbon atoms and branched-chain alkyl having 3 to 10 carbon atoms. The number of carbon atoms of alkyl may be, for example, 1, 2, 3, 4, 5, 6, 7, 8, 9, or 10. Specific examples of alkyl include, but are not limited to, methyl, ethyl, n-propyl, isopropyl, n-butyl, isobutyl, tert-butyl, n-pentyl, isopentyl, neo-pentyl, n-hexyl, n-octyl, 2-ethylhexyl, nonyl, decyl, 3,7-dimethyloctyl, and the like.

In the present application, halogen may be, for example, fluorine, chlorine, bromine, iodine.

In the present application, specific examples of trialkylsilyl include, but are not limited to, trimethylsilyl, triethylsilyl, and the like.

In the present application, specific examples of haloalkyl include, but are not limited to, trifluoromethyl, and the like.

In the present application, specific examples of deuterated alkyl include, but are not limited to, trideuteromethyl, and the like.

In the present application, an unlocated linkage bond refers to a single bond extending from a ring system, and it indicates that the linkage bond can be linked at one end thereof to any position in the ring system through which the bond passes, and linked at the other end thereof to the rest of the compound molecule.

For example, as shown in Formula (f) below, the naphthalyl group represented by Formula (f) is linked to other positions of the molecule via two unlocated linkage bonds passing through the two rings, which indicates any of possible linkages shown in Formulae (f-1) to (f-10):

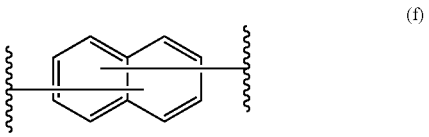

(f)

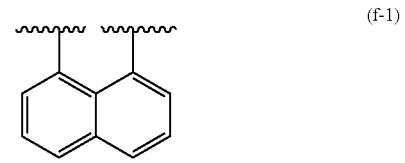

(f-1)

(f-2)

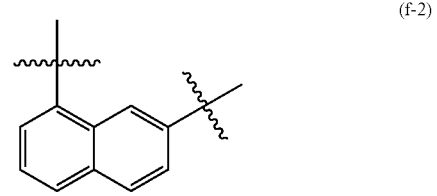

(f-3)

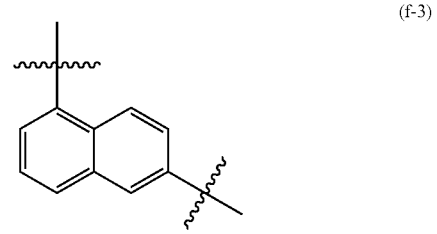

(f-4)

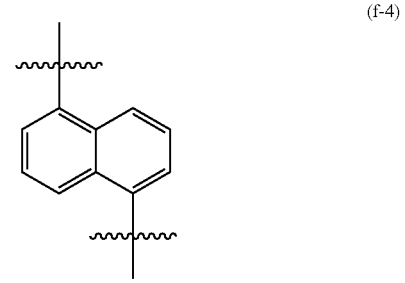

(f-5)

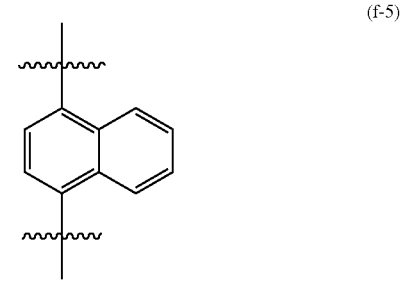

(f-6)

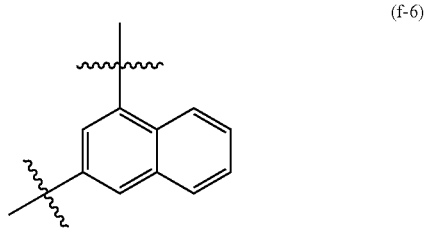

-continued (f-7) 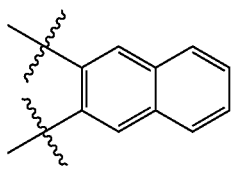

(f-8) 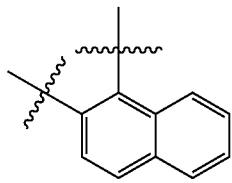

(f-9)
(f-10)
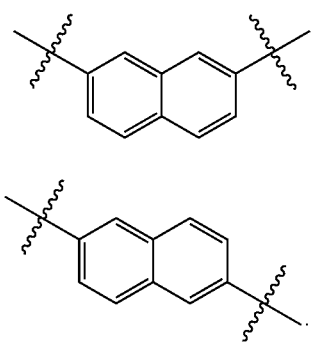

As another example, as shown in Formula (X') below, the dibenzofuranyl group represented by Formula (X') is linked to another position of the molecule via an unlocated linkage bond extending from the center of one benzene ring, which indicates any of possible linkages shown in Formulae (X'-1) to (X'-4):

(X') 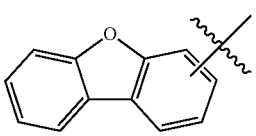

(X'-1) 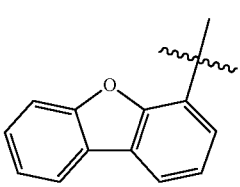

(X'-2) 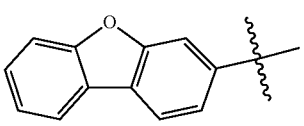

(X'-3) 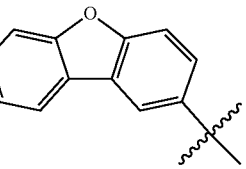

-continued (X'-4) 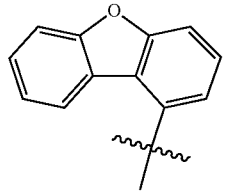

In the present application, $Ar_1$, $Ar_2$, $Ar_3$, and $Ar_4$ are each independently selected from a substituted or unsubstituted aryl having 6, 7, 8, 9, 10, 11, 12, 13, or 14 ring carbon atoms, a substituted or unsubstituted heteroaryl having 5, 6, 7, 8, 9, 10, 11, 12, 13, 14, or 15 ring carbon atoms, or the group shown in Formula 2.

In the present application, the group shown in Formula 2 is specifically selected from the group consisting of the following structures:

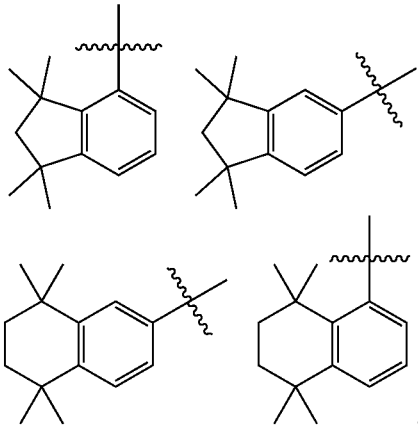

In an embodiment of the present application, $Ar_1$ and $Ar_3$ are identical or different, and are each independently selected from a substituted or unsubstituted aryl having 6 to 14 ring carbon atoms, a substituted or unsubstituted heteroaryl having 5 to 15 ring carbon atoms, or the group shown in Formula 2; and at least one of $Ar_1$ and $Ar_3$ is selected from the group shown in Formula 2.

$Ar_2$ and $Ar_4$ are identical or different, and are each independently selected from a substituted or unsubstituted aryl having 6 to 14 ring carbon atoms, or a substituted or unsubstituted heteroaryl having 5 to 15 ring carbon atoms.

In an embodiment of the present application, L, $L_1$, $L_2$, $L_3$, and $L_4$ are each independently selected from a single bond, or a substituted or unsubstituted arylene having 6 to 20 carbon atoms. For example, L, $L_1$, $L_2$, $L_3$, and $L_4$ are each independently selected from a single bond, or a substituted or unsubstituted arylene having 6, 7, 8, 9, 10, 11, 12, 13, 14, 15, 16, 17, 18, 19, or 20 carbon atoms.

Optionally, the substituents of L, $L_1$, $L_2$, $L_3$, and $L_4$ are each independently selected from deuterium, a fluorine, a cyano, a trialkylsilyl having 3 to 6 carbon atoms, an alkyl having 1 to 5 carbon atoms, an aryl having 6 to 12 carbon atoms, or a heteroaryl having 5 to 12 carbon atoms.

Optionally, L, $L_1$, $L_2$, $L_3$, and $L_4$ are each independently selected from a single bond, a substituted or unsubstituted phenylene, a substituted or unsubstituted naphthylene, or a substituted or unsubstituted biphenylene.

Optionally, the substituents of L, L$_1$, L$_2$, L$_3$, and L$_4$ are each independently selected from deuterium, a fluorine, a cyano, a trimethylsilyl, a methyl, an ethyl, an isopropyl, a tert-butyl, a phenyl, a naphthyl, a biphenyl, a pyridyl, a dibenzofuranyl, a dibenzothiophenyl, or a carbazolyl.

Optionally, L, L$_1$, L$_2$, L$_3$, and L$_4$ are each independently selected from a single bond or a substituted or unsubstituted group V. The unsubstituted group V is selected from the following groups:

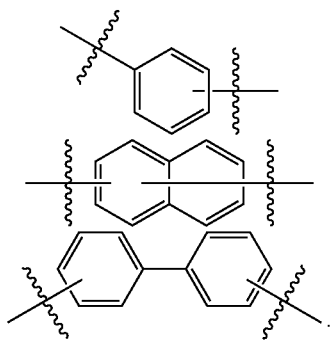

the substituted group V may have one or more substituents, the substituents each independently selected from deuterium, a fluorine, a cyano, a trimethylsilyl, a methyl, an ethyl, an isopropyl, a tert-butyl, a phenyl, a naphthyl, a biphenyl, or a pyridyl; and when the number of the substituents are greater than 1, the substituents are identical or different.

Optionally, L, L$_1$, L$_2$, L$_3$, and L$_4$ are each independently selected from a single bond or the following groups:

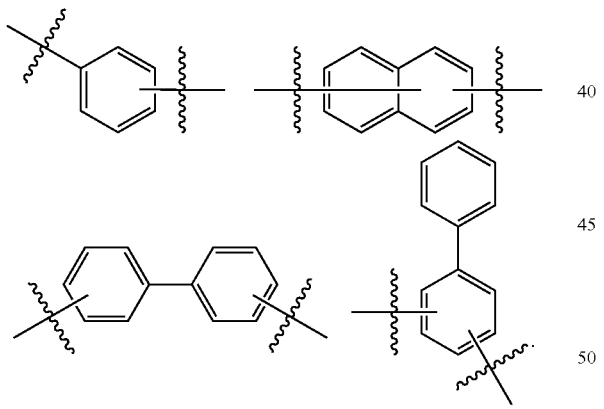

Further optionally, L, L$_1$, L$_2$, L$_3$, and L$_4$ are each independently selected from a single bond or the following groups:

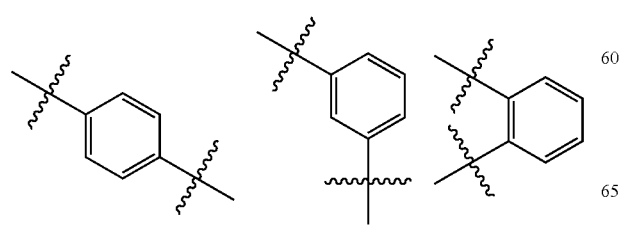

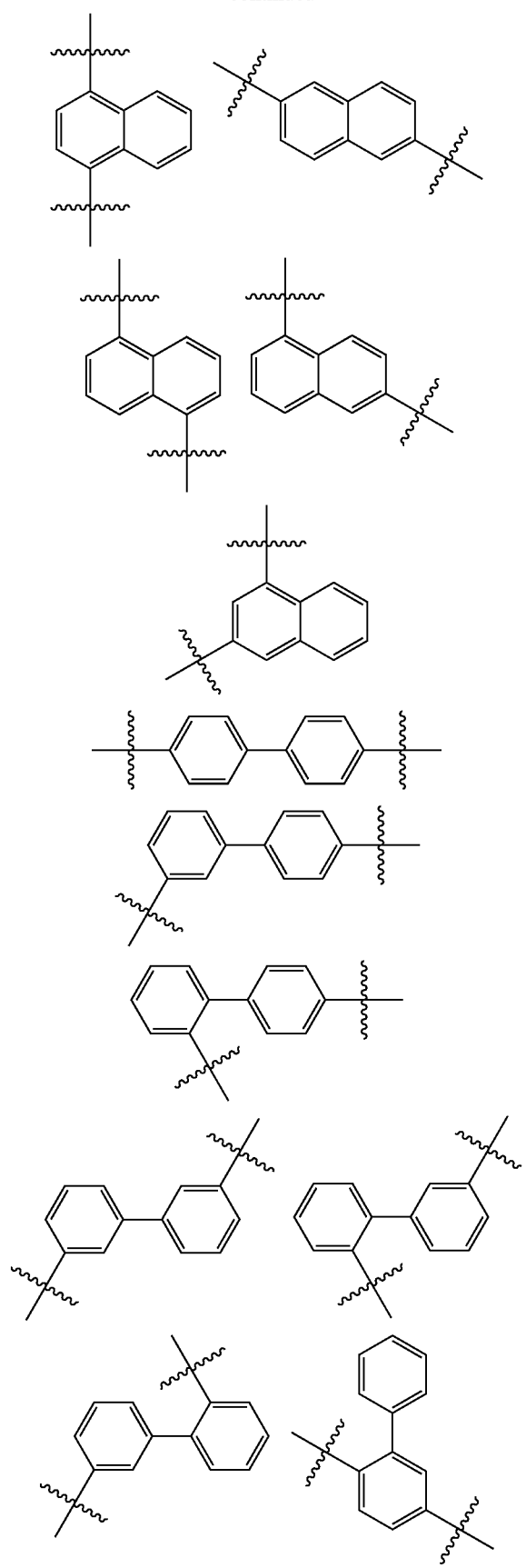

-continued

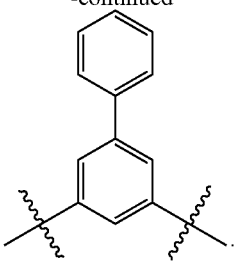

Optionally, L is selected from a single bond or the group consisting of the following groups:

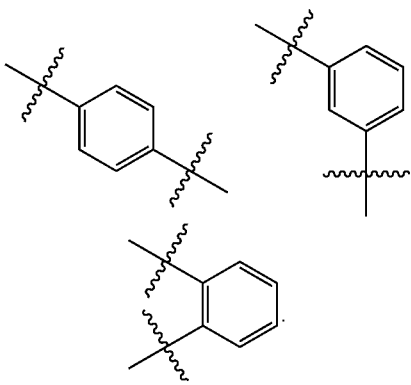

In the present application, specific examples of the substituted or unsubstituted aryl having 6 to 14 ring carbon atoms include, but are not limited to a substituted or unsubstituted phenyl, a substituted or unsubstituted naphthyl, a substituted or unsubstituted biphenyl, a substituted or unsubstituted terphenyl, a substituted or unsubstituted fluorenyl, a substituted or unsubstituted phenanthryl, or a substituted or unsubstituted anthryl.

In the substituted or unsubstituted aryl having 6 to 14 ring carbon atoms, substituents are identical or different, and are each independently selected from deuterium, a fluorine, a cyano, a trialkylsilyl having 3 to 6 carbon atoms, an alkyl having 1 to 4 carbon atoms, a haloalkyl having 1 to 4 carbon atoms, a deuterated alkyl having 1 to 4 carbon atoms, an aryl having 6 to 12 carbon atoms, or a heteroaryl having 5 to 12 carbon atoms. Specific examples of the substituents include, but are not limited to deuterium, a fluorine, a cyano, a trimethylsilyl, a methyl, an ethyl, a n-propyl, an isopropyl, a tert-butyl, a phenyl, a naphthyl, a biphenyl, a carbazolyl, a dibenzofuranyl, a dibenzothiophenyl, or a carbazolyl.

In an embodiment, $Ar_1$, $Ar_2$, $Ar_3$, and $Ar_4$ are each independently selected from a substituted or unsubstituted phenyl, a substituted or unsubstituted naphthyl, a substituted or unsubstituted biphenyl, a substituted or unsubstituted terphenyl, a substituted or unsubstituted fluorenyl, a substituted or unsubstituted phenanthryl, a substituted or unsubstituted anthryl, a substituted or unsubstituted dibenzofuranyl, a substituted or unsubstituted dibenzothiophenyl, a substituted or unsubstituted carbazolyl, or the group shown in Formula 2; and at least one of $Ar_1$ and $Ar_3$ is selected from the group shown in Formula 2.

Optionally, the substituents of $Ar_1$, $Ar_2$, $Ar_3$, and $Ar_4$ are each independently selected from deuterium, a fluorine, a cyano, a trimethylsilyl, a methyl, an ethyl, an isopropyl, a tert-butyl, a phenyl, a naphthyl, a biphenyl, a dibenzofuranyl, a dibenzothiophenyl, or a carbazolyl.

Optionally, $Ar_1$ and $Ar_3$ are each independently selected from a substituted or unsubstituted group W or the group shown in Formula 2, at least one of $Ar_1$ and $Ar_3$ being selected from the group shown in Formula 2; $Ar_2$ and $Ar_4$ are identical or different, and are each independently selected from a substituted or unsubstituted group W. The unsubstituted group W is selected from the following groups:

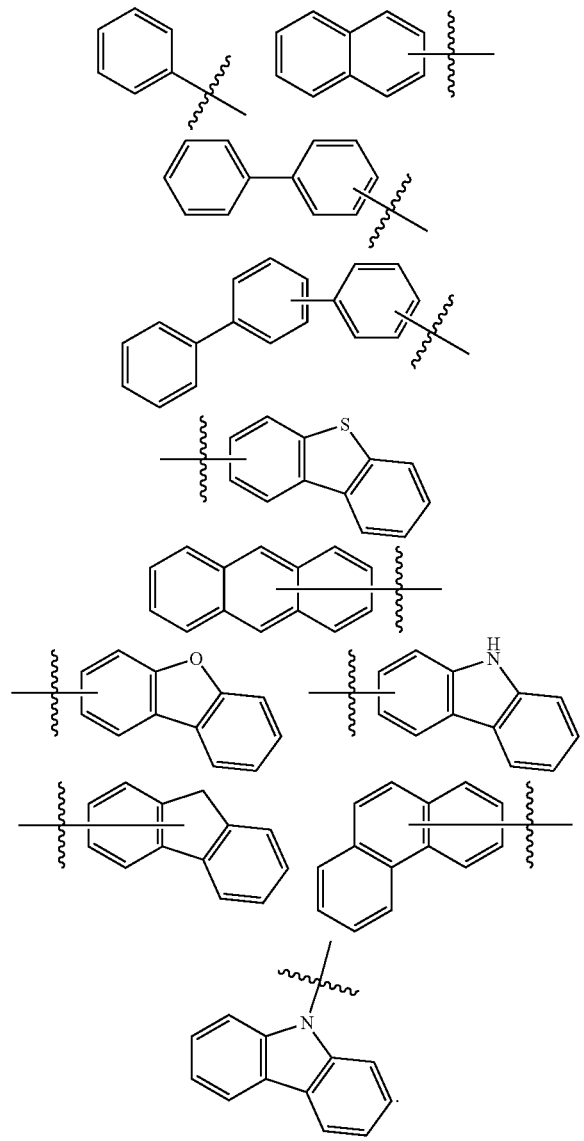

the substituted group W has one or more substituents, the substituents being each independently selected from deuterium, a fluorine, a cyano, a trimethylsilyl, a methyl, an ethyl, an isopropyl, a tert-butyl, a phenyl, a naphthyl, a biphenyl, a dibenzofuranyl, a dibenzothiophenyl, or a carbazolyl; and when the number of the substituents is greater than 1, the substituents are identical or different.

Optionally, $Ar_1$ and $Ar_3$ are identical or different, and are each independently selected from the following groups:

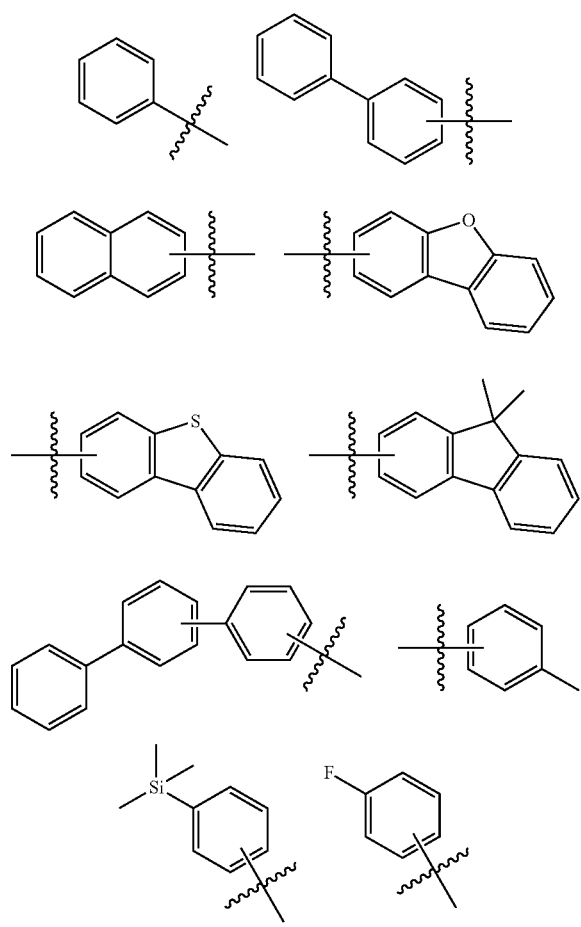
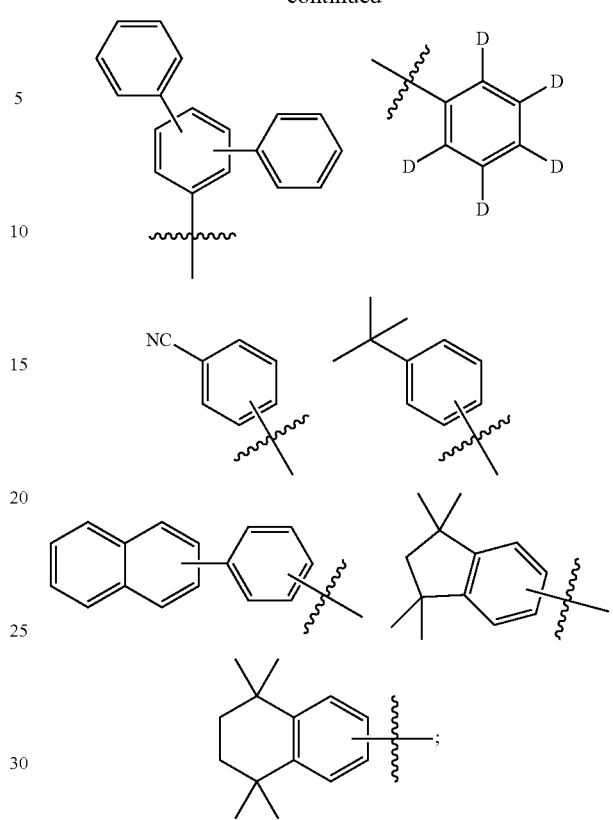
and at least one of Ar₁ and Ar₃ is selected from or
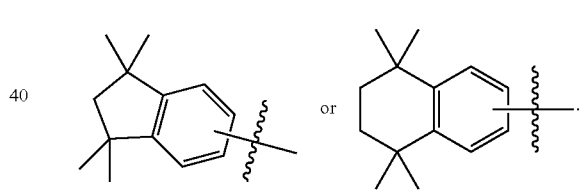
Optionally, Ar₂ and Ar₄ are identical or different, and are each independently selected from the following groups:
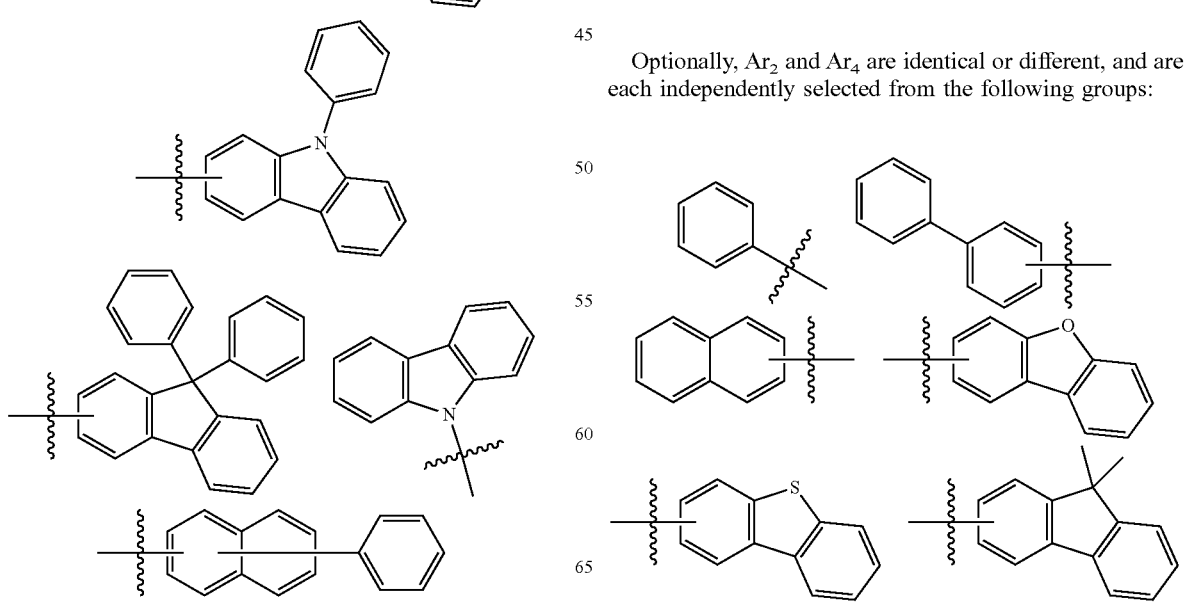

-continued
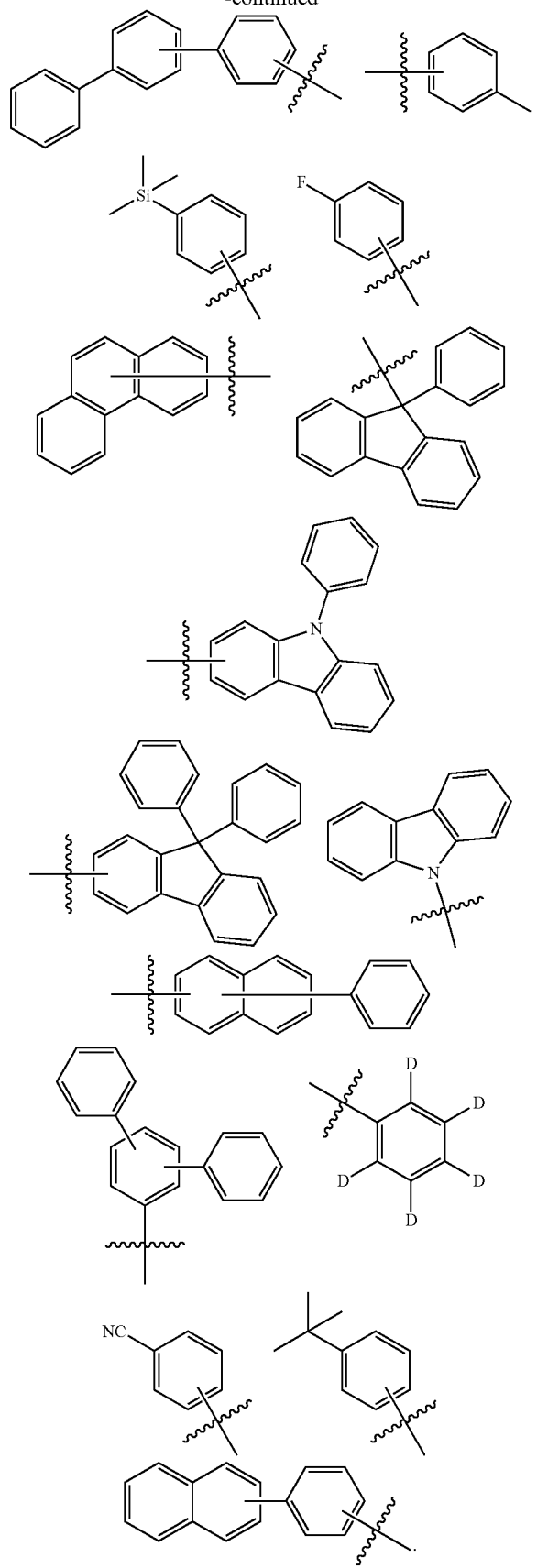
Optionally, Ar₁, Ar₂, Ar₃, and Ar₄ are each independently selected from the following groups:
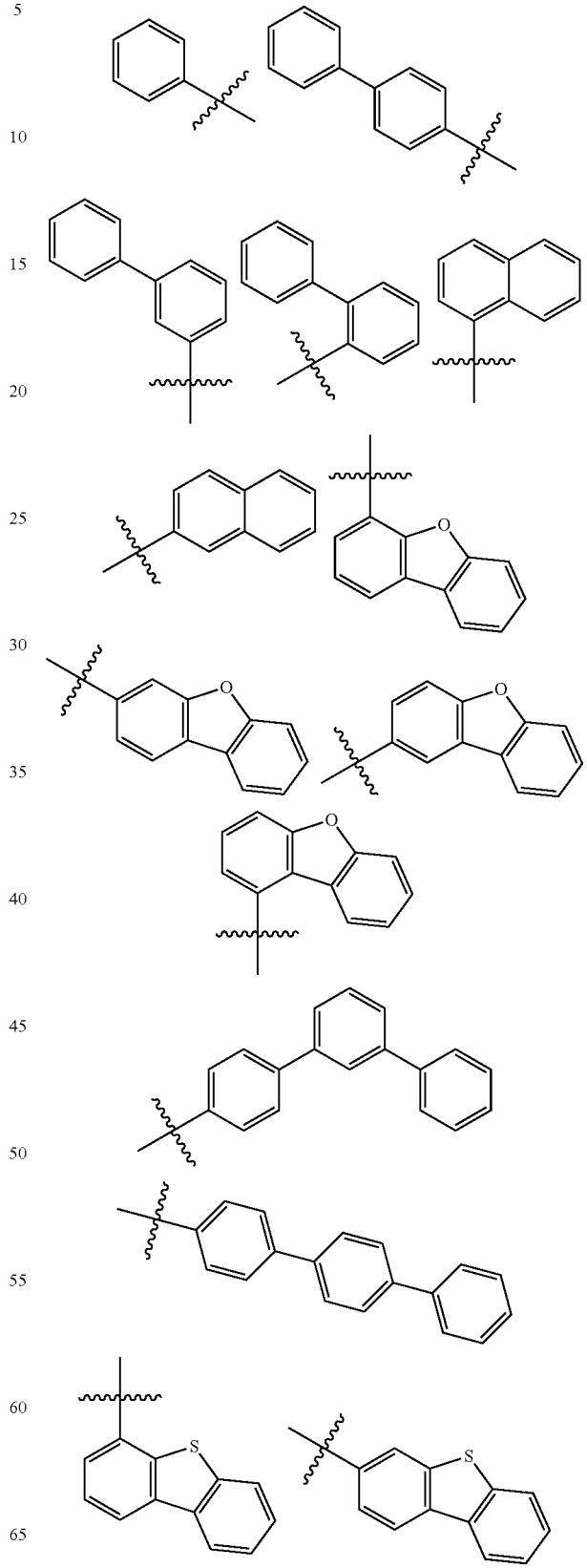

-continued
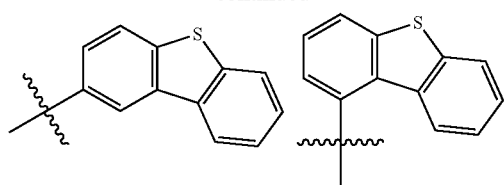
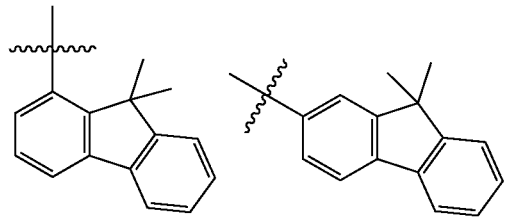
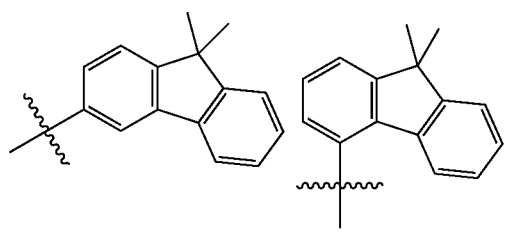
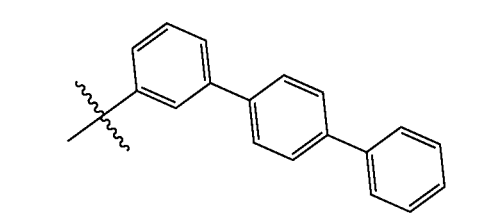
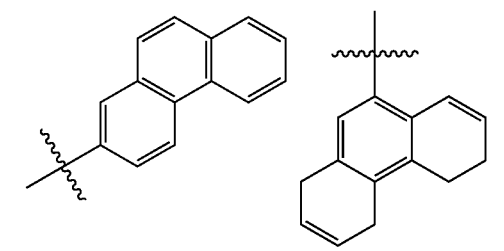
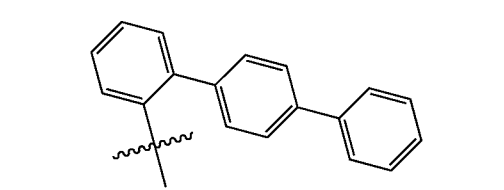
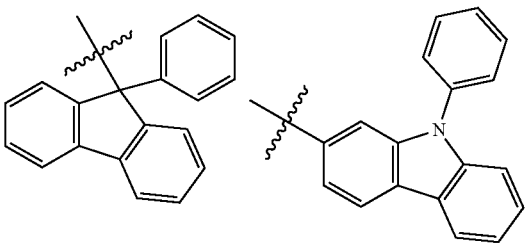
-continued
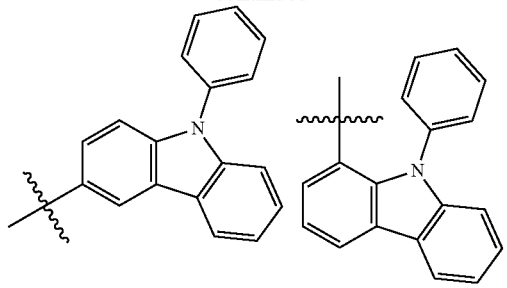
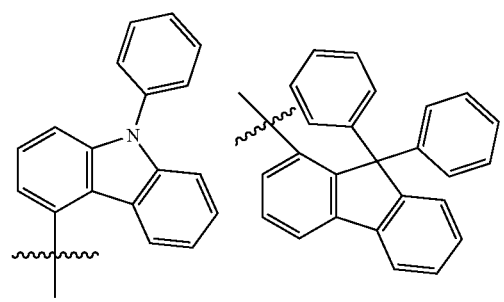
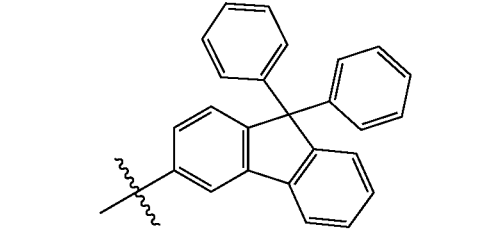
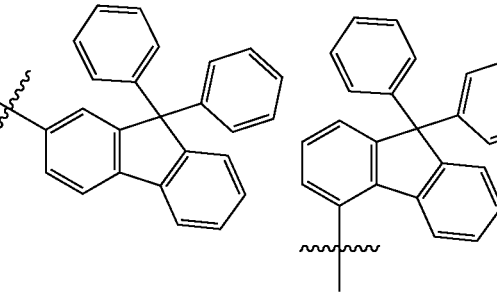
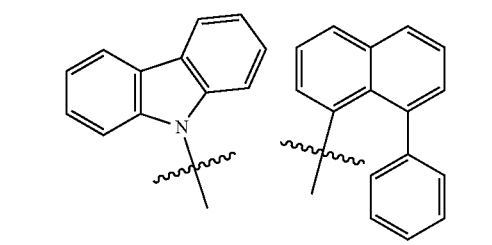
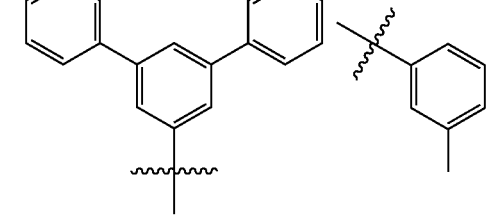

-continued
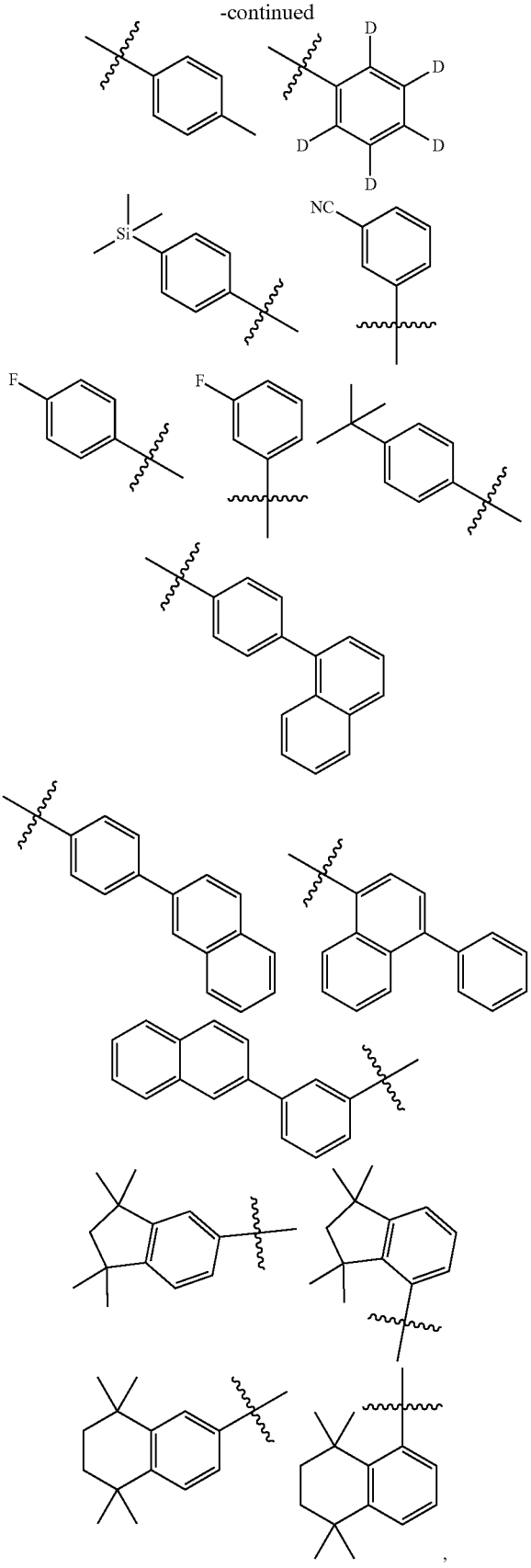
and at least one of $Ar_1$ and $Ar_3$ is selected from
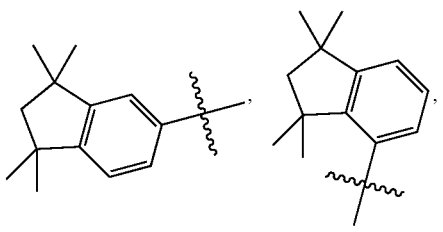
Optionally, $Ar_2$ and $Ar_4$ are not
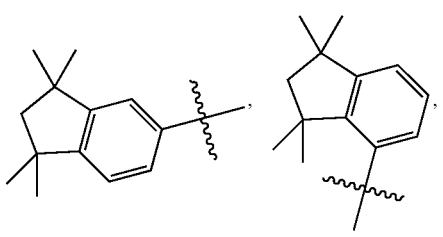
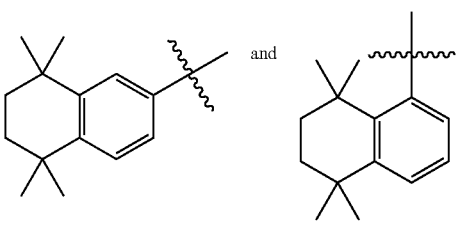
Optionally, the organic compound is selected from the following compounds:
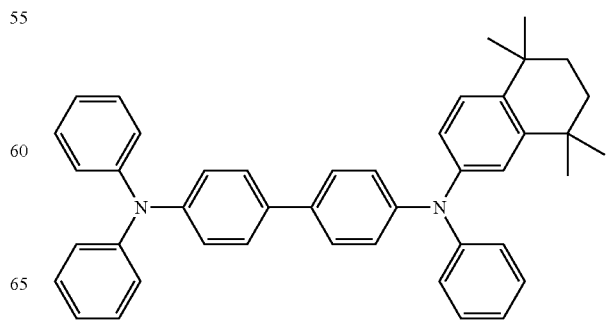
A-1

A-2
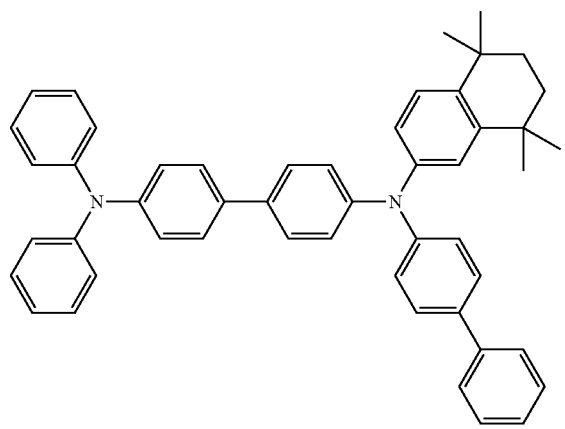
A-3
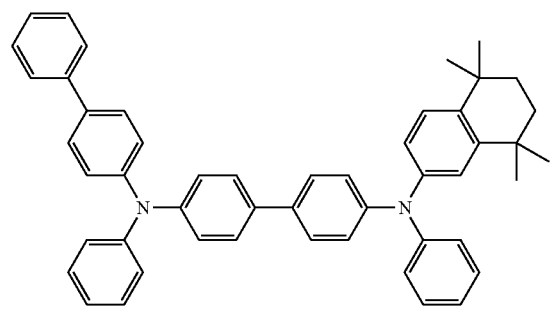
A-4
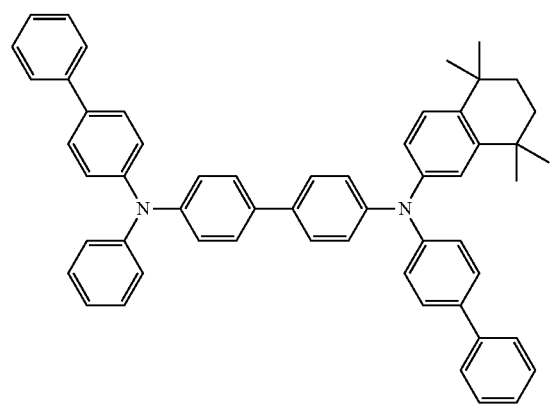
A-5
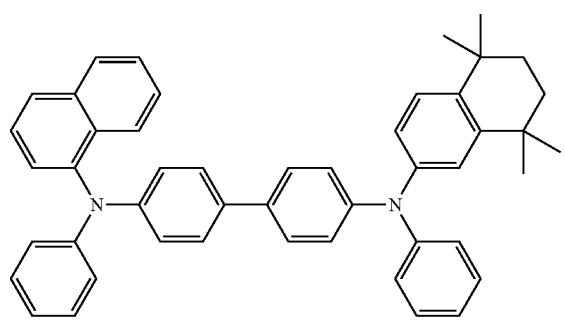
A-6
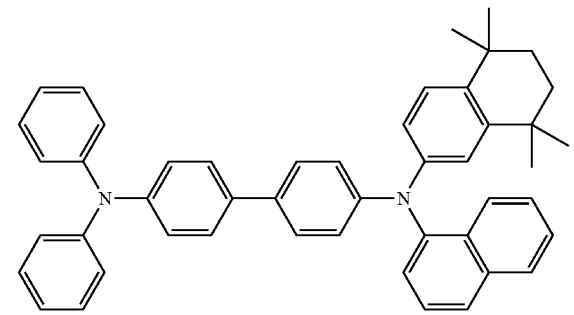
A-7
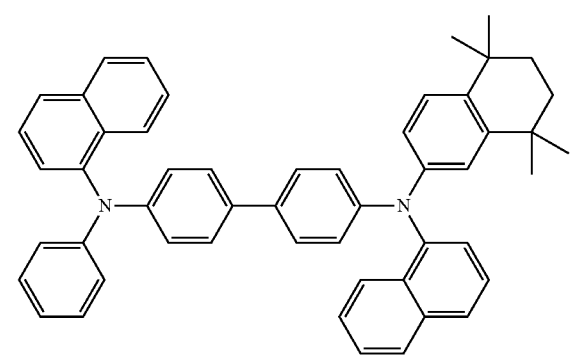
A-8
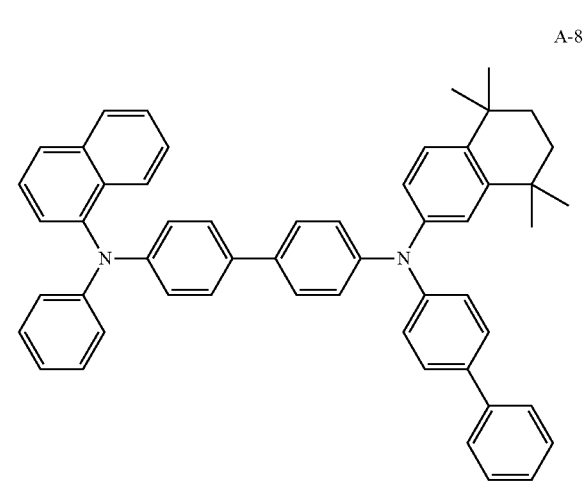
A-9
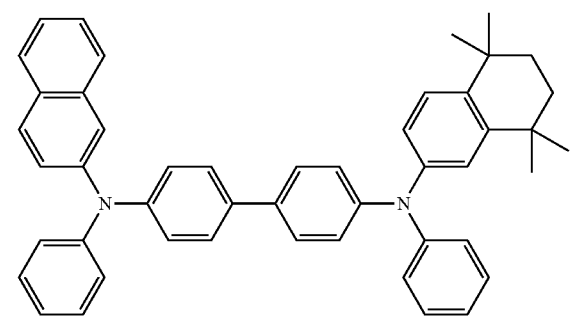

A-10
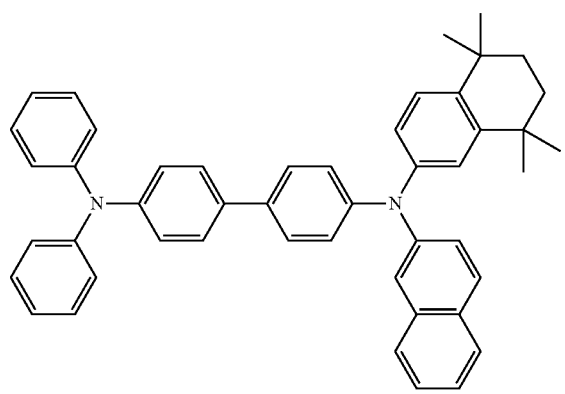
A-14
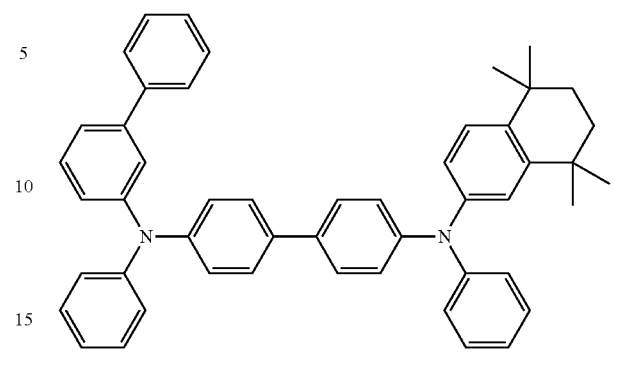
A-11
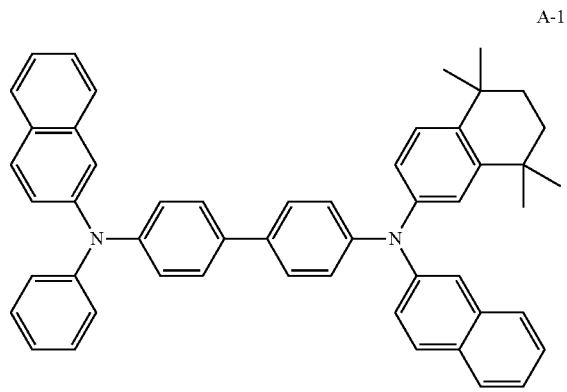
A-15
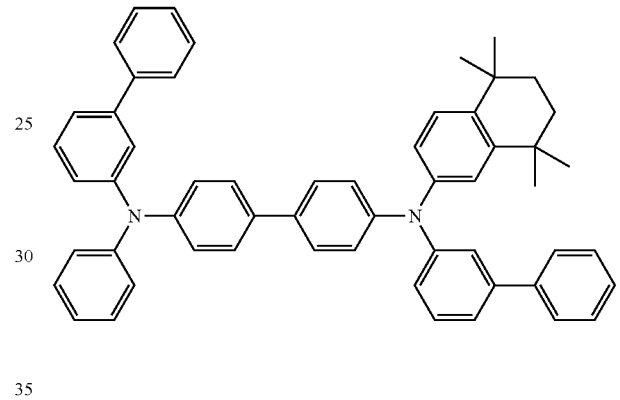
A-12
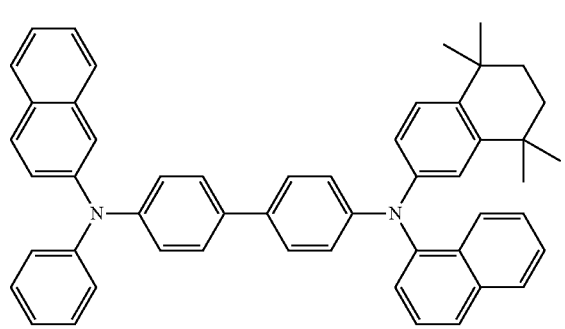
A-16
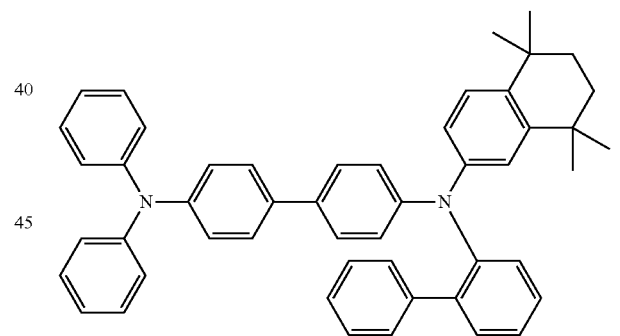
A-13
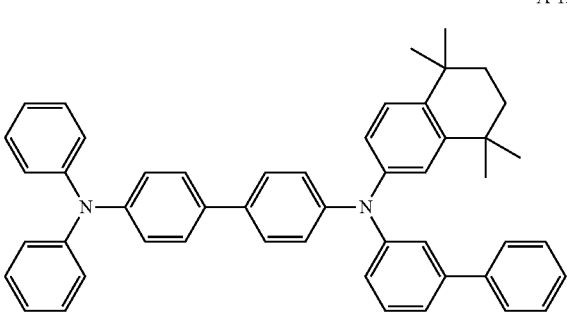
A-17
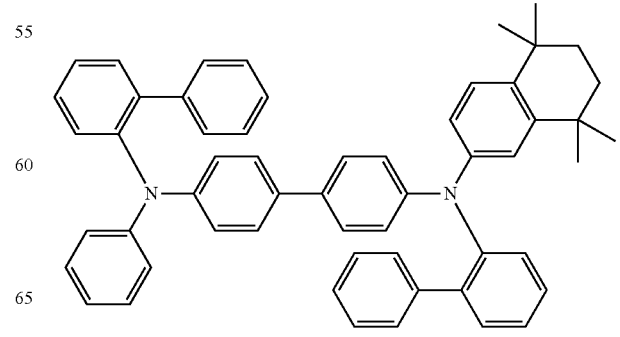

A-18
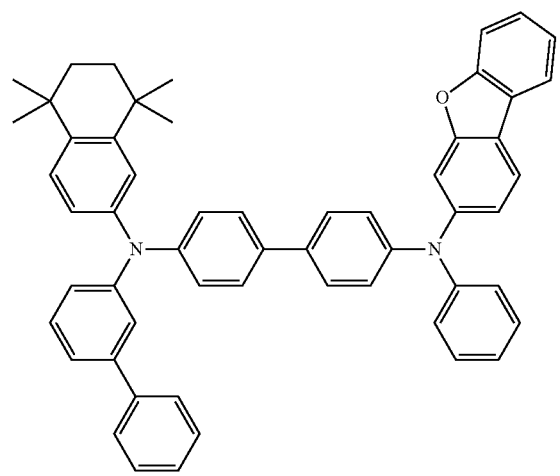
A-21
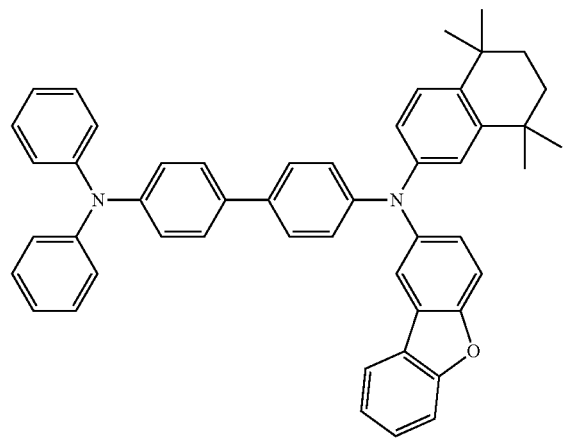
A-19
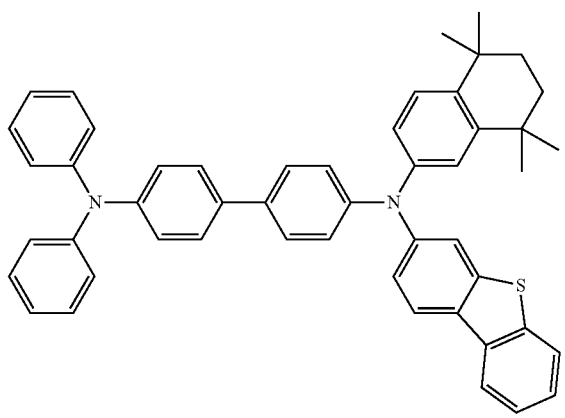
A-22
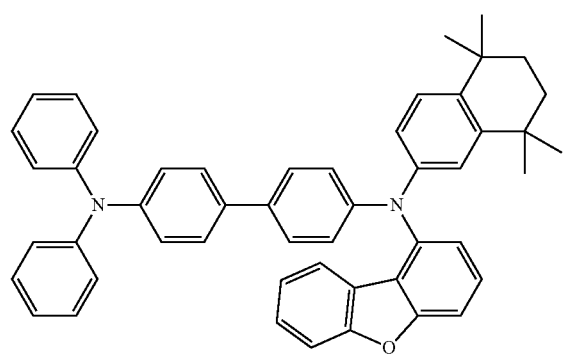
A-20
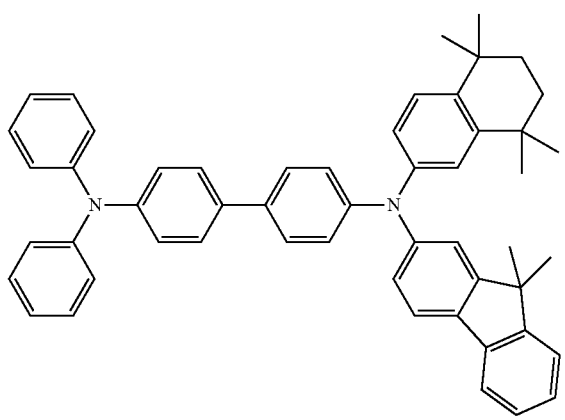
A-23
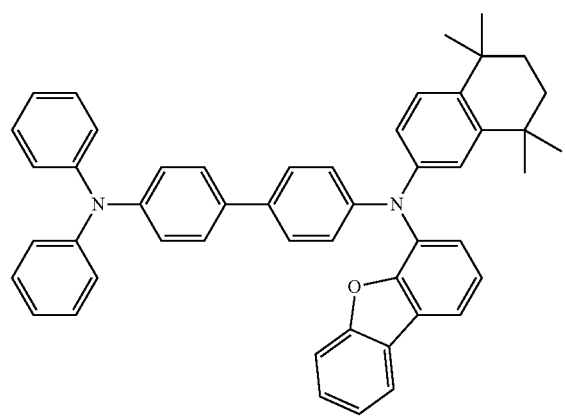

A-24
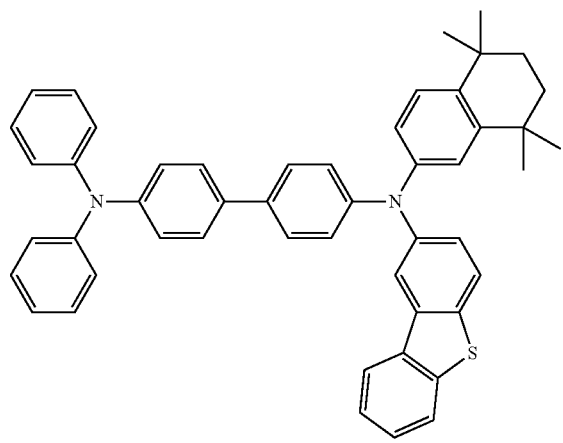
A-27
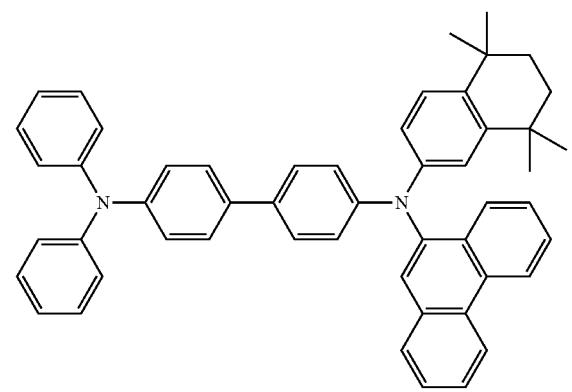
A-25
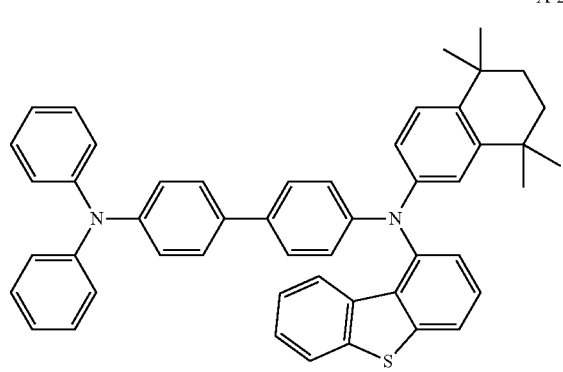
A-28
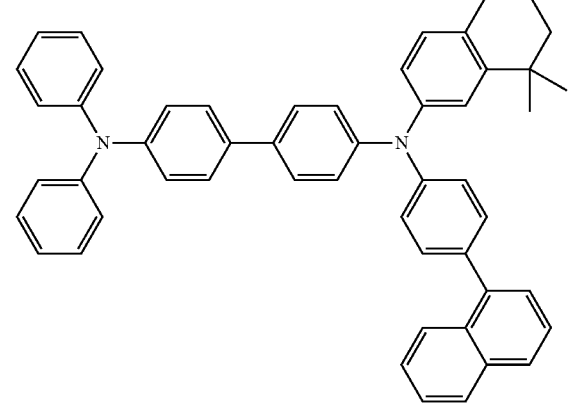
A-26
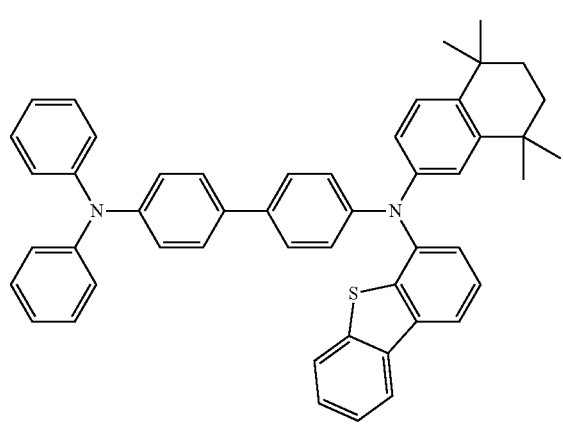
A-29
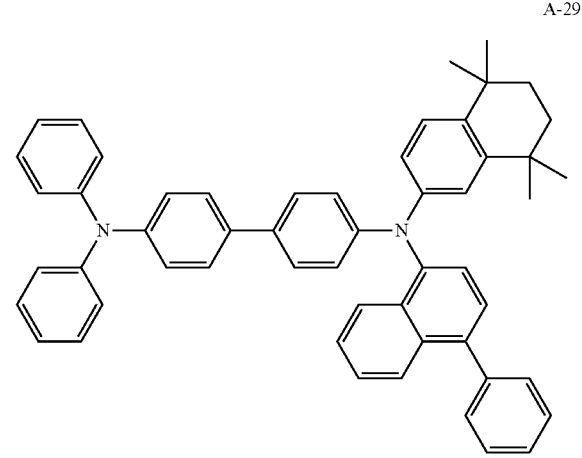

A-30
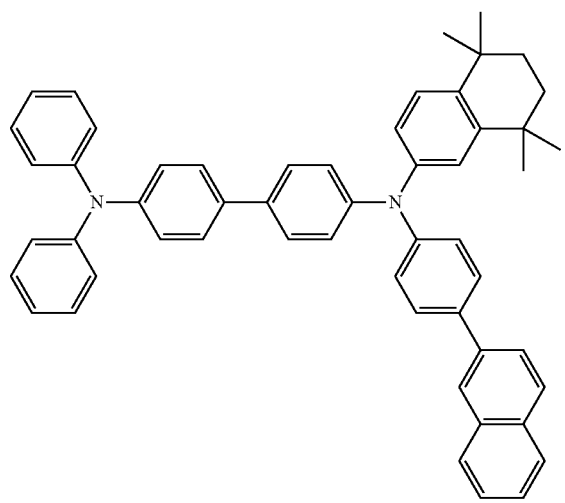
A-33
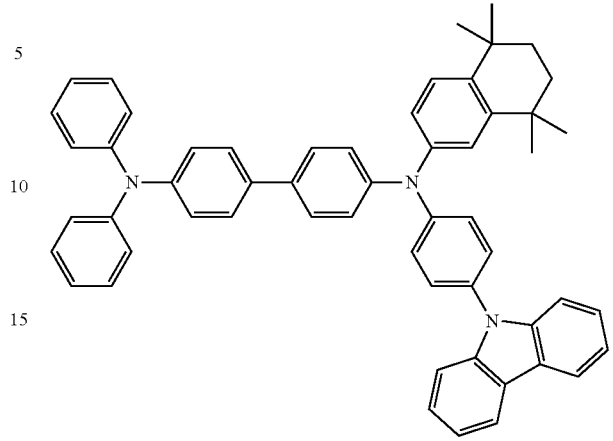
A-31
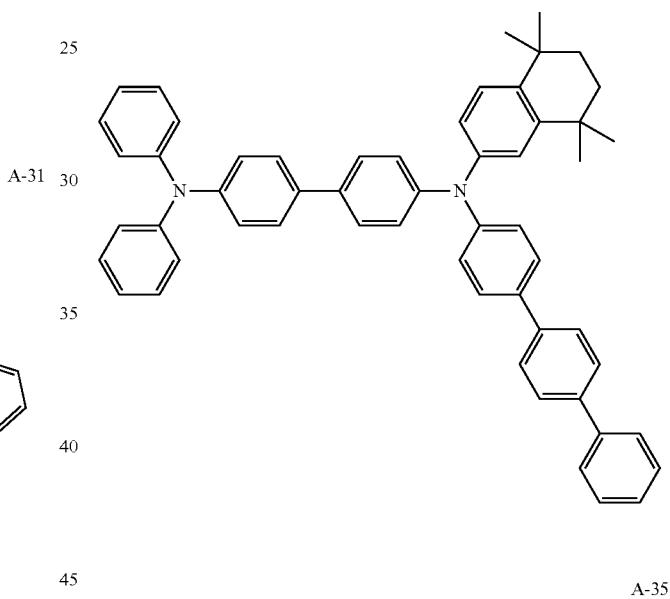
A-34
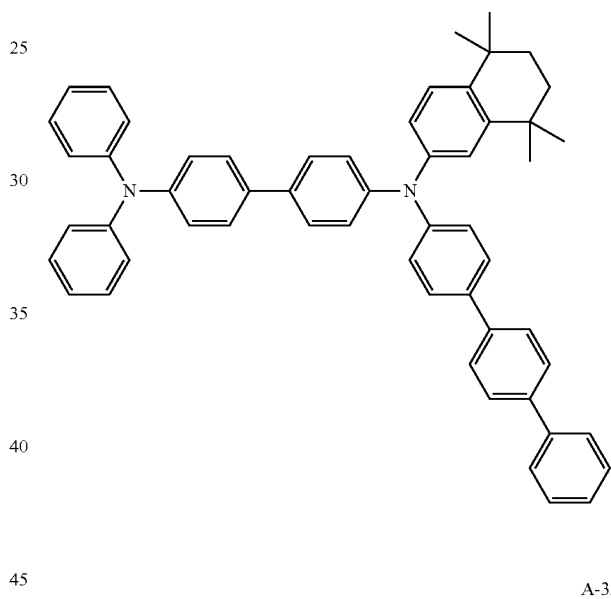
A-32
A-35
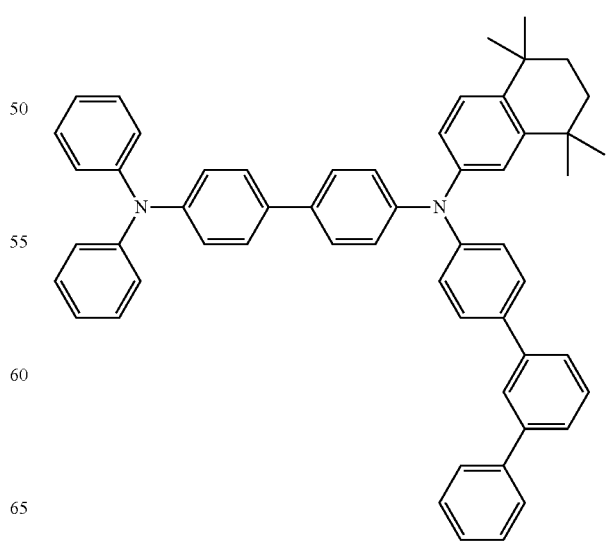

-continued
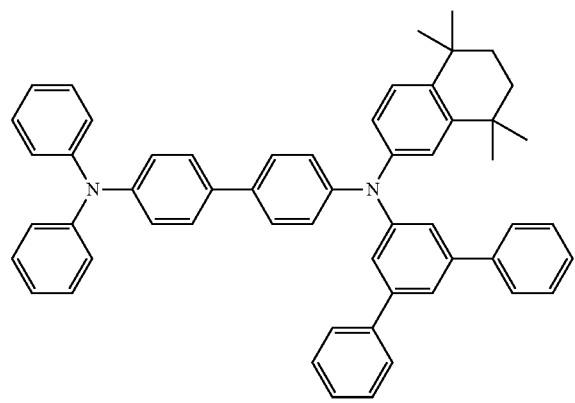
A-36
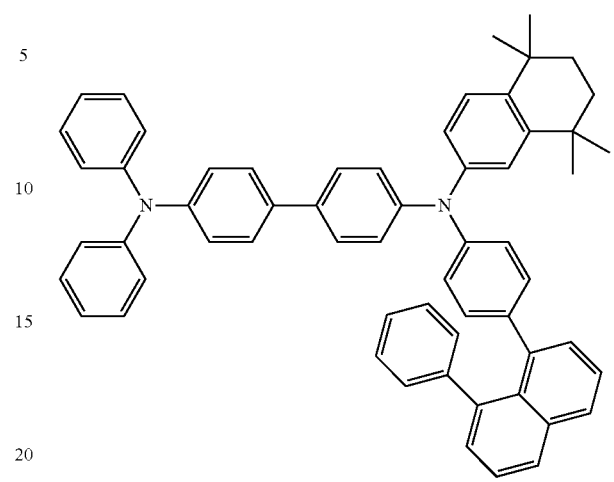
A-39
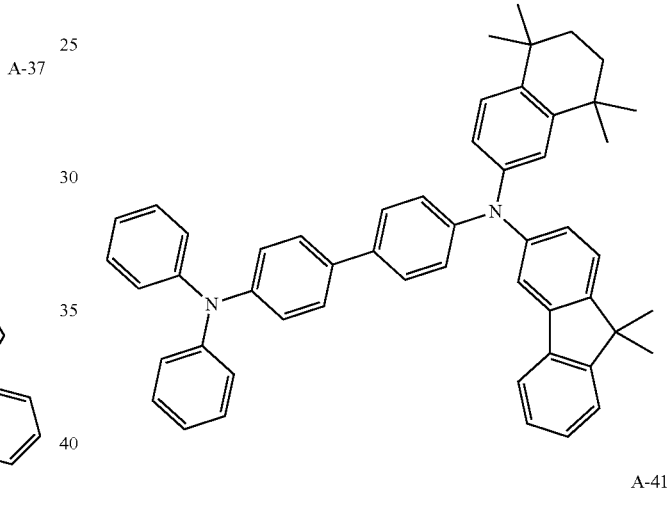
A-37
A-40
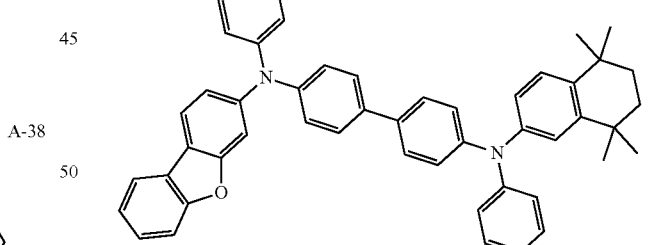
A-38
A-41
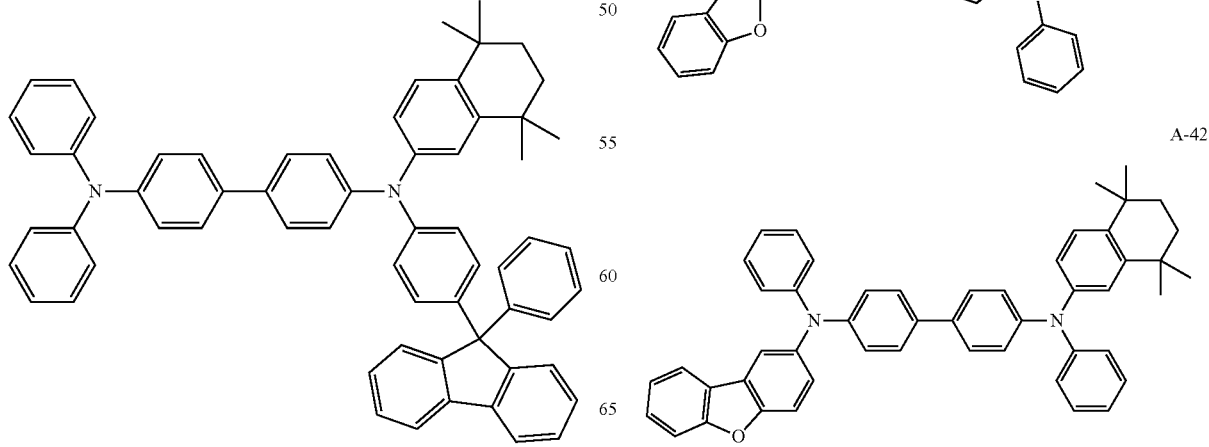
A-42

A-43
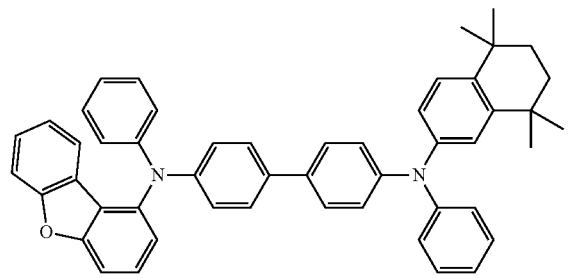
A-44
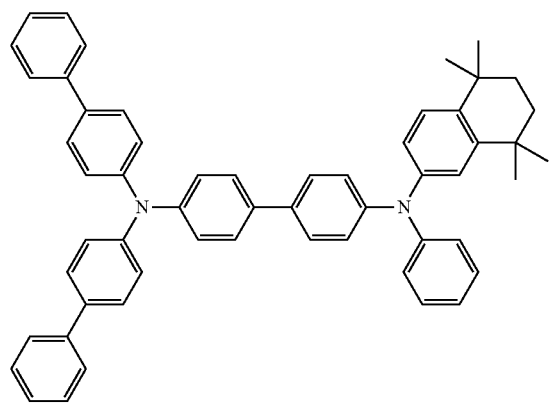
A-45
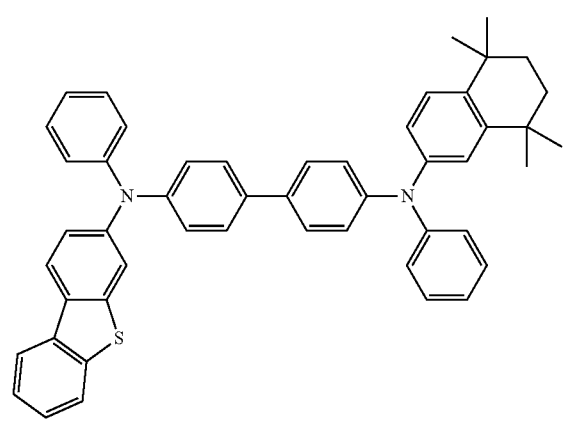
A-46
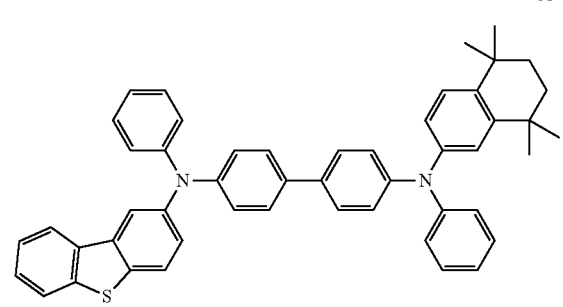
A-47
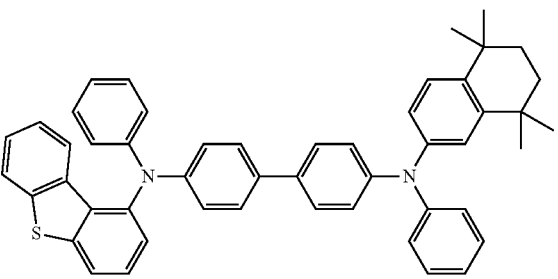
A-48
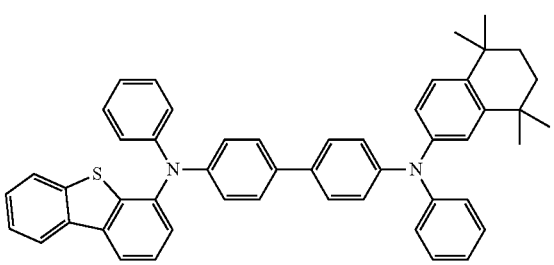
A-49
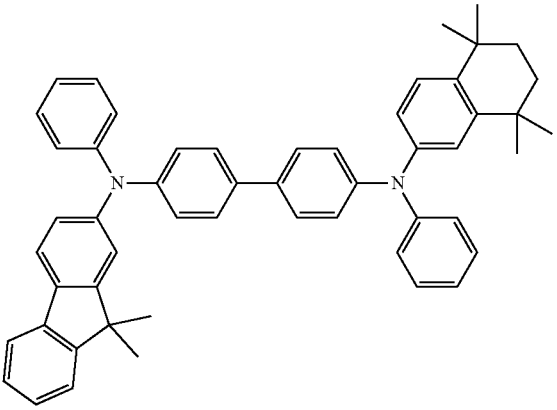
A-50
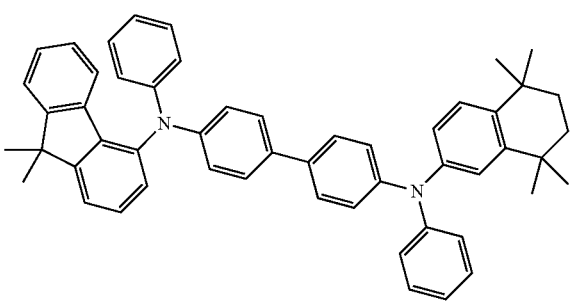

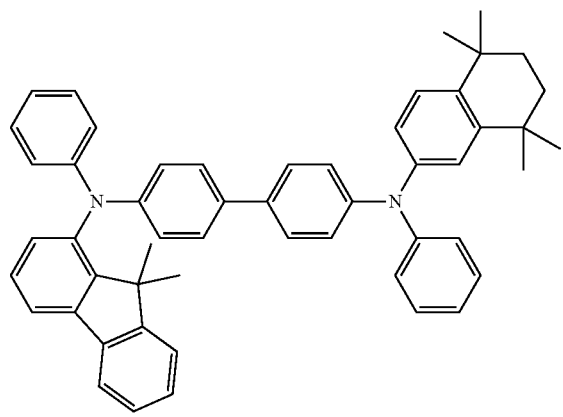
A-51
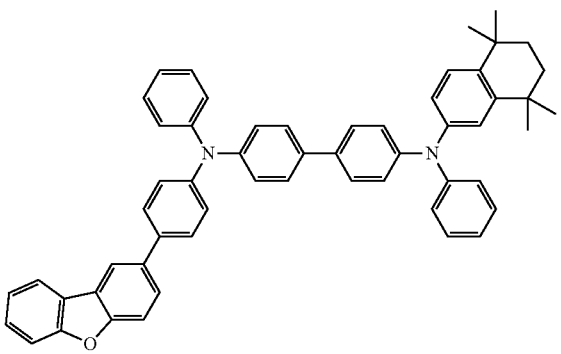
A-55
A-52
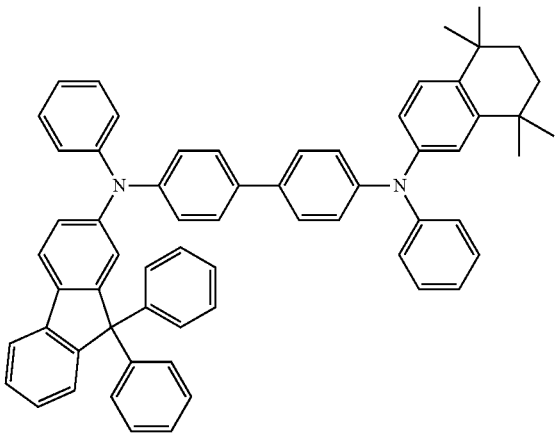
A-56
A-53
A-57
A-54
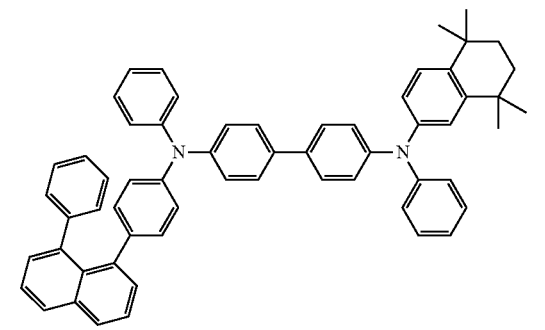
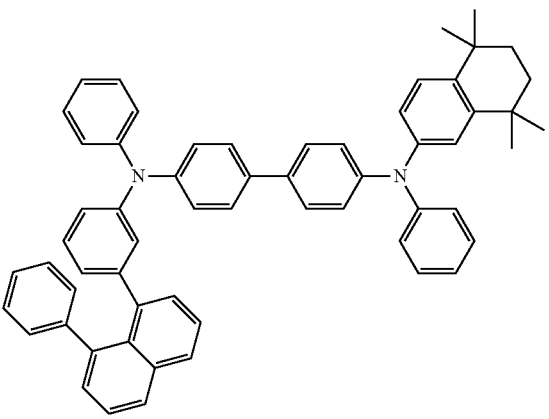
A-58

A-59
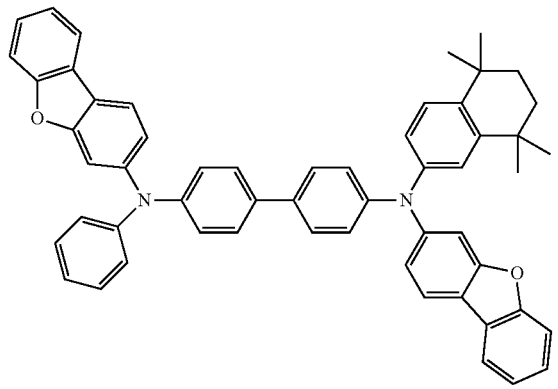
A-63
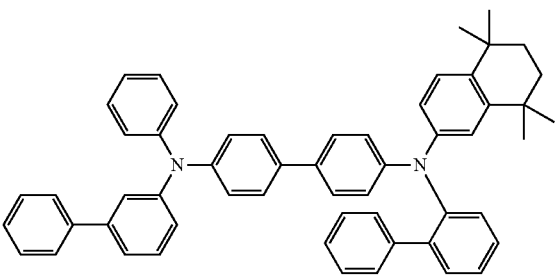
A-60
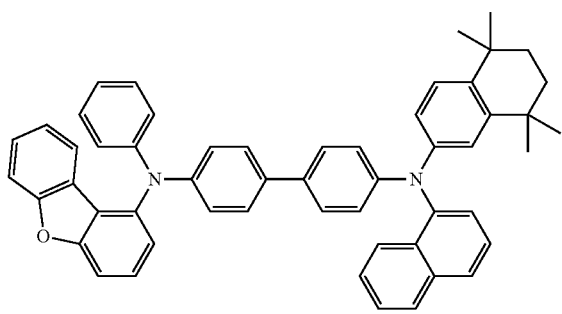
A-64
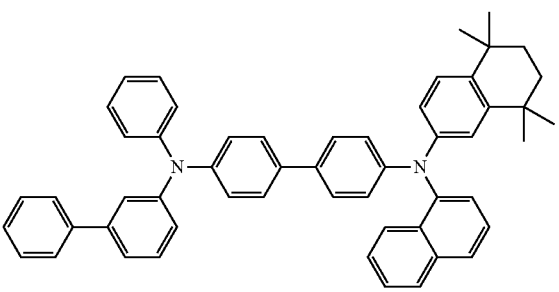
A-61
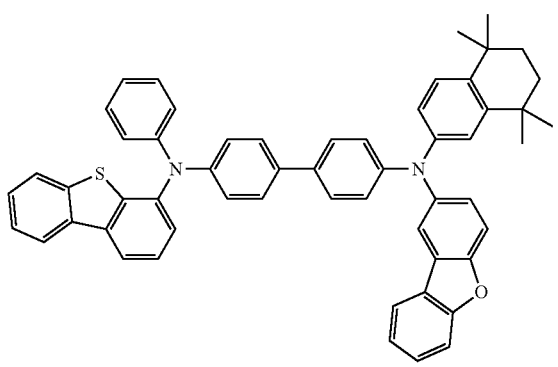
A-65
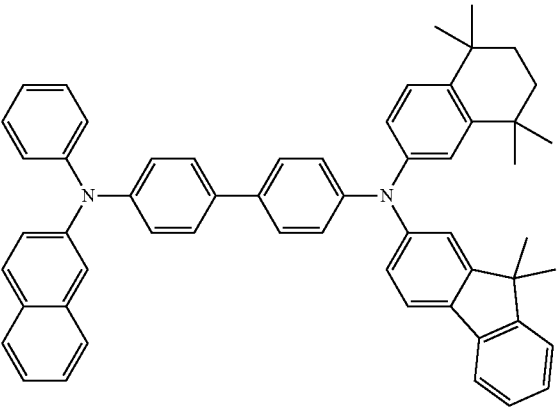
A-62
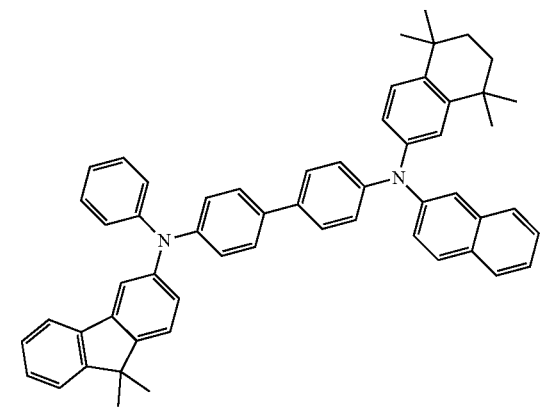
A-66
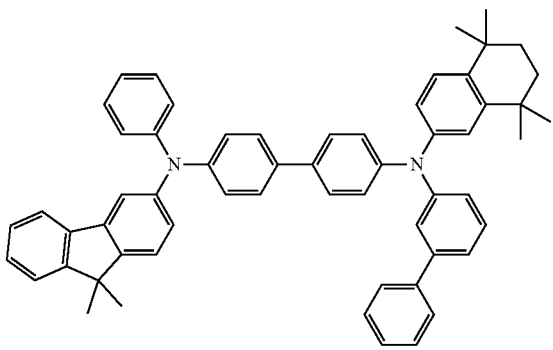

A-67
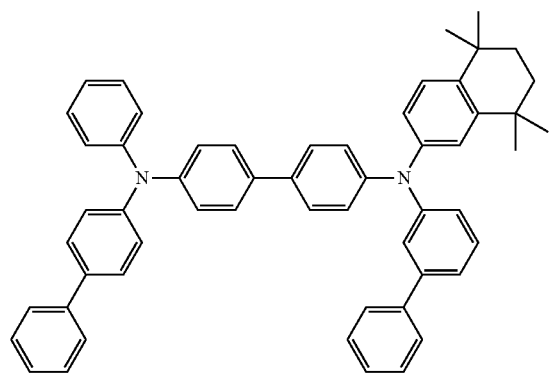
A-68
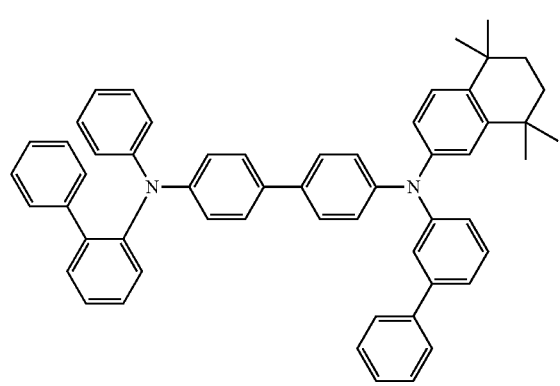
A-69
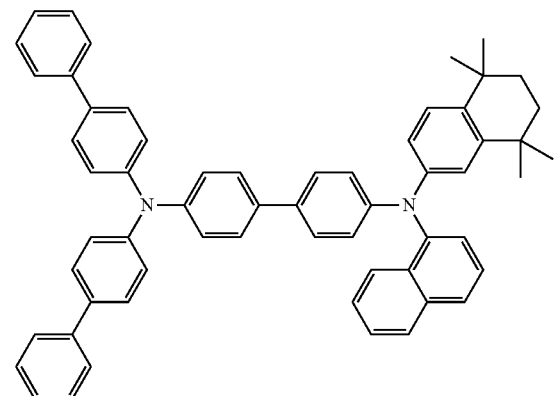
A-70
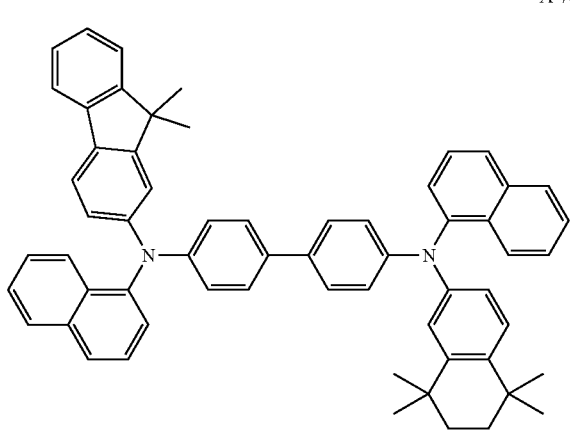
A-71
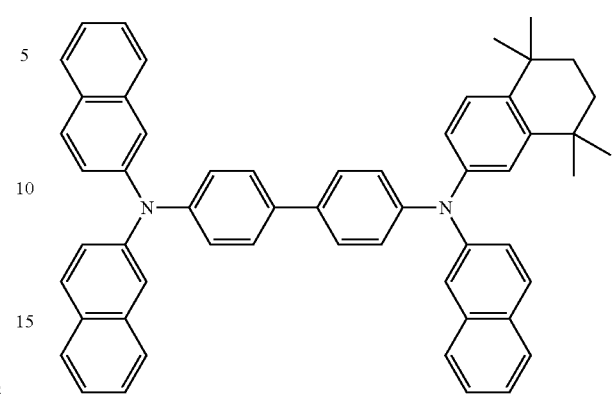
A-72
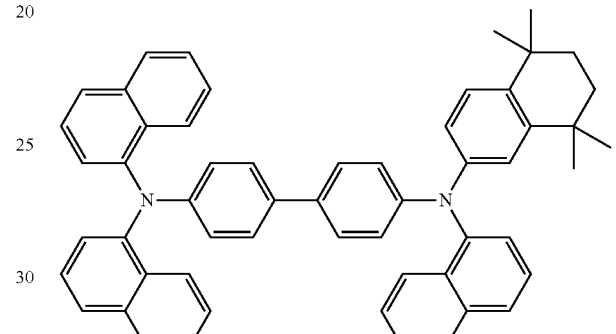
A-73
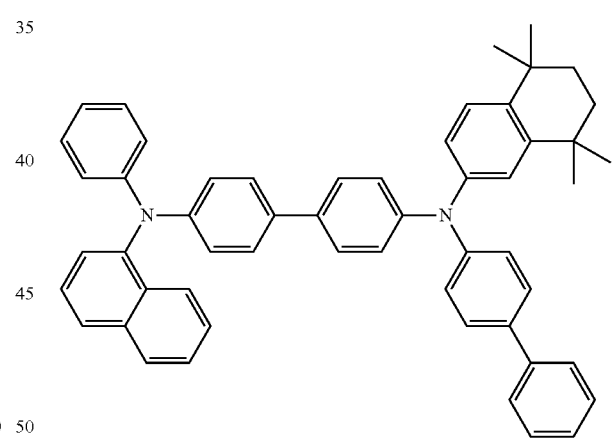
A-74
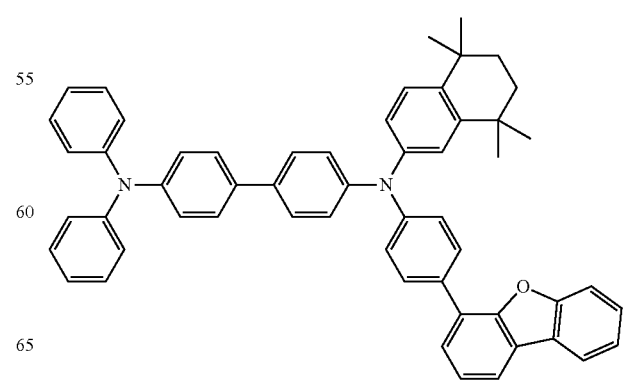

A-75
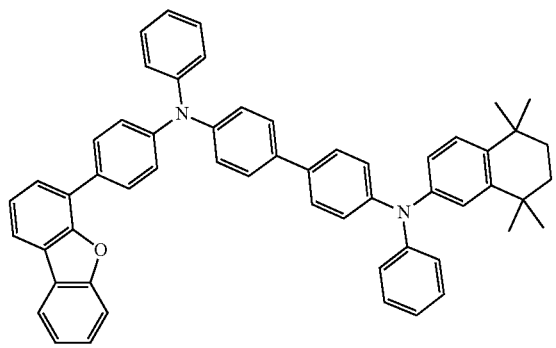
A-81
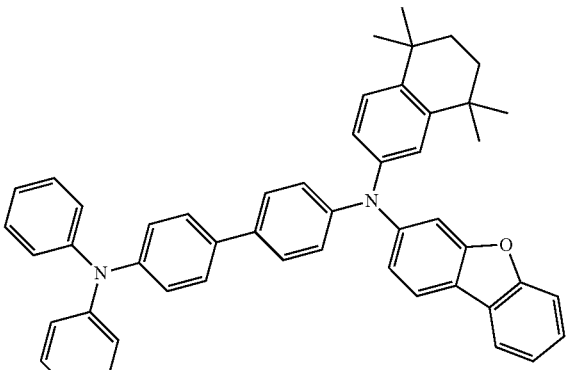
A-78
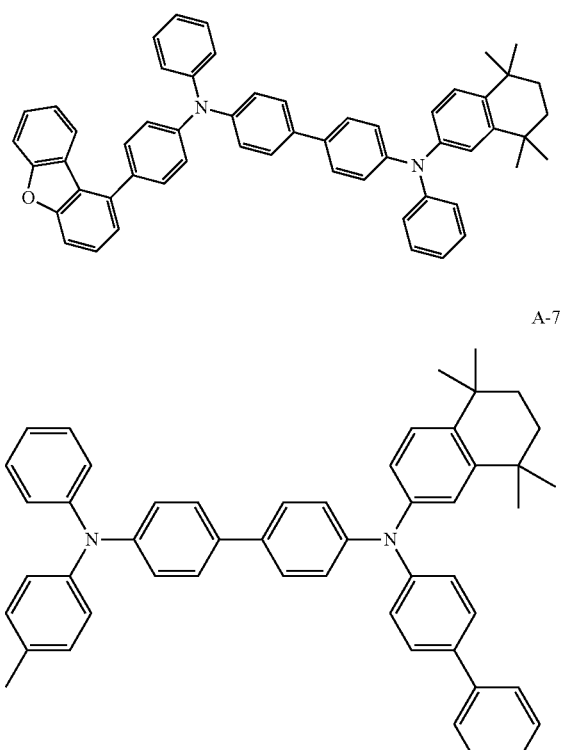
A-82
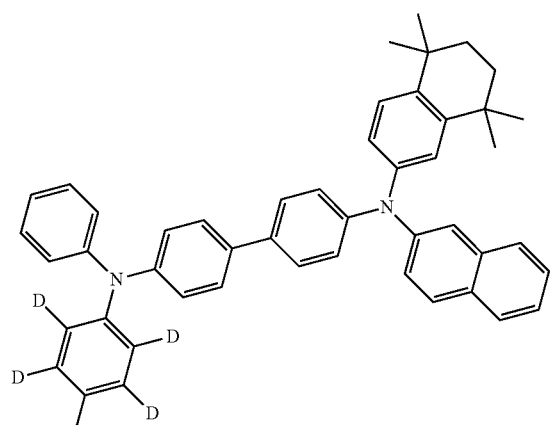
A-79
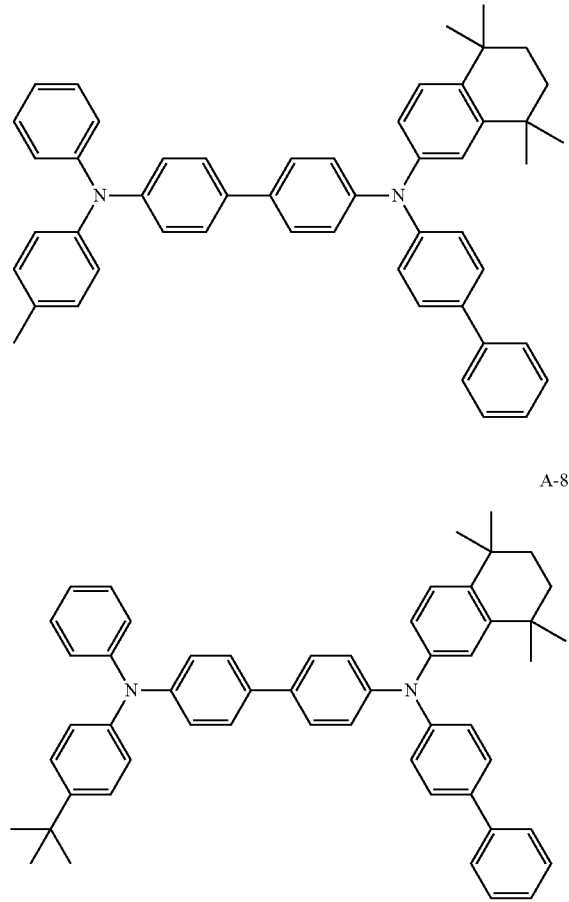
A-80
A-83
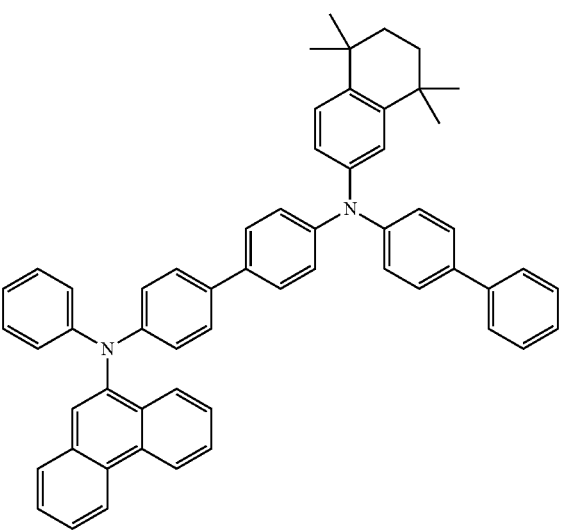

A-85
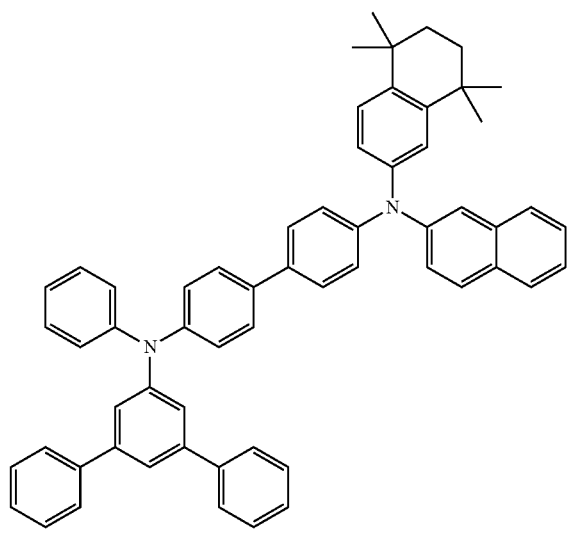
A-86
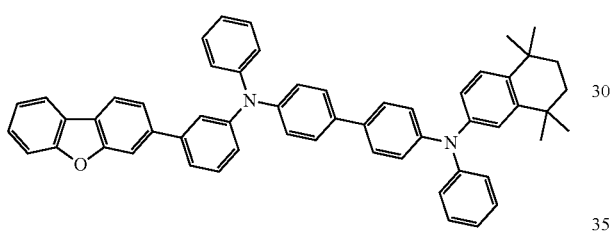
A-87
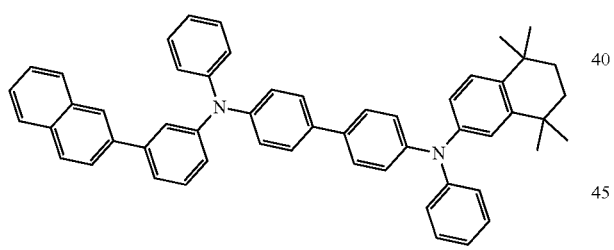
A-88
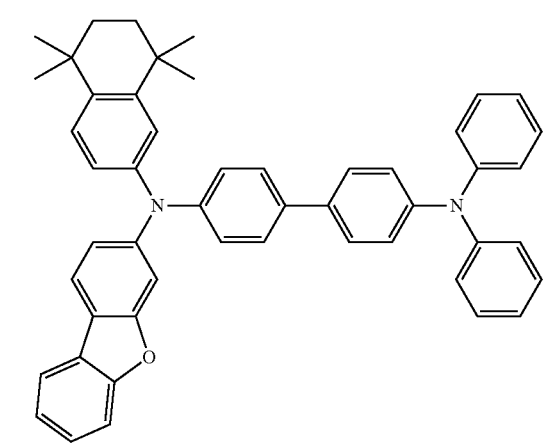
A-89
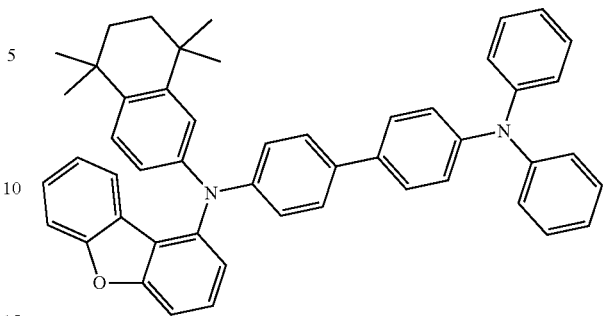
A-90
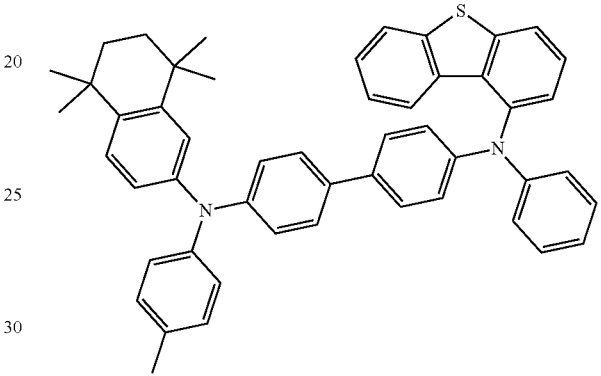
A-91
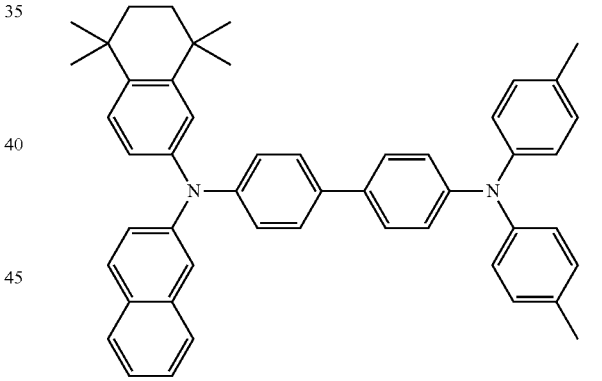
A-92
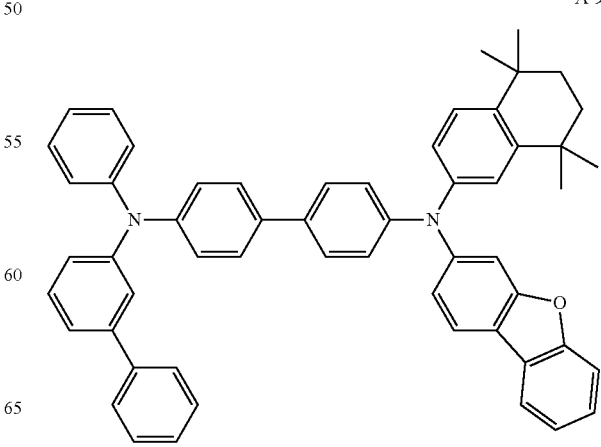

B-1
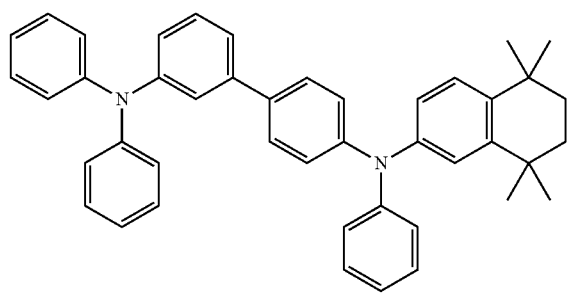
B-5
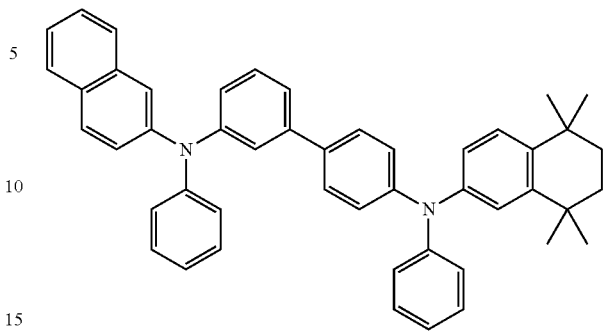
B-2
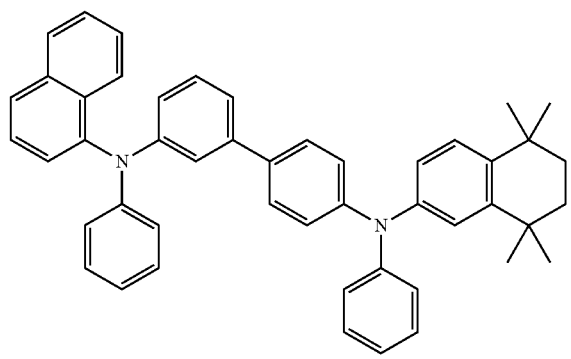
B-6
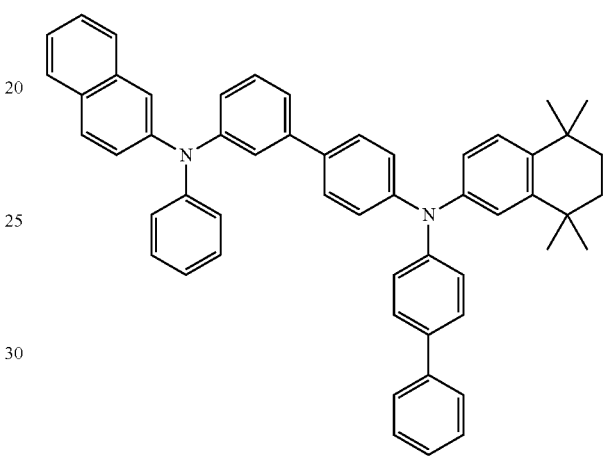
B-3
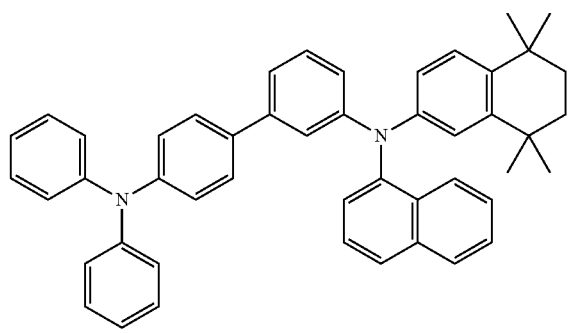
B-7
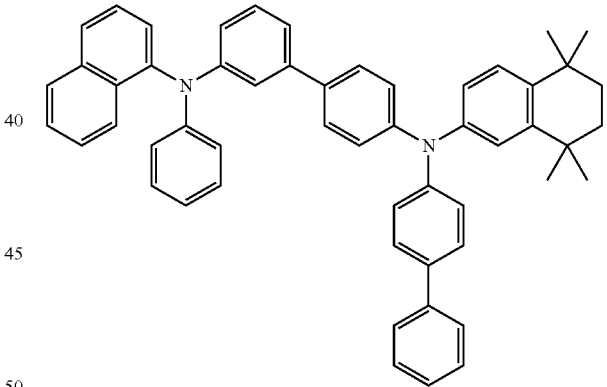
B-4
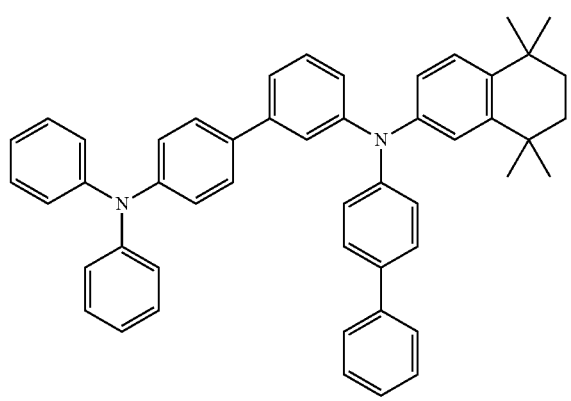
B-8
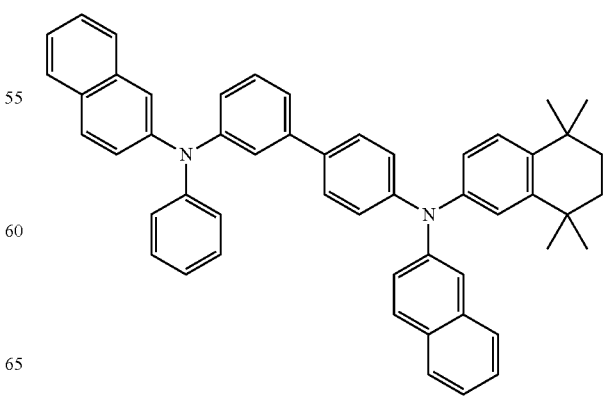

B-9
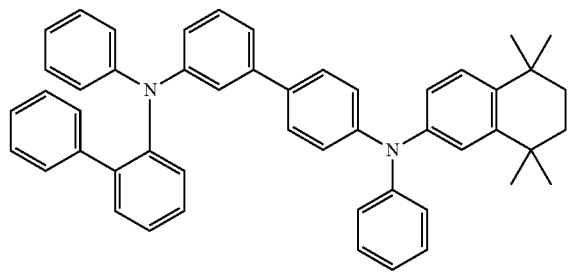
B-10
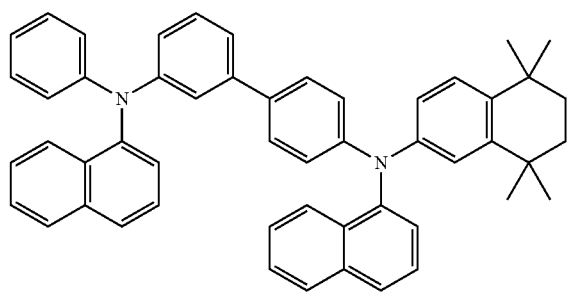
B-11
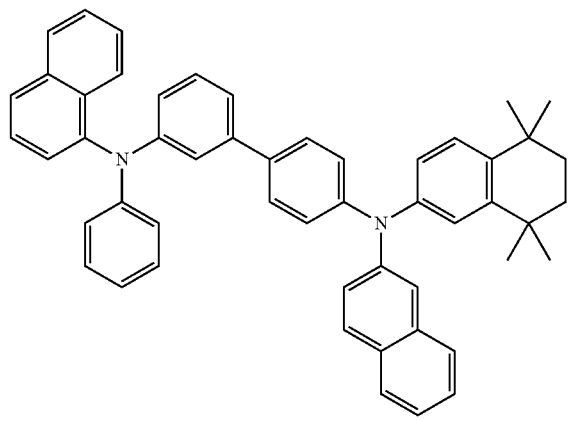
B-12
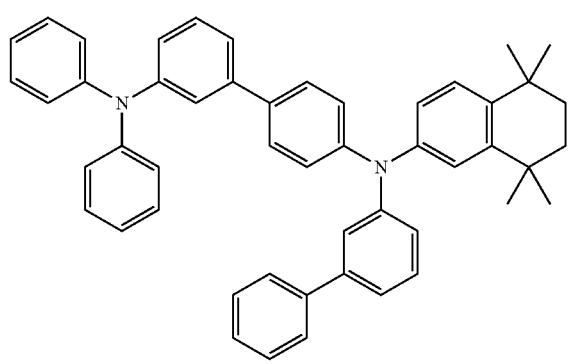
B-13
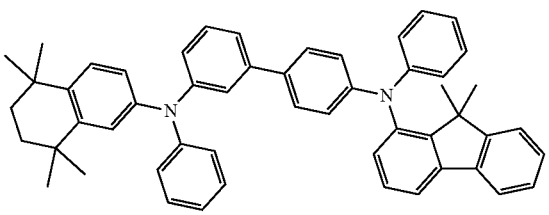
B-14
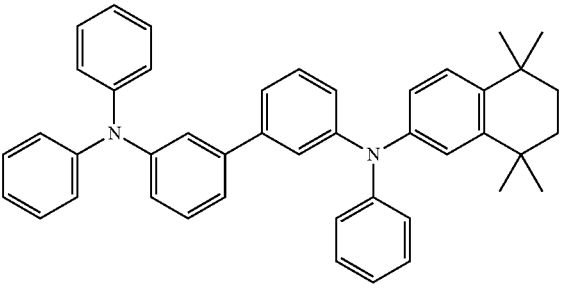
B-15
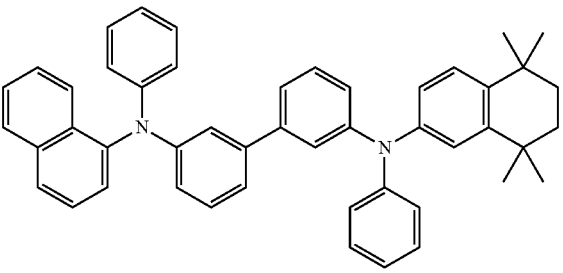
B-16
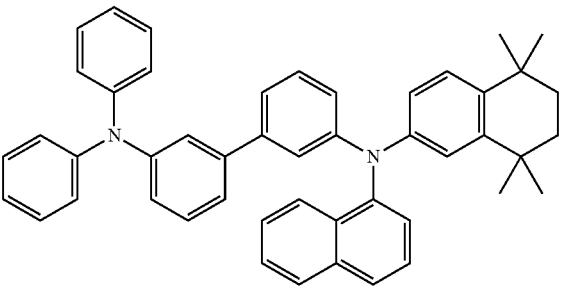
B-17
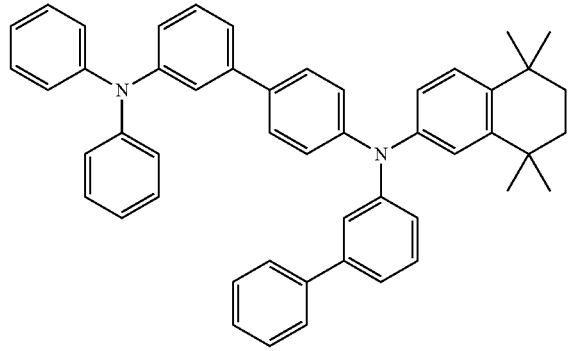

-continued
B-18
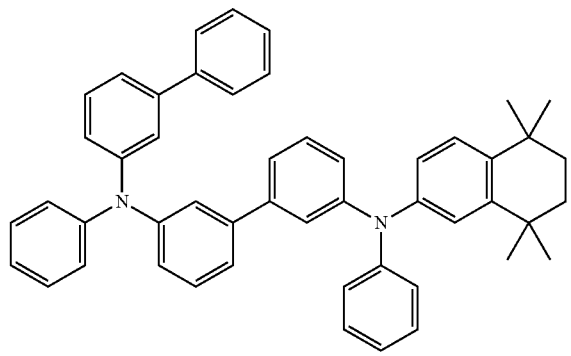
B-22
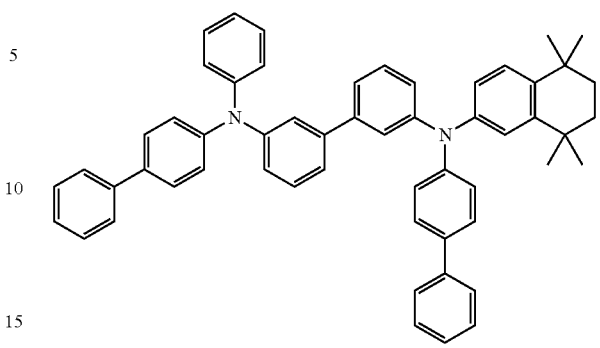
B-19
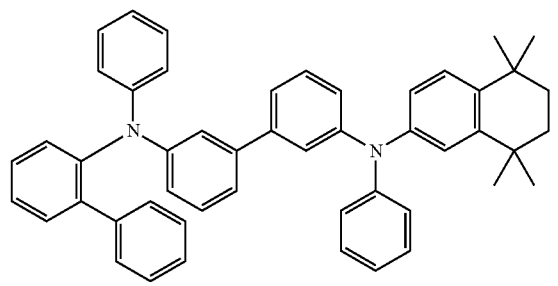
B-23
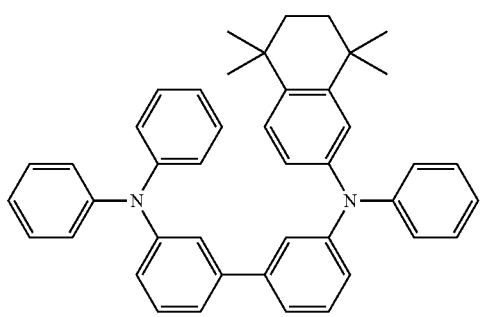
B-20
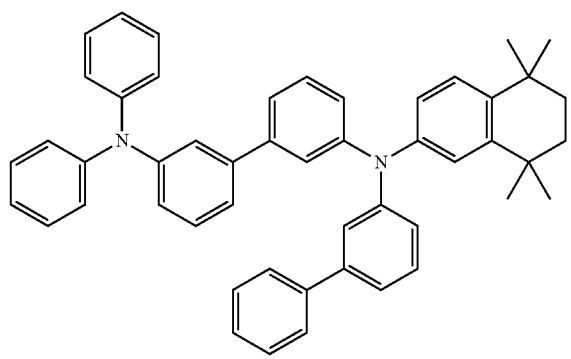
B-24
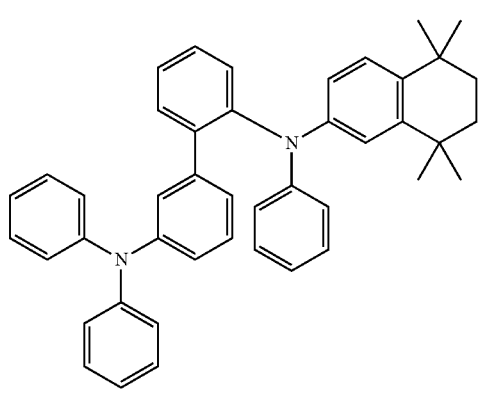
B-21
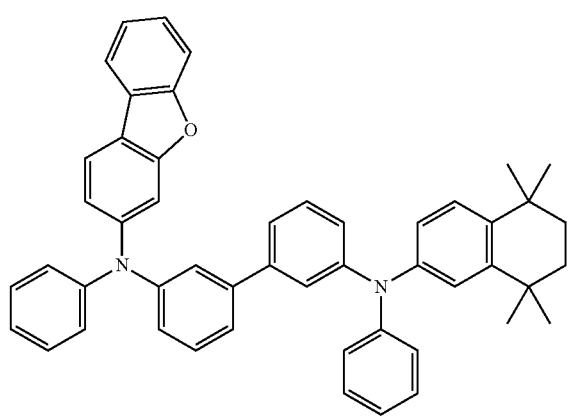
B-25
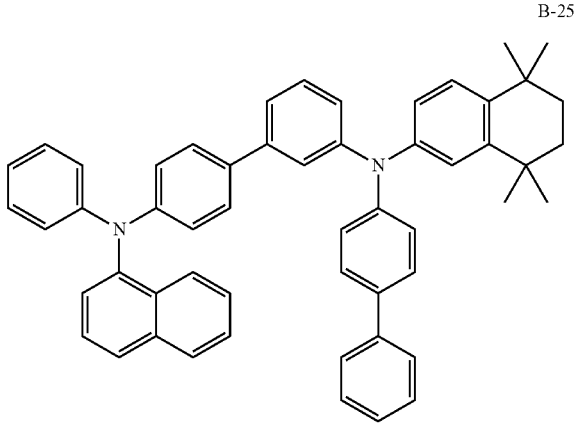 [SMILES: CC1(C)CCC(C)(C)c2cc(N(c3ccc(-c4ccccc4)cc3)c3cccc(-c4ccc(N(c5ccccc5)c5ccccc5)cc4)c3)ccc21]

-continued
B-26
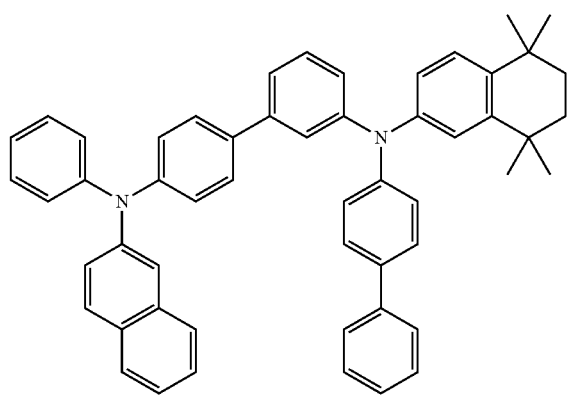
B-27
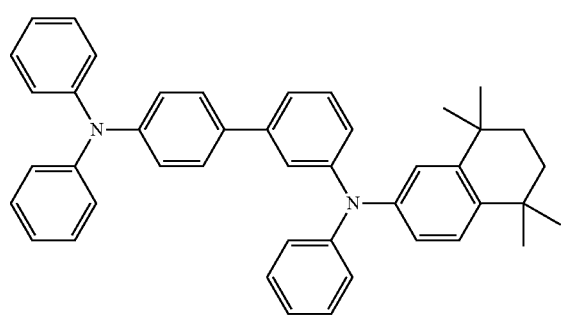
B-28
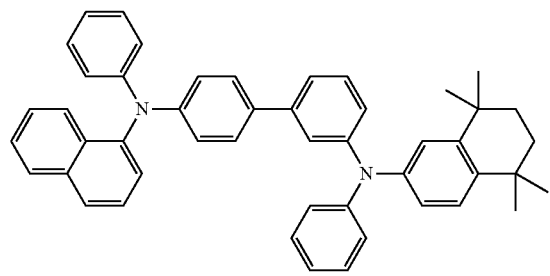
B-29
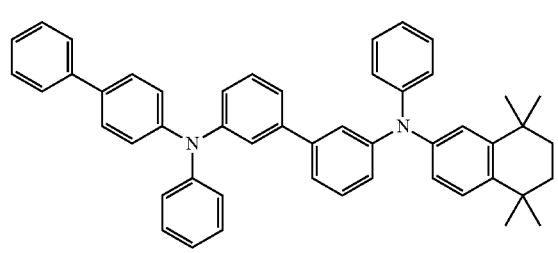
-continued
B-30
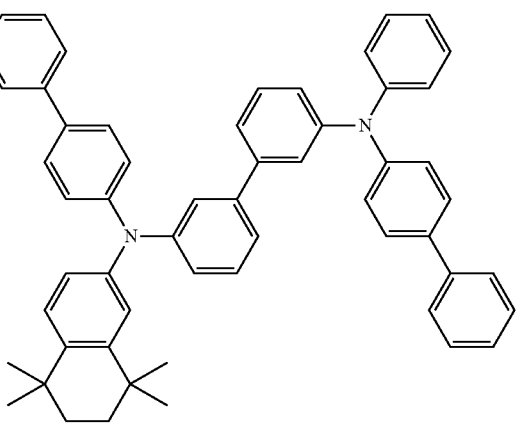
B-31
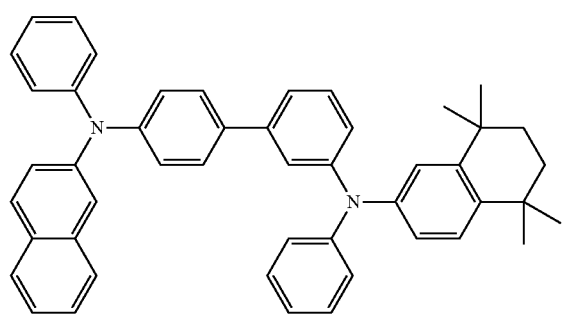
B-32
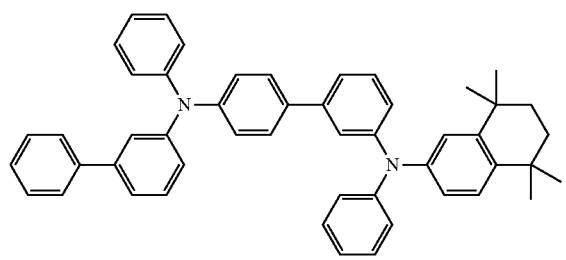
B-33

B-34
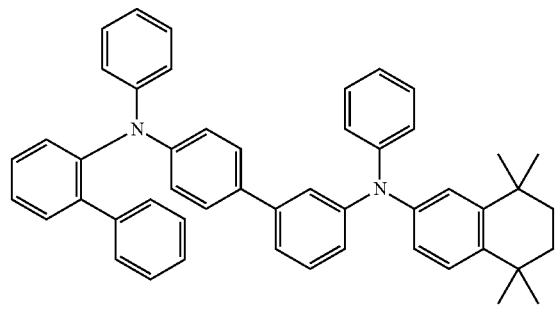
B-35
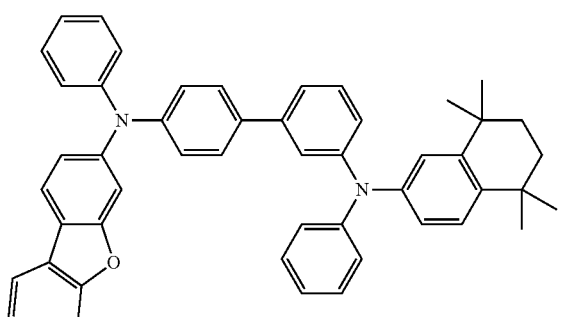
B-36
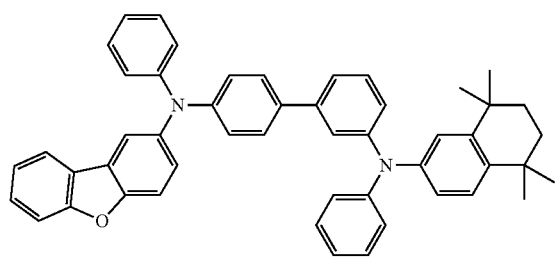
B-37
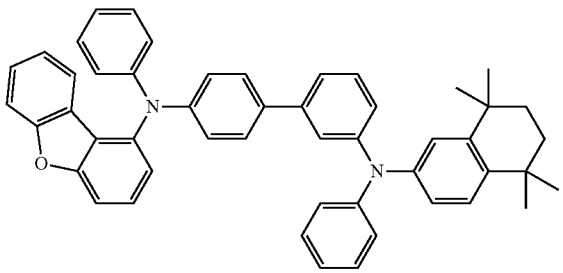
B-38
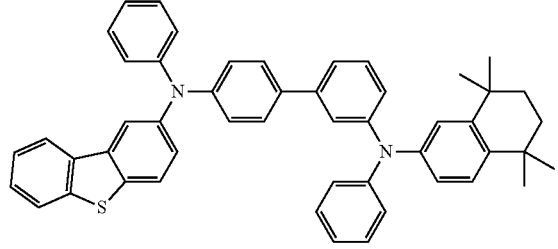
B-39
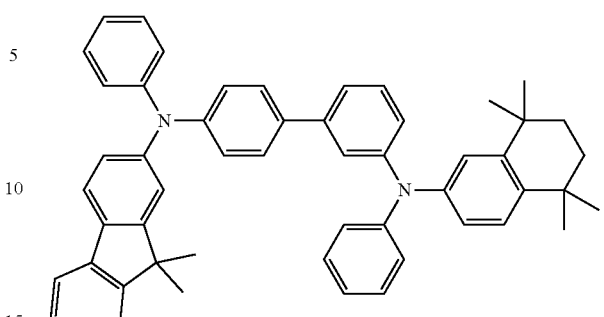
B-40
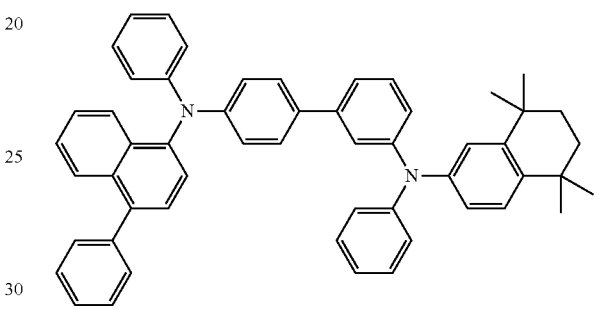
B-41
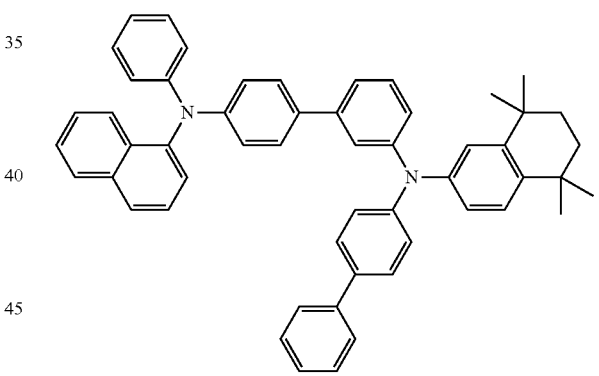
B-42
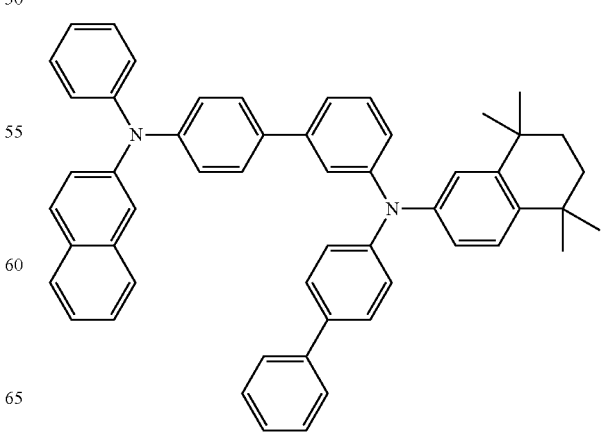

-continued
B-43
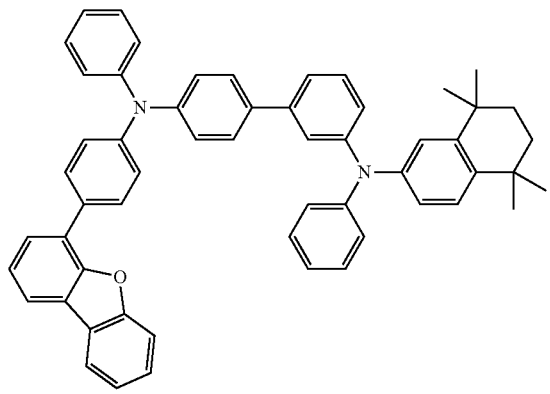
B-44
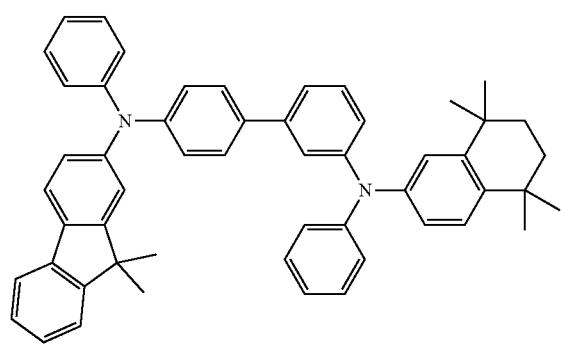
B-45
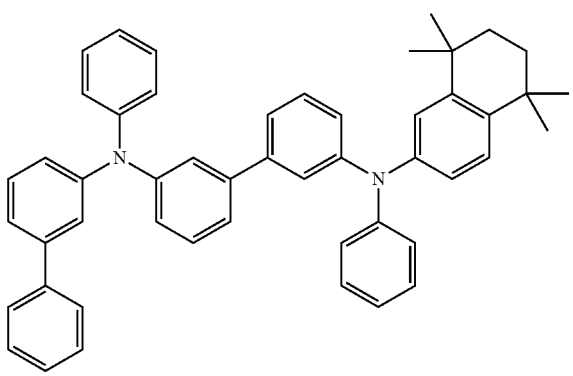
B-46
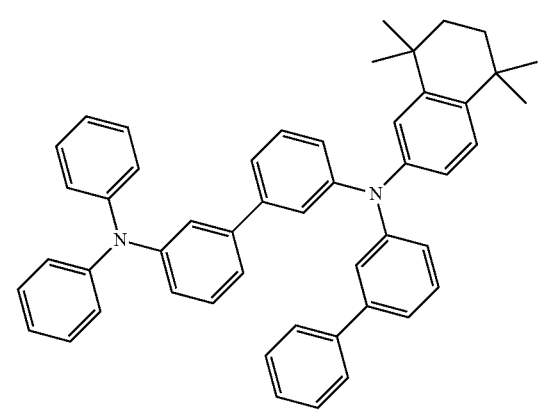
-continued
B-47
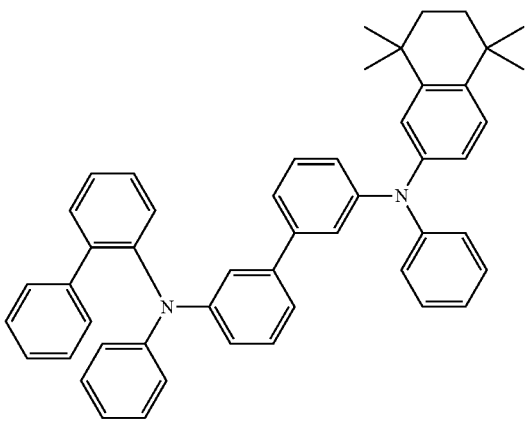
B-48
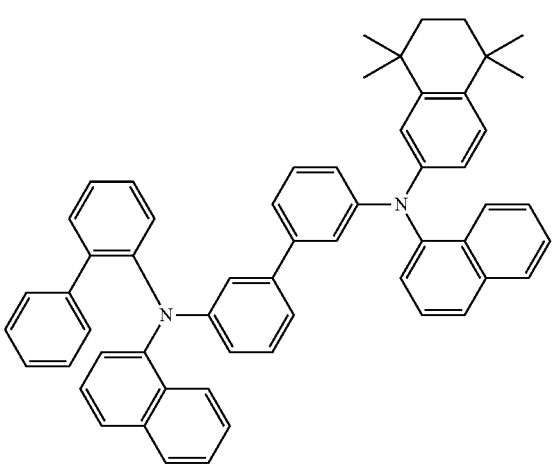
C-1
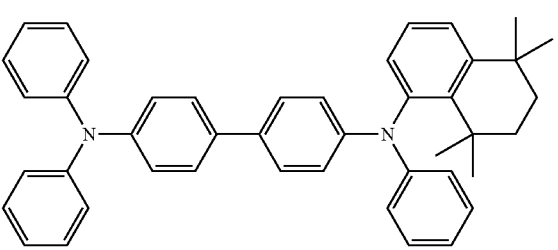
C-2
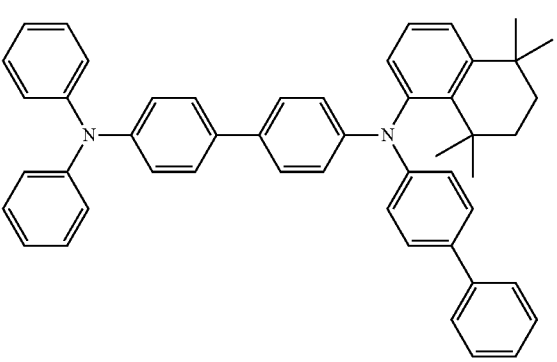

C-3
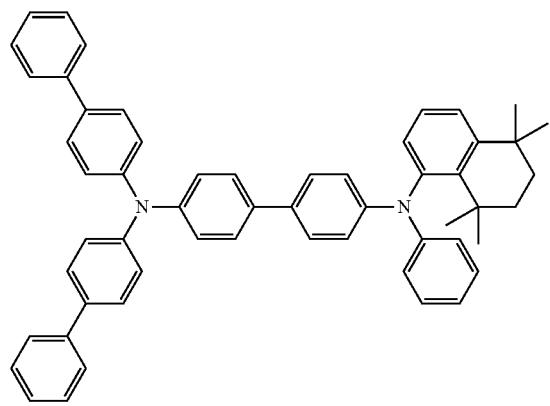
C-4
C-7
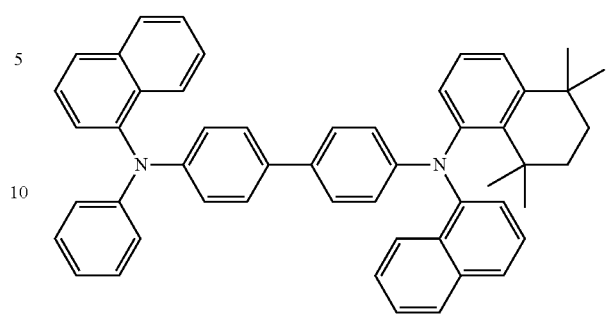
C-8
C-5
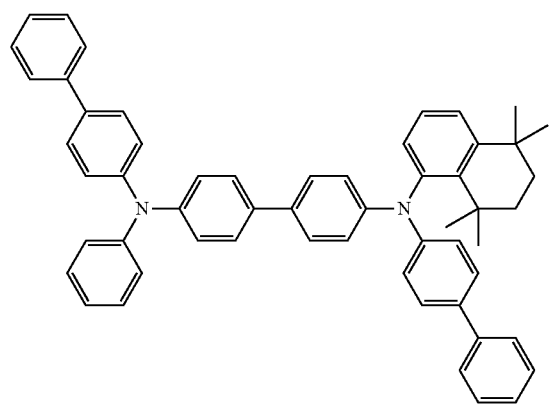
C-9
C-6
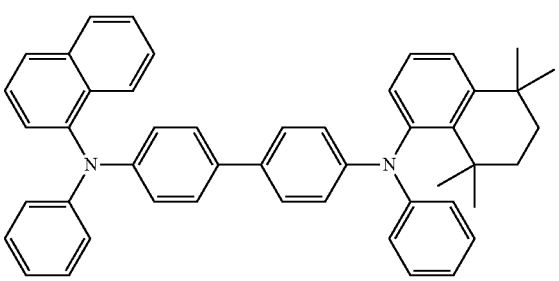
C-10
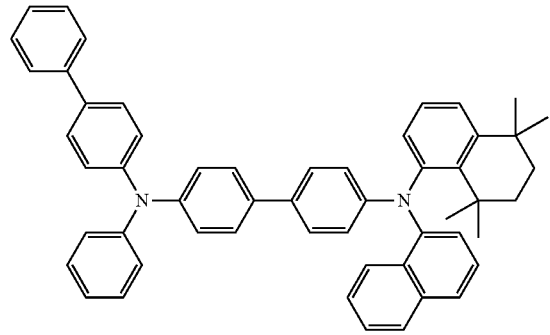

C-11
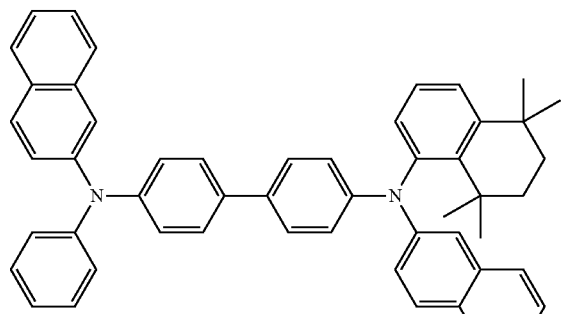
C-12
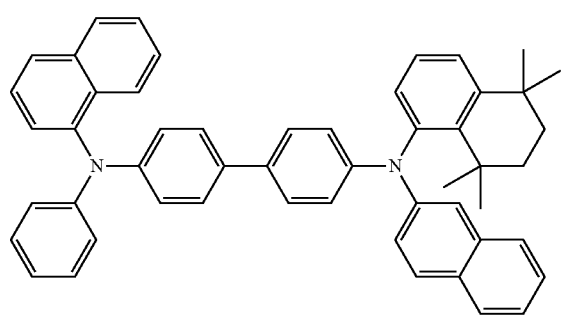
C-13
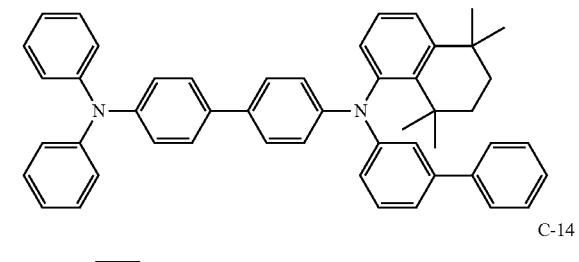
C-14
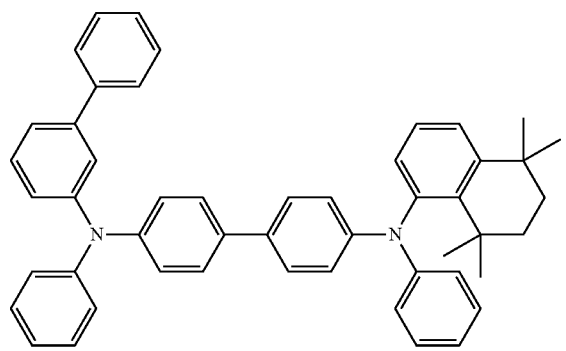
C-15
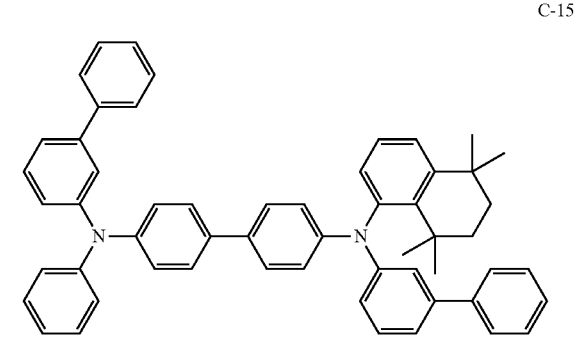
C-16
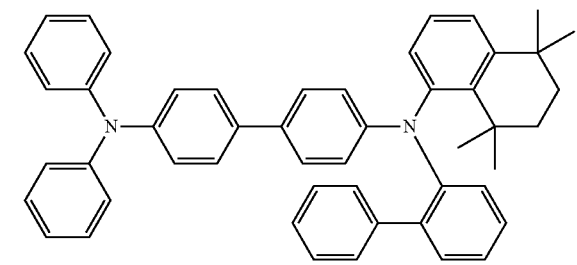
C-17
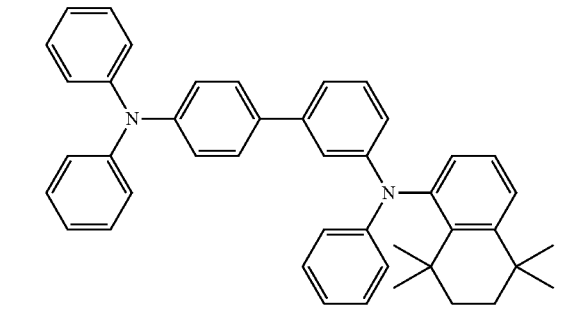
C-18
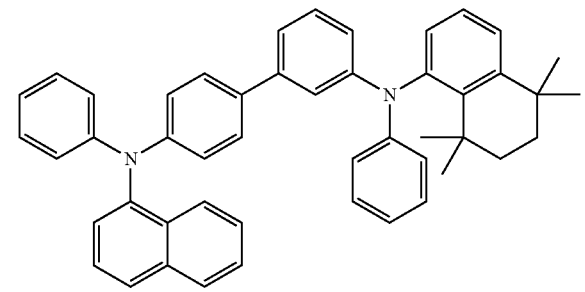
C-19
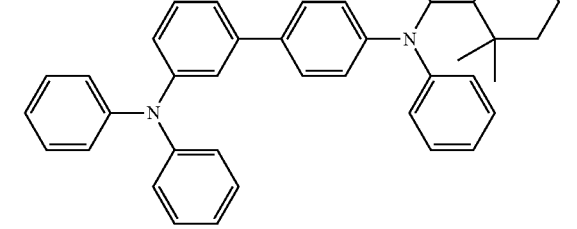
C-20

-continued
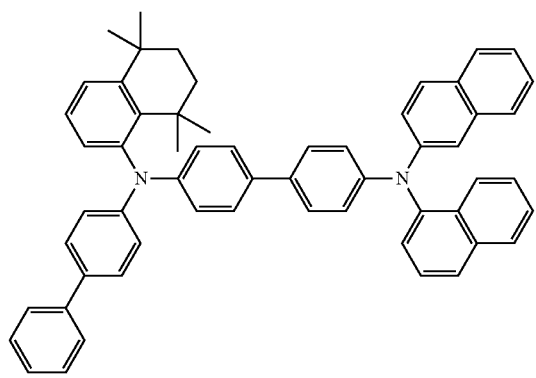
C-21
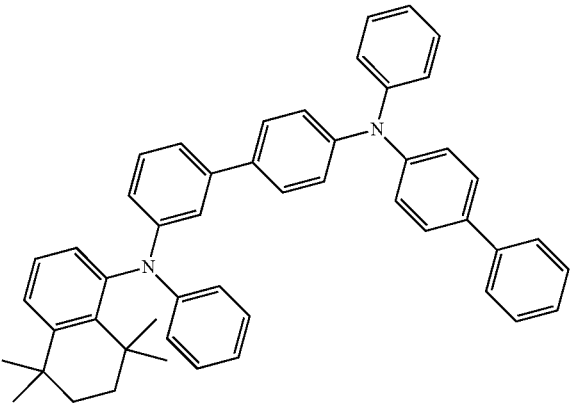
C-23
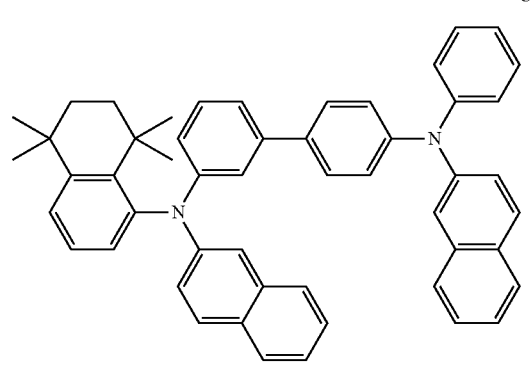
C-22
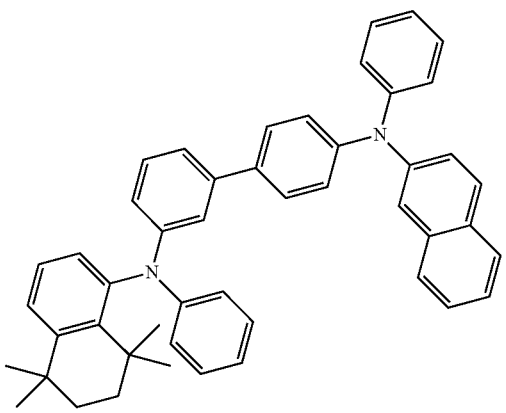
C-24
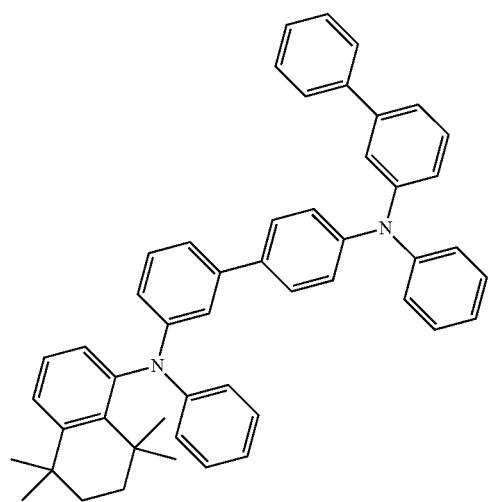
C-25
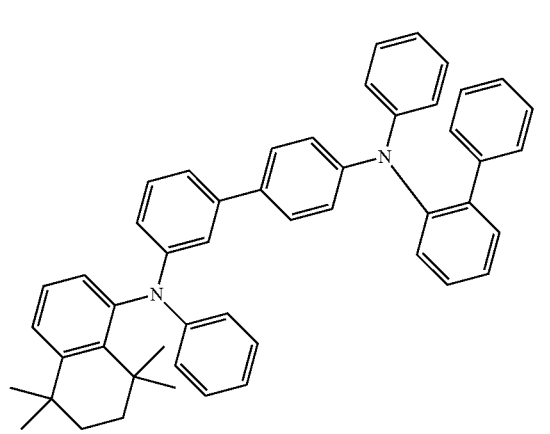
C-26

-continued
C-27
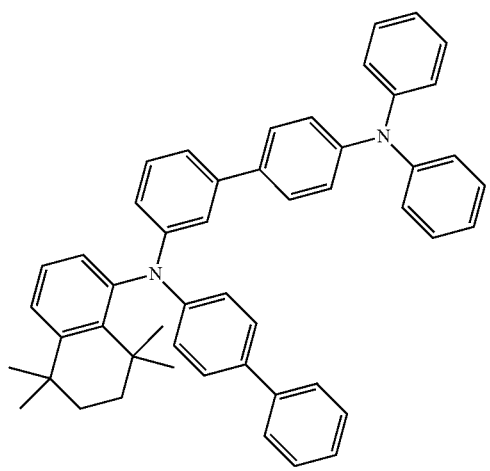
C-28
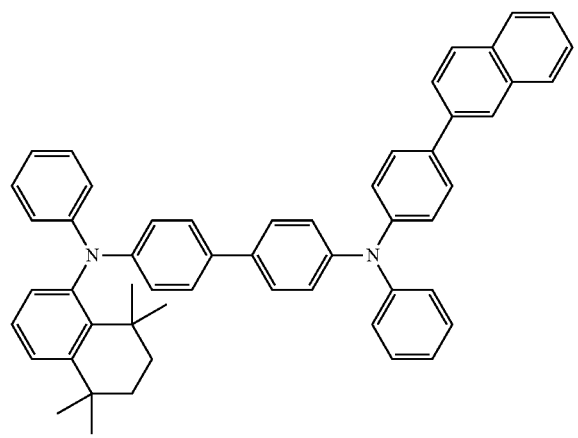
C-29
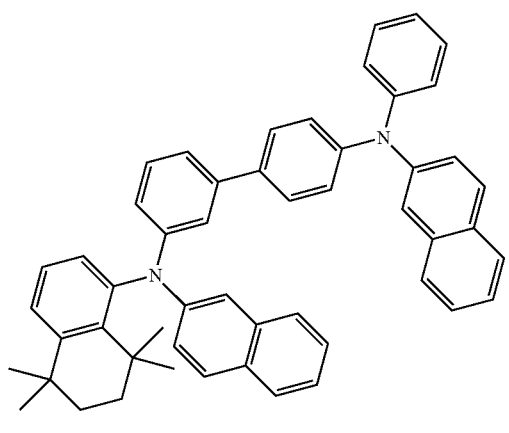
C-30
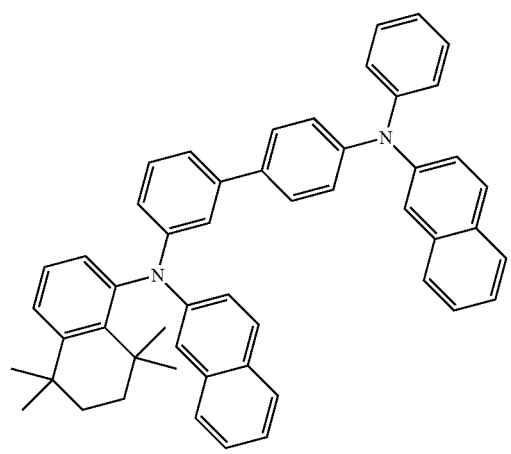
C-31
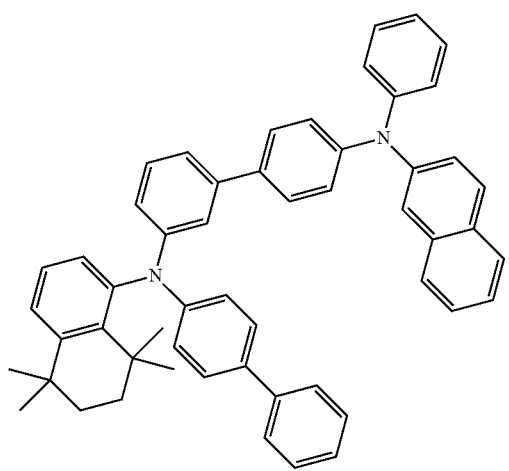
C-32
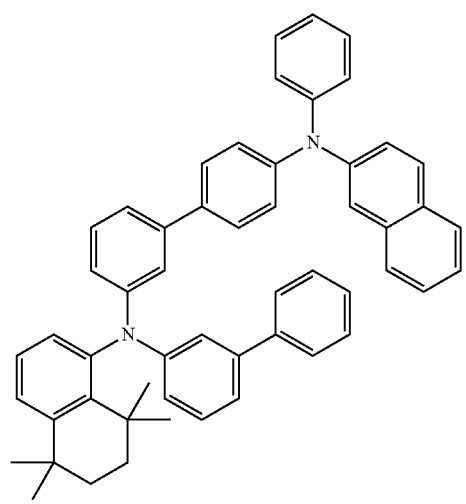

-continued
C-33
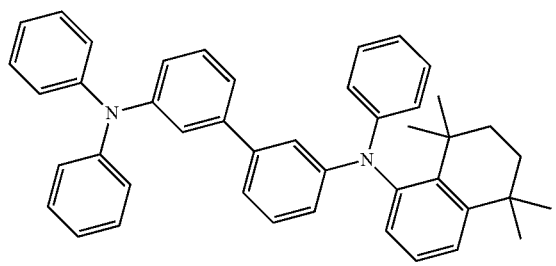
C-34
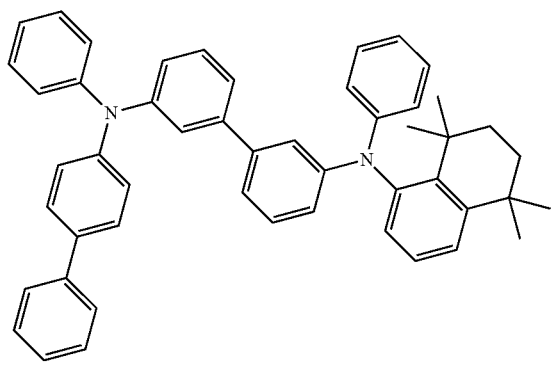
C-35
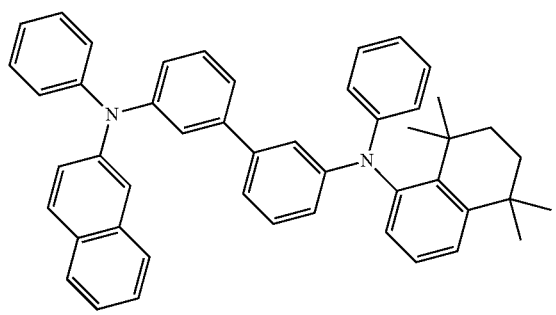
C-36
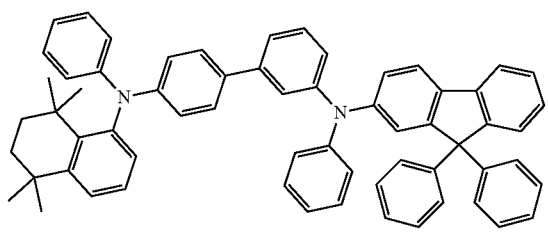
C-37
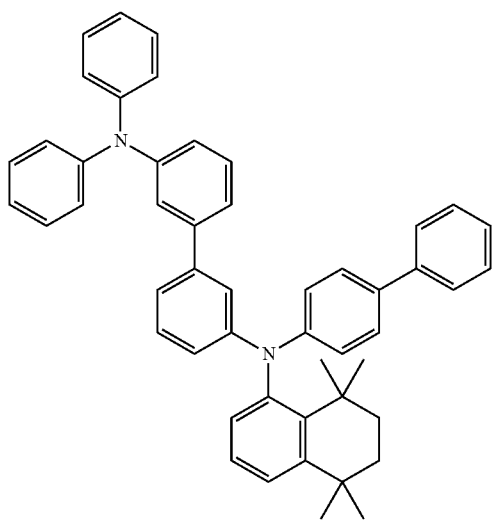
C-38
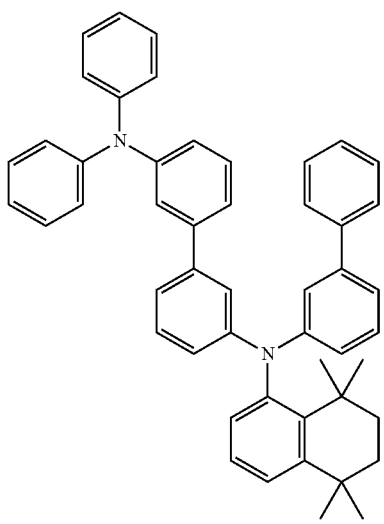

-continued
C-39
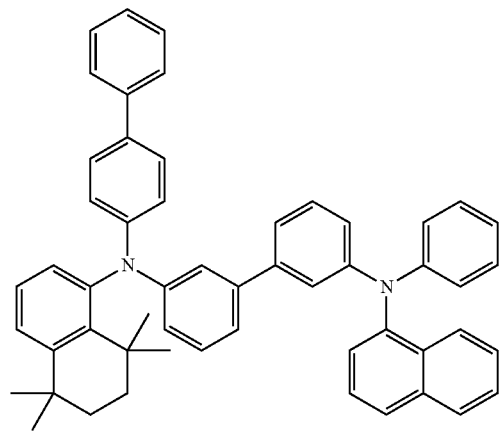
C-40
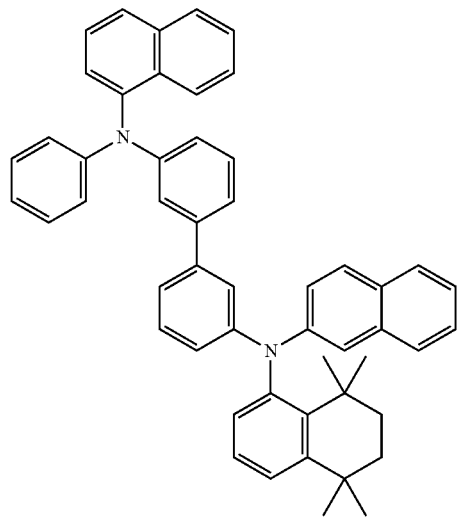
C-41
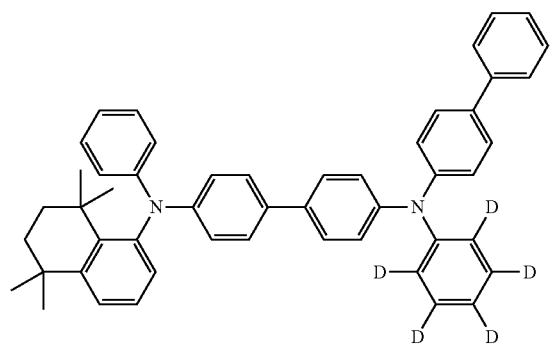
C-42
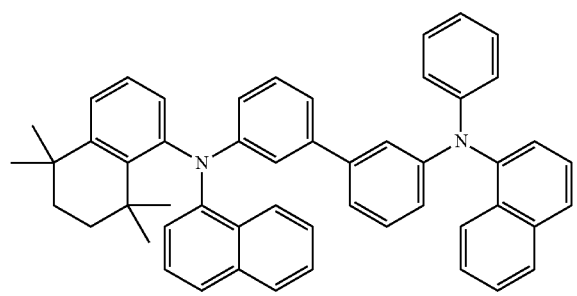
C-43
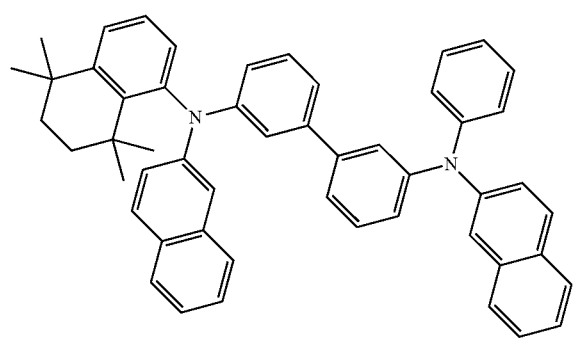
C-44
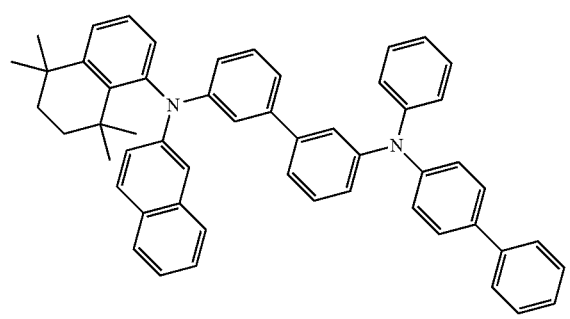

-continued
D-1
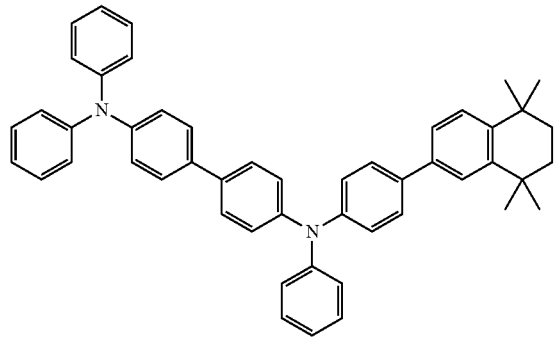
D-2
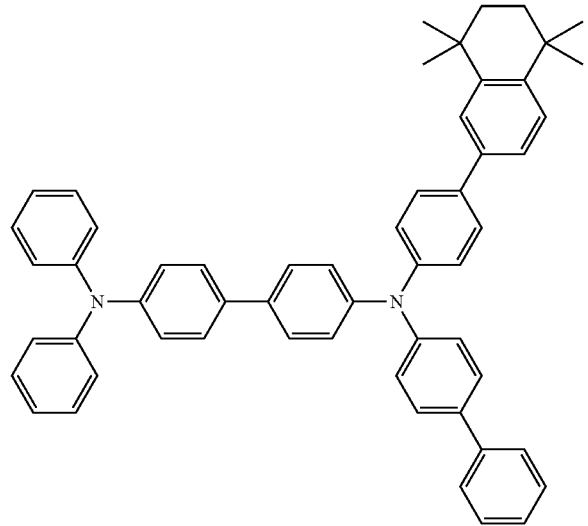
D-3
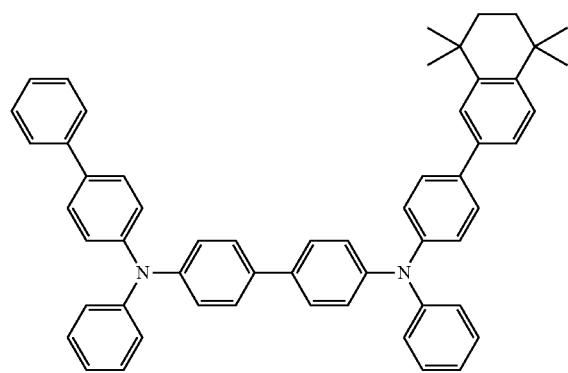
D-4
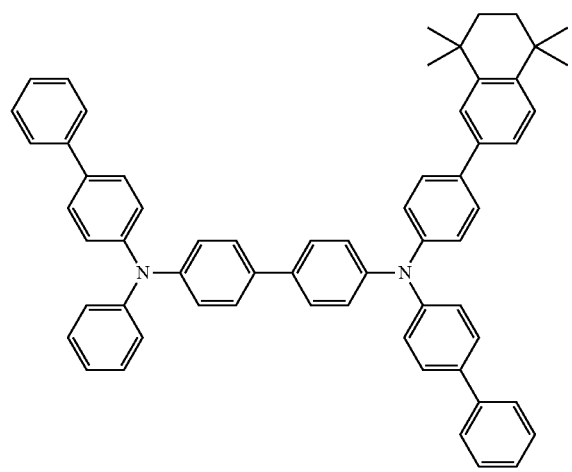
D-5
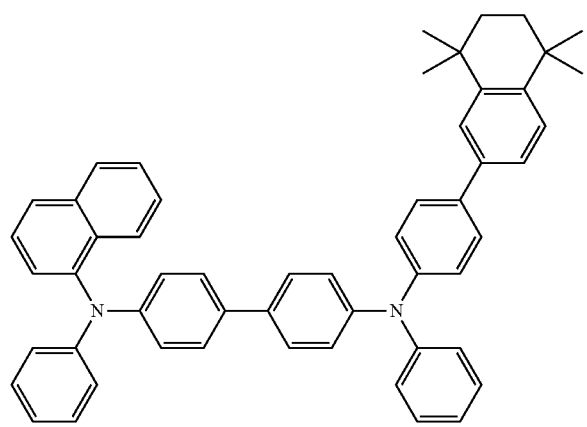
D-6
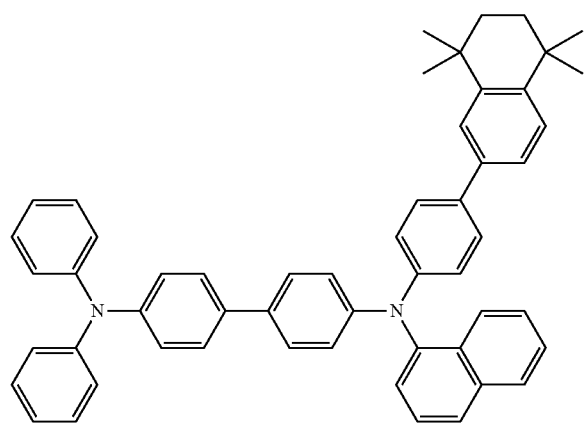

-continued
D-7
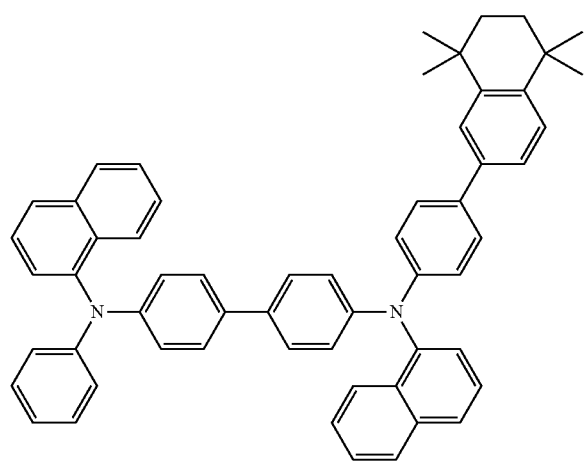
D-8
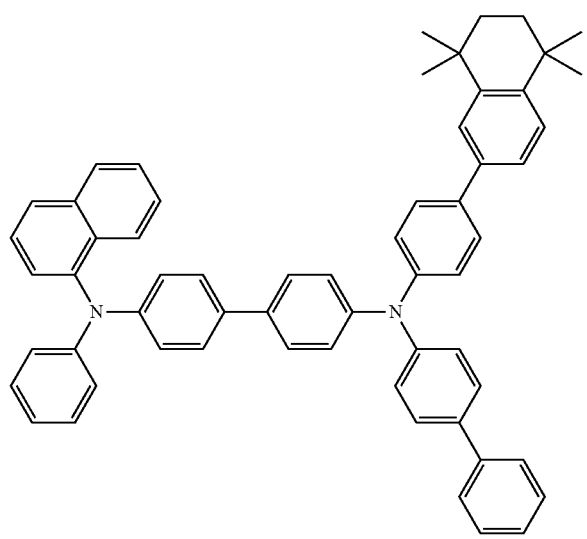
D-9
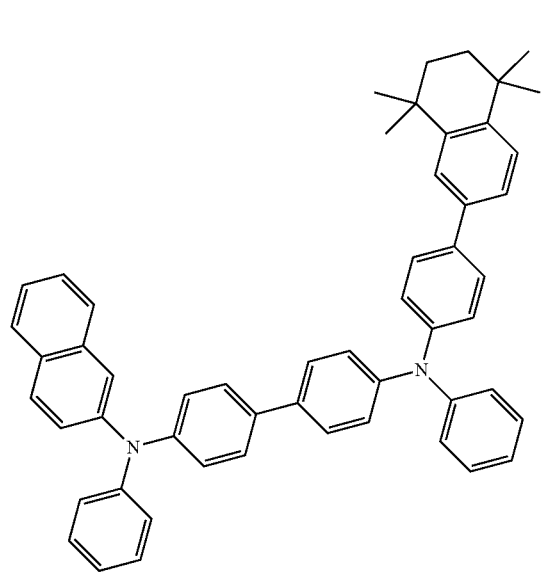
D-10
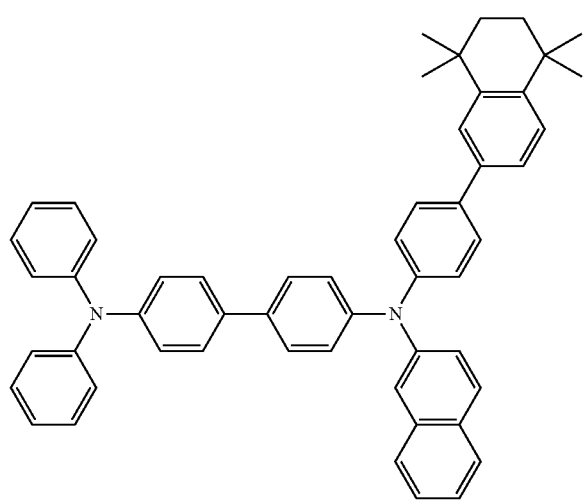
D-11
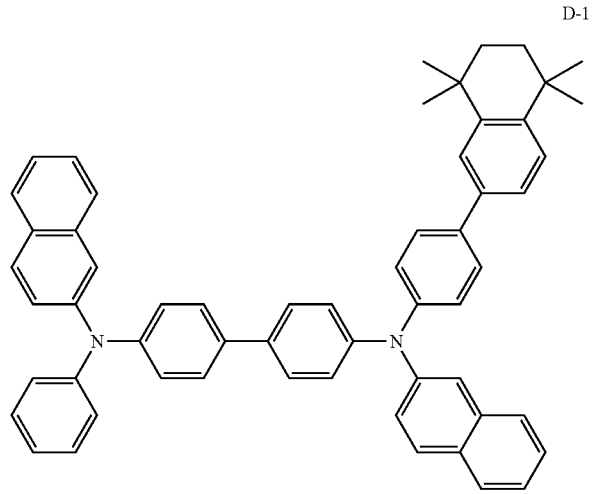
D-12
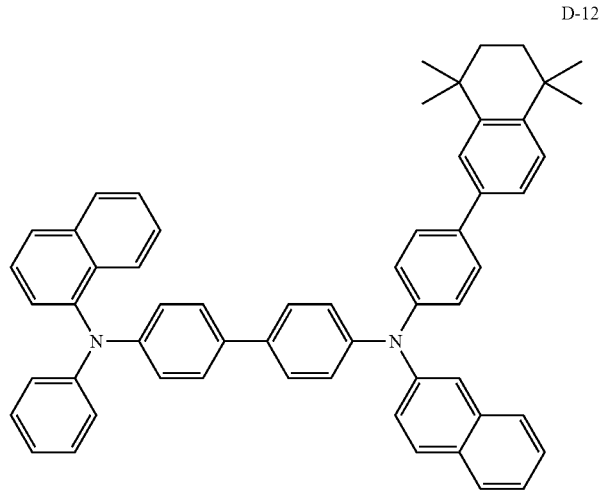

-continued
D-13
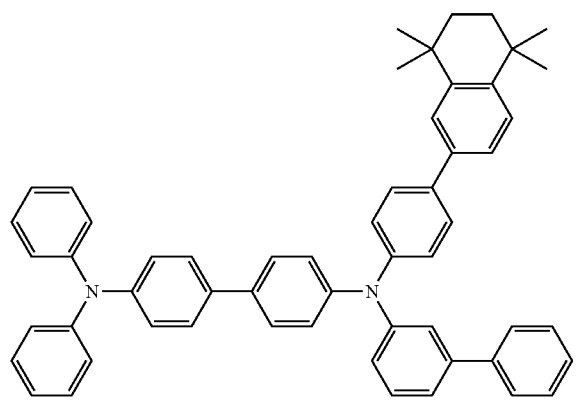
D-14
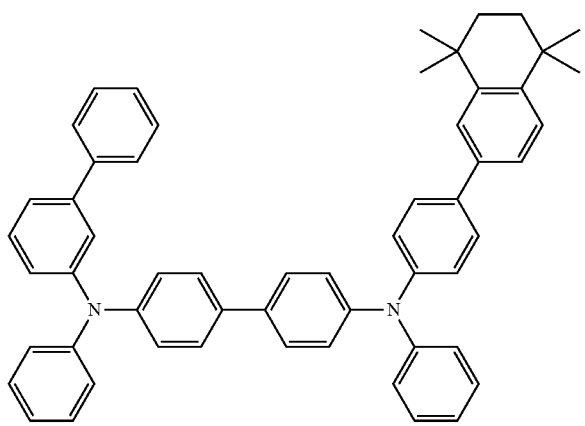
D-15
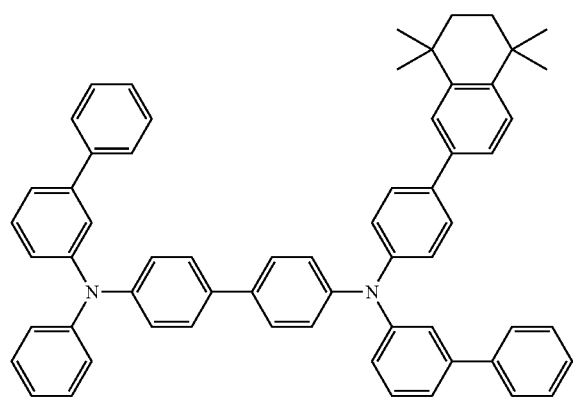
D-16
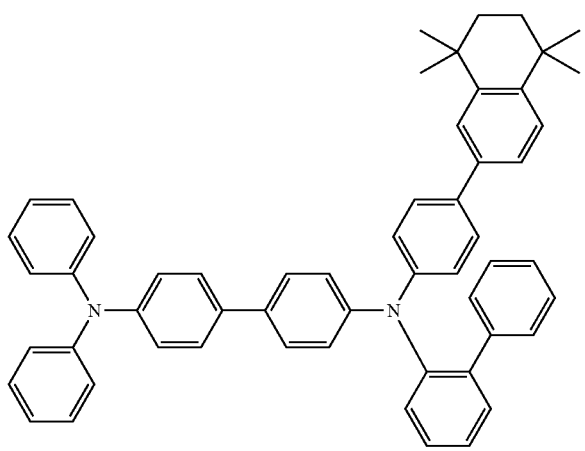
D-17
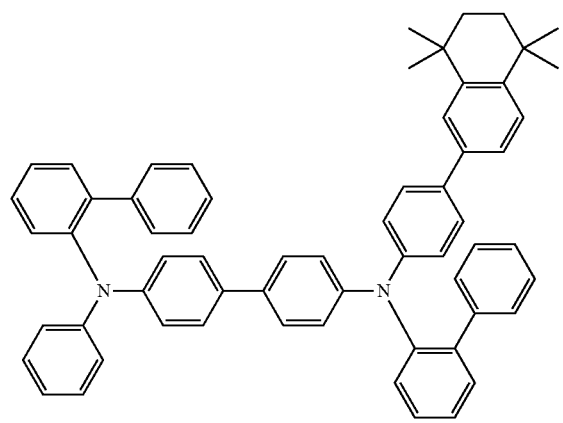
D-18
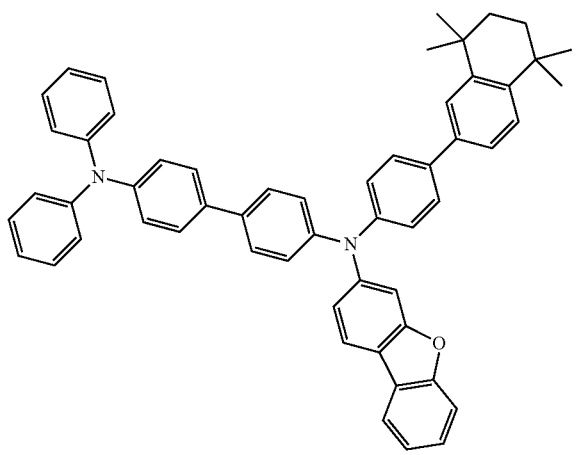

-continued
D-19
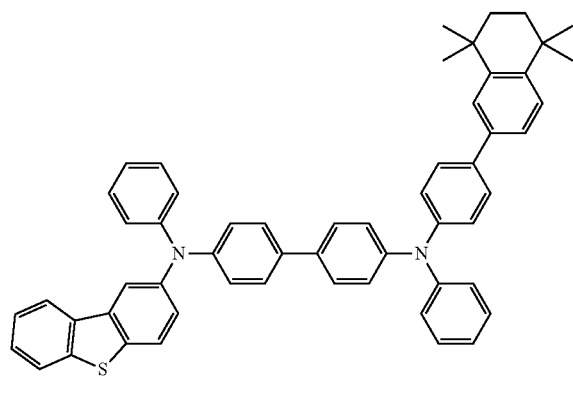
D-20
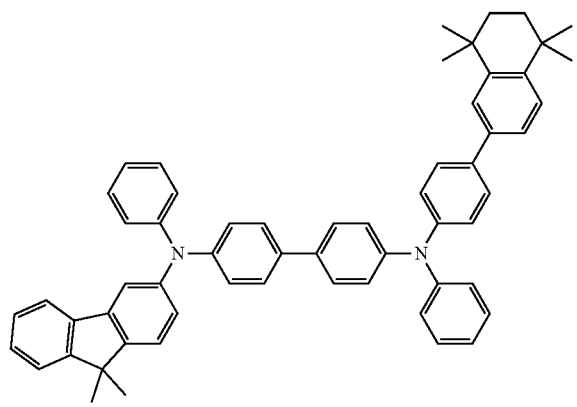
D-21
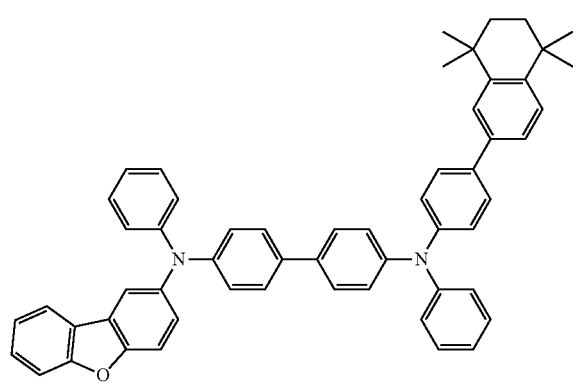
D-22
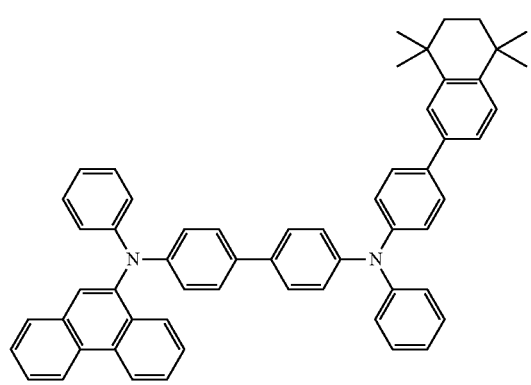
D-23
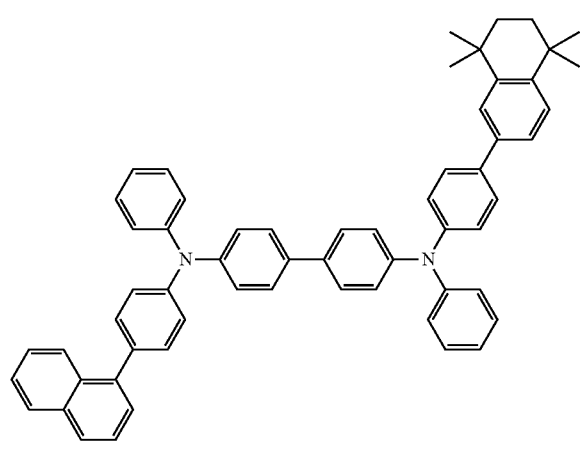
D-24
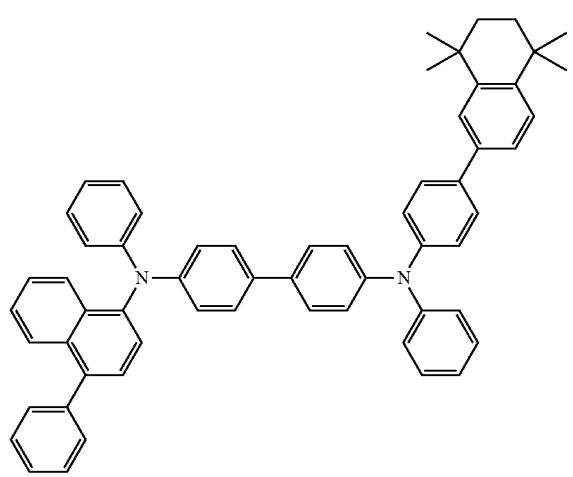

-continued
D-25
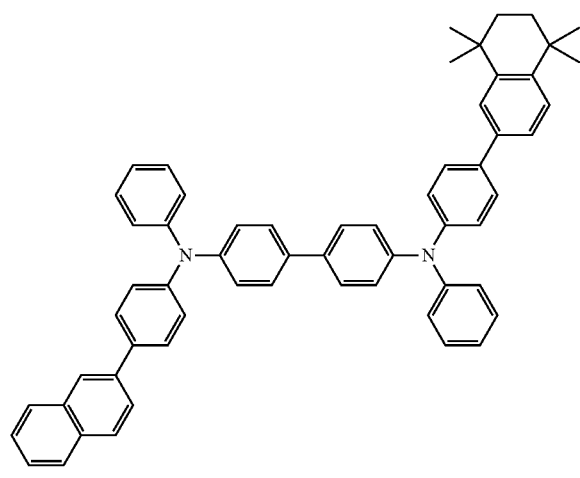
D-26
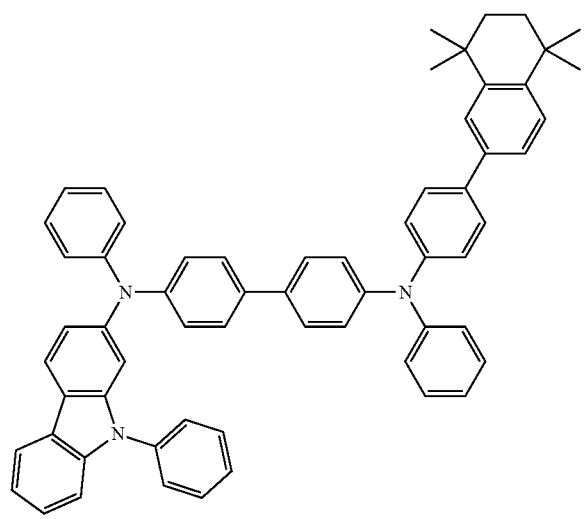
D-27
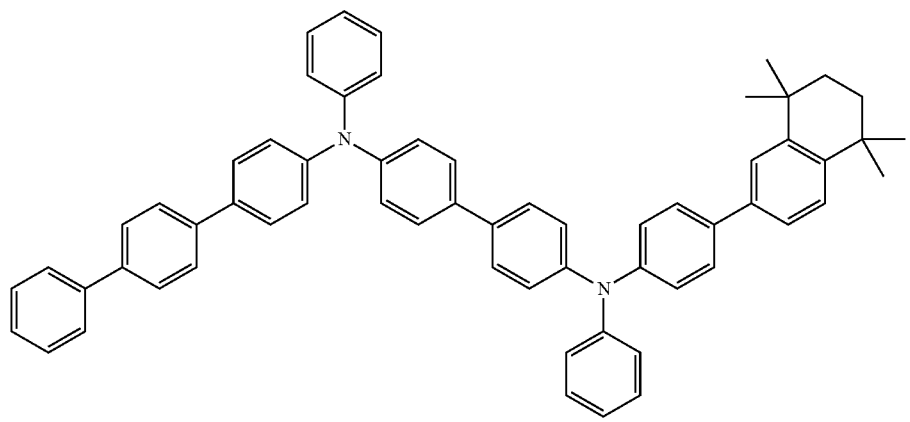
D-28
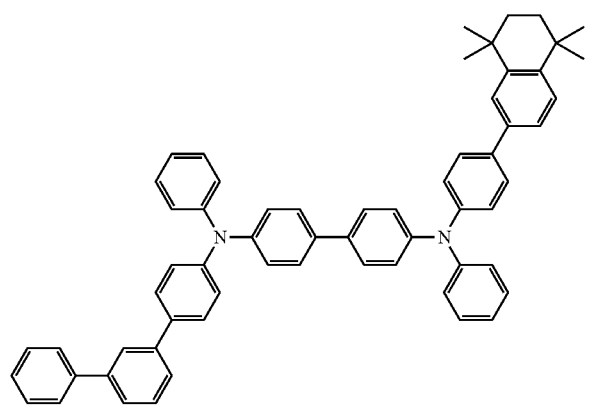
D-29
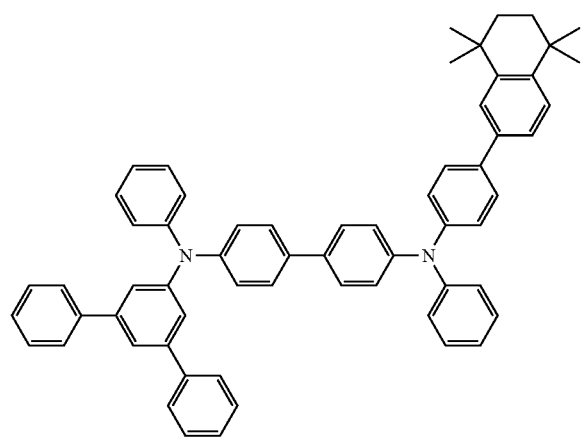

-continued
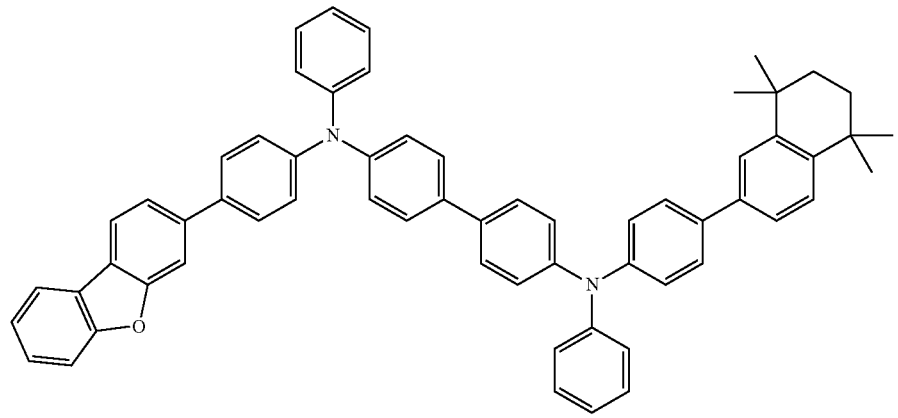
D-30
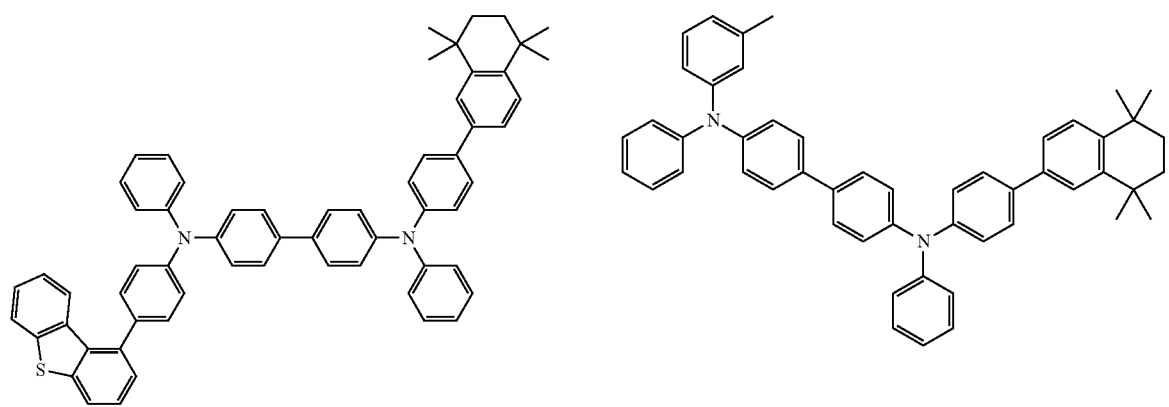
D-31    D-32

D-33
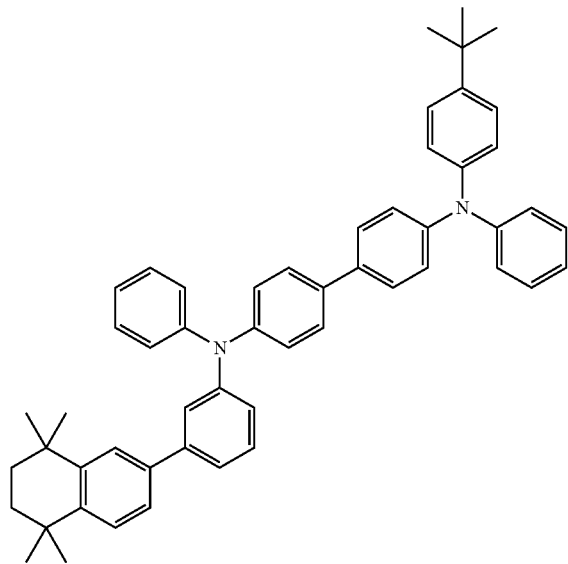
D-34
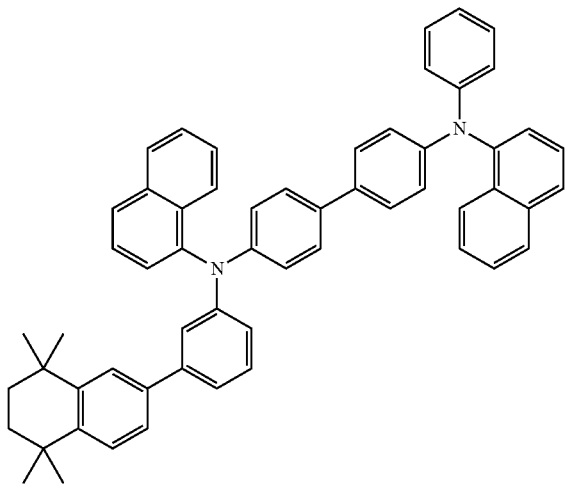
D-35
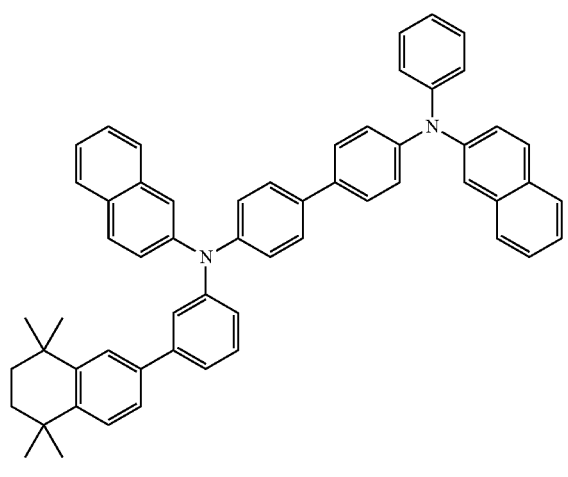
D-36
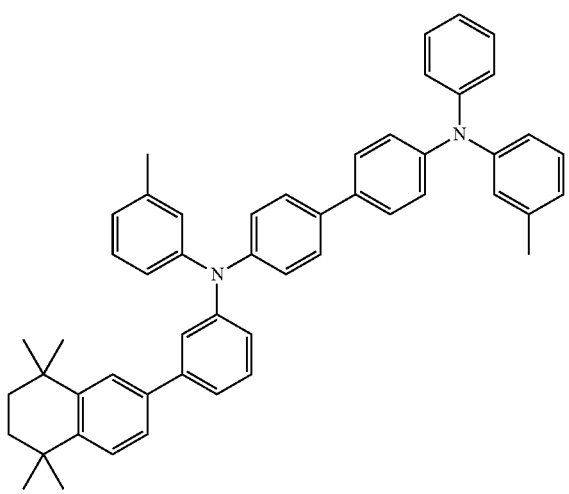

E-1
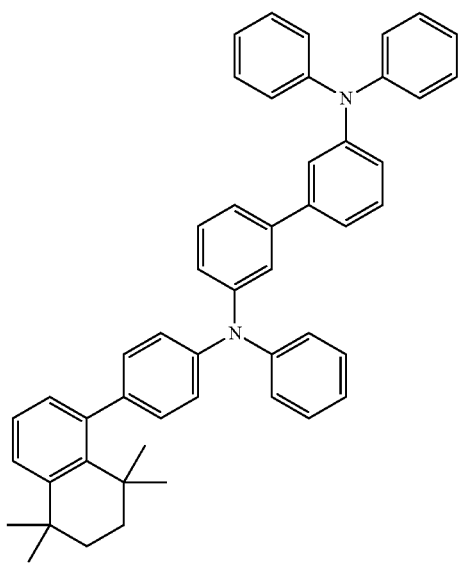
E-2
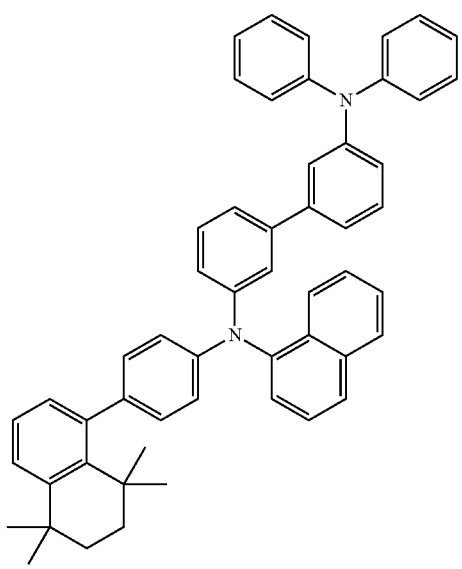
E-3
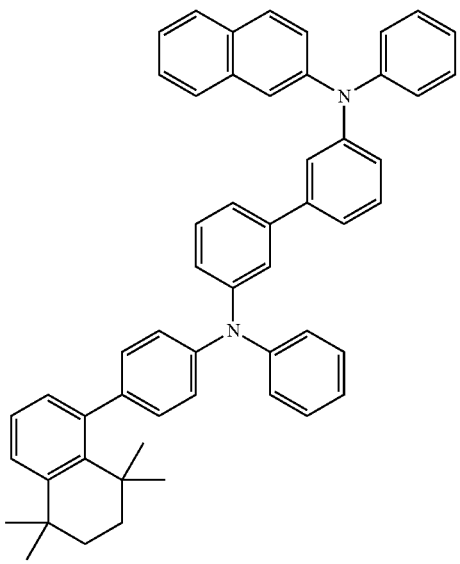
E-4
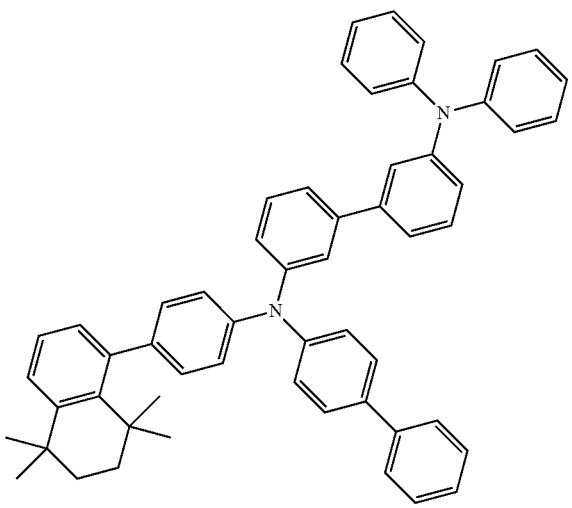
E-5
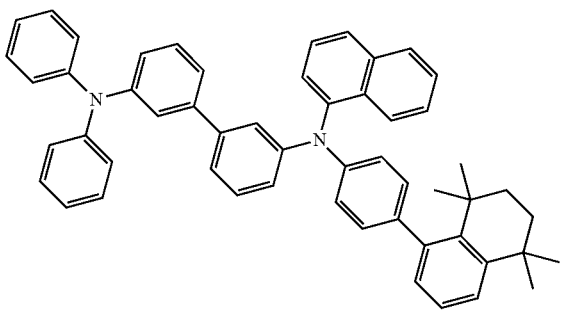

E-6
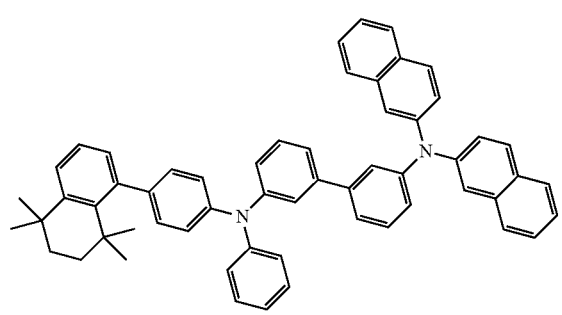
E-7
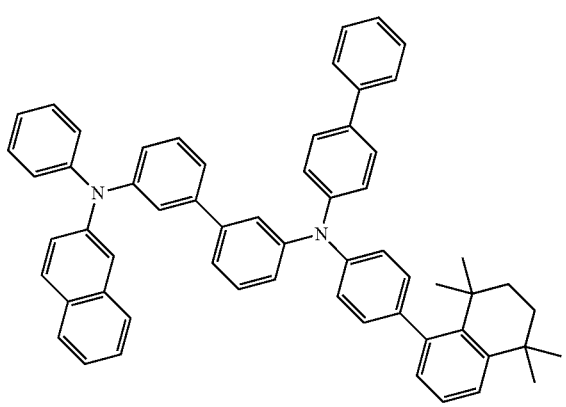
E-8
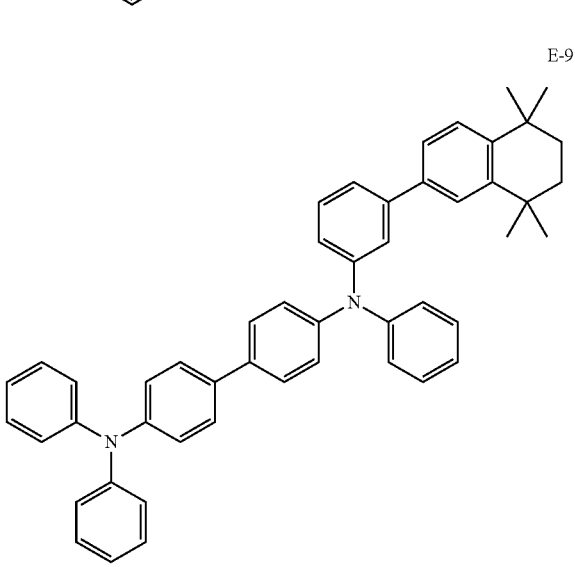
E-9
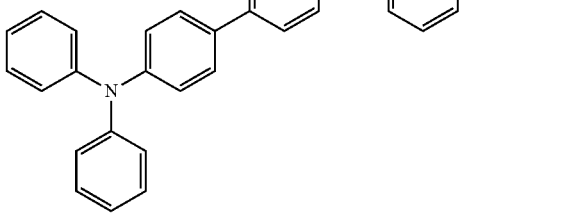
E-10
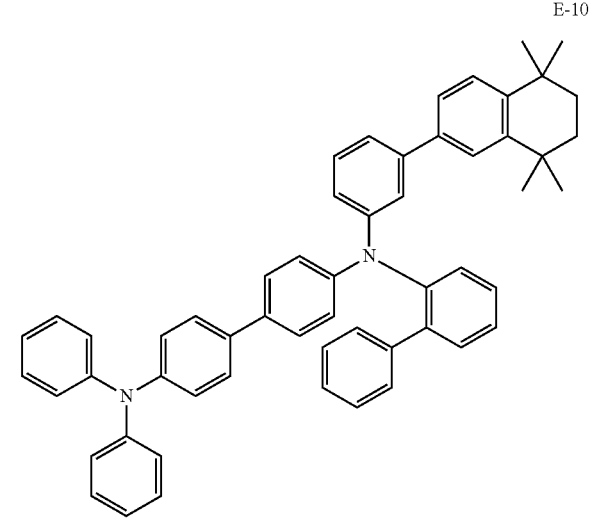
E-11
E-12

E-13
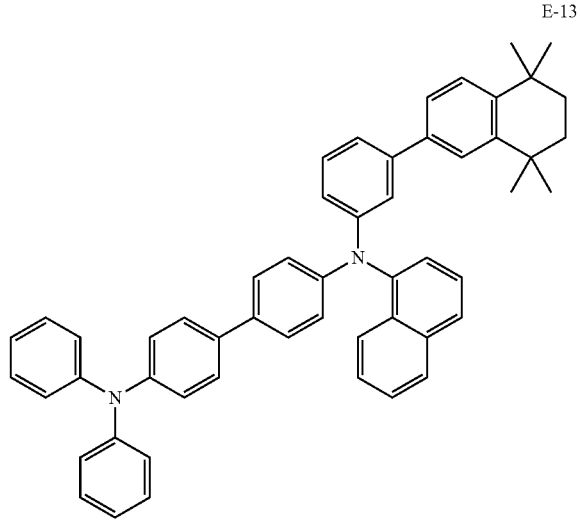
E-14
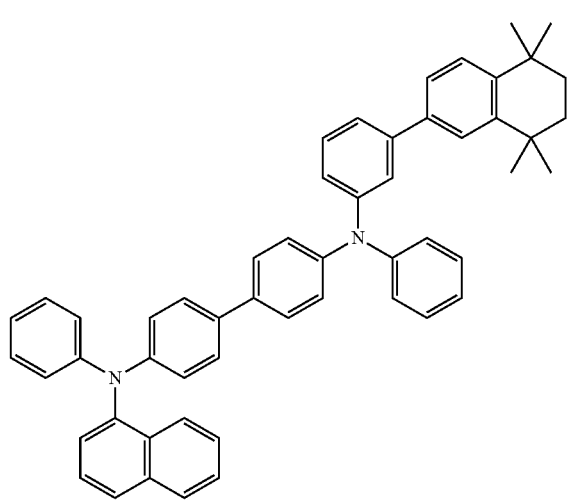
E-15
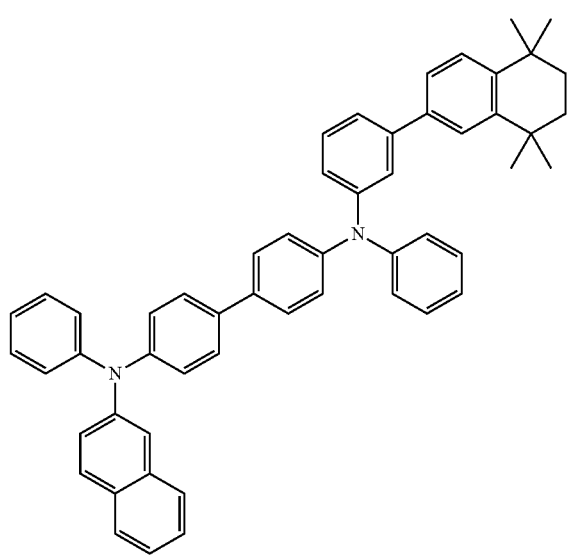
E-16
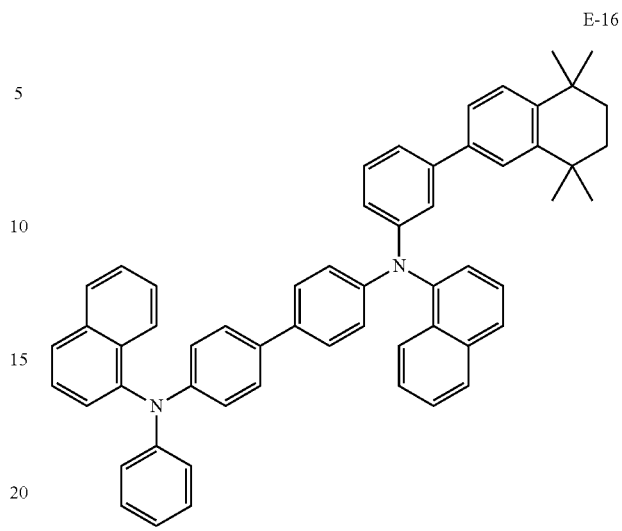
E-17
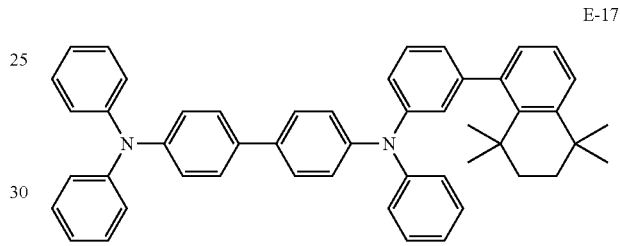
E-18
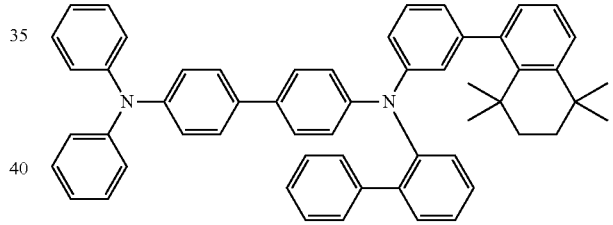
E-19
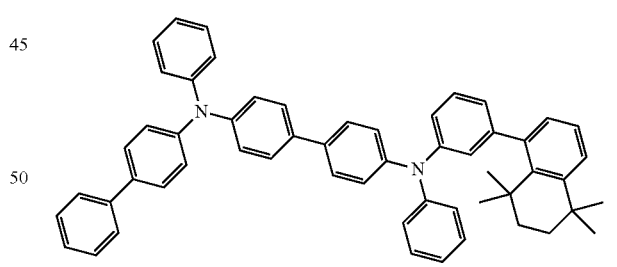
E-20
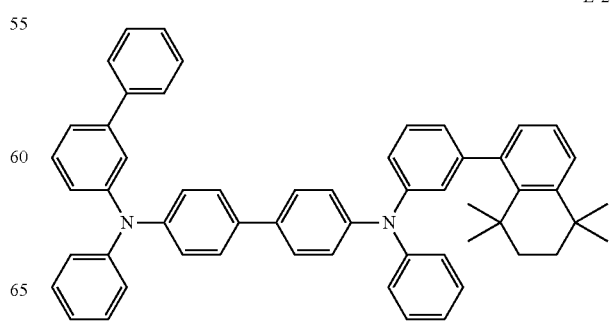

E-21
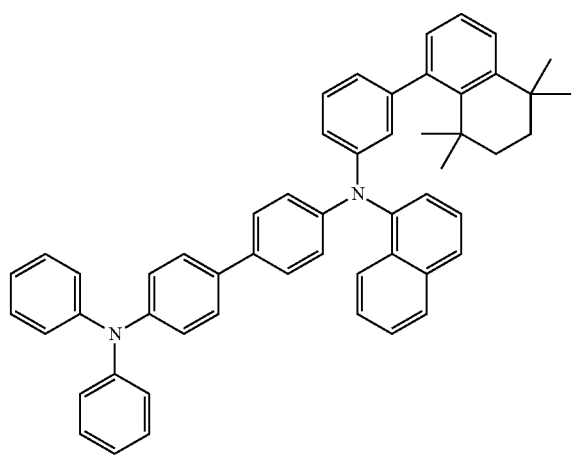
E-22
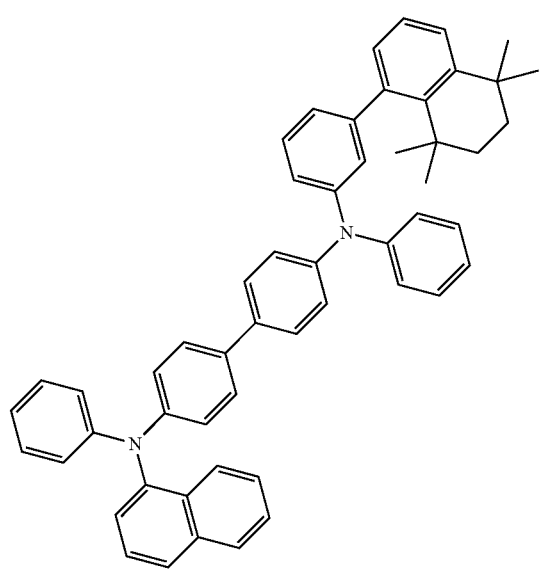
E-23
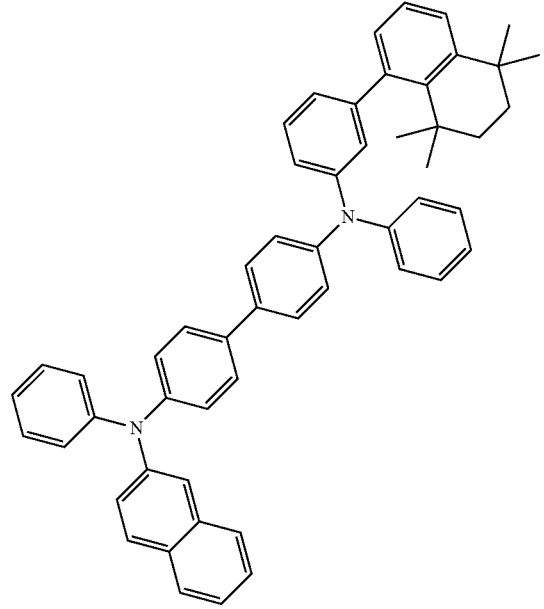
E-24
F-1
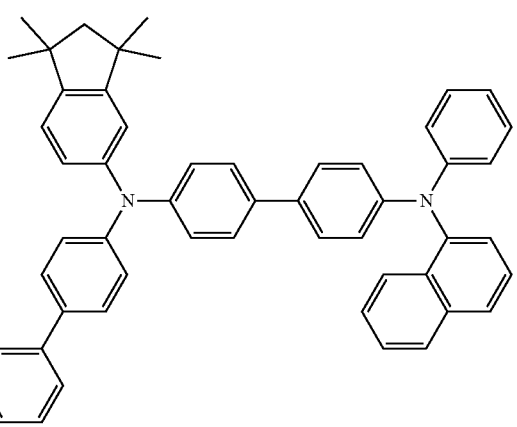

F-2
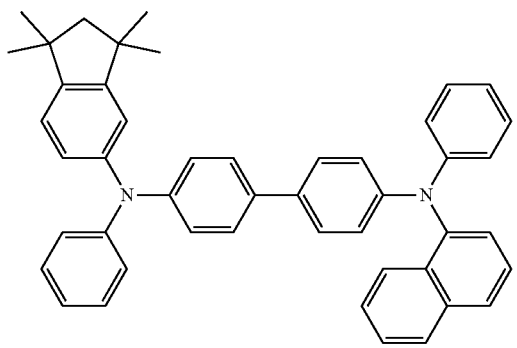
F-3
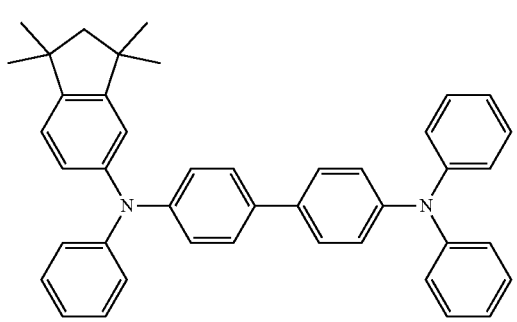
F-4
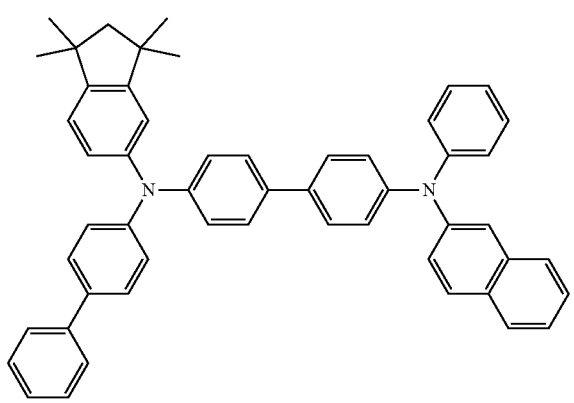
F-5
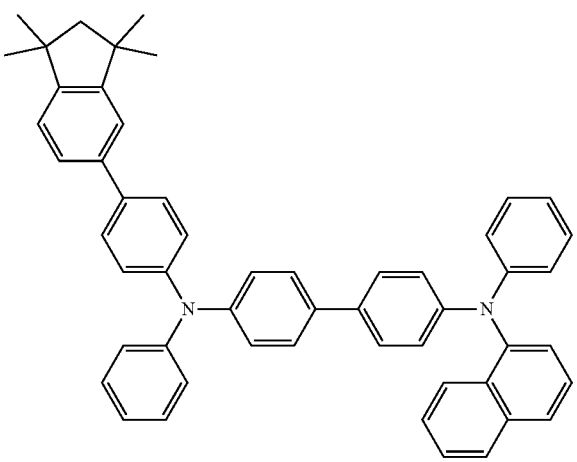
F-6
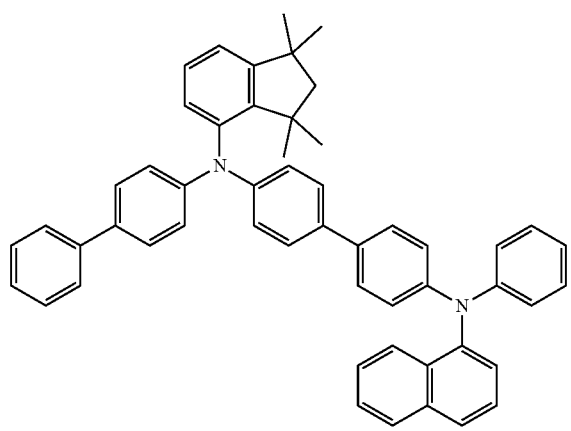
F-7
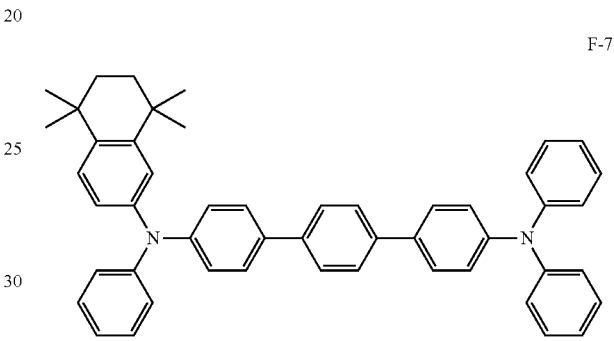
F-8
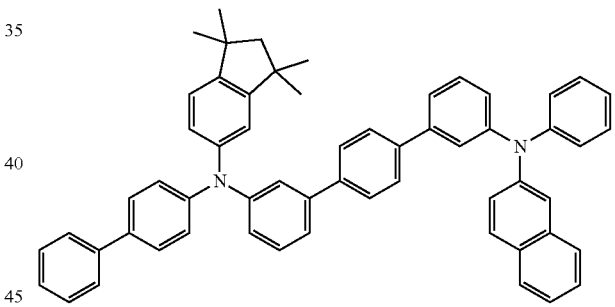
F-9
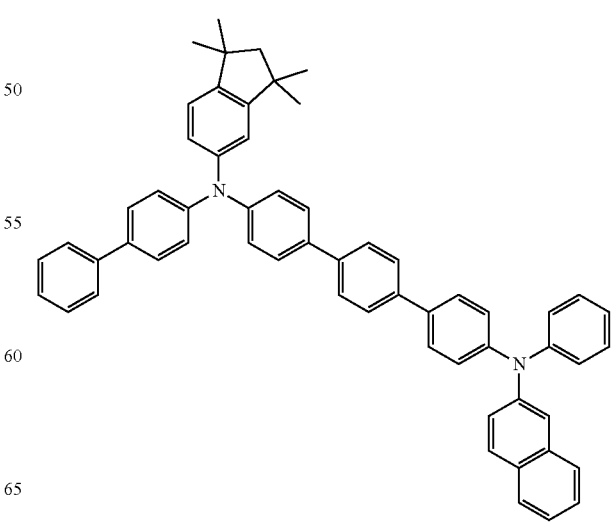

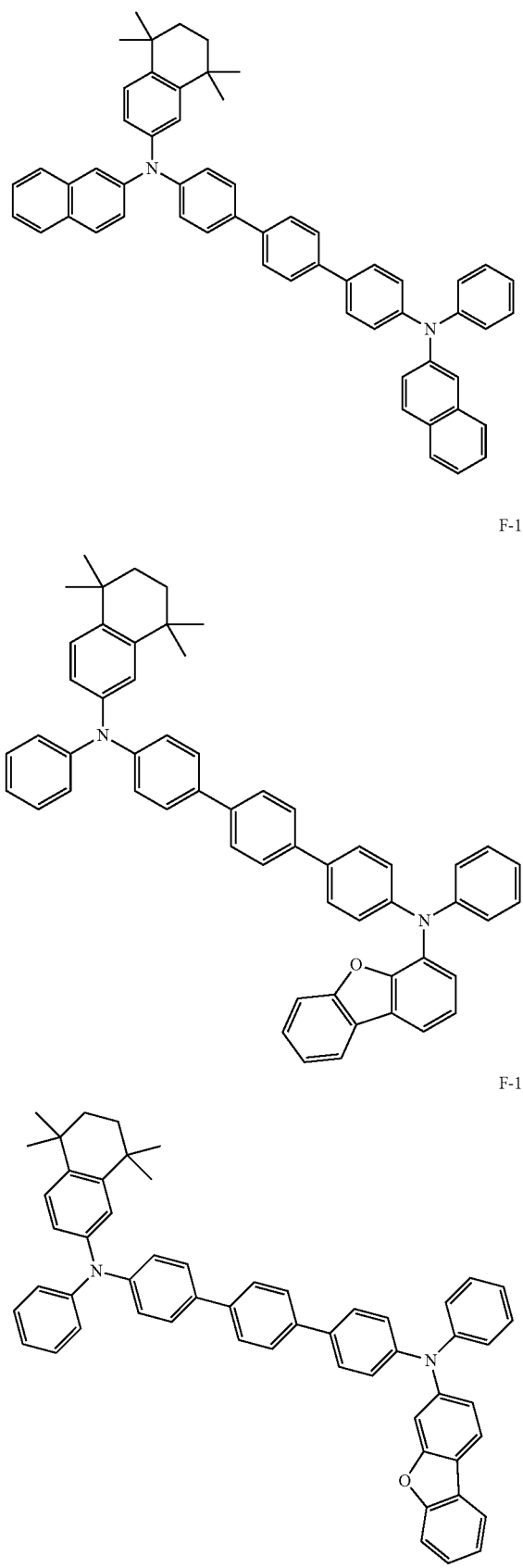
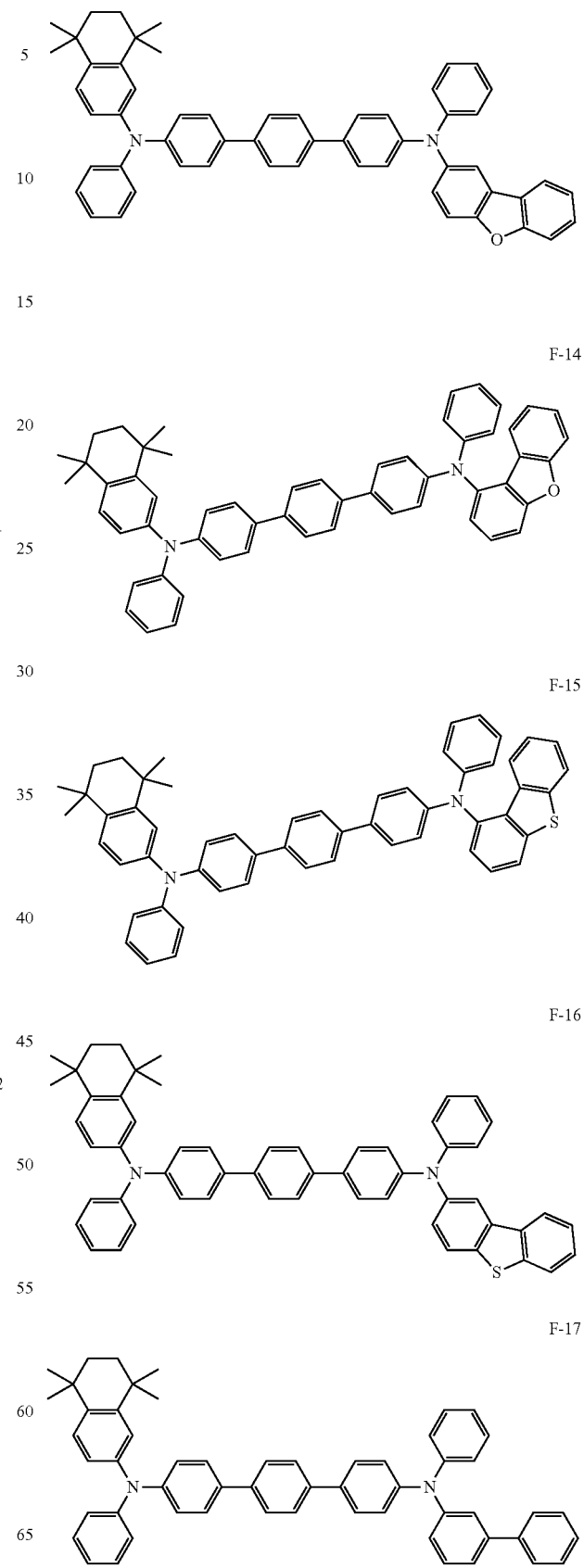

-continued
F-18
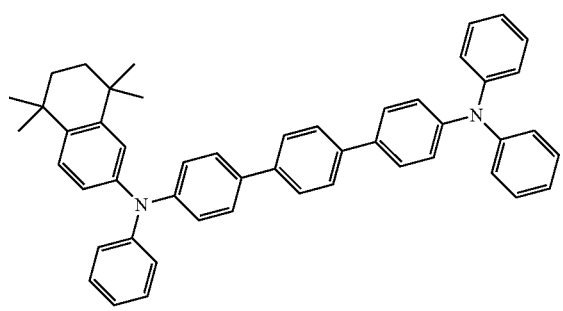
F-19
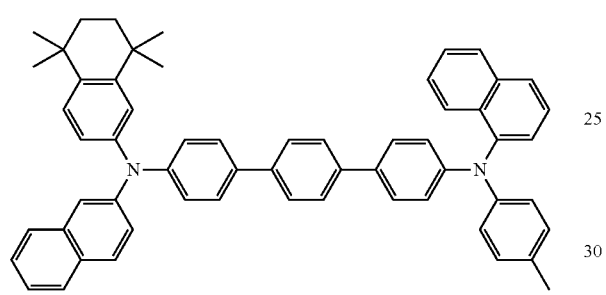
F-20
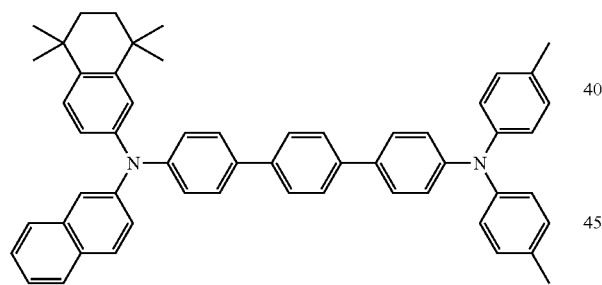
F-21
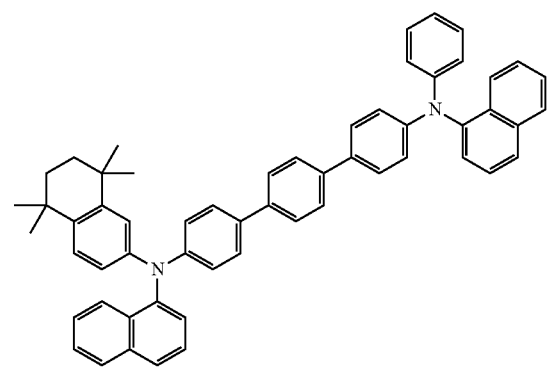
F-22
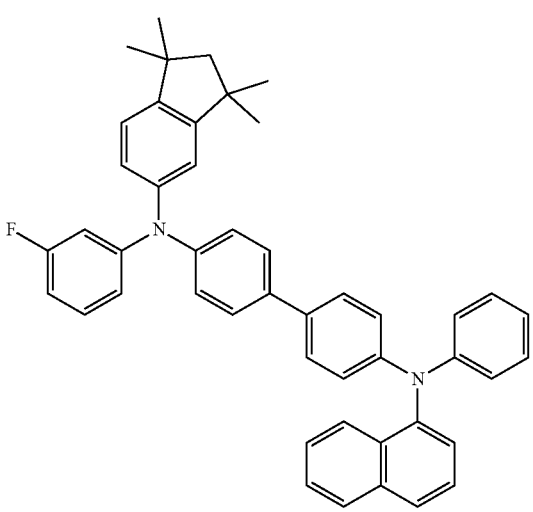
F-23
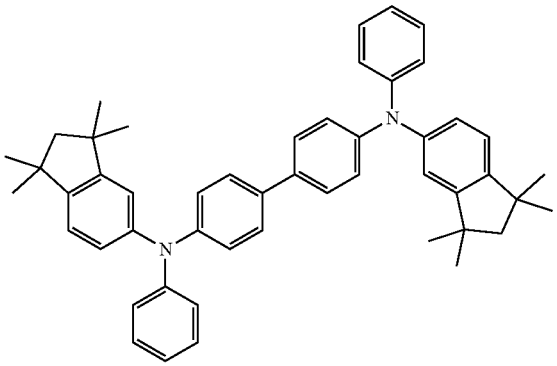
F-24
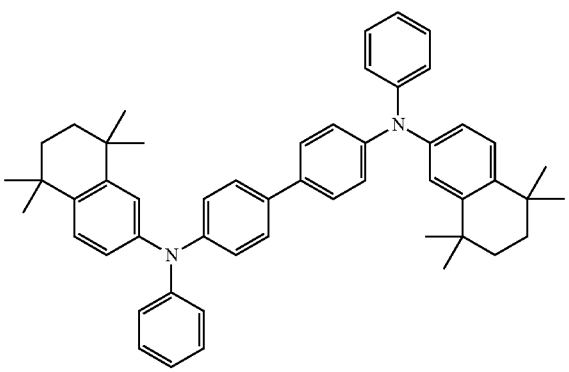

F-25

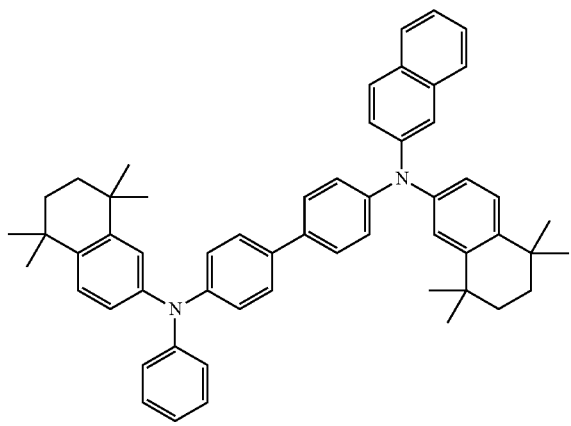

F-28

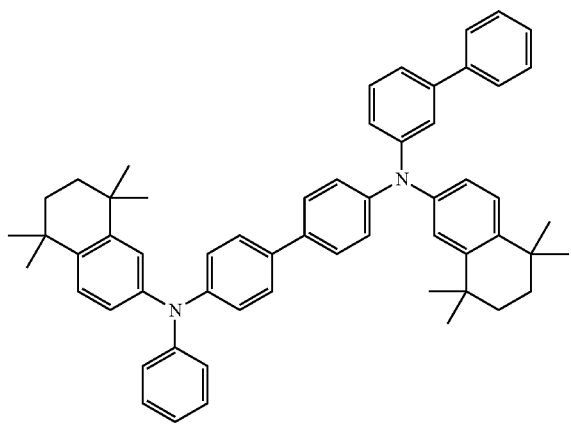

F-29

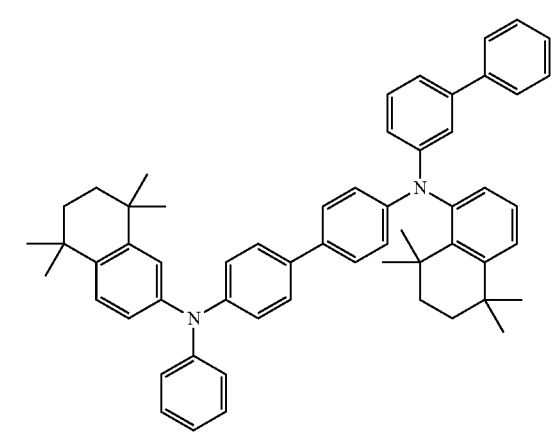

F-30

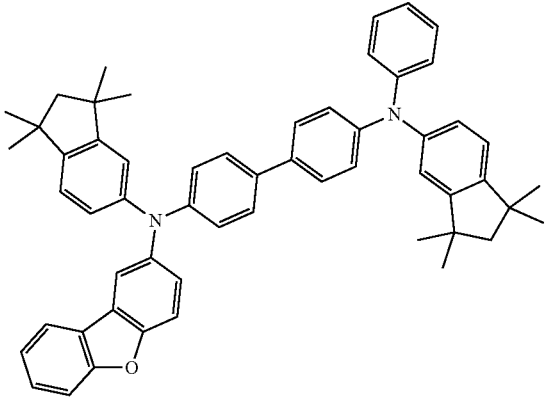

In a second aspect, the present application provides an electronic component comprising an anode and a cathode disposed opposite each other, and a functional layer disposed between the anode and the cathode. The functional layer comprises the organic compound of the present application.

Optionally, the functional layer includes a hole transport layer comprising the organic compound.

Optionally, the electronic component is an organic electroluminescent device or a photoelectric conversion device.

Further optionally, the electronic component is an organic electroluminescent device. The hole transport layer includes a first hole transport layer and a second hole transport layer. The first hole transport layer is closer to the anode than the second hole transport layer, wherein the first hole transport layer comprises the organic compound.

In an embodiment, the organic electroluminescent device is a blue light organic electroluminescent device.

In an embodiment, the electronic component is an organic electroluminescent device. As shown in FIG. 1, the organic electroluminescent device may include an anode 100, a first hole transport layer 321, a second hole transport layer 322, an organic light emitting layer 330, an electron transport layer 340, and a cathode 200 that are stacked sequentially.

Optionally, the anode 100 comprises an anode material, which are preferably materials having a large work function that facilitate hole injection into the functional layer. Specific examples of the anode material include, but are not limited to: metals such as nickel, platinum, vanadium, chromium, copper, zinc, and gold; and alloys thereof; metal oxides such as zinc oxide, indium oxide, indium tin oxide (ITO), and indium zinc oxide (IZO); combinations of metals and oxides, such as ZnO:Al or $SnO_2$:Sb; and conductive polymers such as poly(3-methylthiophene), poly[3,4-(ethylene-1,2-dioxy)thiophene] (PEDT), polypyrrole, and polyaniline. A transparent electrode containing indium tin oxide (ITO) as the anode is preferably included.

Optionally, the first hole transport layer 321 is composed of the organic compound of the present application.

The second hole transport layer 322 comprises one or more hole transport materials. The hole transport materials may be selected from carbazole polymers, carbazole-linked triarylamine compounds, or other types of compounds, which can be selected by those skilled in the art by referring to the existing technologies. For example, the material of the second hole transport layer is selected from the group consisting of the following compounds:

HT-1
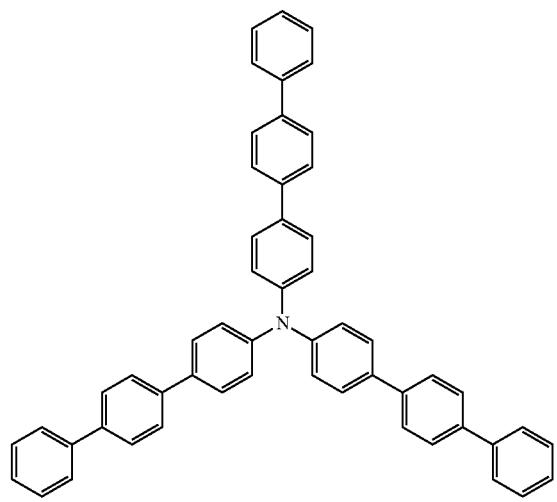
HT-4
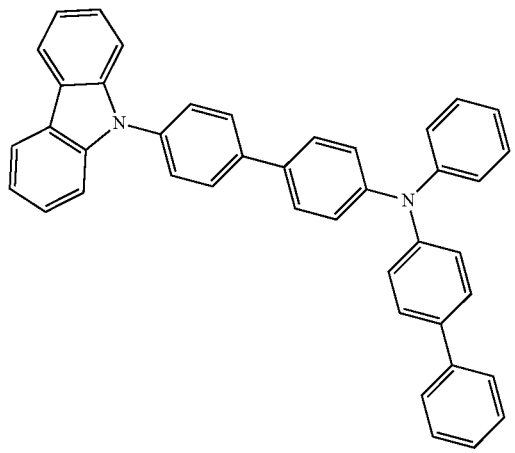
HT-2
HT-5
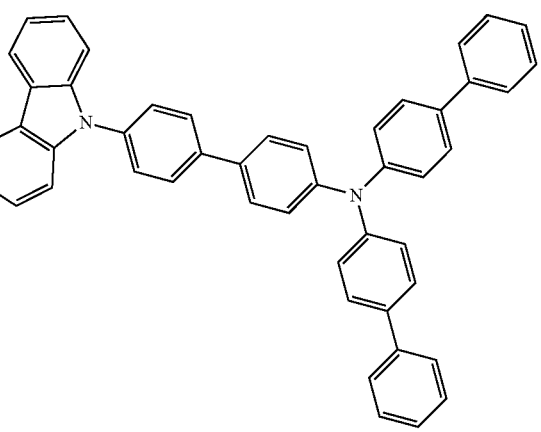
HT-3
HT-6
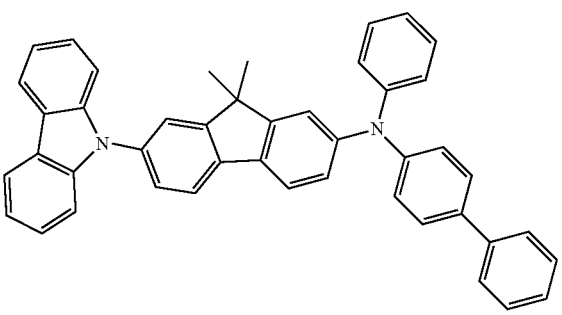

HT-7
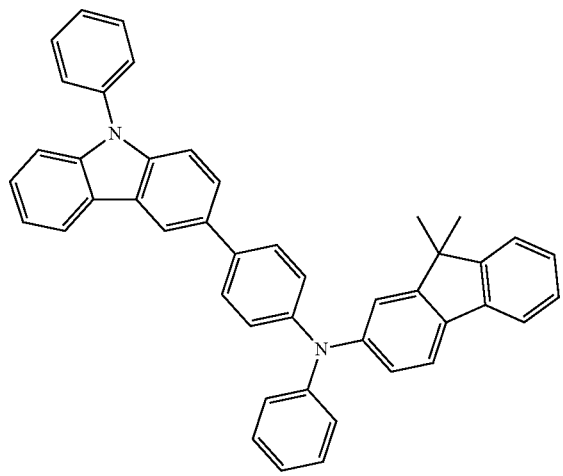
HT-8
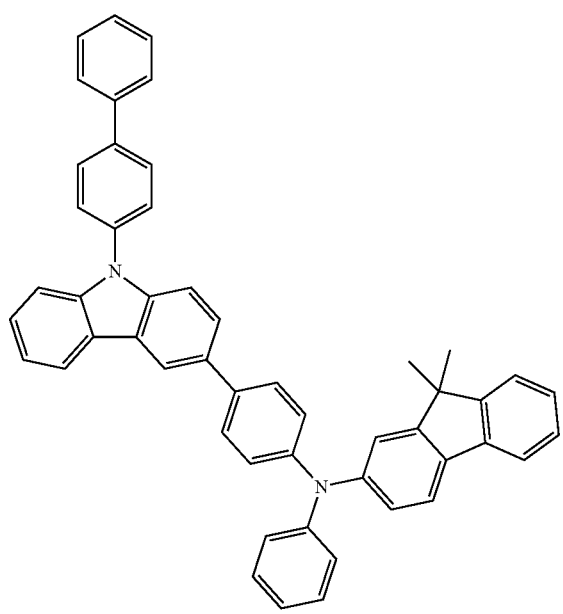
HT-9
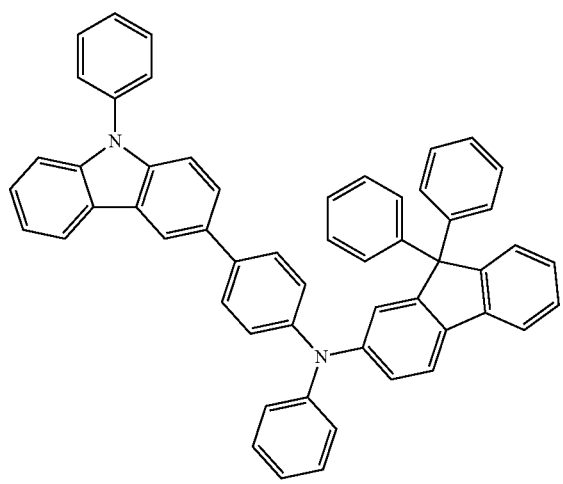
HT-10
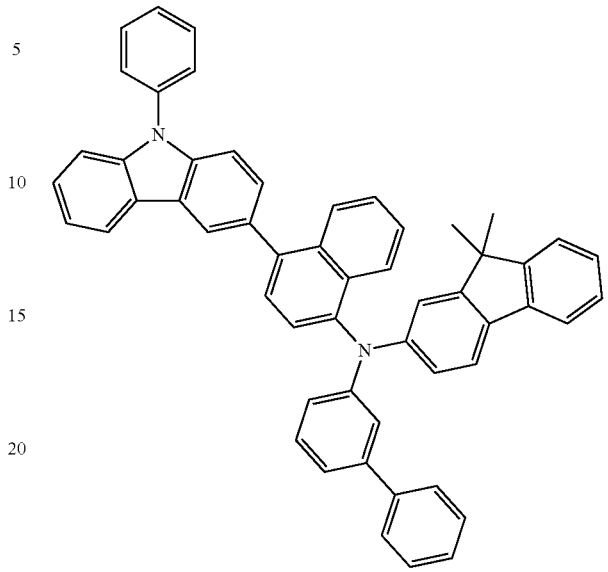
HT-11
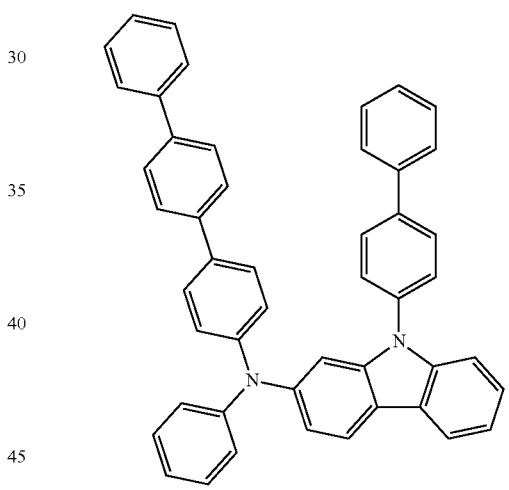
HT-12
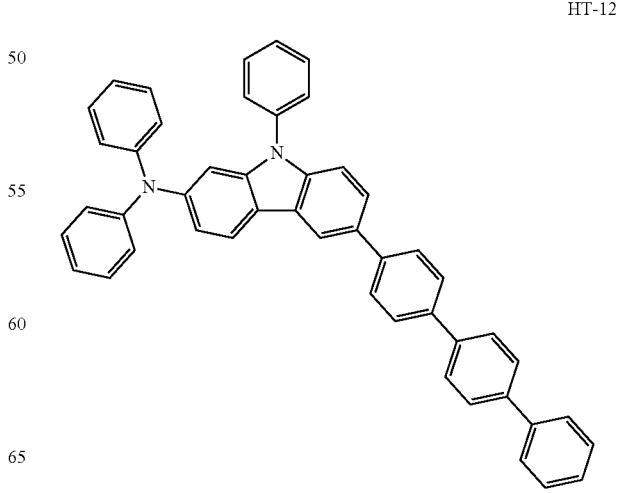

HT-13

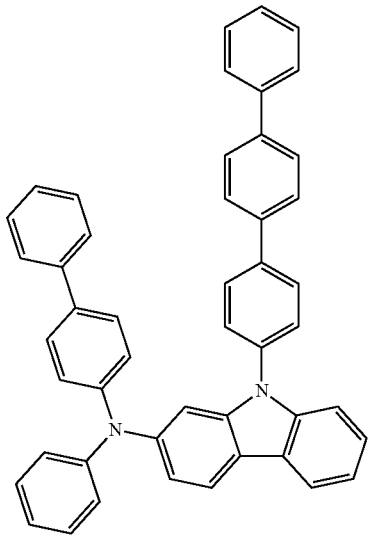

HT-16

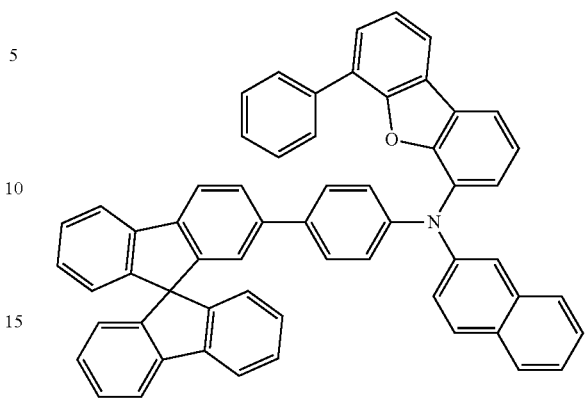

HT-14

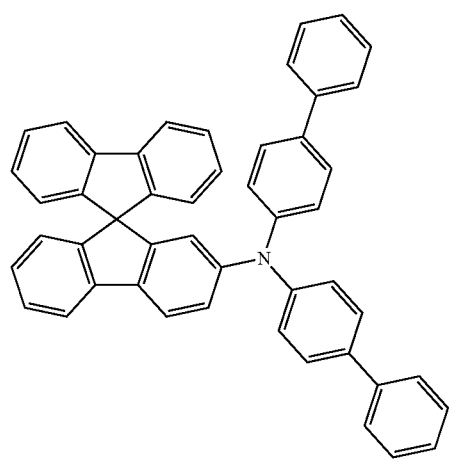

HT-15

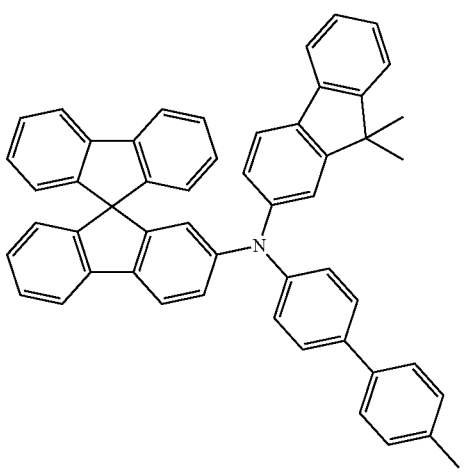

In a specific embodiment, the second hole transport layer 322 is composed of HT-7.

Optionally, the organic light emitting layer 330 may be composed of a single light emitting material, or may comprise a host material and a doping material. Optionally, the organic light emitting layer 330 is composed of a host material and a doping material. Holes injected into the organic light emitting layer 330 and electrons injected into the organic light emitting layer 330 can be combined in the organic light emitting layer 330 to form excitons. The excitons transmit energy to the host material, and the host material transmits the energy to the doping material, thereby enabling the doping material to emit light.

The host material of the organic light emitting layer 330 may be a metal chelating compound, a stilbene derivative, a 9,10-anthracene aromatic compound (α,β-ADN), an aromatic amine derivative, a dibenzofuran derivative, or other types of materials, which is not specially limited in the present application.

In an embodiment of the present application, the host material of the organic light emitting layer 330 is α, β-ADN.

The doping material of the organic light emitting layer 330 may be selected by referring to the existing technology, and may be, for example, selected from an iridium (III) organometallic complex, a platinum (II) organometallic complex, a ruthenium (II) complex, or the like. Specific examples of the doping material include, but are not limited to:

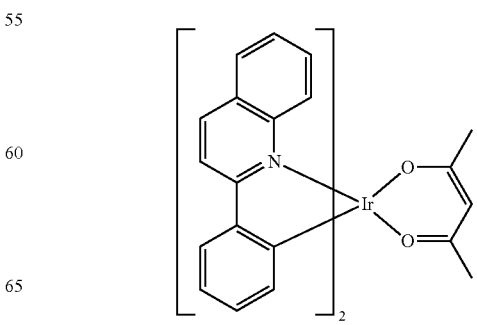

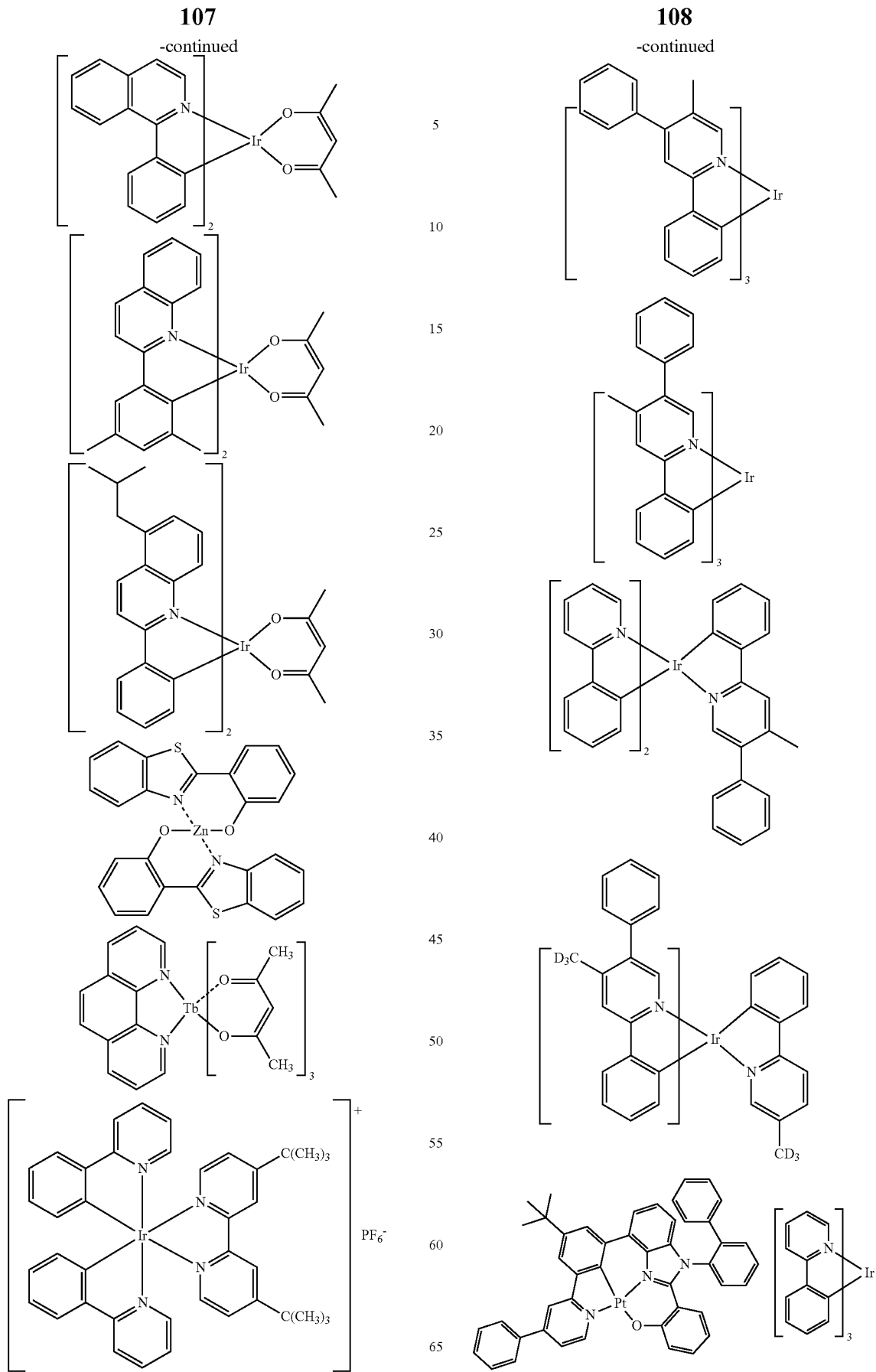

-continued

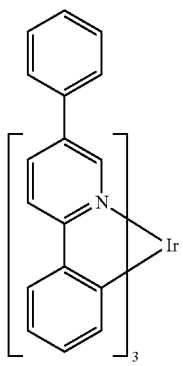

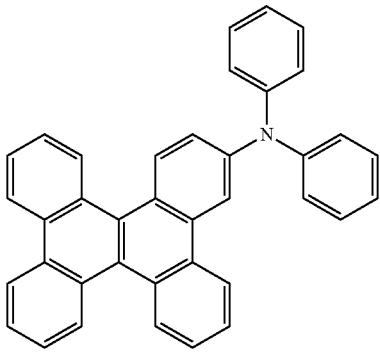

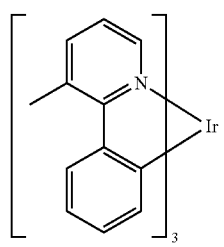

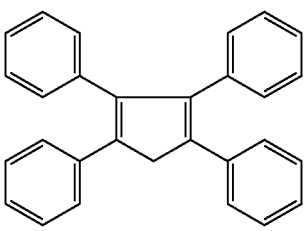

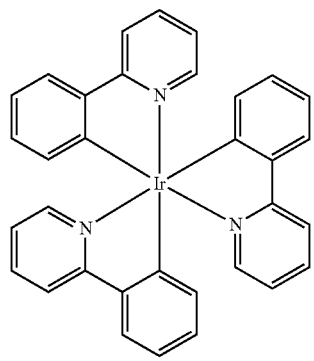

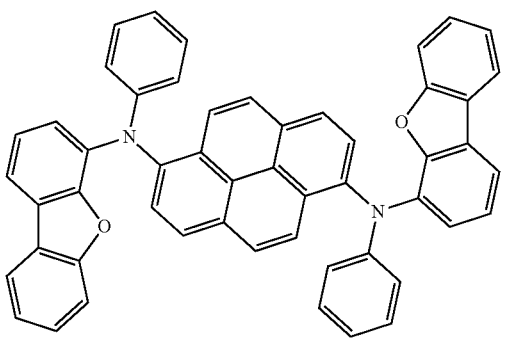

BD

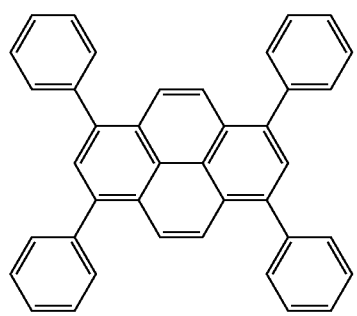

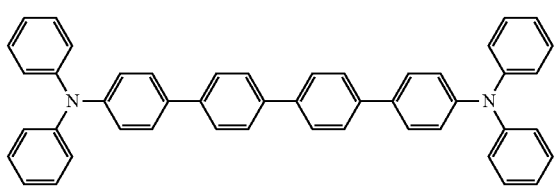

In an embodiment of the present application, the doping material of the organic light emitting layer 330 is BD.

Optionally, the electron transport layer 340 may be a single-layer structure, or a multi-layer structure, and may comprise one or more electron transport materials. The electron transport materials may typically include metal complexes and/or nitrogen-containing heterocyclic derivatives. The metal complex material may, for example, be selected from LiQ, Alq$_3$, Bepq$_2$, or the like. The nitrogen-containing heterocyclic derivative may be an aromatic ring having a nitrogen-containing 6-membered ring or 5-membered ring skeleton, a fused aromatic ring compound having a nitrogen-containing 6-membered ring or 5-membered ring skeleton, or the like, specific examples include, but are not limited to, 1,10-phenanthroline compounds such as Bphen, NBphen, DBimiBphen, BimiBphen, and the like; or azaaryl-containing anthracene, triazine or pyrimidine compounds having a structure shown below. In an embodiment of the present application, the electron transport layer 340 may be composed of ET-18 and LiQ.

ET-1
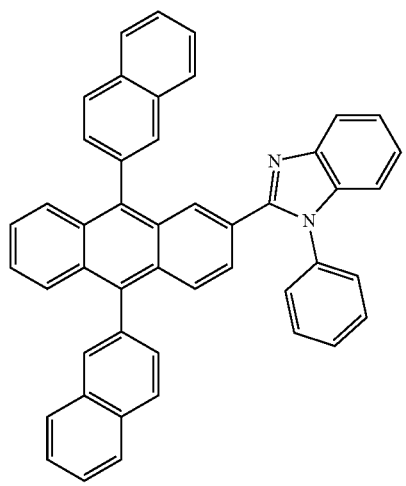
ET-2
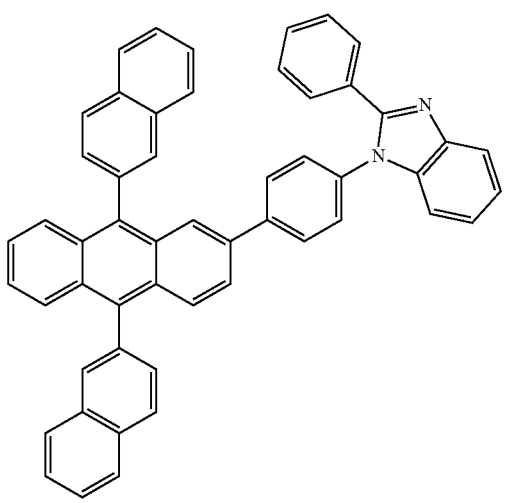
ET-3
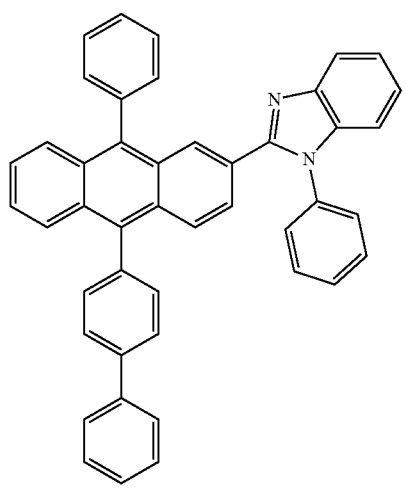
ET-4
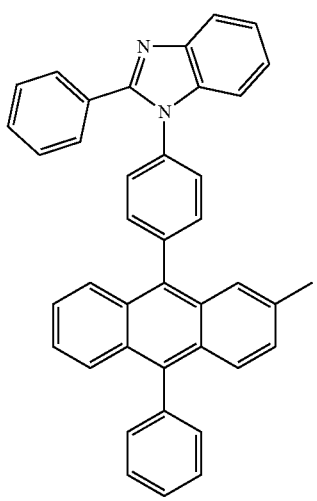
ET-5
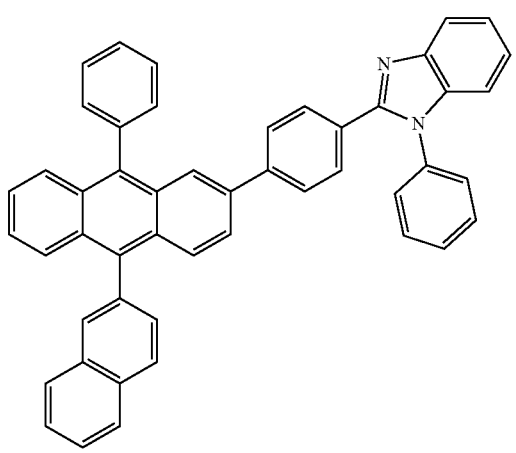
ET-6
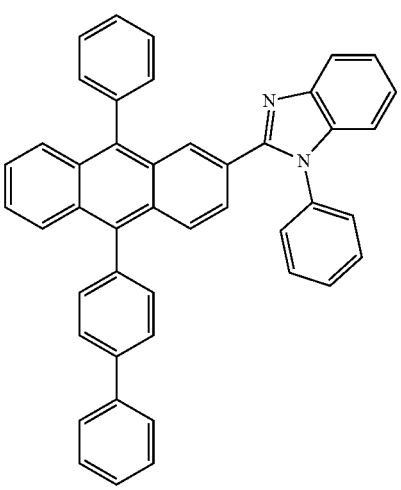

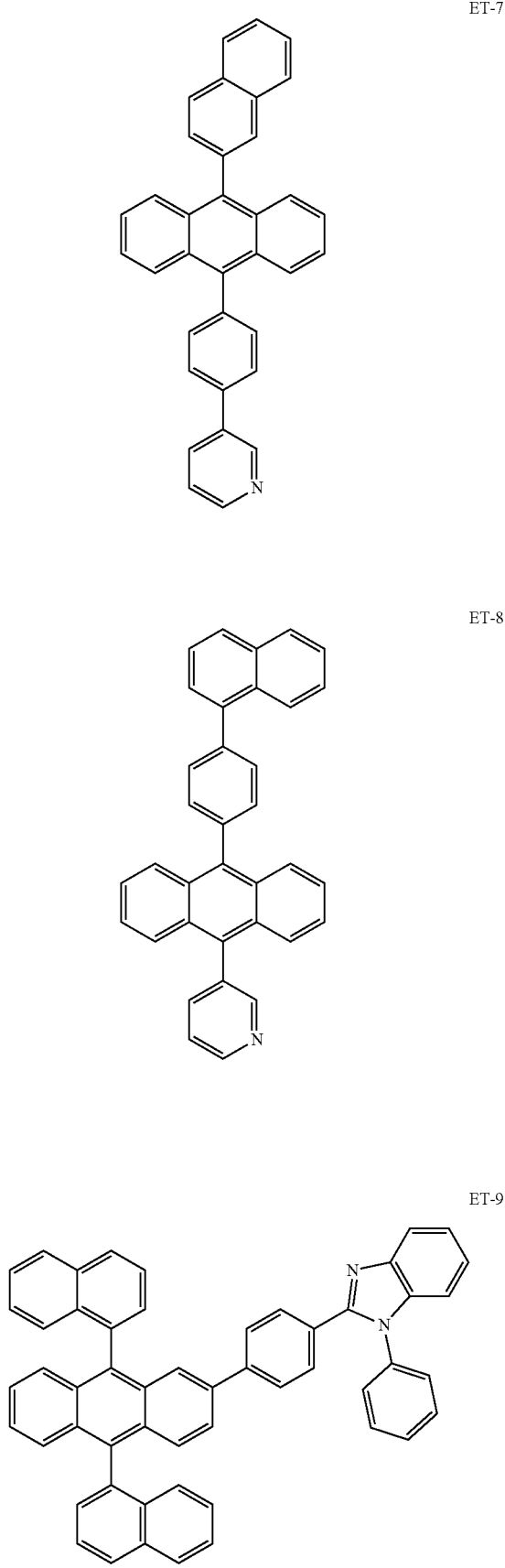

ET-14

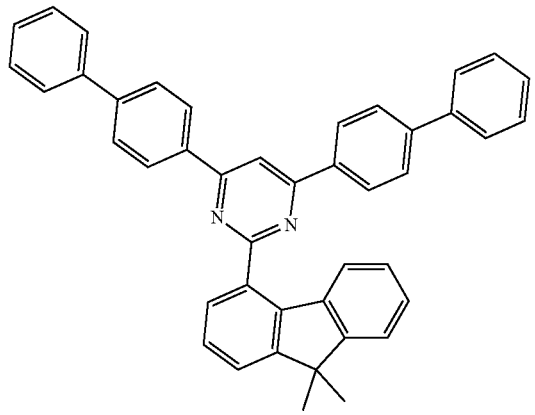

ET-15

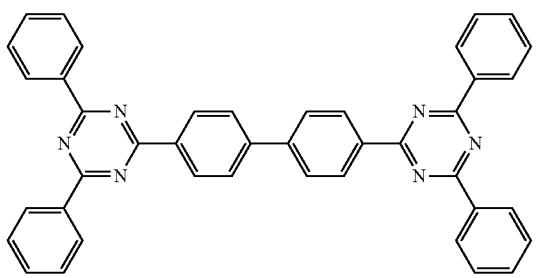

ET-16

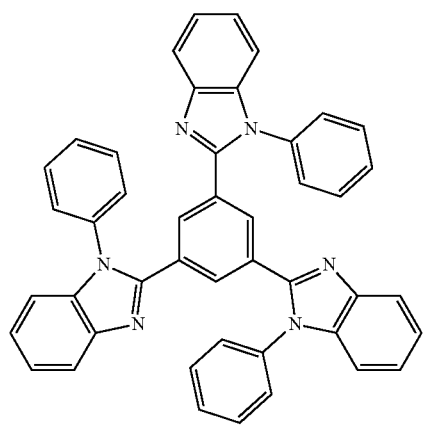

ET-17

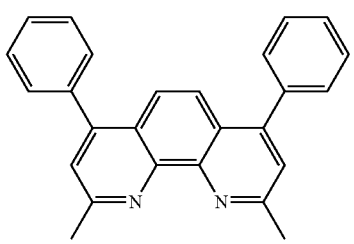

ET-18

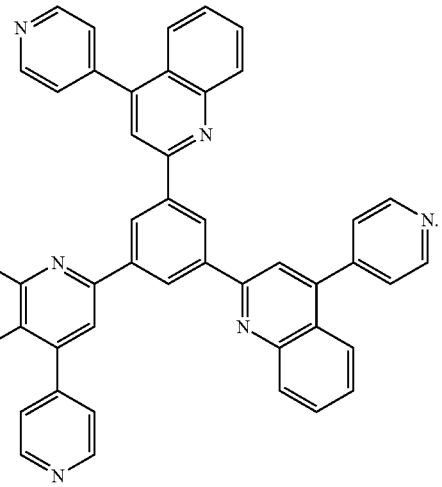

In the present application, the cathode 200 may comprise a cathode material, which is a material with a small work function that facilitates electron injection into the functional layer. Specific examples of the cathode material include, but are not limited to, metals such as magnesium, calcium, sodium, potassium, titanium, indium, yttrium, lithium, gadolinium, aluminum, silver, tin, lead, and alloys thereof; or multilayer materials such as LiF/Al, Liq/Al, LiO$_2$/Al, LiF/Ca, LiF/Al, and BaF$_2$/Ca. A metal electrode including magnesium and silver as the cathode is preferably included.

Optionally, as shown in FIG. 1, a hole injection layer 310 may be further provided between the anode 100 and the hole transport layer 321 to enhance the ability to inject holes into the hole transport layer 321. The hole injection layer 310 may be composed of a material selected from benzidine derivatives, starburst arylamine compounds, phthalocyanine derivatives, or other materials, which is not specially limited in the present application. For example, the compound contained in the hole injection layer 310 is selected from the group consisting of the following compounds:

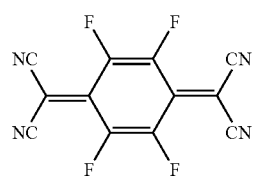

F4-TCNQ

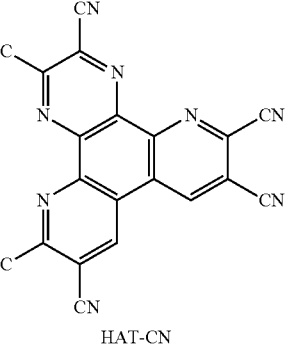

HAT-CN

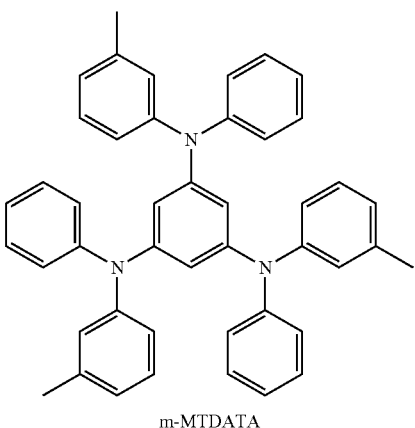

m-MTDATA

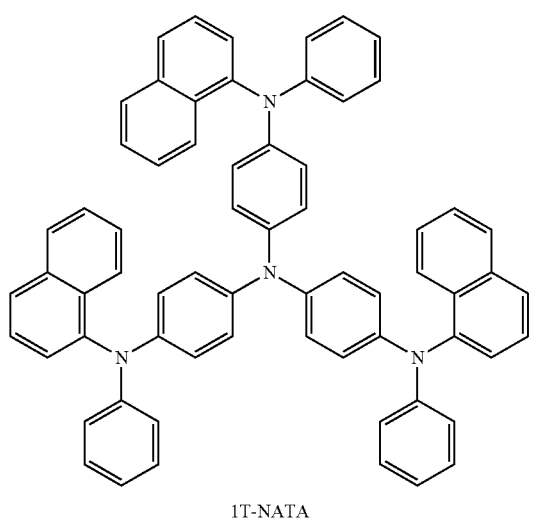

1T-NATA

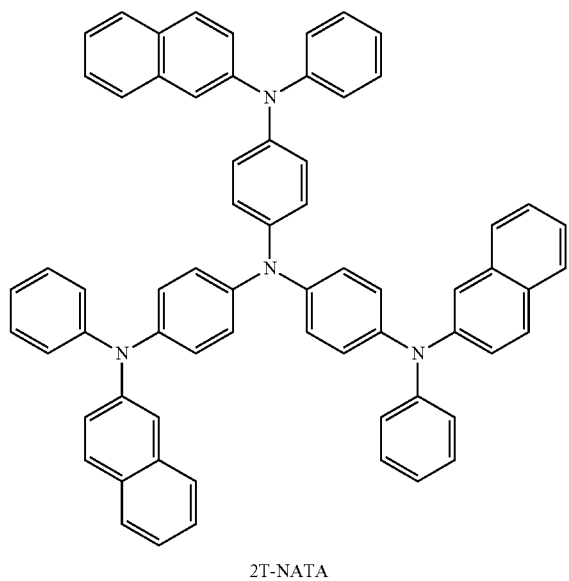

2T-NATA

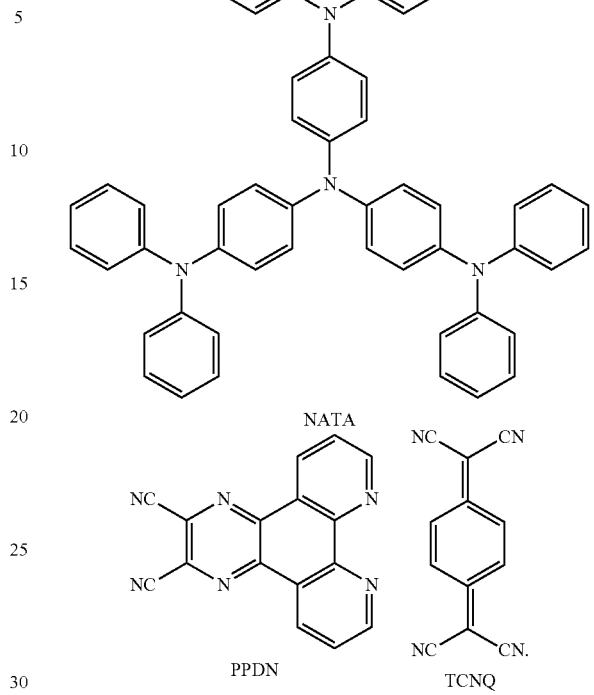

NATA

PPDN

TCNQ

In a specific embodiment of the present application, the hole injection layer 310 is composed of F4-TCNQ.

Optionally, a hole blocking layer may be further provided between the organic light emitting layer 330 and the electron transport layer 340 to keep carriers from the anode in the organic light emitting layer, so as to improve the balance of the carriers. For example, the hole blocking layer may be composed of BTB.

Optionally, as shown in FIG. 1, an electron injection layer 350 may be further provided between the cathode 200 and the electron transport layer 340 to enhance the ability to inject electrons into the electron transport layer 340. The electron injection layer 350 may comprise an inorganic material such as an alkali metal sulfide, an alkali metal halide, and the like. or may comprise a complex of an alkali metal and an organic substance. For example, the electron injection layer 350 may comprise Yb.

Figure 3:
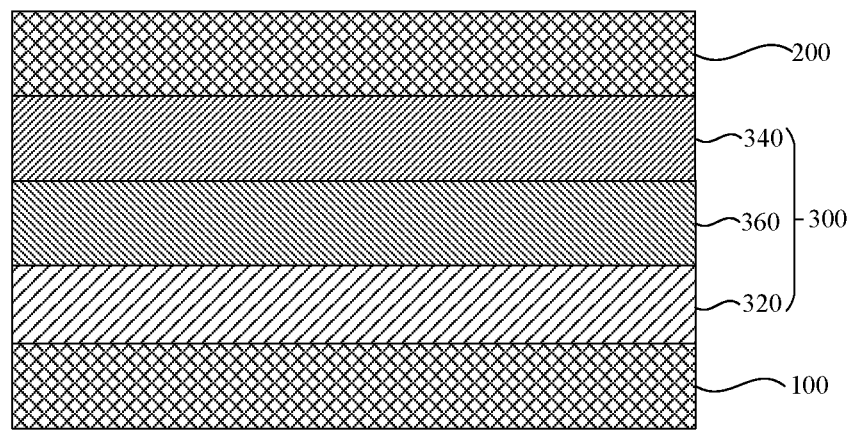
FIG. 3 is a schematic structural diagram of a photoelectric conversion device according to an embodiment of the present application.

According to another embodiment, the electronic component is a photoelectric conversion device. As shown in FIG. 3, the photoelectric conversion device may include an anode 100 and a cathode 200 disposed opposite each other, and a functional layer 300 disposed between the anode 100 and the cathode 200. The functional layer 300 comprises the organic compound provided in the present application.

According to a specific embodiment, as shown in FIG. 3, the photoelectric conversion device may include an anode 100, a hole transport layer 320, a photoelectric conversion layer 360, an electron transport layer 340, and a cathode 200 that are stacked in sequence.

Optionally, the photoelectric conversion device may be a solar cell, especially an organic thin-film solar cell. For example, in an embodiment of the present application, the solar cell may include an anode, a hole transport layer, a photoelectric conversion layer, an electron transport layer, and a cathode that are stacked in sequence, wherein the hole transport layer 320 comprises the organic compound of the present application.

In a third aspect, the present application provides an electronic apparatus comprising the electronic component provided in the second aspect of the present application.

Figure 2:
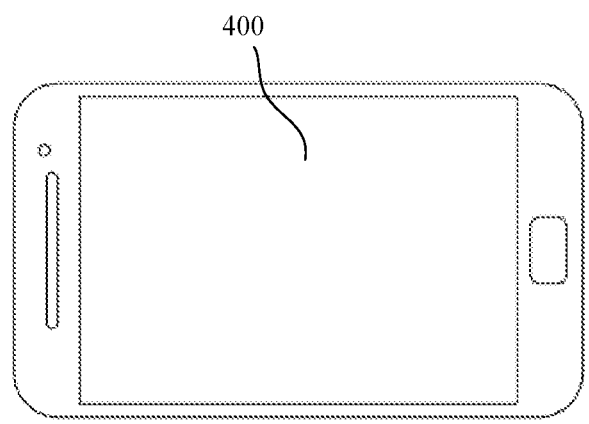
FIG. 2 is a schematic structural diagram of a first electronic apparatus according to an embodiment of the present application.

According to an embodiment, as shown in FIG. 2, the electronic apparatus is a first electronic apparatus 400. The first electronic apparatus 400 includes the above described organic electroluminescent device. The first electronic apparatus 400 may be, for example, a display device, a lighting device, an optical communication device, or other types of electronic apparatuses, which, for example, may include, but are not limited to, computer screens, mobile phone screens, televisions, electronic paper, emergency lamps, optical modules, and the like.

Figure 4:
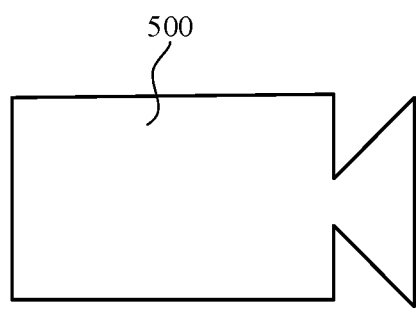
FIG. 4 is a schematic structural diagram of a second electronic apparatus according to an embodiment of the present application.

According to another embodiment, as shown in FIG. 4, the electronic apparatus is a second electronic apparatus 500. The second electronic apparatus 500 includes the photoelectric conversion device described above. The second electronic apparatus 500 may be, for example, a solar power generation apparatus, a light detector, a fingerprint recognition apparatus, an optical module, a CCD camera, or other types of electronic apparatuses.

A synthesis method of the organic compound of the present application is described in detail below in conjunction with Synthesis Examples, but the present application is not limited thereto in any way.

Synthesis Examples

Those skilled in the art should appreciate that chemical reactions described in the present application may be used properly to prepare many organic compounds of the present application, and other methods that can be used to prepare the compounds of the present application are all considered to be within the scope of the present application. For example, the synthesis of those non-exemplary compounds of the present application may be successfully accomplished by those skilled in the art by modifying the method, for example, by properly protecting an interfering group, by utilizing other known reagents other than those described in the present application, or by making some conventional modifications to reaction conditions. Compounds for which a synthesis method is not mentioned in the present application are commercially available raw material products.

1. Synthesis of IM X-1

Synthesis of IM X-1 was illustrated by taking the synthesis of IM a-1 as an example.

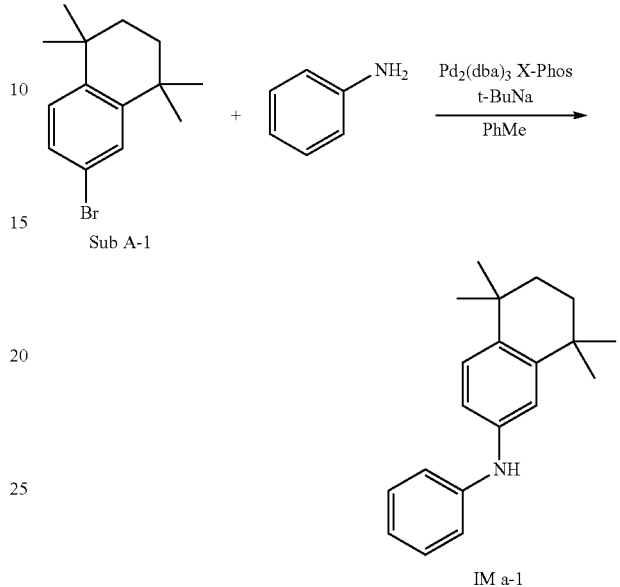

Raw material Sub A-1 (50 g, 187 mmol), aniline (19.17 g, 206 mmol), tris(dibenzylideneacetonyl)dipalladium (1.71 g, 1.87 mmol), 2-dicyclohexylphosphino-2',4',6'-triisopropylbiphenyl (1.77 g, 3.74 mmol), and sodium tert-butoxide (26.97 g, 281 mmol) were added to toluene (400 mL), heated to 108° C. under nitrogen protection, stirred for 4 hours, and then cooled to room temperature. The reaction solution was washed with deionized water to pH=7, dried by adding anhydrous magnesium sulfate, and filtered. The resulting filtrate was passed through a short silica gel column, followed by removing the solvent under reduced pressure. The resulting crude product was purified by recrystallization using a mixture of dichloromethane/n-heptane to obtain IM a-1 as a solid (44 g, yield 84%).

IM X-1 was synthesized with reference to the synthesis method of IM a-1, except that Sub A-1 was replaced with the raw material I, and that aniline was replaced with the raw material II. The raw materials I and raw materials II used, the correspondingly synthesized IM X-1, as well as the yields of the reactions are shown in Table 1.

TABLE 1

| 2. Synthesis of IM X-2 | | | |
|---|---|---|---|
| Raw material I | Raw material II | IM X-1 | Yield/% |
| ![structure with Br] | ![NH2 biphenyl] | ![IM b-1] | 81 |

TABLE 1-continued

2. Synthesis of IM X-2

| Raw material I | Raw material II | IM X-1 | Yield/% |
|---|---|---|---|
| (6-bromo-1,1,4,4-tetramethyltetralin) | 1-naphthylamine | IM c-1 | 77 |
| (6-bromo-1,1,4,4-tetramethyltetralin) | 2-naphthylamine | IM d-1 | 82 |
| (6-bromo-1,1,4,4-tetramethyltetralin) | 3-aminobiphenyl | IM e-1 | 80 |
| (6-bromo-1,1,4,4-tetramethyltetralin) | 4-methylaniline | IM m-1 | 75 |
| (6-bromo-1,1,4,4-tetramethyltetralin) | 3-aminodibenzofuran | IM n-1 | 70 |
| (5-bromo-1,1,4,4-tetramethyltetralin) | aniline | IM f-1 | 72 |
| (5-bromo-1,1,4,4-tetramethyltetralin) | 4-aminobiphenyl | IM g-1 | 74 |
| (5-bromo-1,1,4,4-tetramethyltetralin) | 1-naphthylamine | IM h-1 | 76 |

TABLE 1-continued

2. Synthesis of IM X-2

| Raw material I | Raw material II | IM X-1 | Yield/% |
|---|---|---|---|
| 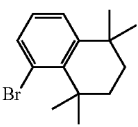 | 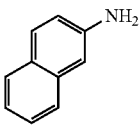 [SMILES: Nc1ccc2ccccc2c1] | 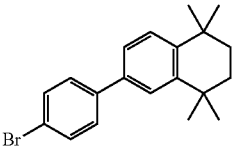 [SMILES: CC1(C)CCC(C)(C)c2cc(-c3ccc(Br)cc3)ccc21]<br>IM i-1 | 77 |
| 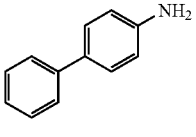 [SMILES: Nc1ccc(-c2ccccc2)cc1] | 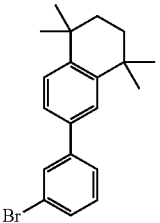 [SMILES: CC1(C)CCC(C)(C)c2cc(-c3cccc(Br)c3)ccc21] | 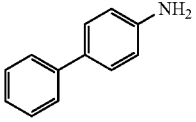 [SMILES: Nc1ccc(-c2ccccc2)cc1]<br>IM j-1 | 85 |
| 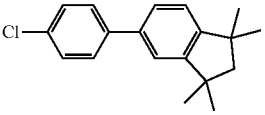 [SMILES: CC1(C)CC(C)(C)c2cc(-c3ccc(Cl)cc3)ccc21] | 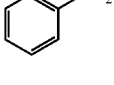 | 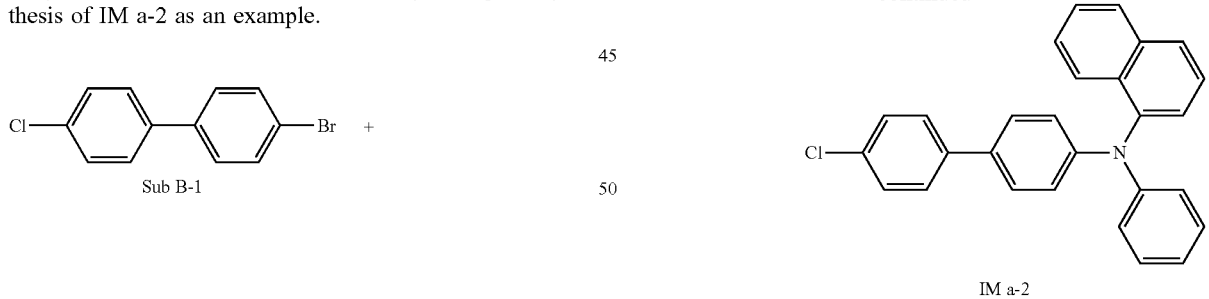<br>IM k-1 | 79 |
| 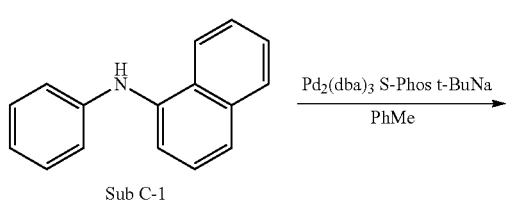 |  | <br>IM l-1 | 82 |

Synthesis of IM X-2 was illustrated by taking the synthesis of IM a-2 as an example.

Sub B-1

Sub C-1

-continued

IM a-2

Raw material Sub B-1 (20 g, 74.75 mmol), raw material Sub C-1 (15.57 g, 71.01 mmol), tris(dibenzylideneacetonyl)dipalladium (0.68 g, 0.75 mmol), 2-dicyclohexylphosphino-2',6'-dimethoxybiphenyl (0.61 g, 1.49 mmol), and sodium tert-butoxide (10.77 g, 112.13 mmol) were added to toluene (160 mL), heated to 108° C. under nitrogen protection, stirred for 2 hours, and then cooled to room temperature. The reaction solution was washed with water to pH=7, dried by adding magnesium sulfate, and then filtered. The resulting filtrate was subjected to removal of the solvent under reduced pressure. The resulting product was purified by recrystallization using a mixture of dichloromethane/n-heptane to obtain IM a-2 as a solid (19 g, yield 66%).

IM X-2 was synthesized with reference to the synthesis method of IM a-2, except that Sub B-1 was replaced with the raw material III, and that Sub C-1 was replaced with the raw material IV. The main raw materials used, the correspondingly synthesized IM X-2, and the yields are shown in Table 2.

TABLE 2

| Raw material III | Raw material IV | IM X-2 | Yield/% |
|---|---|---|---|
| (structure) | (structure) | IM b-2 | 70 |
| (structure) | (structure) | IM c-2 | 66 |
| (structure) | (structure) | IM d-2 | 69 |
| (structure) | (structure) | IM e-2 | 70 |
| (structure) | (structure) | IM f-2 | 50 |

TABLE 2-continued

| Raw material III | Raw material IV | IM X-2 | Yield/% |
|---|---|---|---|
| 4'-chloro-4-bromobiphenyl | N-([1,1'-biphenyl]-4-yl)-[1,1'-biphenyl]-4-amine | IM g-2 | 54 |
| 4'-chloro-4-bromobiphenyl | N-(naphthalen-1-yl)naphthalen-2-amine | IM h-2 | 62 |
| 4'-chloro-4-bromobiphenyl | 4-methyl-N-(p-tolyl)aniline | IM m-2 | 59 |
| 4'-chloro-4-bromobiphenyl | 4-tert-butyl-N-phenylaniline | IM n-2 | 64 |
| 4'-chloro-4-bromobiphenyl | N-([1,1'-biphenyl]-4-yl)phenyl-d5-amine | IM o-2 | 67 |

TABLE 2-continued

| Raw material III | Raw material IV | IM X-2 | Yield/% |
| --- | --- | --- | --- |
| (structure) | (structure) | IM p-2 | 59 |
| (structure) | (structure) | IM r-2 | 56 |
| (structure) | (structure) | IM i-2 | 63 |
| (structure) | (structure) | IM j-2 | 65 |
| (structure) | (structure) | IM l-2 | 58 |

TABLE 2-continued
| Raw material III | Raw material IV | IM X-2 | Yield/% |
|---|---|---|---|
|  | 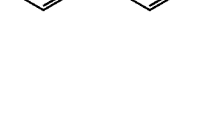 | 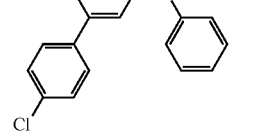<br>IM k-2 | 67 |
|  |  | 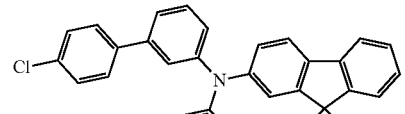<br>IM q-2 | 53 |
| 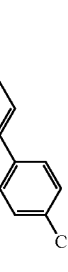 | 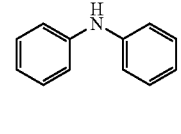 [SMILES: c1ccc(Nc2ccccc2)cc1] | 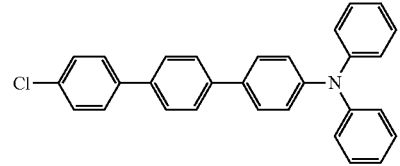<br>IM s-2 | 60 |
| 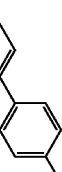 |  | 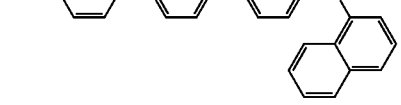<br>IM t-2 | 65 |

Synthesis of Compounds

Synthesis Example 1: Synthesis of Compound A-5

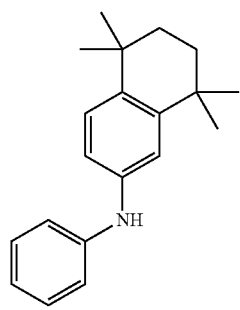

IM a-1

+

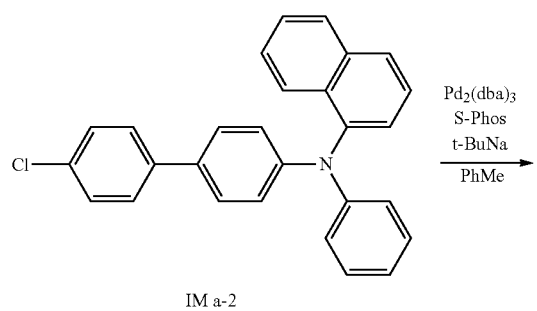

IM a-2

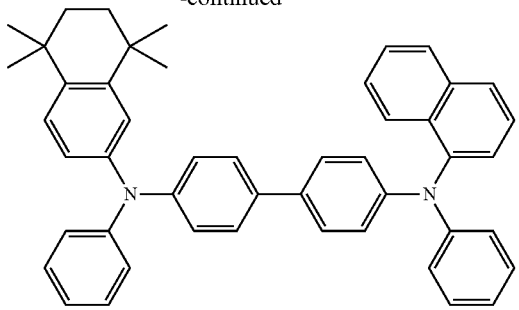

A-5

IM a-1 (13 g, 46.5 mmol), IM a-2 (18.89 g, 46.5 mmol), tris(dibenzylideneacetonyl) dipalladium (0.43 g, 0.46 mmol), 2-dicyclohexylphosphino-2',6'-dimethoxybiphenyl (0.38 g, 0.93 mmol), and sodium tert-butoxide (6.7 g, 69.78 mmol) were added to toluene (100 mL), heated to 108° C. under nitrogen protection, stirred for 3 hours, and then cooled to room temperature. The reaction solution was filtered, and the resulting filtrate was subjected to removal of the solvent under reduced pressure. The resulting crude product was purified by silica gel column chromatography using dichloromethane/n-heptane (v/v) (1:3) as a mobile phase, and then purified by recrystallization using a mixture of dichloromethane/ethyl acetate to obtain Compound A-5 as a white solid (19.5 g, yield 64.5%); mass spectrometry (m/z)=649.4[M+H]$^+$.

NMR data for Compound A-5:

$^1$H-NMR (400 MHz, CD$_2$Cl$_2$): 8.44 (d, 1H), 8.17 (d, 1H), 7.86-7.78 (m, 6H), 7.62-7.42 (m, 6H), 7.35 (d, 1H), 7.27 (s, 1H), 7.19-6.82 (m, 12H), 2.23-1.93 (m, 4H), 1.85 (d, 12H).

Synthesis Examples 2 to 25

Compounds shown in Table 3 were synthesized with reference to the synthesis method of Compound A-5, except that IM a-1 was replaced with IM X-1, and that IM a-2 was replaced with IM X-2. The intermediates used, the correspondingly synthesized compounds, the yields and mass spectrometry (MS) characterization results are shown in Table 3.

TABLE 3

| Synthesis Example | IM X-1 | IM X-2 |
|---|---|---|
| 2 |  IM a-1 |  IM c-2 |

TABLE 3-continued
| | | | |
|---|---|---|---|
| 3 | 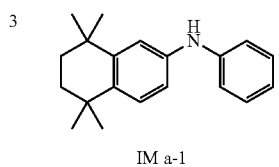<br>IM a-1 | 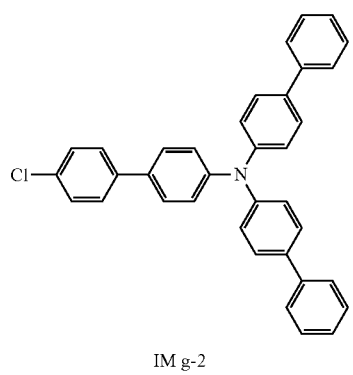 [SMILES: Clc1ccc(-c2ccc(N(c3ccc(-c4ccccc4)cc3)c3ccc(-c4ccccc4)cc3)cc2)cc1]<br>IM g-2 | |
| 4 | 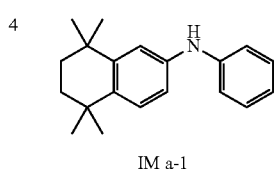<br>IM a-1 | 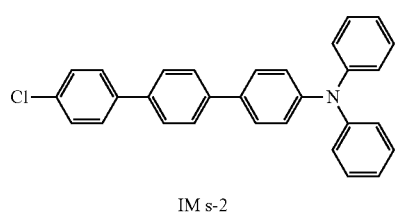 [SMILES: Clc1ccc(-c2ccc(-c3ccc(N(c4ccccc4)c4ccccc4)cc3)cc2)cc1]<br>IM s-2 | |
| 5 | 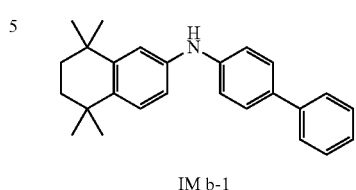<br>IM b-1 | 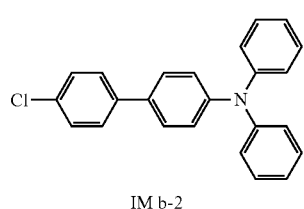 [SMILES: Clc1ccc(-c2ccc(N(c3ccccc3)c3ccccc3)cc2)cc1]<br>IM b-2 | |
| 6 | 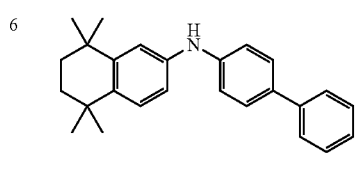<br>IM b-1 | 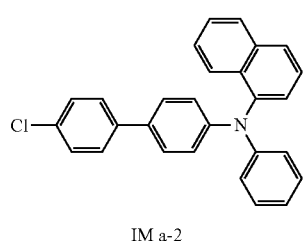 [SMILES: Clc1ccc(-c2ccc(N(c3ccccc3)c3cccc4ccccc34)cc2)cc1]<br>IM a-2 | |
| 7 | 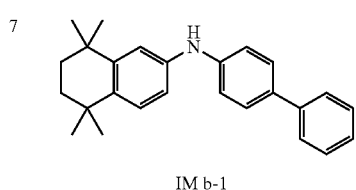<br>IM b-1 | 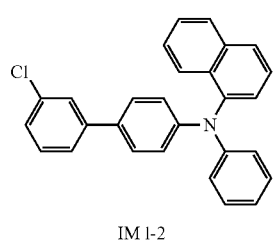 [SMILES: Clc1cccc(-c2ccc(N(c3ccccc3)c3cccc4ccccc34)cc2)c1]<br>IM l-2 | |
| 8 | 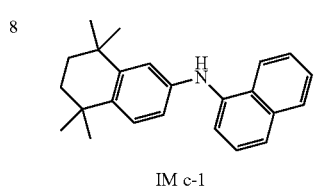<br>IM c-1 | 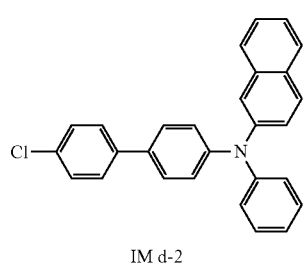 [SMILES: Clc1ccc(-c2ccc(N(c3ccccc3)c3ccc4ccccc4c3)cc2)cc1]<br>IM d-2 | |

TABLE 3-continued
| | | | |
|---|---|---|---|
| 9 | 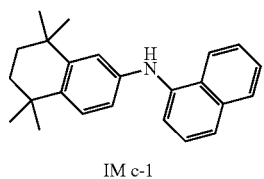 [SMILES: CC1(C)CCC(C)(C)c2cc(Nc3cccc4ccccc34)ccc21]<br>IM c-1 | | 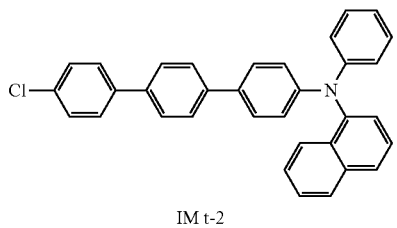 [SMILES: Clc1ccc(-c2ccc(-c3ccc(N(c4ccccc4)c4cccc5ccccc45)cc3)cc2)cc1]<br>IM t-2 |
| 10 | 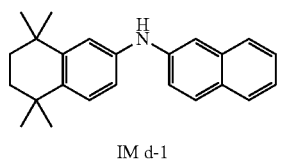 [SMILES: CC1(C)CCC(C)(C)c2cc(Nc3ccc4ccccc4c3)ccc21]<br>IM d-1 | | 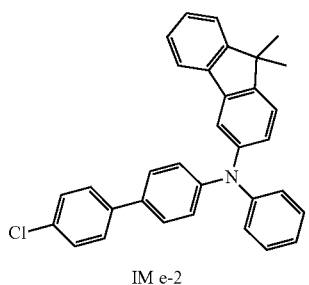 [SMILES: CC1(C)c2ccccc2-c2cc(N(c3ccccc3)c3ccc(-c4ccc(Cl)cc4)cc3)ccc21]<br>IM e-2 |
| 11 | 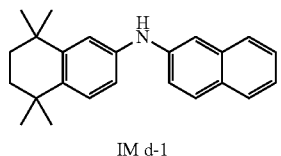 [SMILES: CC1(C)CCC(C)(C)c2cc(Nc3ccc4ccccc4c3)ccc21]<br>IM d-1 | | 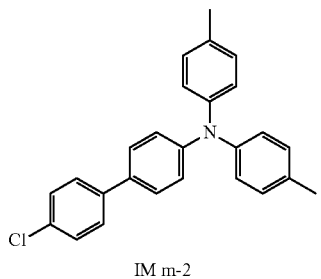 [SMILES: Cc1ccc(N(c2ccc(C)cc2)c2ccc(-c3ccc(Cl)cc3)cc2)cc1]<br>IM m-2 |
| 12 | 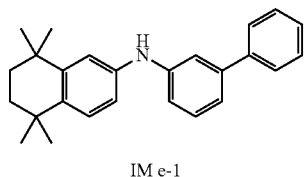 [SMILES: CC1(C)CCC(C)(C)c2cc(Nc3cccc(-c4ccccc4)c3)ccc21]<br>IM e-1 | | 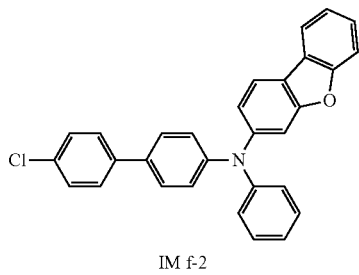 [SMILES: Clc1ccc(-c2ccc(N(c3ccccc3)c3ccc4c(c3)oc3ccccc34)cc2)cc1]<br>IM f-2 |
| 13 | 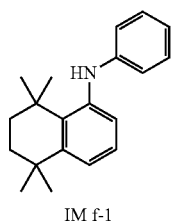 [SMILES: CC1(C)CCC(C)(C)c2c(Nc3ccccc3)cccc21]<br>IM f-1 | | 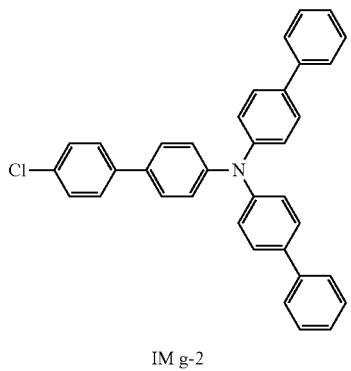 [SMILES: Clc1ccc(-c2ccc(N(c3ccc(-c4ccccc4)cc3)c3ccc(-c4ccccc4)cc3)cc2)cc1]<br>IM g-2 |

TABLE 3-continued
| | | |
|---|---|---|
| 14 | 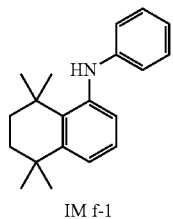 [SMILES: CC1(C)CCC(C)(C)c2c(Nc3ccccc3)cccc21]<br>IM f-1 | 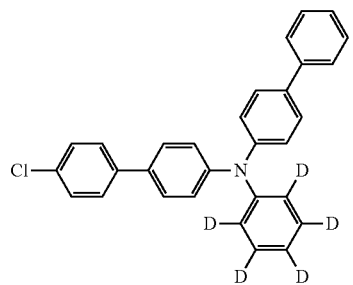<br>IM o-2 |
| 15 | 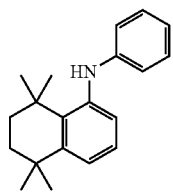<br>IM f-1 | 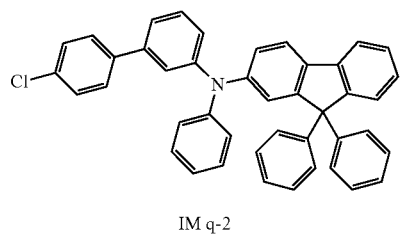 [SMILES: Clc1ccc(-c2cccc(N(c3ccccc3)c3ccc4c(c3)C(c3ccccc3)(c3ccccc3)c3ccccc3-4)c2)cc1]<br>IM q-2 |
| 16 | 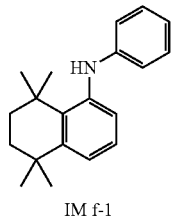 [SMILES: CC1(C)CCC(C)(C)c2c(Nc3ccccc3)cccc21]<br>IM f-1 | 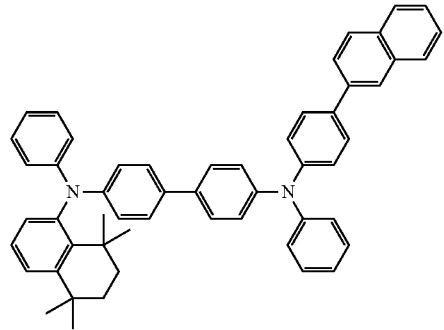<br>C-28 |
| 17 | 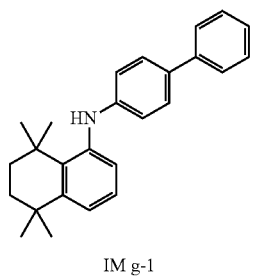 [SMILES: CC1(C)CCC(C)(C)c2c(Nc3ccc(-c4ccccc4)cc3)cccc21]<br>IM g-1 | 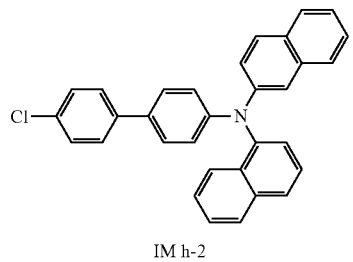 [SMILES: Clc1ccc(-c2ccc(N(c3ccc4ccccc4c3)c3cccc4ccccc34)cc2)cc1]<br>IM h-2 |
| 18 | 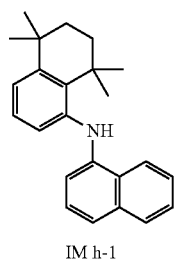 [SMILES: CC1(C)CCC(C)(C)c2c(Nc3cccc4ccccc34)cccc21]<br>IM h-1 | 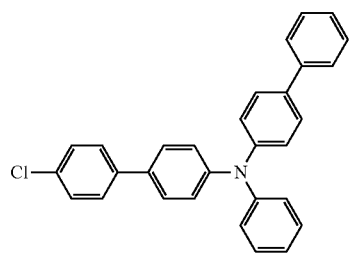<br>IM c-2 |

TABLE 3-continued
| | | | |
|---|---|---|---|
| 19 | 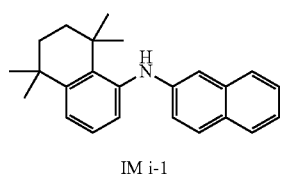 [SMILES: CC1(C)CCC(C)(C)c2c(Nc3ccc4ccccc4c3)cccc21]<br>IM i-1 | 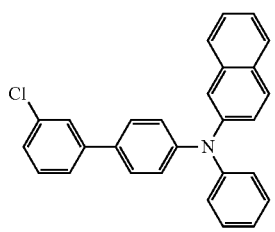<br>IM j-2 | |
| 20 | 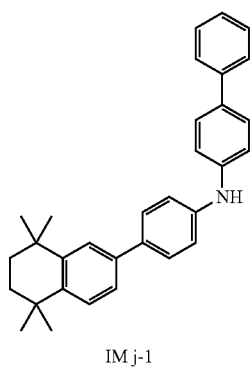 [SMILES: CC1(C)CCC(C)(C)c2cc(-c3ccc(Nc4ccc(-c5ccccc5)cc4)cc3)ccc21]<br>IM j-1 | 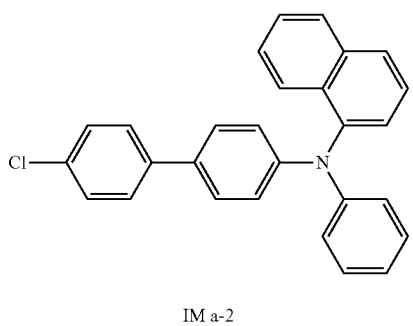 [SMILES: Clc1ccc(-c2ccc(N(c3ccccc3)c3cccc4ccccc34)cc2)cc1]<br>IM a-2 | |
| 21 | 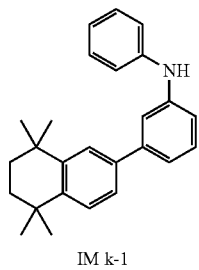 [SMILES: CC1(C)CCC(C)(C)c2cc(-c3cccc(Nc4ccccc4)c3)ccc21]<br>IM k-1 | 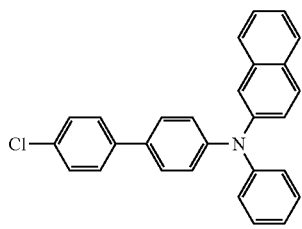<br>IM d-2 | |
| 22 | 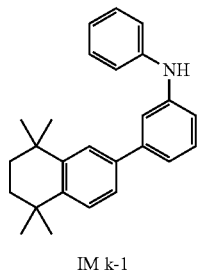 [SMILES: CC1(C)CCC(C)(C)c2cc(-c3cccc(Nc4ccccc4)c3)ccc21]<br>IM k-1 | 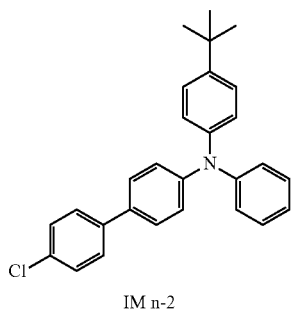 [SMILES: CC(C)(C)c1ccc(N(c2ccccc2)c2ccc(-c3ccc(Cl)cc3)cc2)cc1]<br>IM n-2 | |
| 23 | 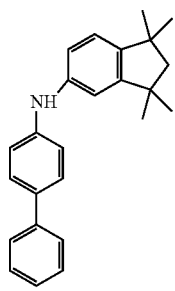<br>IM l-1 | 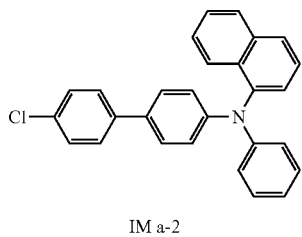 [SMILES: Clc1ccc(-c2ccc(N(c3ccccc3)c3cccc4ccccc34)cc2)cc1]<br>IM a-2 | |

TABLE 3-continued
| | | | | |
|---|---|---|---|---|
| 24 | 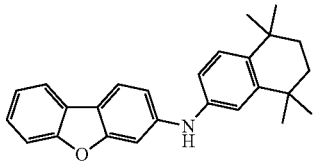\nIM n-1 | | 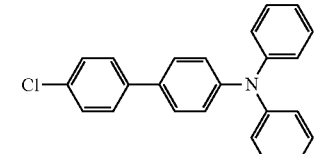\nIM b-2 | |
| 25 | 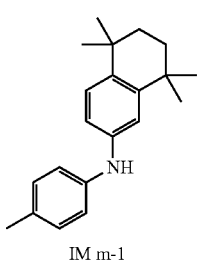\nIM m-1 | | 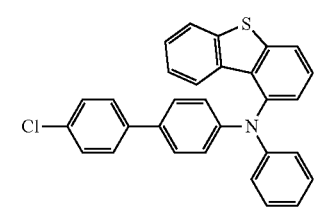\nIM p-2 | |
| Synthesis Example | Compound | Yield/% | MS (m/z)/ [M + H]+ |
|---|---|---|---|
| 2 | 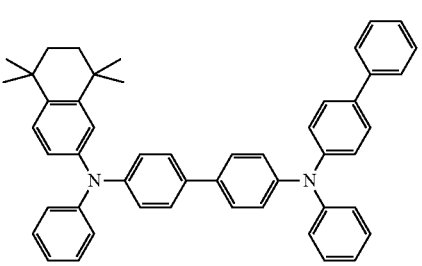\nA-3 | 68 | 675.4 |
| 3 | 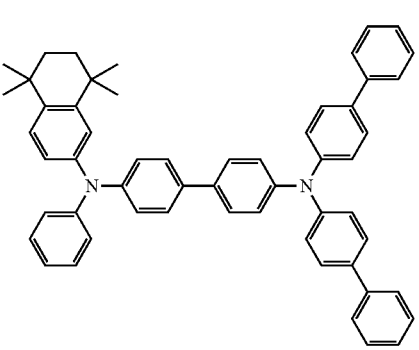\nA-44 | 61 | 751.4 |
| 4 | 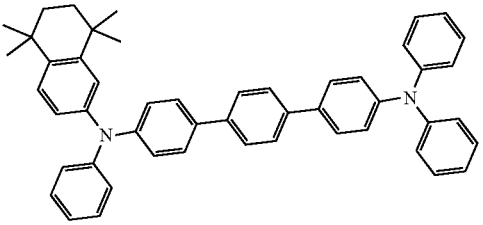\nF-18 | 67 | 675.4 |

TABLE 3-continued

| | | | | |
|---|---|---|---|---|
| 5 | A-2 | | 64 | 675.4 |
| 6 | A-8 | | 70 | 725.4 |
| 7 | B-41 | | 51 | 725.4 |
| 8 | A-12 | | 67 | 699.4 |
| 9 | F-21 | | 70 | 775.4 |

TABLE 3-continued
| 10 | 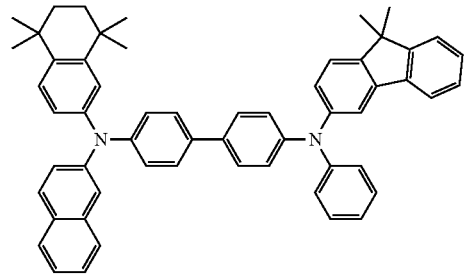
A-62 | 55 | 765.4 |
| 11 | 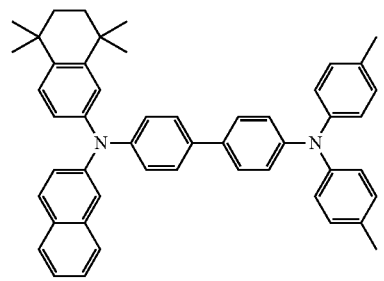
A-91 | 70 | 677.4 |
| 12 | 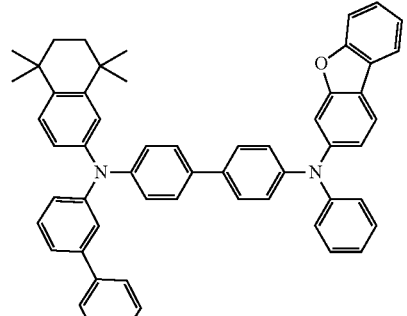
A-18 | 59 | 765.4 |
| 13 | 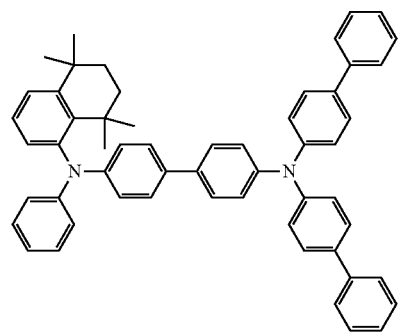
C-3 | 52 | 751.4 |

TABLE 3-continued
| | | | |
|---|---|---|---|
| 14 | 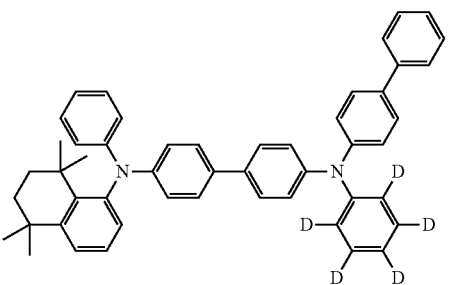 C-41 | 68 | 680.4 |
| 15 | 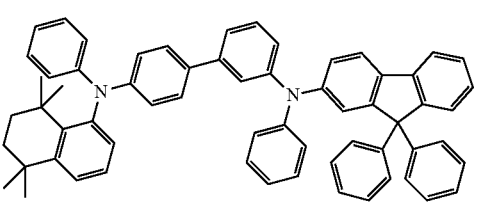 C-36 | 60 | 839.4 |
| 16 | 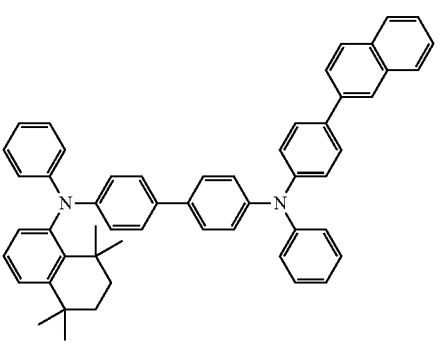 C-28 | 61 | 725.4 |
| 17 | 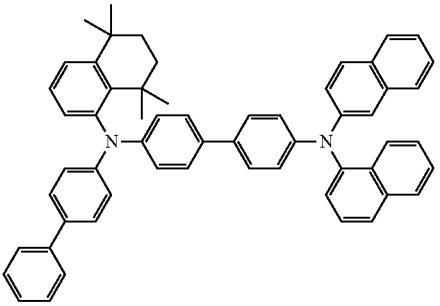 C-21 | 60 | 775.4 |
| 18 | 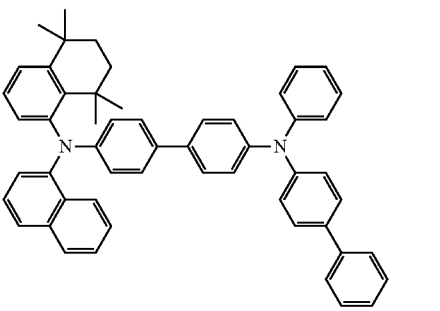 C-6 | 61 | 725.4 |

TABLE 3-continued
| | | | | |
|---|---|---|---|---|
| 19 | 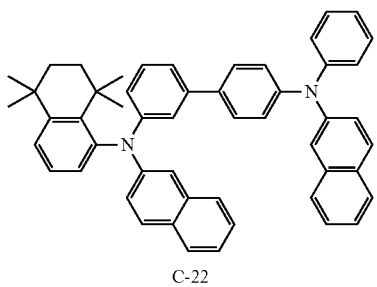<br>C-22 | | 55 | 699.4 |
| 20 | 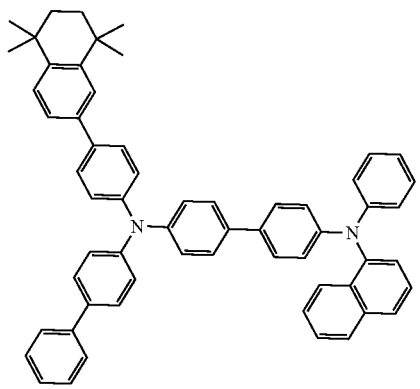<br>D-8 | | 71 | 801.4 |
| 21 | 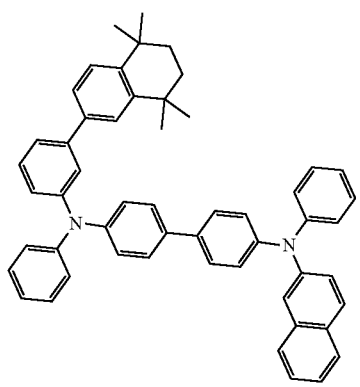<br>E-15 | | 70 | 725.4 |
| 22 | 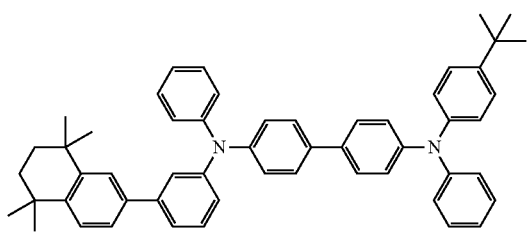<br>D-33 | | 62 | 731.4 |

TABLE 3-continued

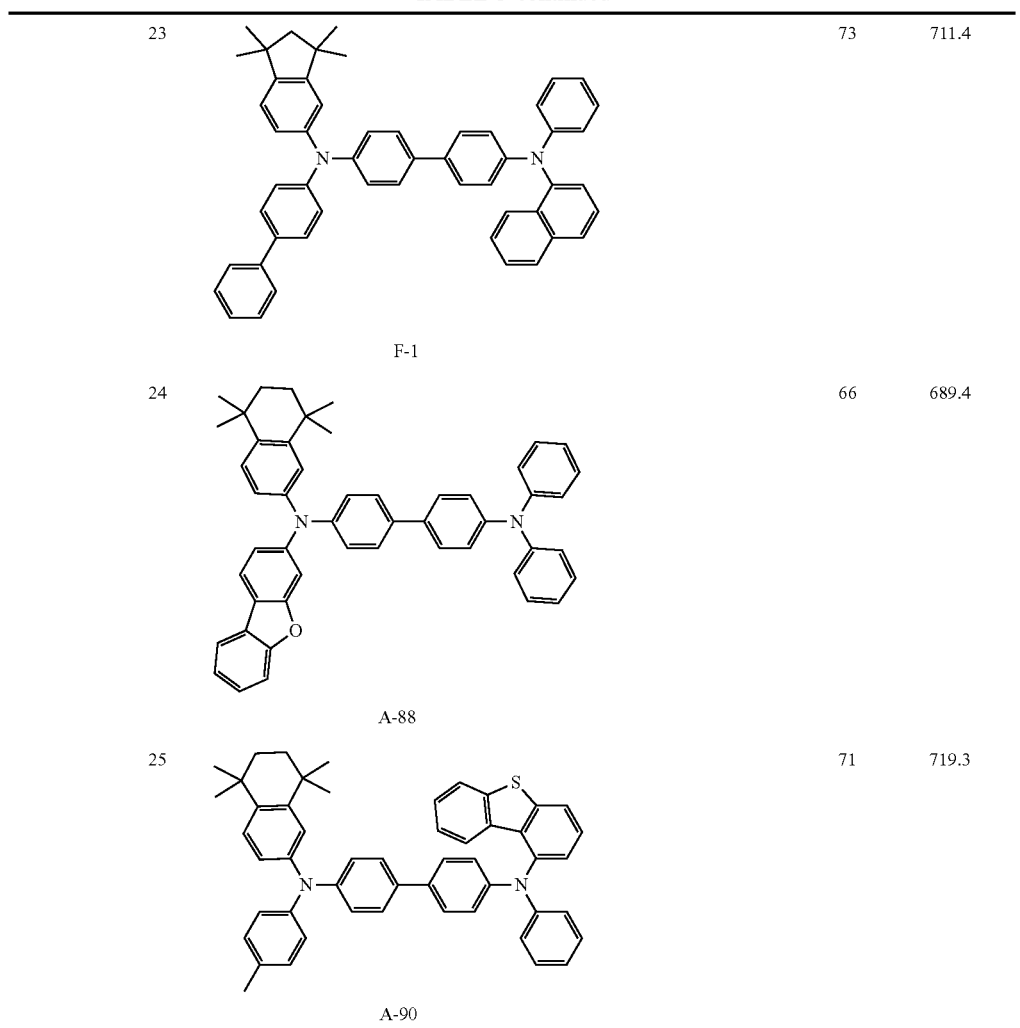

| | | |
|---|---|---|
| 23 F-1 | 73 | 711.4 |
| 24 A-88 | 66 | 689.4 |
| 25 A-90 | 71 | 719.3 |

NMR data for Compound F-21:
$^1$H-NMR (400 MHz, $CD_2Cl_2$): 8.42-8.35 (m, 2H), 8.08 (d, 2H), 7.92-7.53 (m, 18H), 7.44 (d, 1H), 7.38 (d, 1H), 7.31-6.95 (m, 10H), 2.26-2.01 (m, 4H), 1.90 (d, 12H).

Fabrication and Evaluation of Organic Electroluminescent Devices

Example 1: Blue Light-Emitting Organic Electroluminescent Device

An anode was prepared by the following processes. An Ag/ITO/Ag substrate (manufactured by Corning), with thicknesses of Ag/ITO/Ag being 100 Å, 1300 Å, and 100 Å, respectively, was cut to have dimensions of 40 mm×40 mm×0.7 mm, and then fabricated by photoetching processes into an experimental substrate with patterns of an anode, and of an insulation layer, followed by surface treatment using ultraviolet ozone and $O_2:N_2$ plasma to increase the work function of the anode (experimental substrate) and to descum.

F4-TCNQ was deposited by vacuum evaporation on the experimental substrate (anode) to form a hole injection layer (HIL) having a thickness of 100 Å, and Compound A-5 was deposited by evaporation on the hole injection layer to form a first hole transport layer (HTL-1) having a thickness of 1100 Å.

HT-7 was deposited by vacuum evaporation on the first hole transport layer to form a second hole transport layer (HTL-2) having a thickness of 50 Å.

α,β-AND and BD were co-deposited by evaporation on the second hole transport layer at an evaporation rate ratio of 99%:1% to form an organic light emitting layer (EML) having a thickness of 220 Å.

BTB was deposited by vacuum evaporation on the organic light emitting layer to form a hole blocking layer (HBL) having a thickness of 50 Å.

ET-18 and LiQ were co-deposited by evaporation on the hole blocking layer at an evaporation rate ratio of 1:1 to form an electron transport layer (ETL) having a thickness of 300 Å. Yb was deposited by evaporation on the electron transport layer to form an electron injection layer (EIL) having a thickness of 10 Å. Then magnesium (Mg) and silver (Ag) were mixed at an evaporation rate ratio of 1:9 and deposited by vacuum evaporation on the electron injection layer to form a cathode having a thickness of 120 Å.

Furthermore, CP-1 was deposited by evaporation on the above cathode to form an organic capping layer (CPL)

having a thickness of 680 Å, thereby completing the fabrication of an organic electroluminescent device.

Examples 2 to 25

Organic electroluminescent devices were fabricated by the same method as used in Example 1, except that Compound A-5 was replaced with Compounds shown in Table 4 below when a first hole transport layer was formed.

Comparative Examples 1 to 5

Organic electroluminescent devices were fabricated by the same method as used in Example 1, except that Compound A-5 was replaced with Compounds a to e shown in Table 4 below when a first hole transport layer was formed.

Structures of the materials used in the above Examples and Comparative Examples are shown in Table 4 below.

TABLE 4

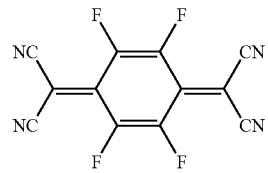 [SMILES: N#CC(C#N)=c1c(F)c(F)c(=C(C#N)C#N)c(F)c1F]

F4-TCNQ

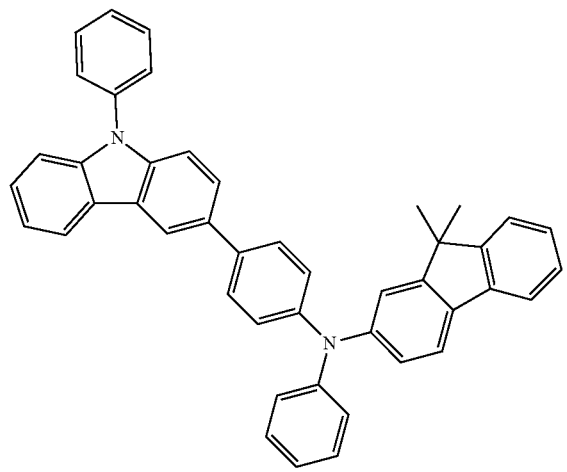 [SMILES: CC1(C)c2ccccc2-c2ccc(N(c3ccccc3)c3ccc(-c4ccc5c(c4)c4ccccc4n5-c4ccccc4)cc3)cc21]

HT-7

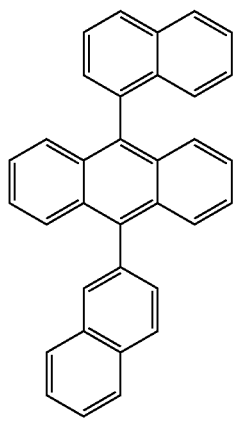 [SMILES: c1ccc2cc(-c3c4ccccc4c(-c4cccc5ccccc45)c4ccccc34)ccc2c1]

α, β -ADN

TABLE 4-continued
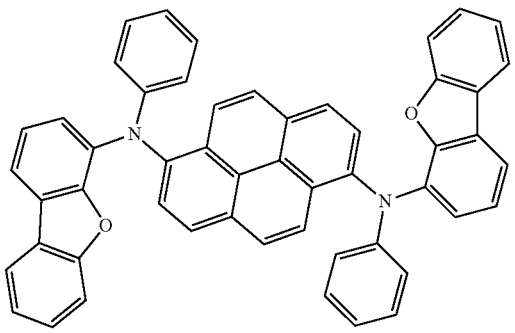 [SMILES: c1ccc(N(c2ccc3ccc4c(N(c5ccccc5)c5cccc6c5oc5ccccc56)ccc5ccc2c3c54)c2cccc3c2oc2ccccc23)cc1]
BD
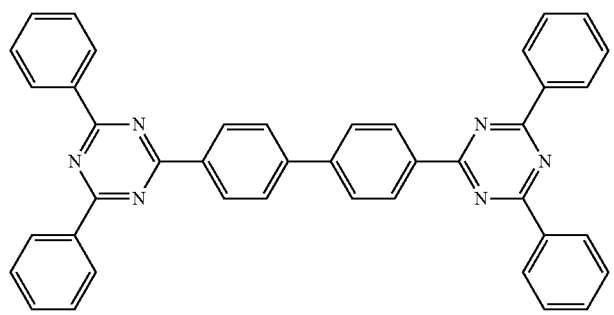 [SMILES: c1ccc(-c2nc(-c3ccccc3)nc(-c3ccc(-c4ccc(-c5nc(-c6ccccc6)nc(-c6ccccc6)n5)cc4)cc3)n2)cc1]
BTB
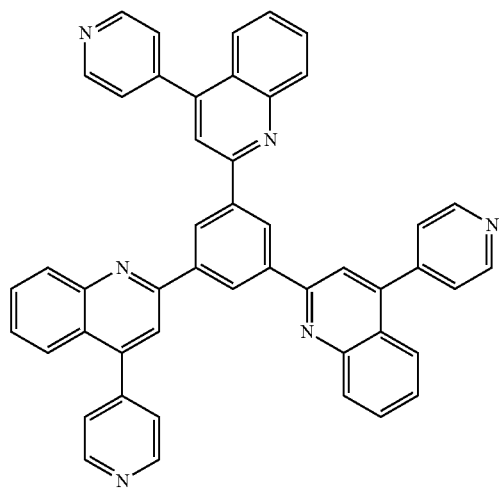 [SMILES: c1ccc2c(-c3ccncc3)cc(-c3cc(-c4cc(-c5ccncc5)c5ccccc5n4)cc(-c4cc(-c5ccncc5)c5ccccc5n4)c3)nc2c1]
ET-18
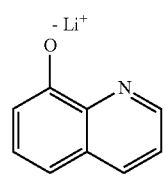
LiQ TABLE 4-continued
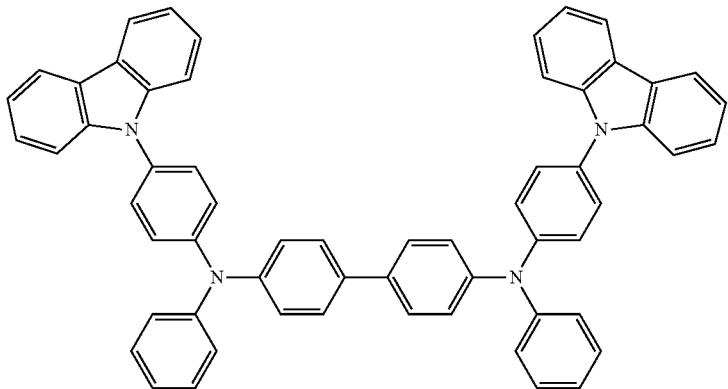 [SMILES: c1ccc(N(c2ccc(-c3ccc(N(c4ccccc4)c4ccc(-n5c6ccccc6c6ccccc65)cc4)cc3)cc2)c2ccc(-n3c4ccccc4c4ccccc43)cc2)cc1]
CP-1
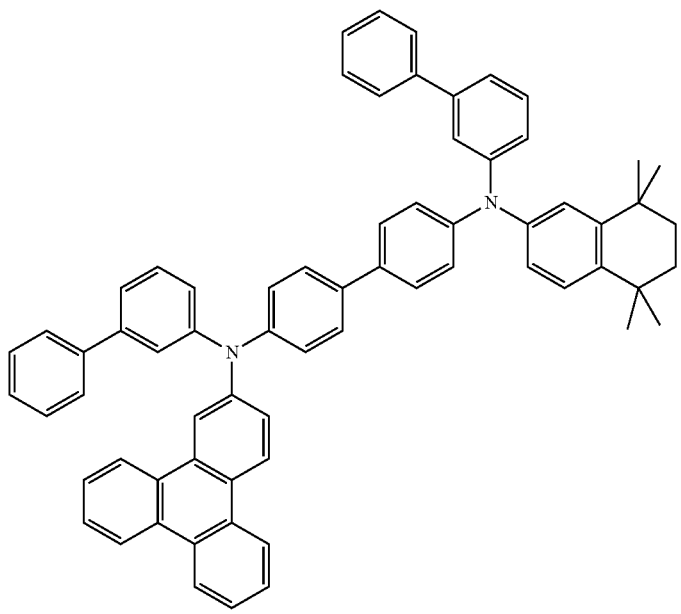 [SMILES: CC1(C)CCC(C)(C)c2cc(N(c3ccc(-c4ccc(N(c5cccc(-c6ccccc6)c5)c5ccc6c7ccccc7c7ccccc7c6c5)cc4)cc3)c3cccc(-c4ccccc4)c3)ccc21]
Compound a
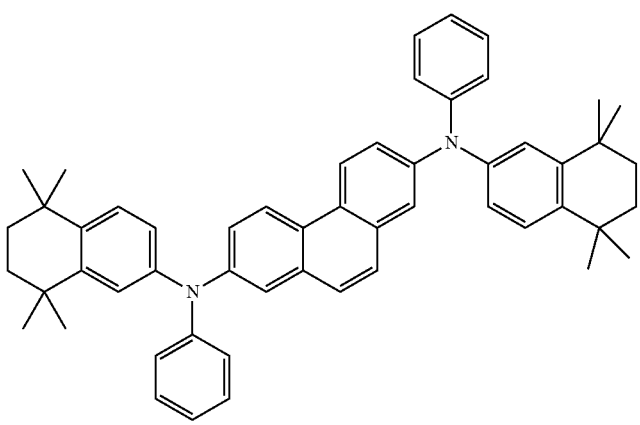 [SMILES: CC1(C)CCC(C)(C)c2cc(N(c3ccccc3)c3ccc4c(ccc5cc(N(c6ccccc6)c6ccc7c(c6)C(C)(C)CCC7(C)C)ccc54)c3)ccc21]
Compound b TABLE 4-continued

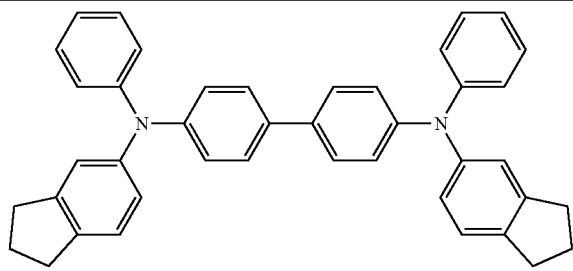

Compound c

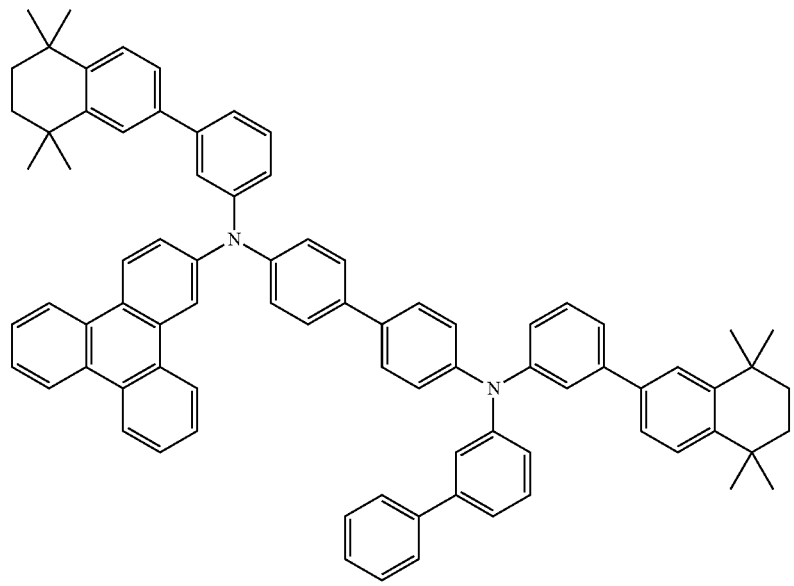 [SMILES: CC1(C)CCC(C)(C)c2cc(-c3cccc(N(c4ccc(-c5ccc(N(c6cccc(-c7ccc8c(c7)C(C)(C)CCC8(C)C)c6)c6ccc7c8ccccc8c8ccccc8c7c6)cc5)cc4)c4cccc(-c5ccccc5)c4)c3)ccc21]

Compound d

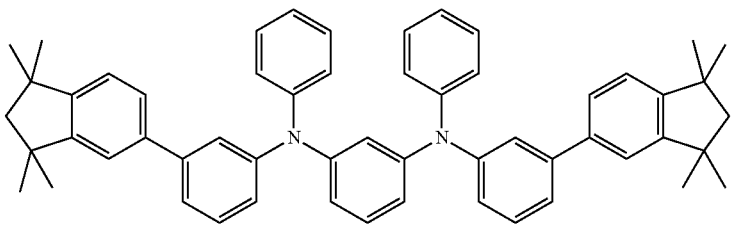 [SMILES: CC1(C)CC(C)(C)c2cc(-c3cccc(N(c4ccccc4)c4cccc(N(c5ccccc5)c5cccc(-c6ccc7c(c6)C(C)(C)CC7(C)C)c5)c4)c3)ccc21]

Compound e

The organic electroluminescent devices fabricated above were tested for their performance under the condition of 20 mA/cm². Results are shown in Table 5 below.

TABLE 5

| Example | HTL-1 | Driving voltage (V) | Current efficiency (Cd/A) | Chromaticity coordinate CIEx, CIEy | External quantum efficiency (EQE %) | Lifetime T95(h) |
|---|---|---|---|---|---|---|
| Example 1 | Compound A-5 | 3.98 | 6.81 | 0.140, 0.050 | 14.01 | 218 |
| Example 2 | Compound A-3 | 3.95 | 6.92 | 0.140, 0.050 | 13.60 | 215 |
| Example 3 | Compound A-44 | 3.94 | 6.68 | 0.140, 0.050 | 13.74 | 207 |
| Example 4 | Compound A-2 | 3.90 | 6.86 | 0.140, 0.050 | 14.11 | 194 |
| Example 5 | Compound A-8 | 3.97 | 6.64 | 0.140, 0.050 | 13.66 | 201 |
| Example 6 | Compound B-41 | 3.87 | 6.61 | 0.140, 0.050 | 14.23 | 196 |
| Example 7 | Compound A-12 | 3.99 | 6.81 | 0.140, 0.050 | 13.64 | 214 |

TABLE 5-continued

| Example | HTL-1 | Driving voltage (V) | Current efficiency (Cd/A) | Chromaticity coordinate CIEx, CIEy | External quantum efficiency (EQE %) | Lifetime T95(h) |
|---|---|---|---|---|---|---|
| Example 8 | Compound A-62 | 3.89 | 6.67 | 0.140, 0.050 | 13.68 | 258 |
| Example 9 | Compound A-18 | 3.92 | 6.82 | 0.140, 0.050 | 14.03 | 249 |
| Example 10 | Compound C-3 | 3.97 | 6.93 | 0.140, 0.050 | 14.26 | 198 |
| Example 11 | Compound C-21 | 3.90 | 6.69 | 0.140, 0.050 | 13.68 | 199 |
| Example 12 | Compound C-6 | 3.97 | 6.83 | 0.140, 0.050 | 14.05 | 203 |
| Example 13 | Compound C-22 | 3.88 | 6.63 | 0.140, 0.050 | 14.01 | 220 |
| Example 14 | Compound D-8 | 3.93 | 6.58 | 0.140, 0.050 | 13.54 | 200 |
| Example 15 | Compound E-15 | 3.89 | 6.75 | 0.140, 0.050 | 13.91 | 211 |
| Example 16 | Compound F-1 | 3.92 | 6.65 | 0.140, 0.050 | 13.68 | 219 |
| Example 17 | Compound A-88 | 3.96 | 6.80 | 0.140, 0.050 | 13.99 | 260 |
| Example 18 | Compound A-91 | 3.96 | 6.82 | 0.140, 0.050 | 14.03 | 217 |
| Example 19 | Compound D-33 | 3.94 | 6.76 | 0.140, 0.050 | 13.82 | 209 |
| Example 20 | Compound C-41 | 3.92 | 6.82 | 0.140, 0.050 | 14.03 | 212 |
| Example 21 | Compound A-90 | 3.92 | 6.70 | 0.140, 0.050 | 13.78 | 251 |
| Example 22 | Compound C-36 | 3.94 | 6.91 | 0.140, 0.050 | 14.21 | 246 |
| Example 23 | Compound C-28 | 3.93 | 6.92 | 0.140, 0.050 | 14.23 | 204 |
| Example 24 | Compound F-18 | 3.92 | 6.77 | 0.140, 0.050 | 13.93 | 205 |
| Example 25 | Compound F-21 | 3.96 | 6.78 | 0.140, 0.050 | 13.95 | 216 |
| Comparative Example 1 | Compound a | 4.18 | 5.69 | 0.140, 0.050 | 11.70 | 168 |
| Comparative Example 2 | Compound b | 4.24 | 5.51 | 0.140, 0.050 | 11.31 | 156 |
| Comparative Example 3 | Compound c | 4.20 | 5.55 | 0.140, 0.050 | 11.54 | 160 |
| Comparative Example 4 | Compound d | 4.11 | 5.52 | 0.140, 0.050 | 11.35 | 163 |
| Comparative Example 5 | Compound e | 4.16 | 5.48 | 0.140, 0.050 | 11.27 | 155 |

As can be seen from Table 5, in the case that the compounds are each used in the blue light organic electroluminescent devices as the first hole transport layer, the devices in Examples 1 to 25, compared with those in Comparative Examples 1 to 5, exhibit improvement in all properties thereof. Specifically, the current efficiency is increased by at least 15.6%; the external quantum efficiency is increased by at least 15.7%; and the T95 lifetime was prolonged by at least 22.8%.

The above describes in detail optional embodiments of the present application. the present application, however, is not limited to those specific details provided in the above embodiments. A variety of simple variations may be made to the technical solutions of the present application within the scope of the technical concept of the present application, and all such simple variations are within the protection scope of the present application.

The invention claimed is:

1. An organic compound having a structure shown in Formula 1:

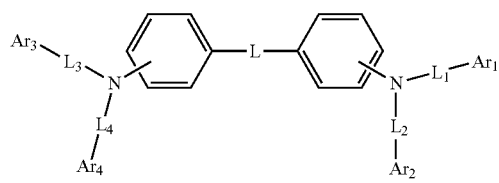

Formula 1 wherein L, $L_1$, $L_2$, $L_3$, and $L_4$ are identical or different, and are each independently selected from a single bond, or an unsubstituted phenylene;

$Ar_1$, $Ar_2$, $Ar_3$, and $Ar_4$ are identical or different, and are each independently selected from a substituted or unsubstituted phenyl, a substituted or unsubstituted naphthyl, a substituted or unsubstituted biphenyl, a substituted or unsubstituted terphenyl, a substituted or unsubstituted fluorenyl, a substituted or unsubstituted dibenzofuranyl, a substituted or unsubstituted dibenzothiophenyl, or a group shown in Formula 2; and at least one of $Ar_1$ and $Ar_3$ is selected from the group shown in Formula 2;

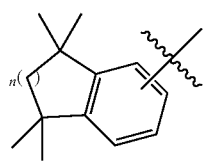

Formula 2 wherein n is 1 or 2;

substituents of $Ar_1$, $Ar_2$, $Ar_3$, and $Ar_4$ are identical or different, and are each independently selected from deuterium, methyl, ethyl, isopropyl, tert-butyl or phenyl.

2. The organic compound according to claim 1, wherein $Ar_1$ and $Ar_3$ are identical or different, and are each independently selected from the group consisting of the following groups:

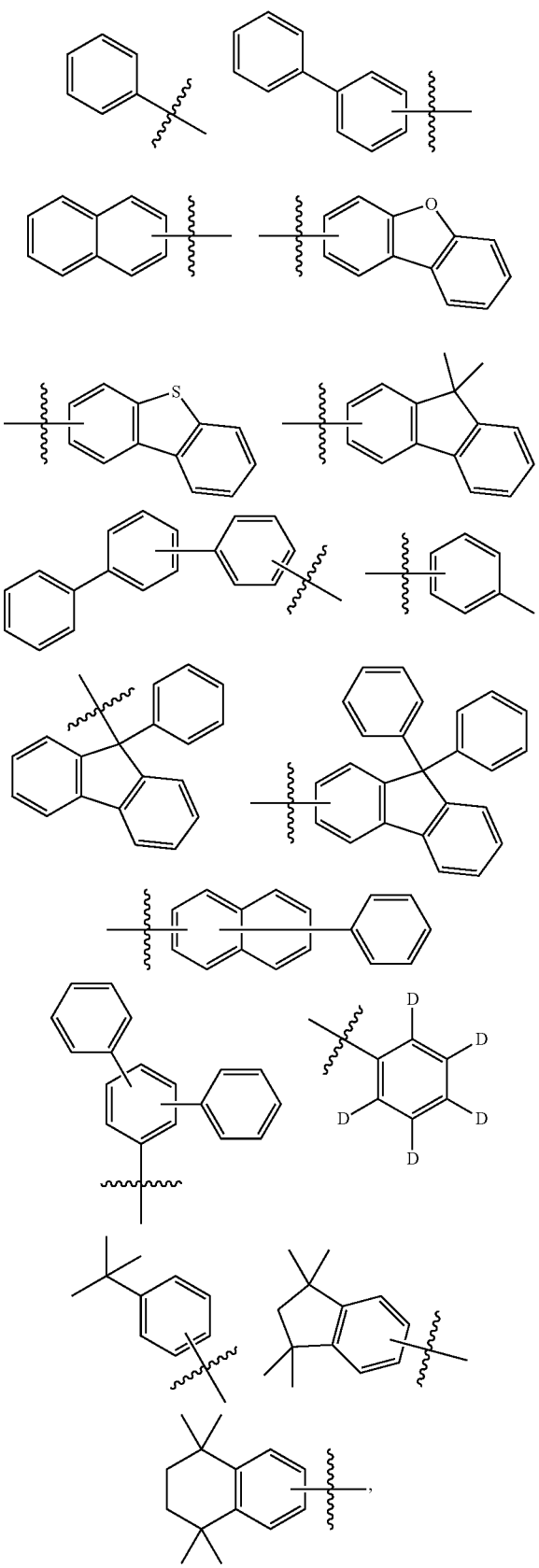
and at least one of Ar₁ and Ar₃ is selected from
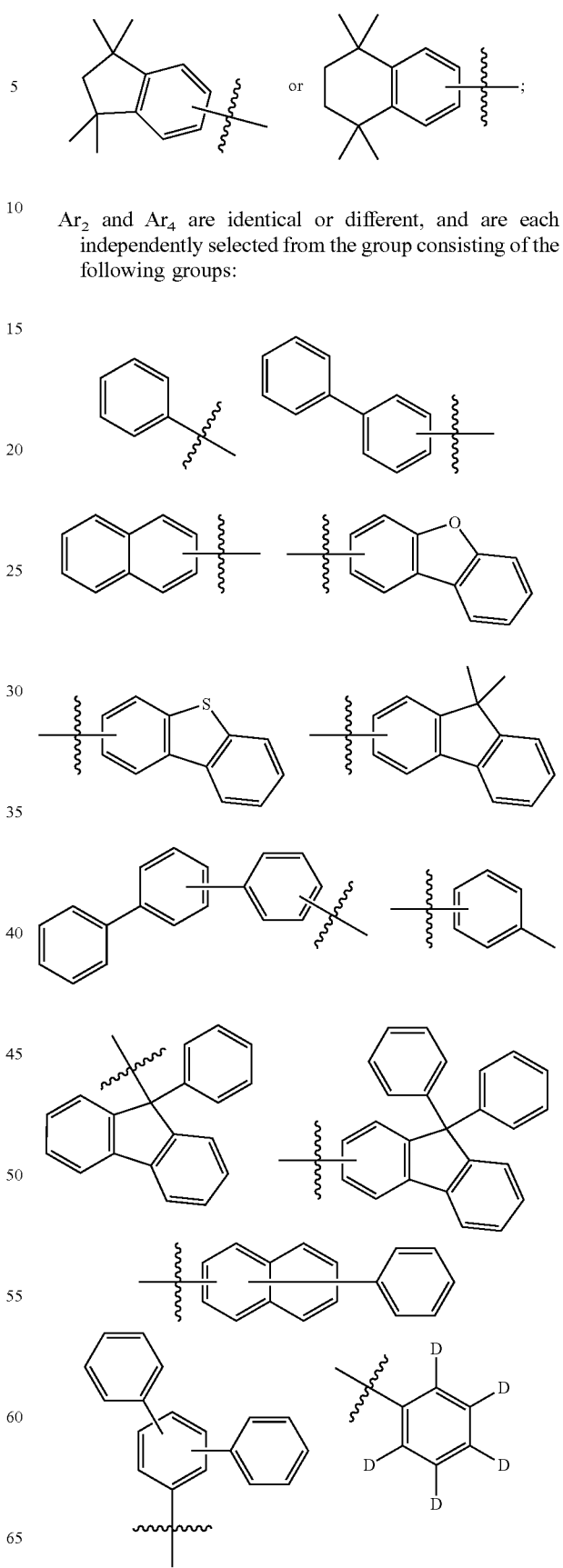
Ar₂ and Ar₄ are identical or different, and are each independently selected from the group consisting of the following groups:

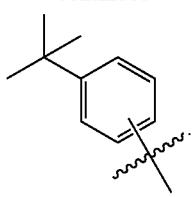
3. The organic compound according to claim 1, wherein the organic compound is selected from the group consisting of the following compounds:
A-1
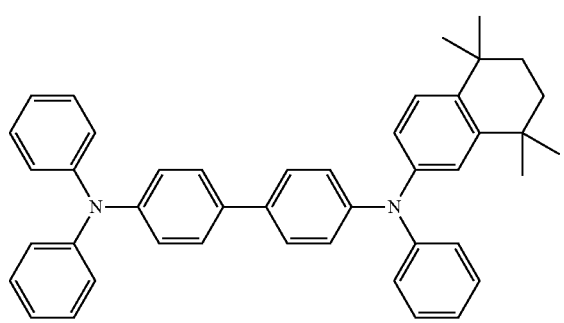
A-2
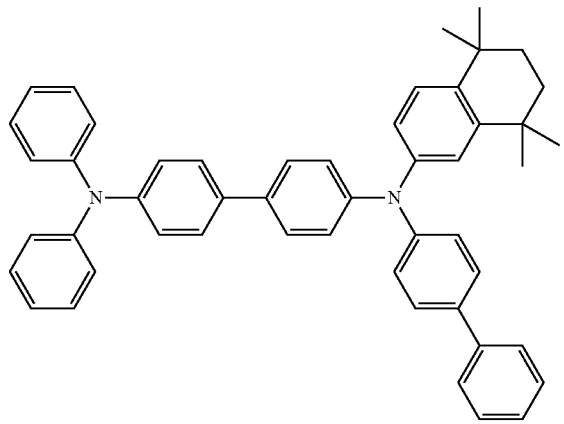
A-3
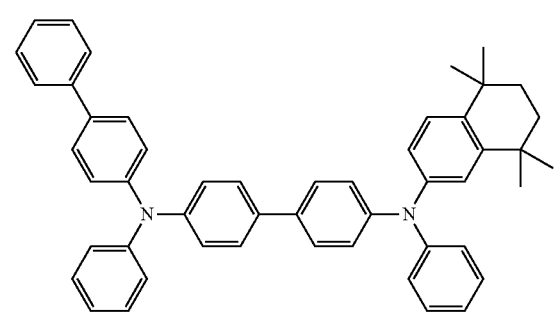
A-4
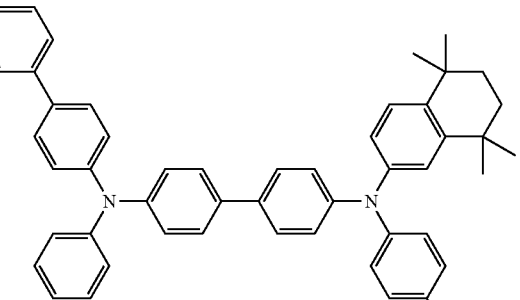
A-5
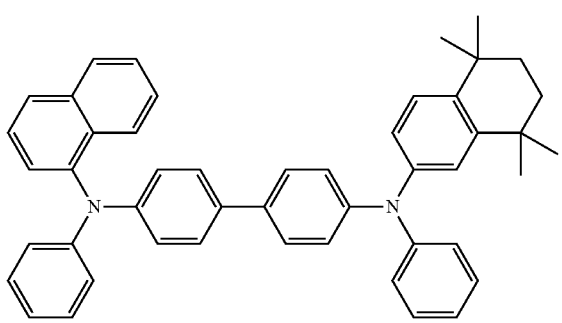
A-6
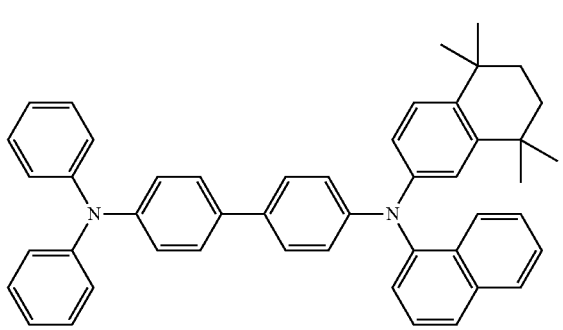
A-7
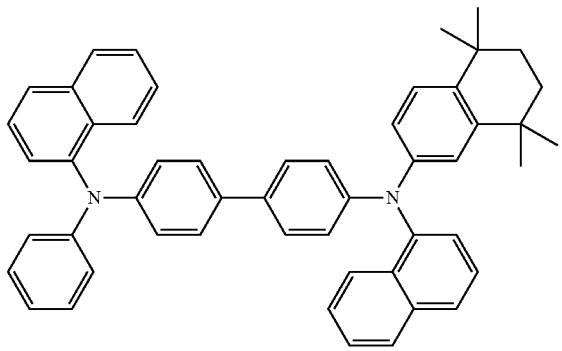

A-8
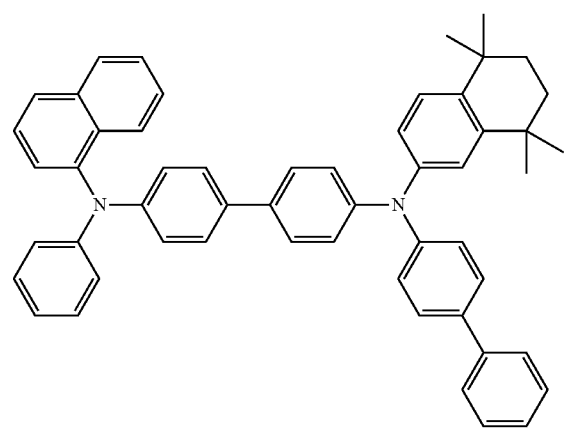
A-9
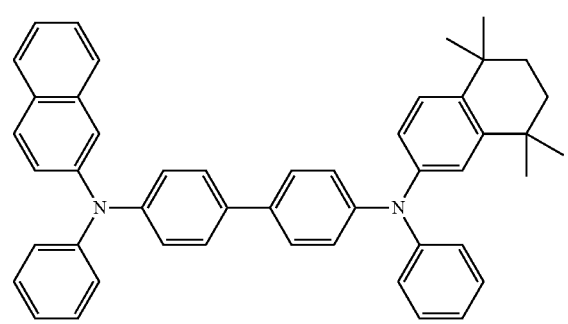
A-10
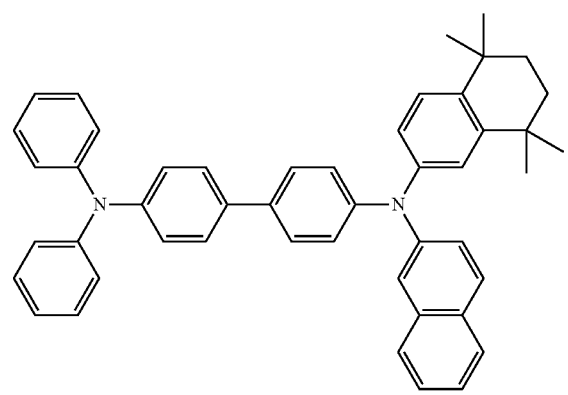
A-11
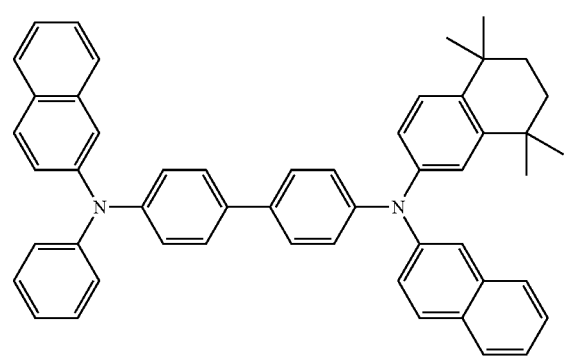
A-12
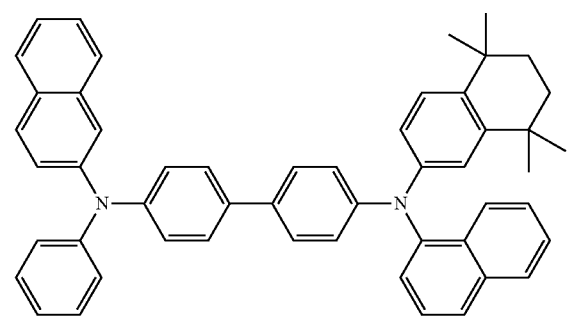
A-13
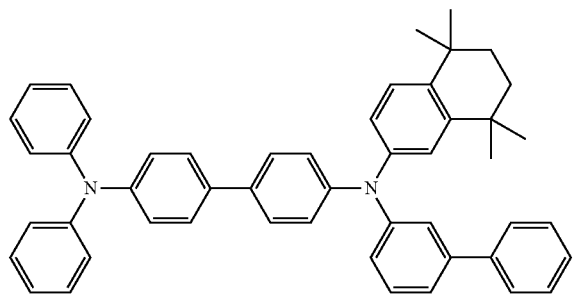
A-14
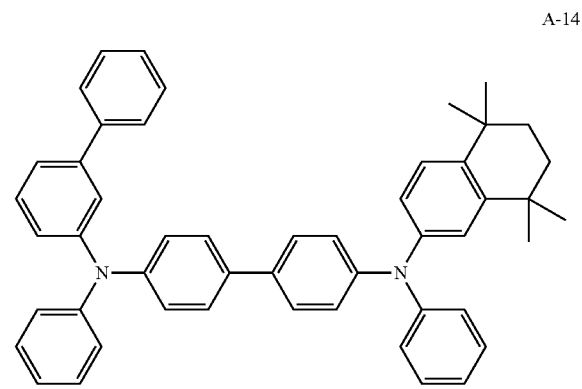
A-15
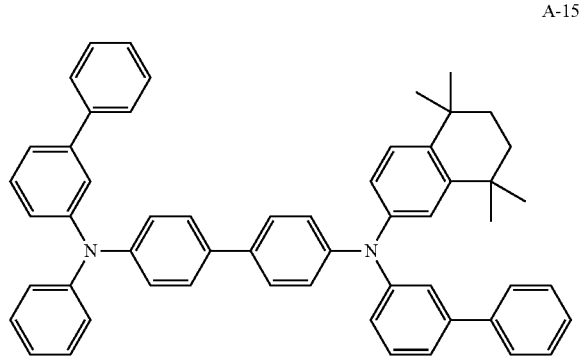

A-16
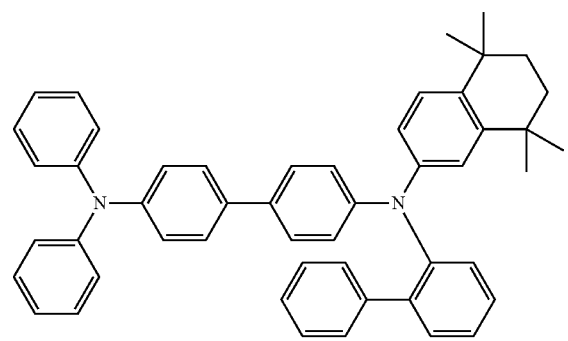
A-17
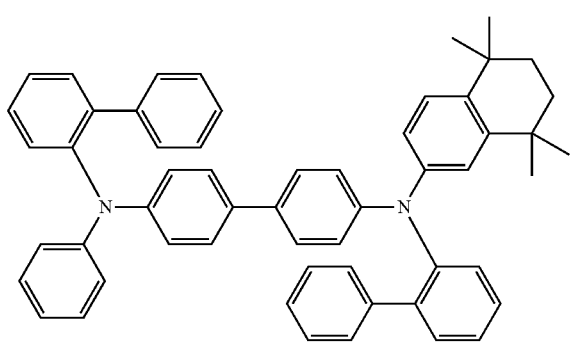
A-18
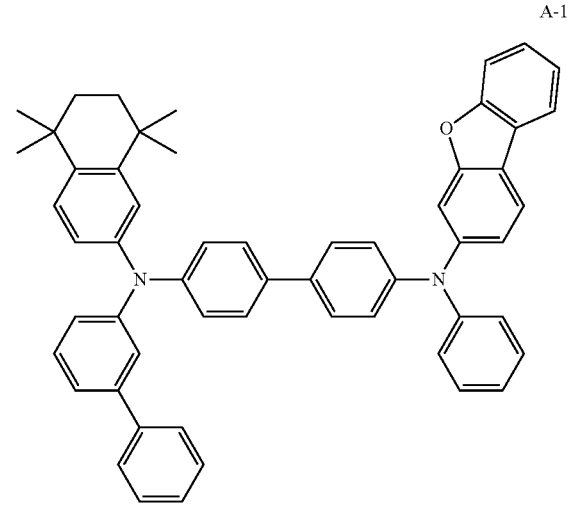
A-19
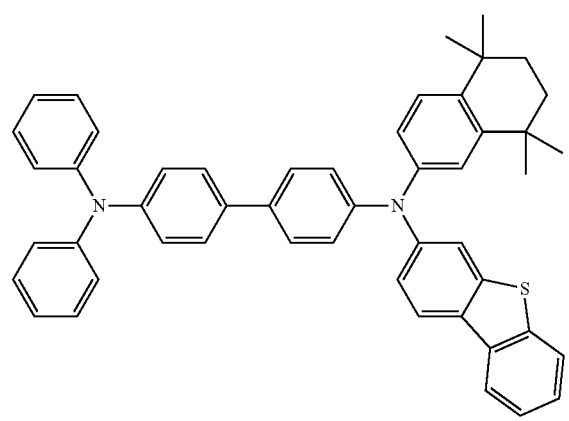
A-20
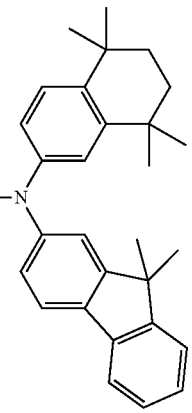
A-21
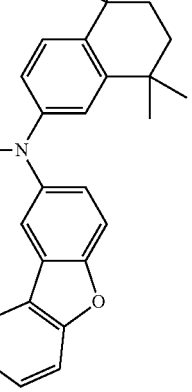
A-22
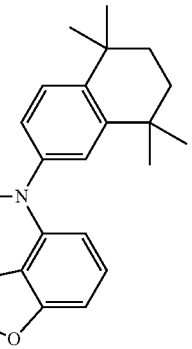

A-23
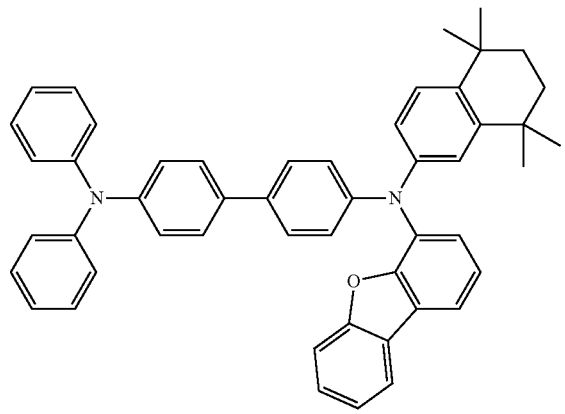
A-26
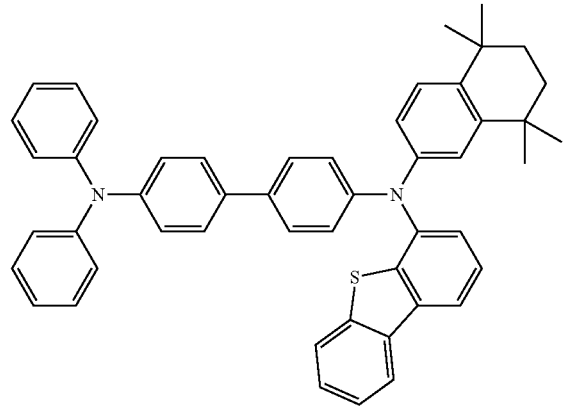
A-24
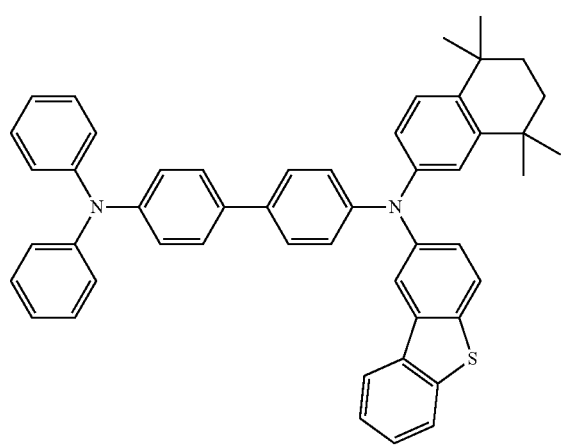
A-28
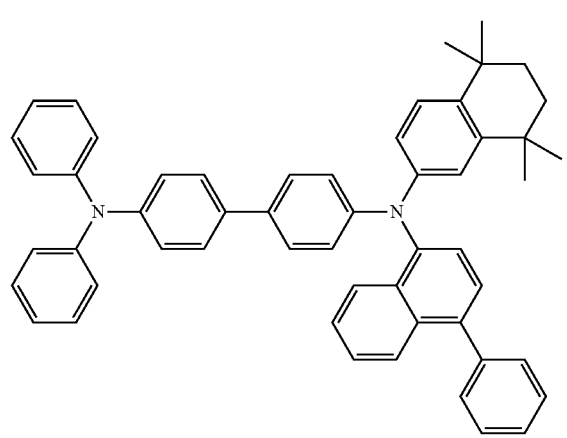
A-25
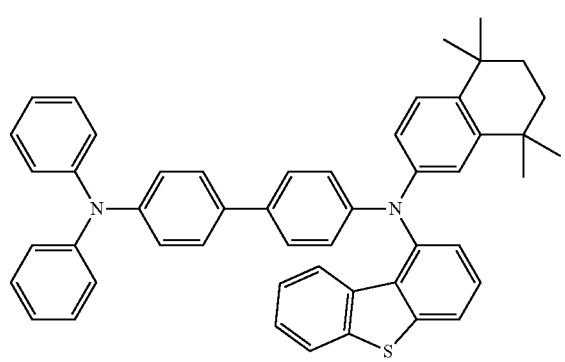
A-29

A-30
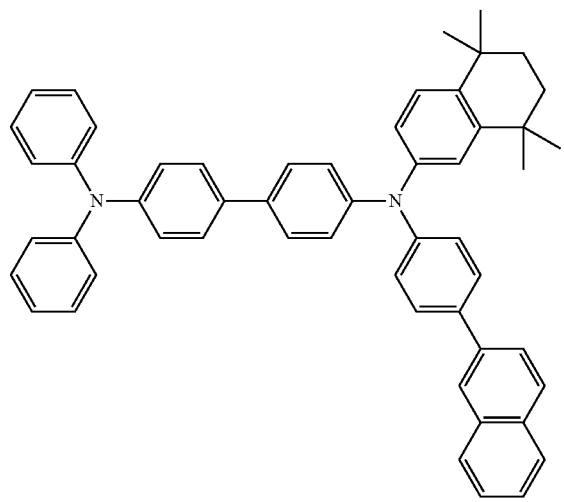
A-36
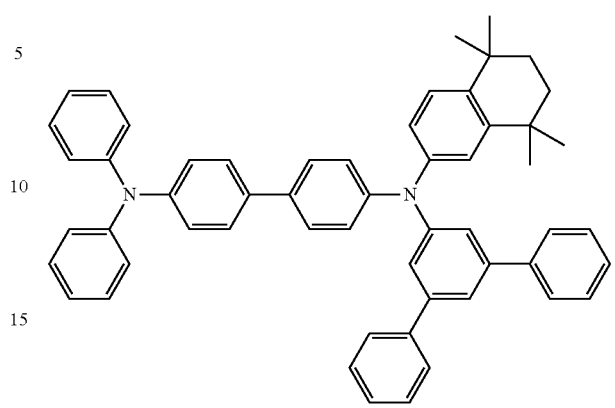
A-34
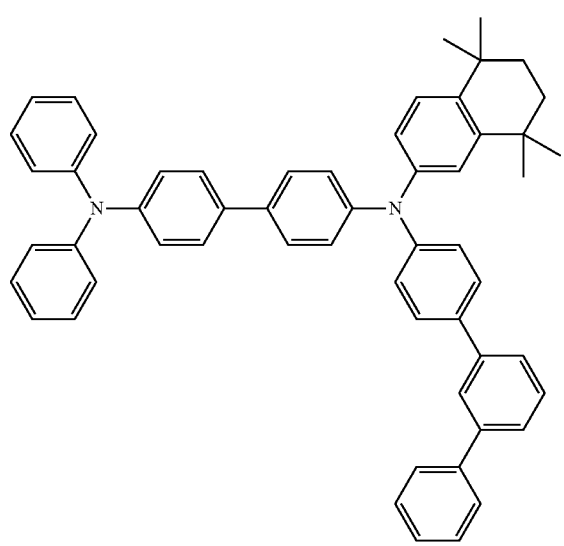
A-37
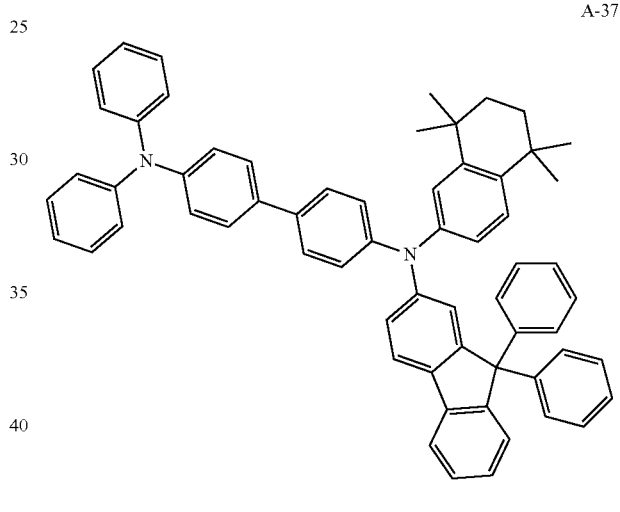
A-35
A-38
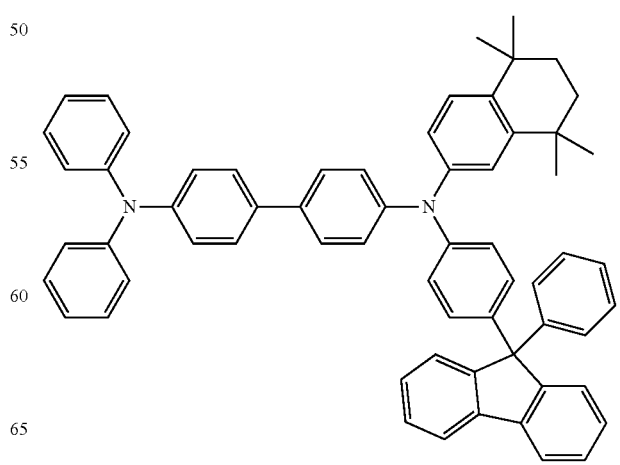

A-39
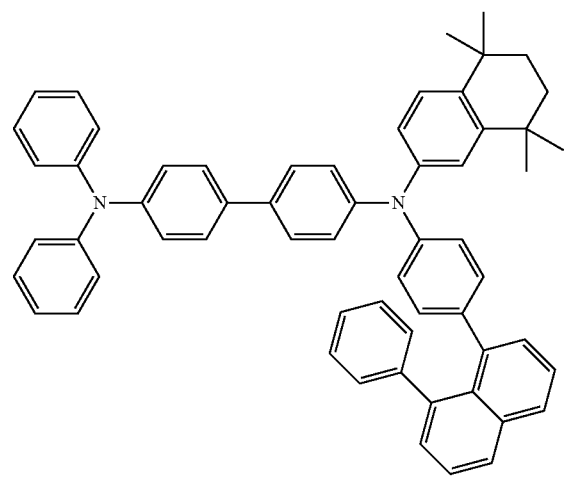
A-43
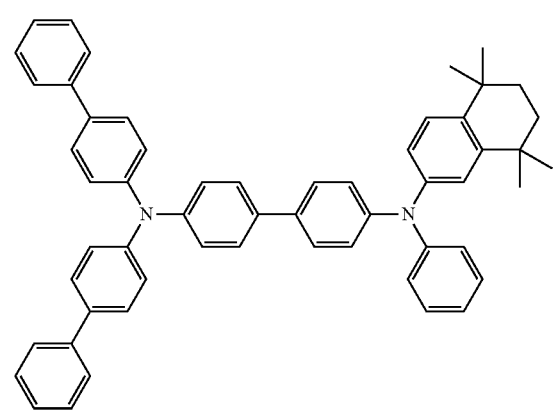
A-40
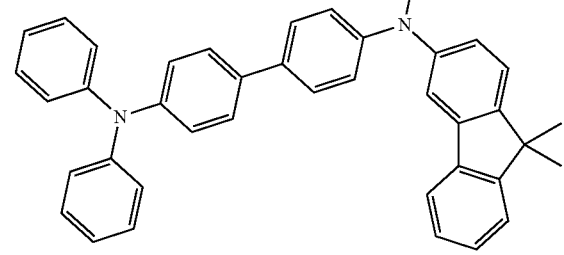
A-44
A-41
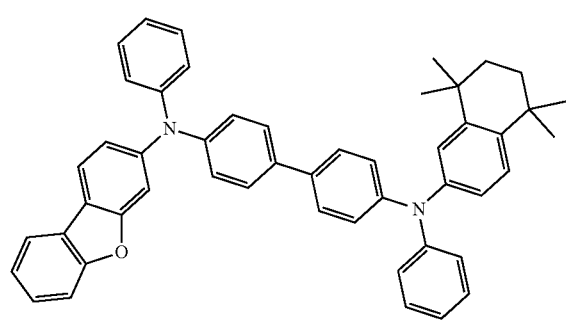
A-45
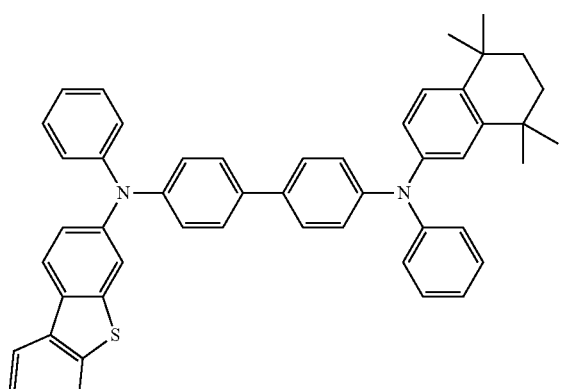
A-42
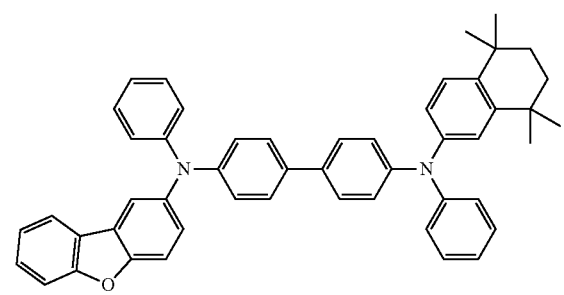
A-46
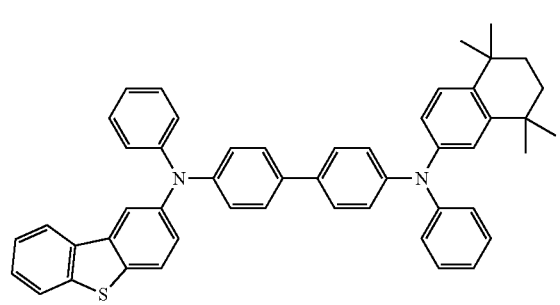

A-47
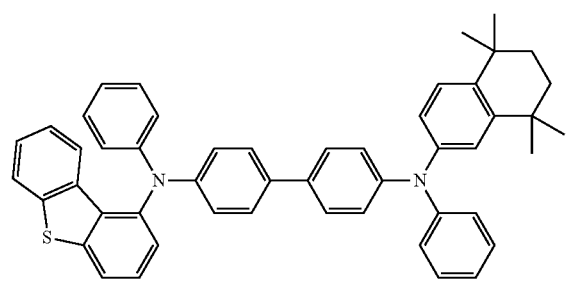
A-48
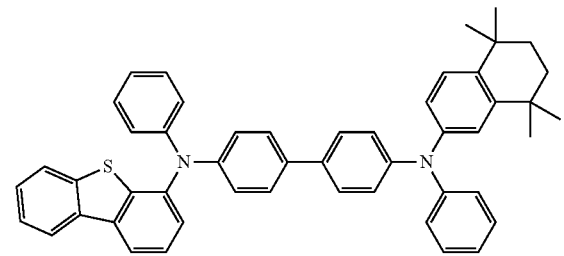
A-49
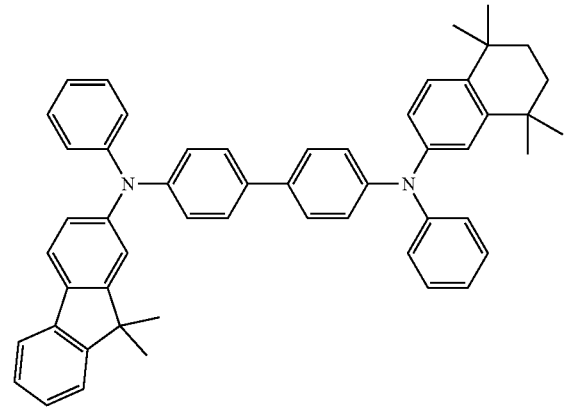
A-50
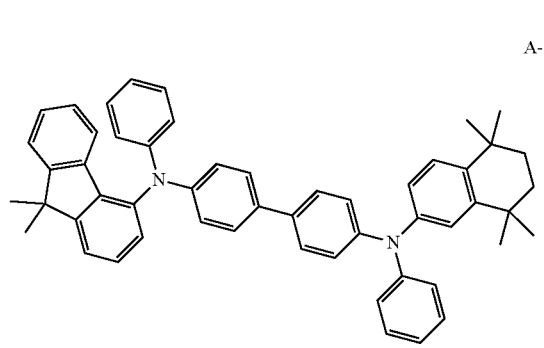
A-51
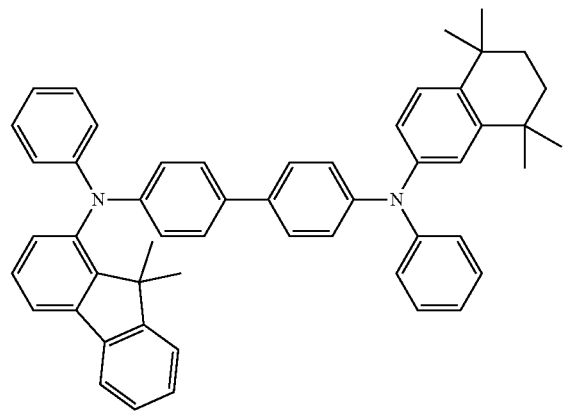
A-52
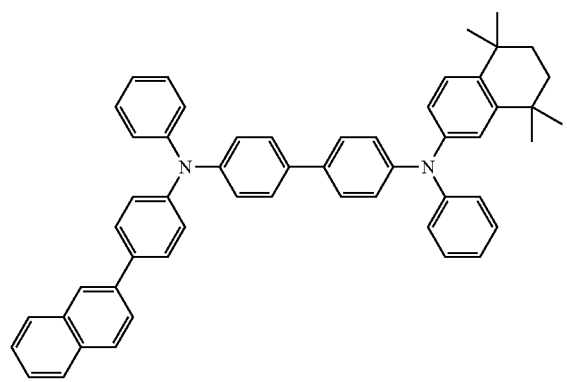
A-54
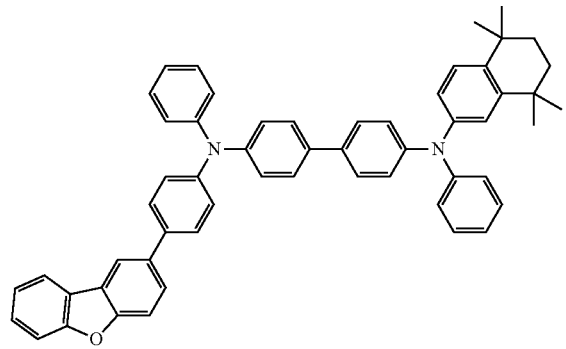
A-55

A-56
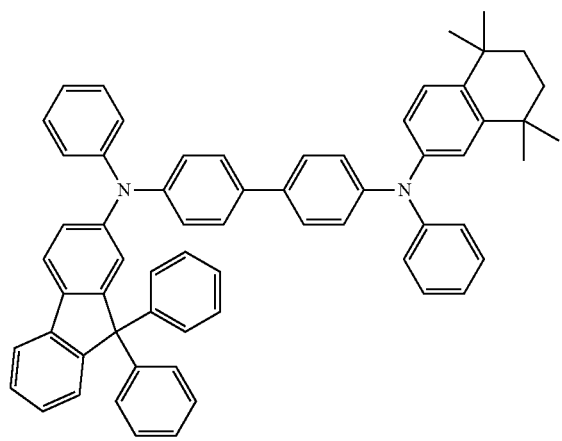
A-59
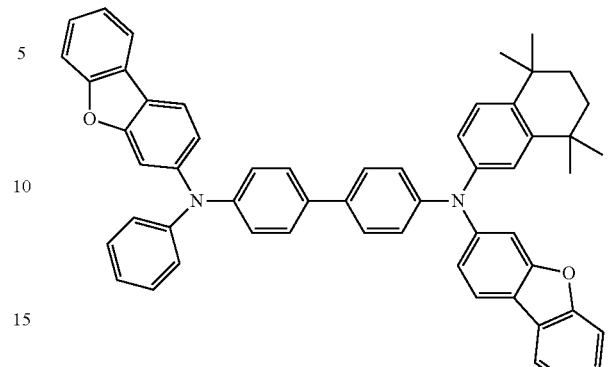
A-57
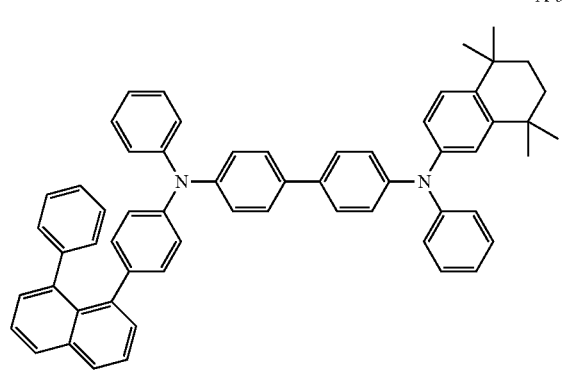
A-60
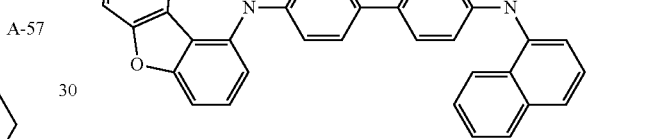
A-61
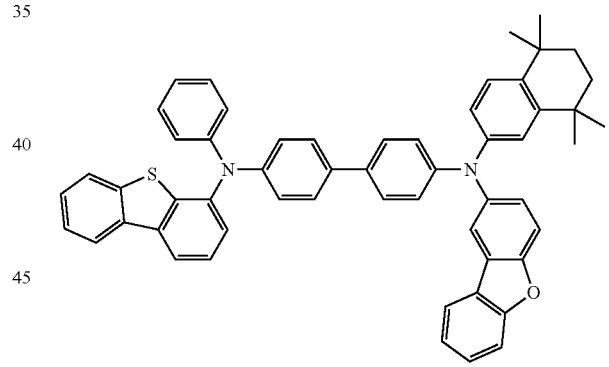
A-58
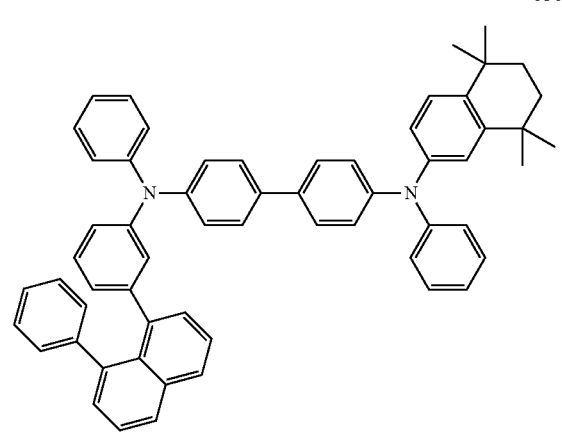
A-62
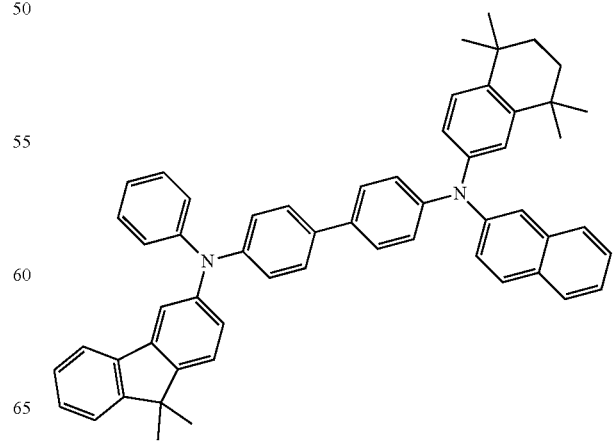

A-63
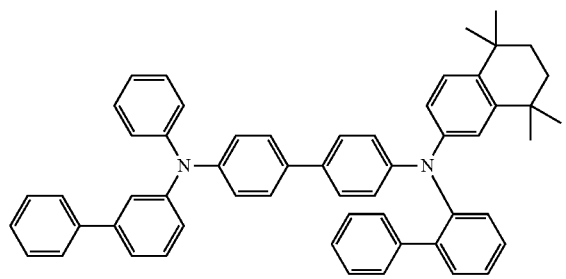
A-64
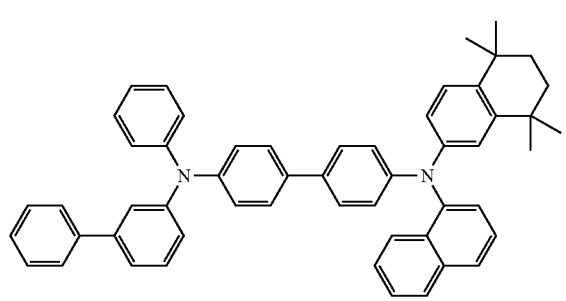
A-65
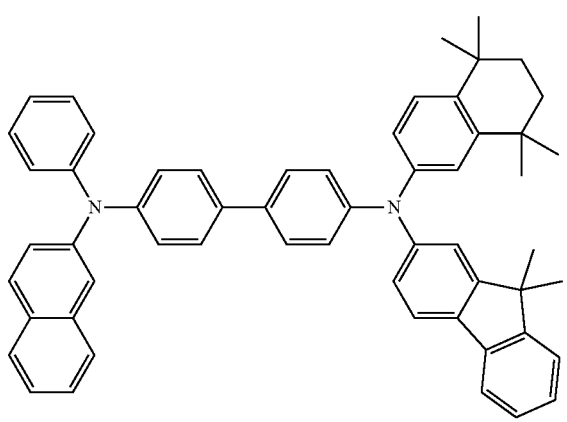
A-66
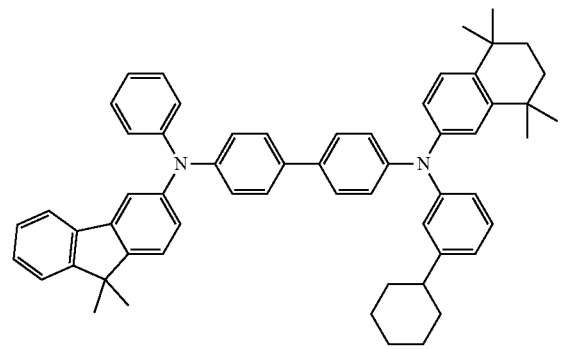
A-67
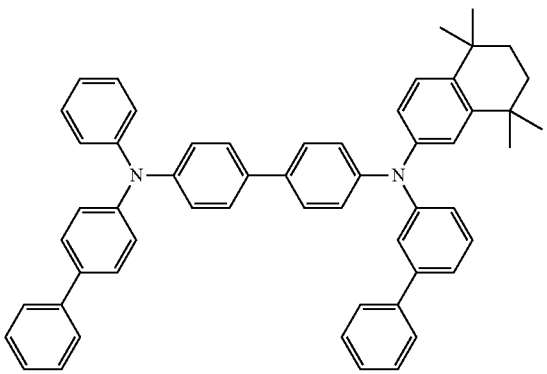
A-68
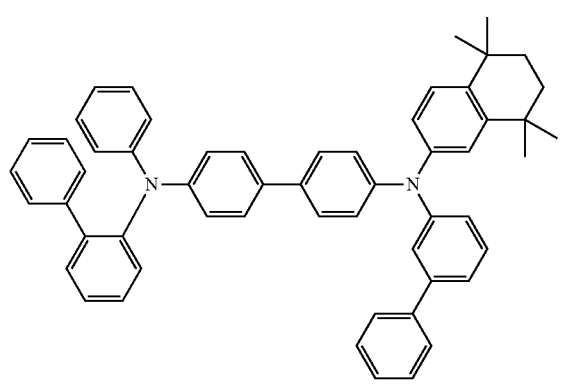
A-69
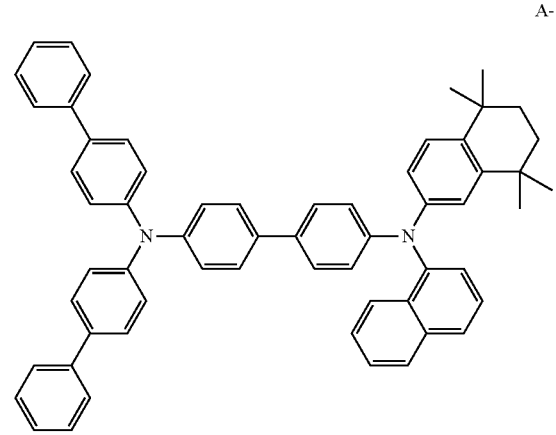
A-70
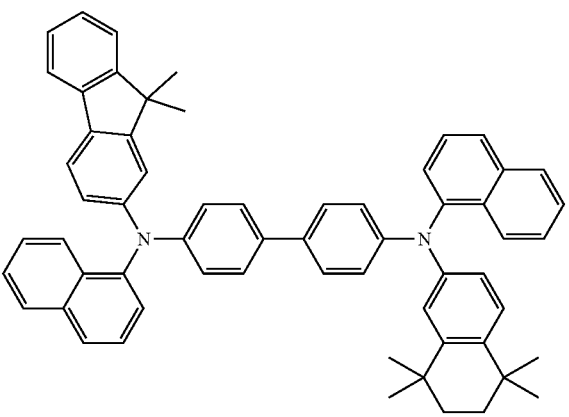

-continued
A-71
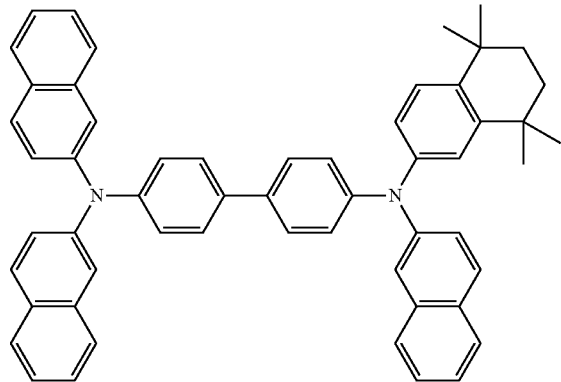
A-72
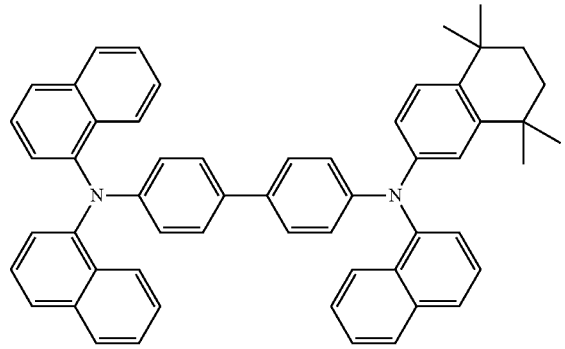
A-73
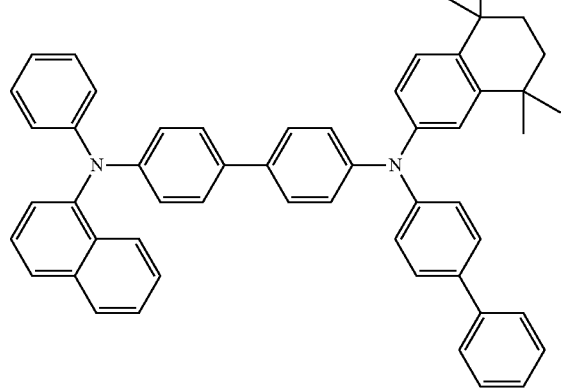
A-74
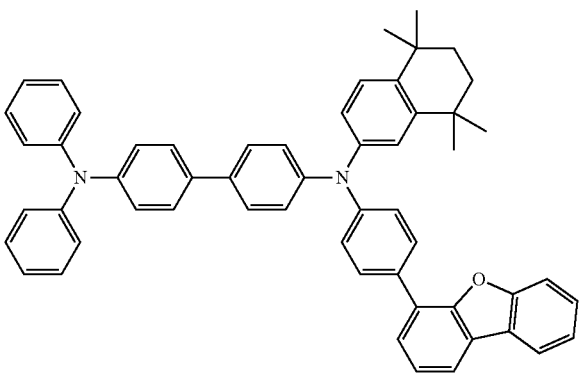
-continued
A-75
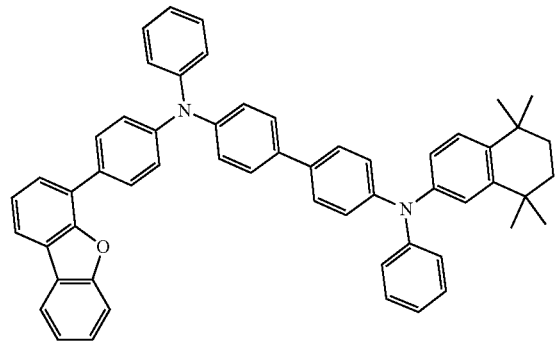
A-78
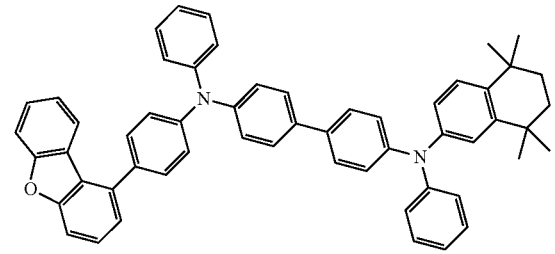
A-79
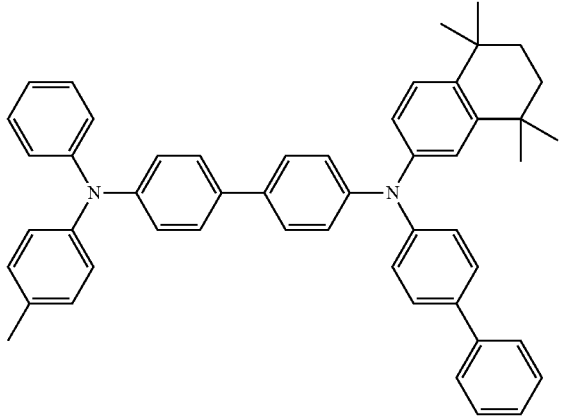
A-80
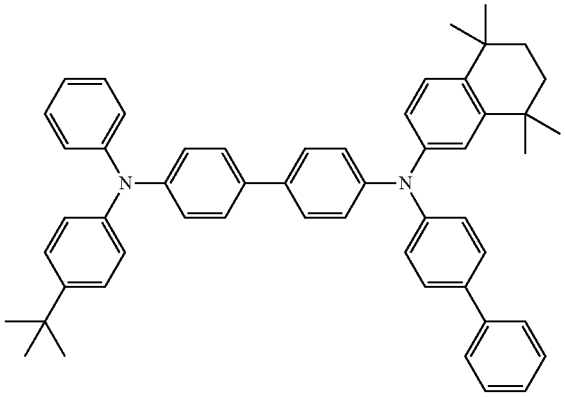

A-82
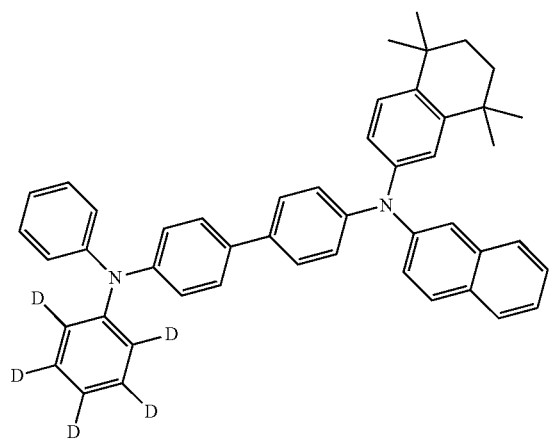
A-85
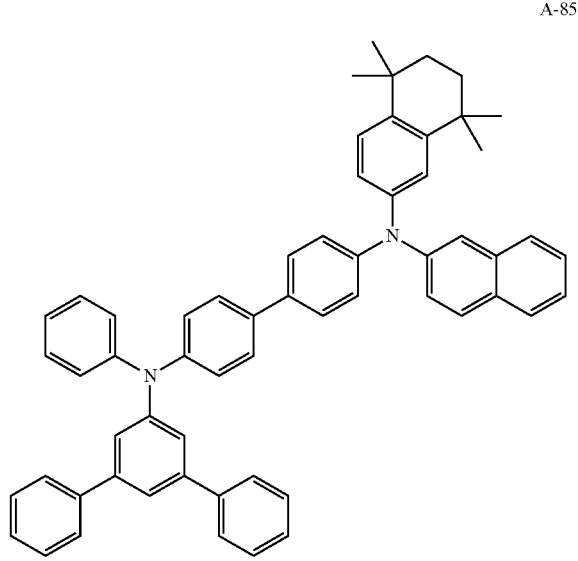
A-86
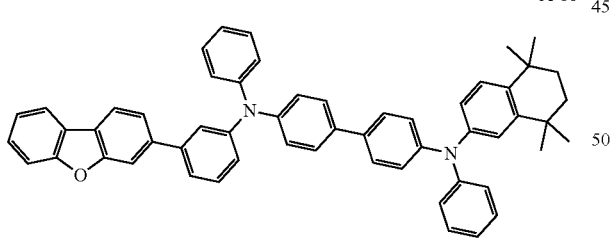
A-87
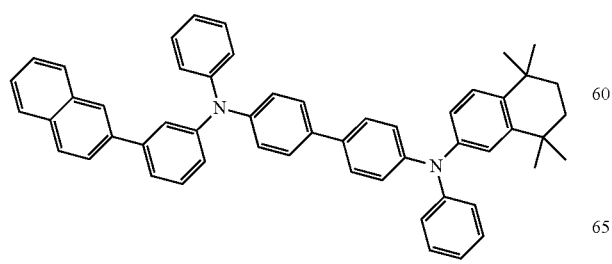
A-88
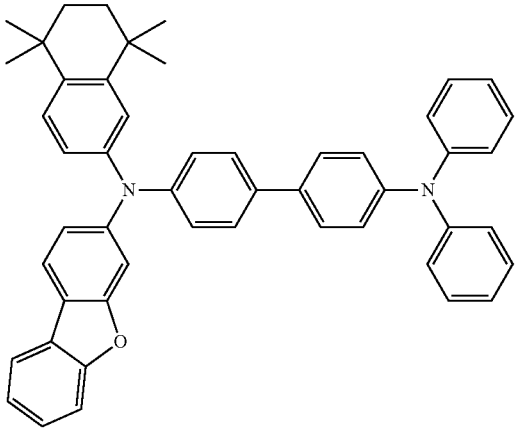
A-89
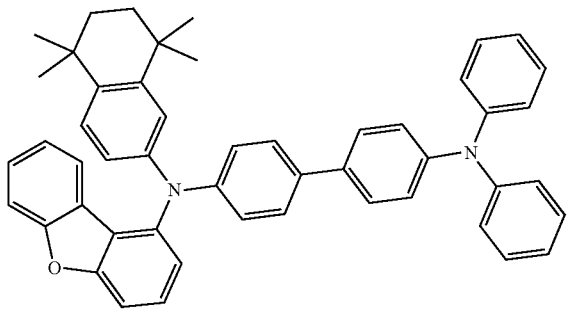
A-90
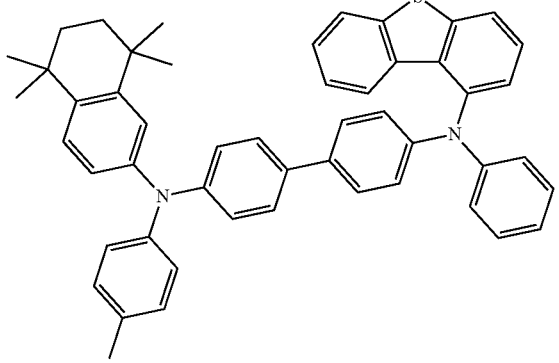
A-91
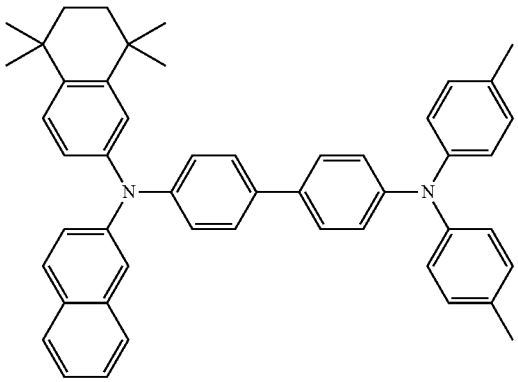

B-1
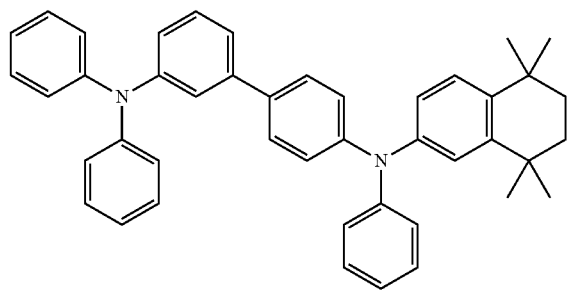
B-2
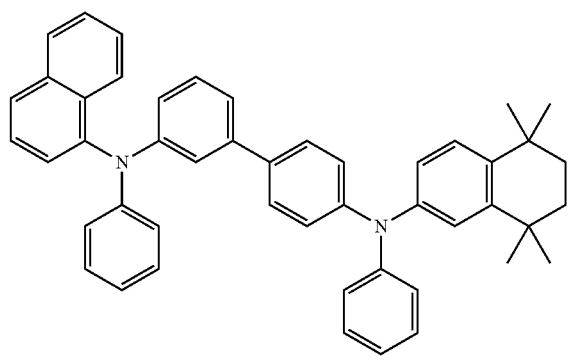
B-3
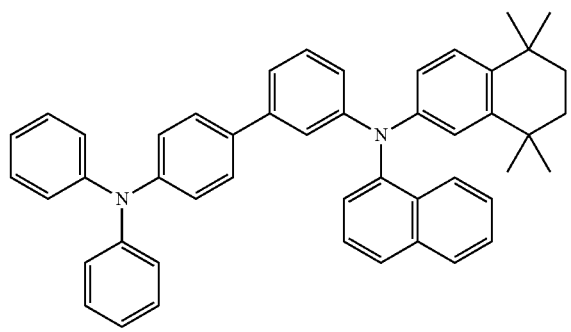
B-4
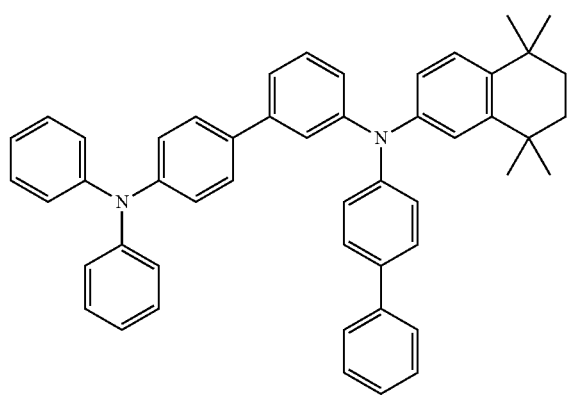
B-5
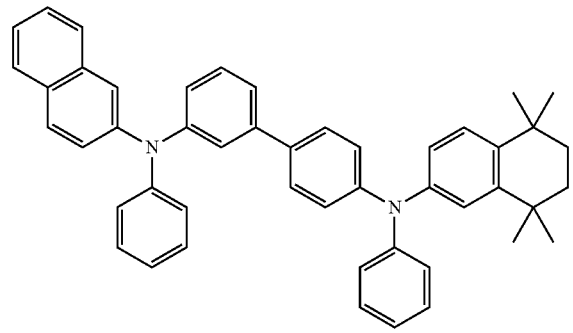
B-6
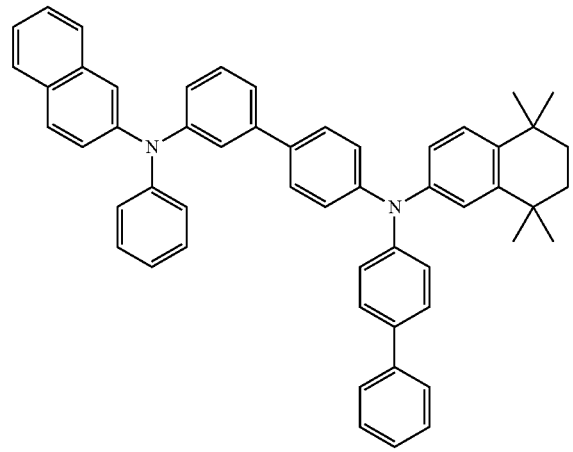
B-7
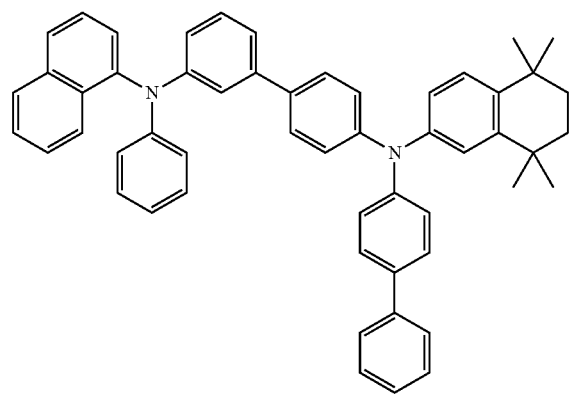
B-8
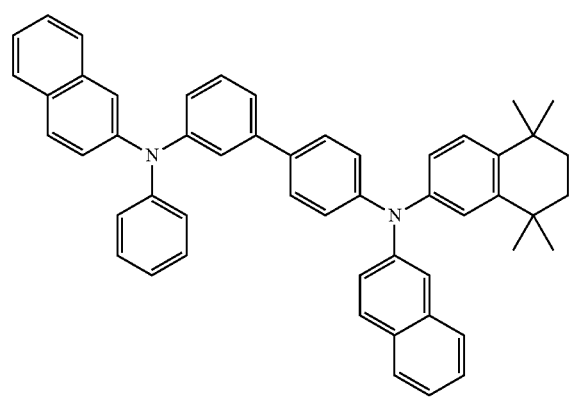

B-9
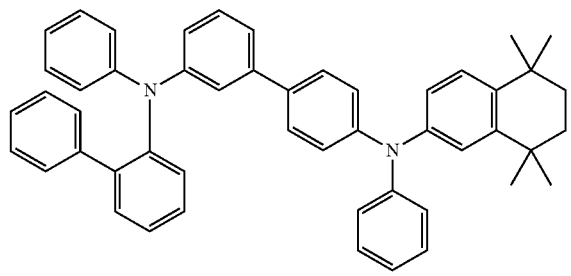
B-10
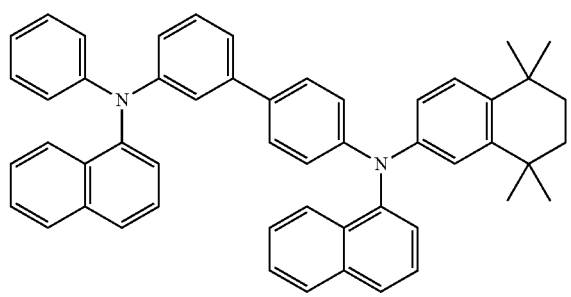
B-11
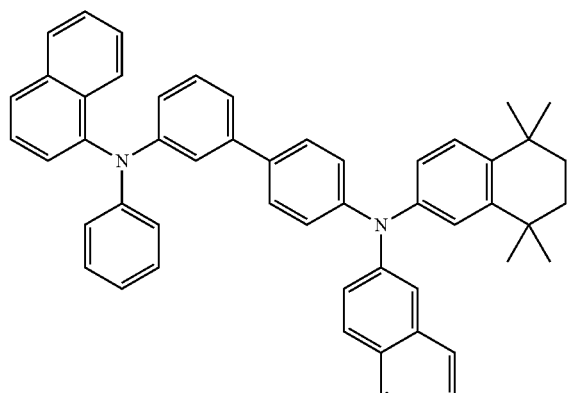
B-12
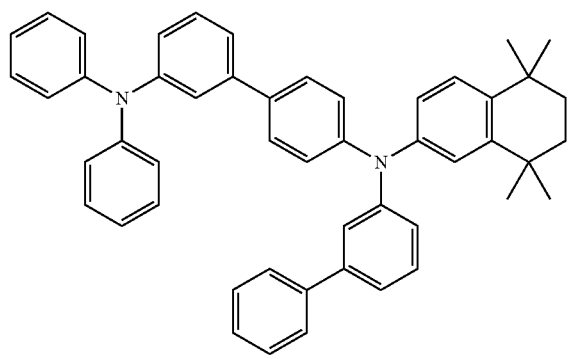
B-13
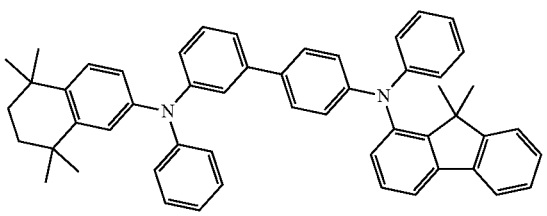
B-14
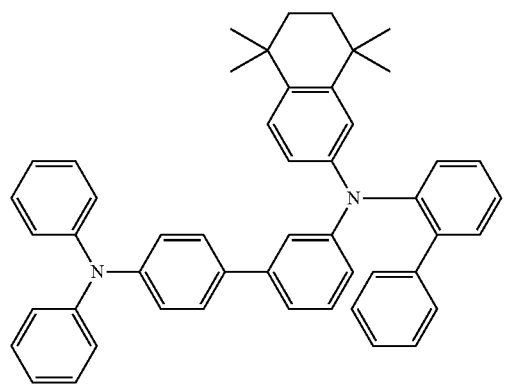
B-15
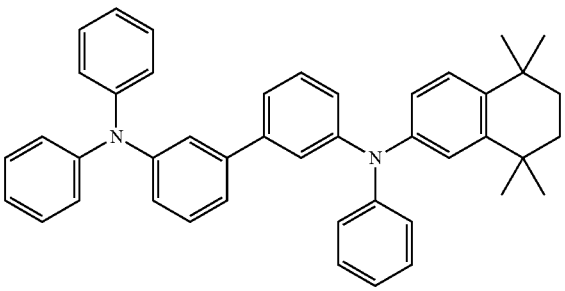
B-16
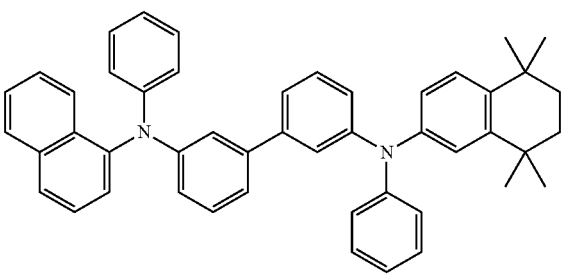
B-17
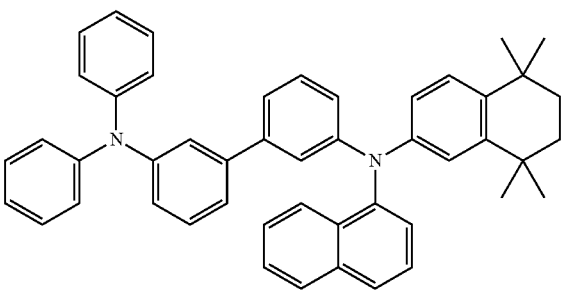

B-18
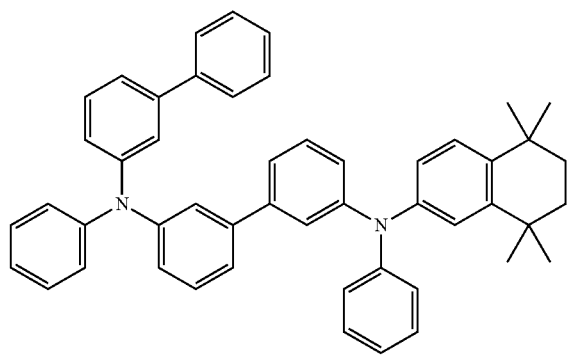
B-22
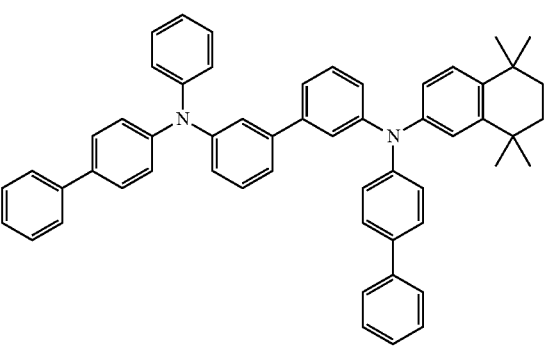
B-19
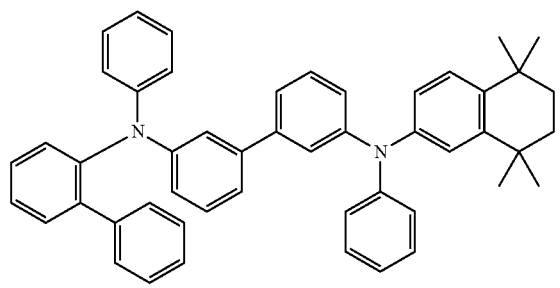
B-23
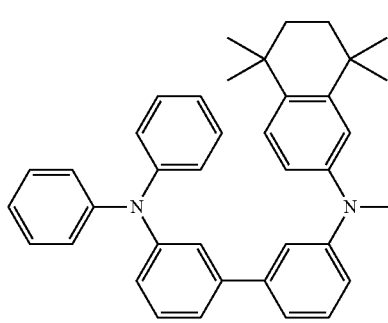
B-20
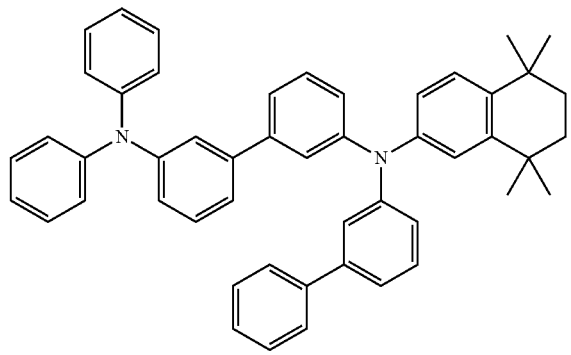
B-24
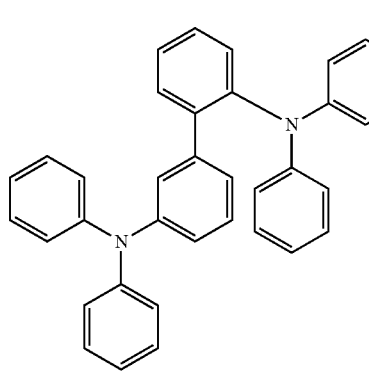
B-21
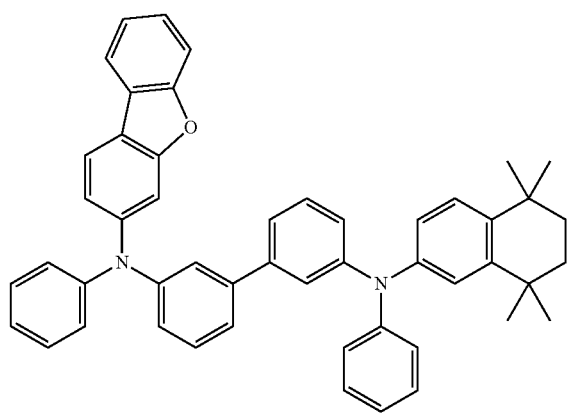
B-25
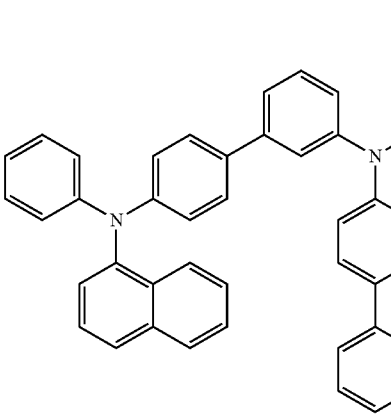

B-26
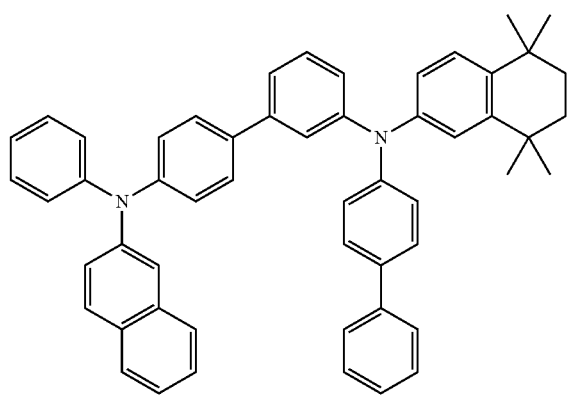
B-30
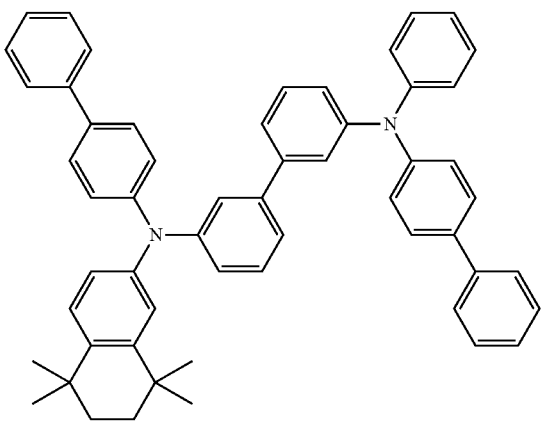
B-27
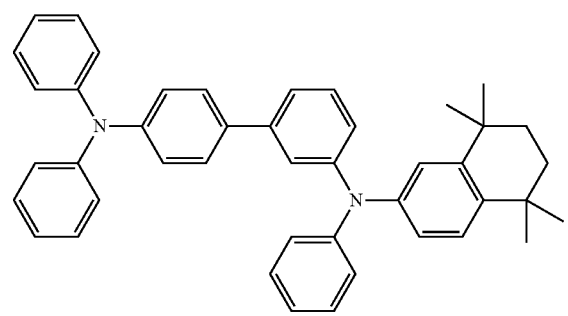
B-31
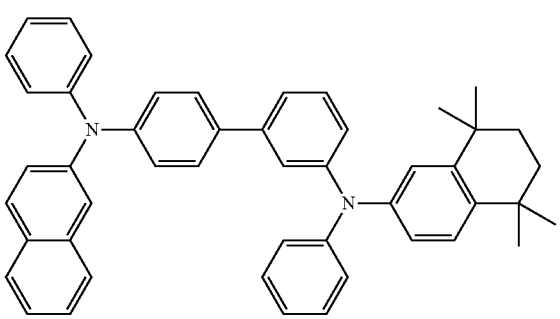
B-28
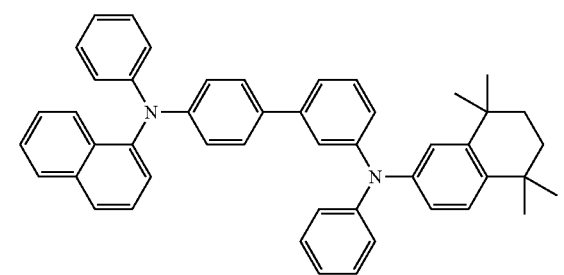
B-32
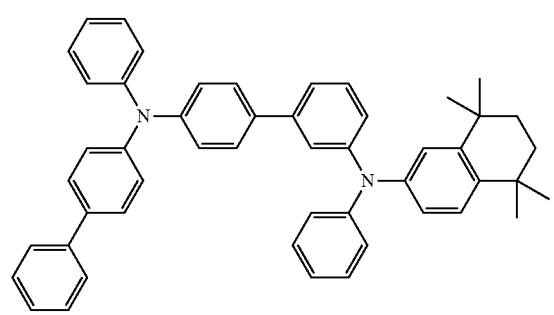
B-29
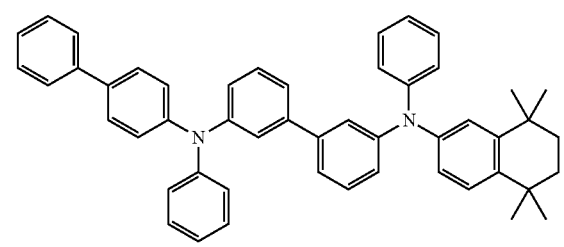
B-33
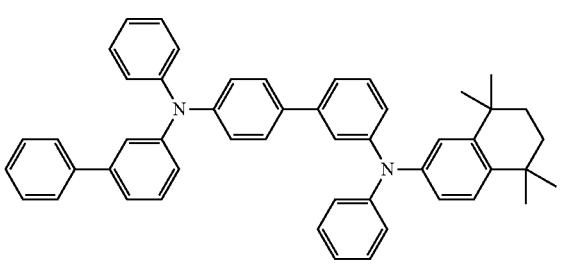

B-34
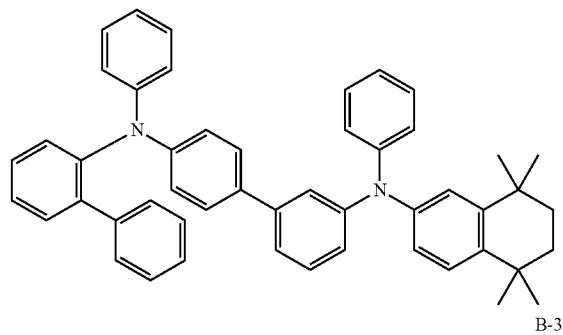
B-35
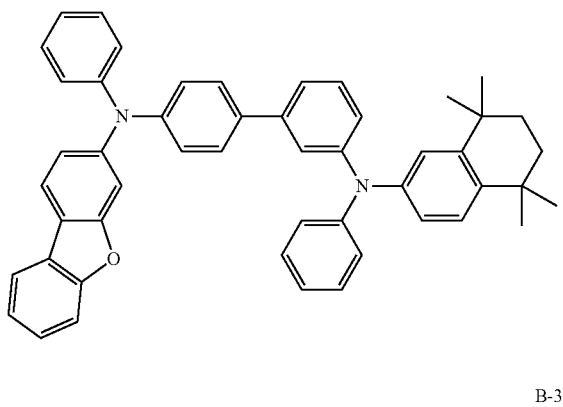
B-36
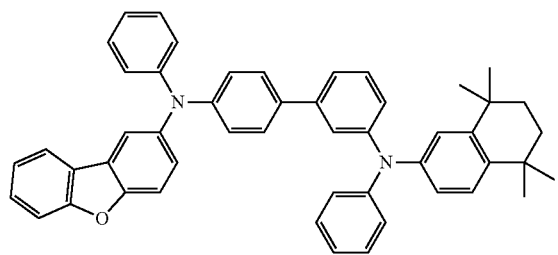
B-37
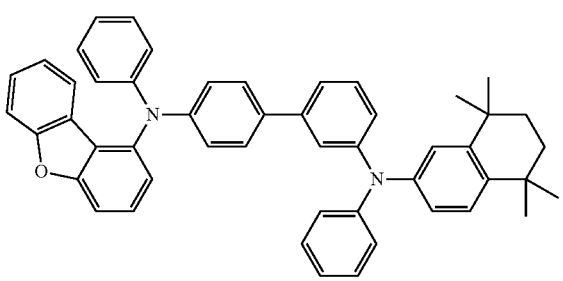
B-38
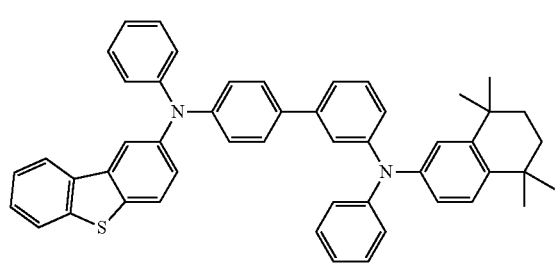
B-39
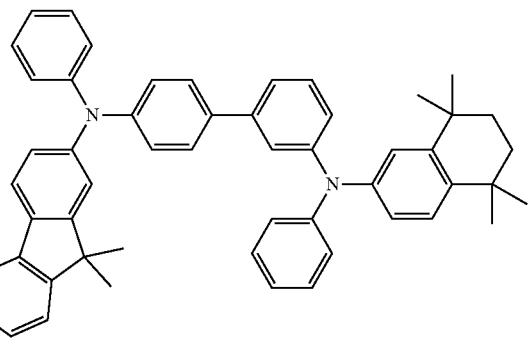
B-40
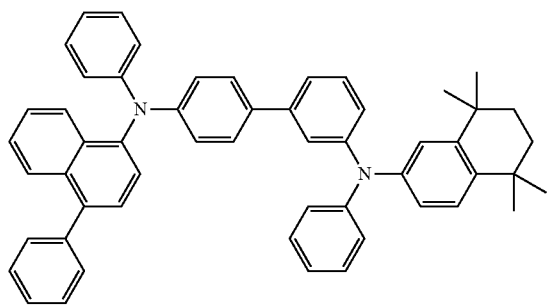
B-41
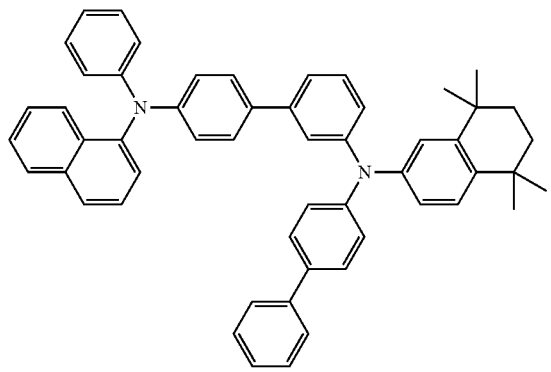
B-42

B-43
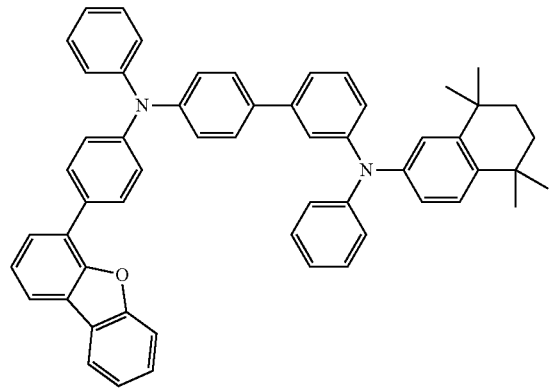
B-44
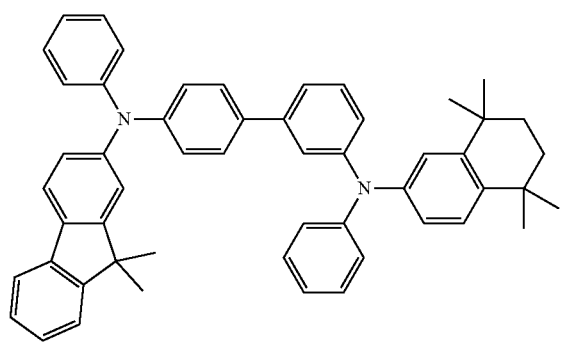
B-45
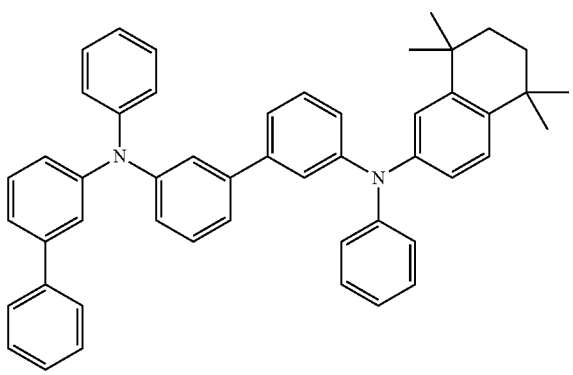
B-46
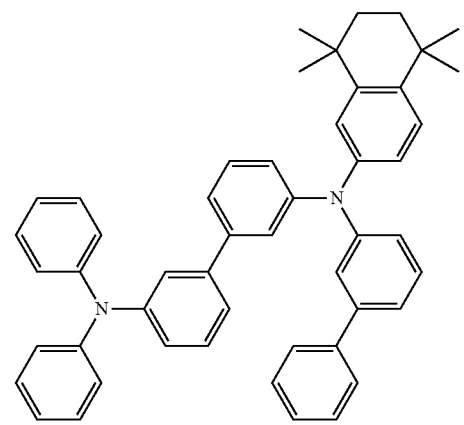
B-47
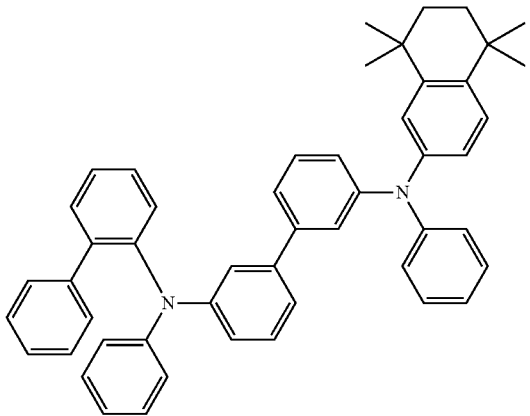
B-48
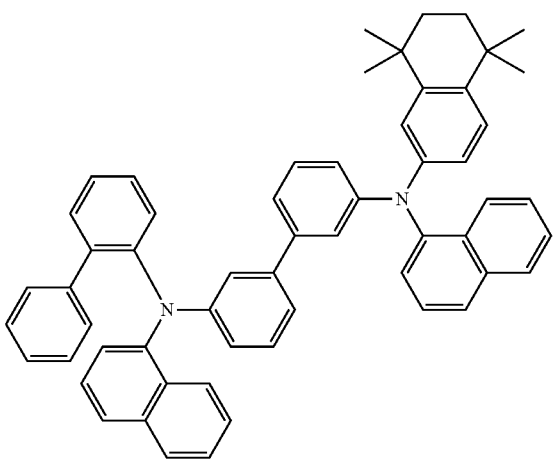
C-1
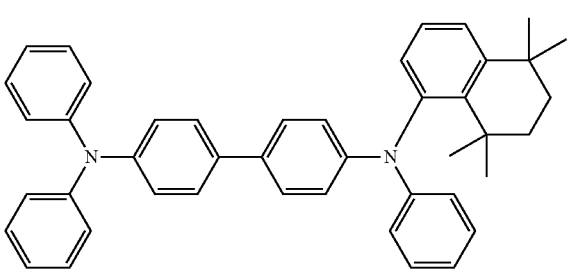
C-2
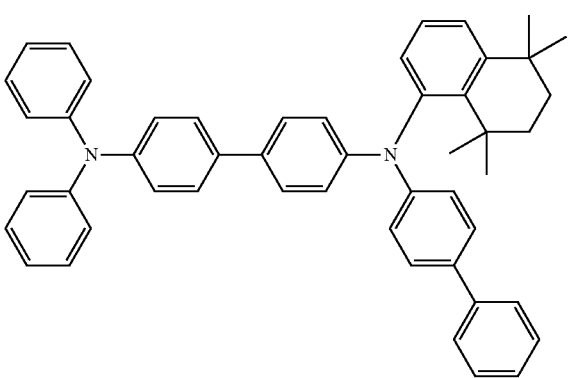

-continued
C-3
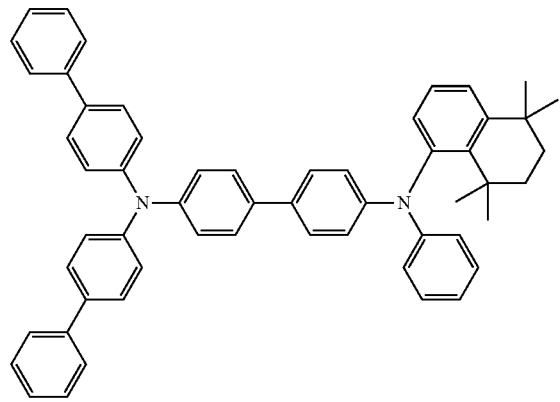
C-7
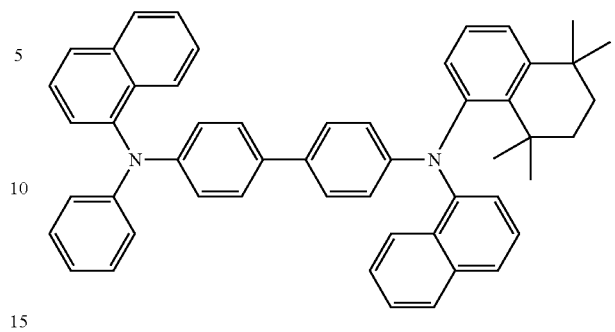
C-4
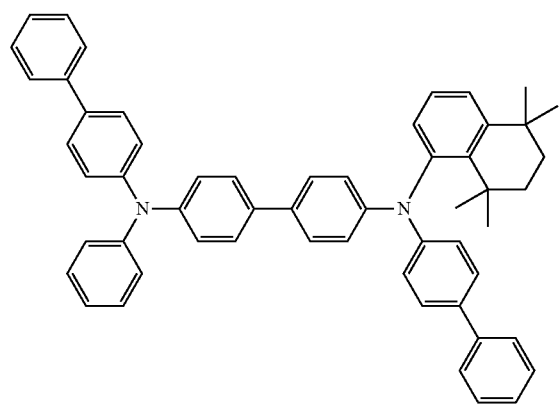
C-8
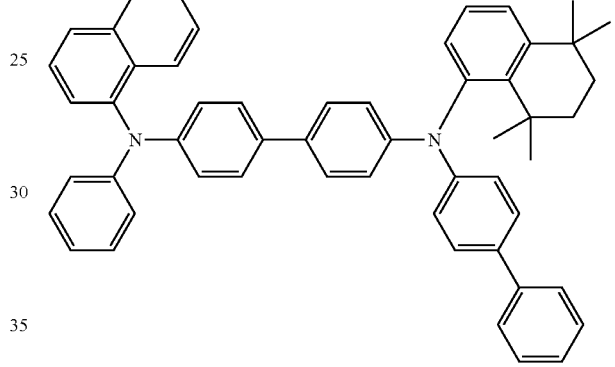
C-5
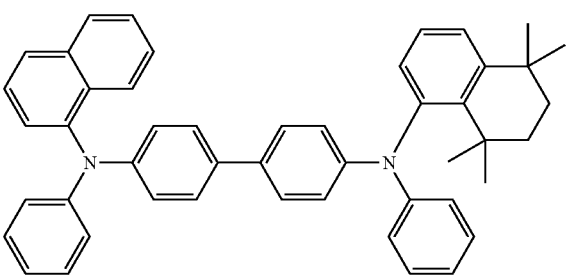
C-9
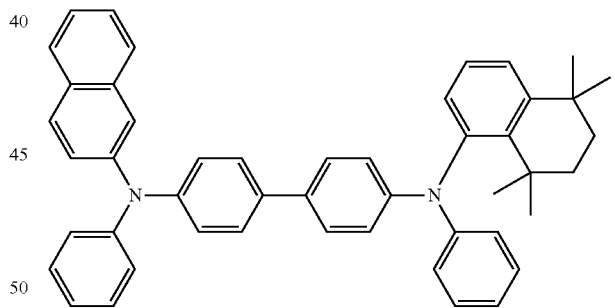
C-6
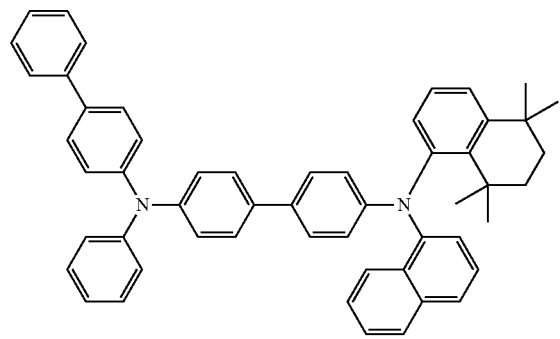
C-10
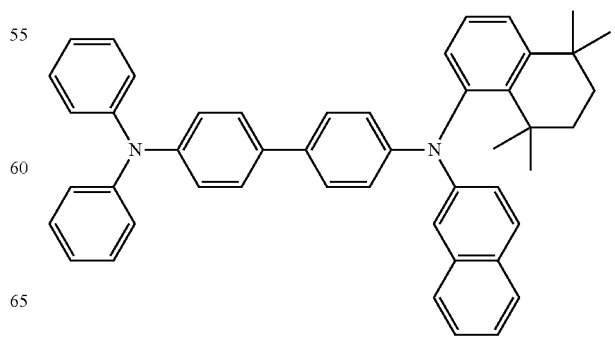

C-11
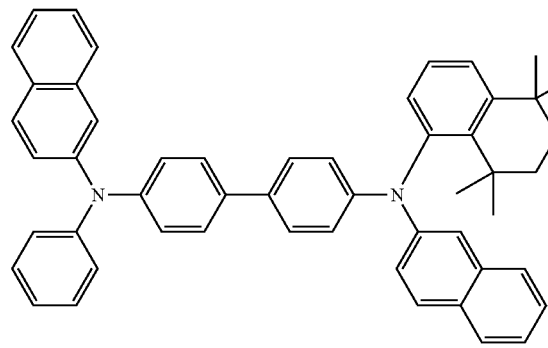
C-15
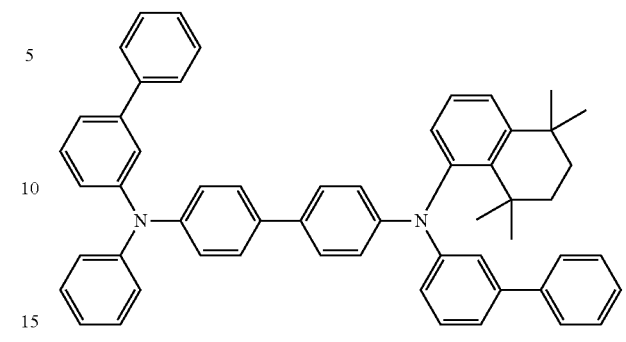
C-12
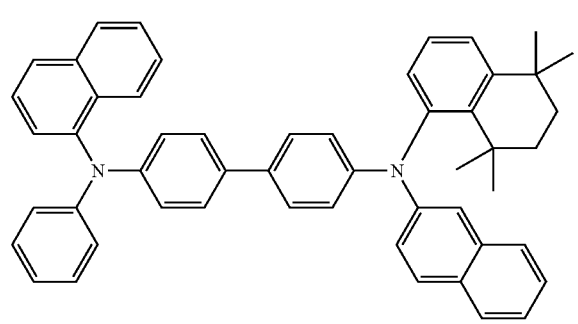
C-16
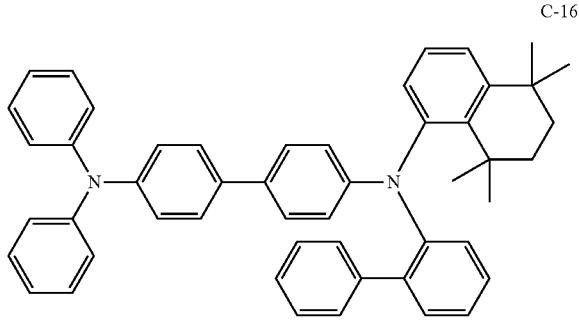
C-13
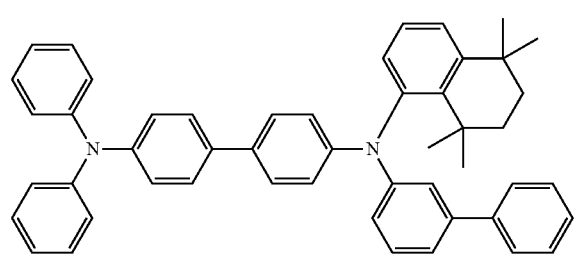
C-17
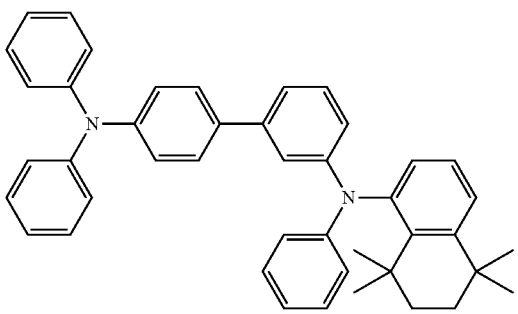
C-14
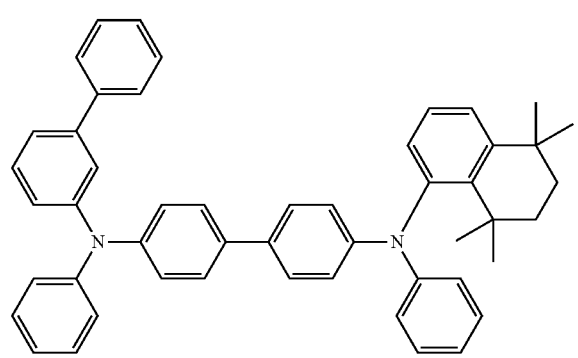
C-18
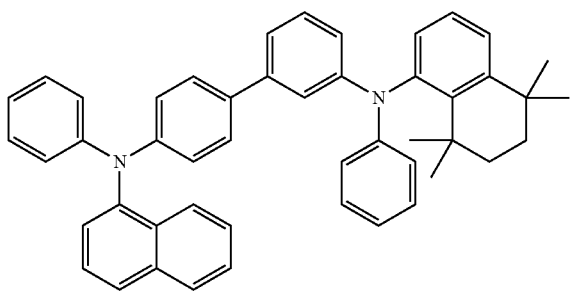

C-19
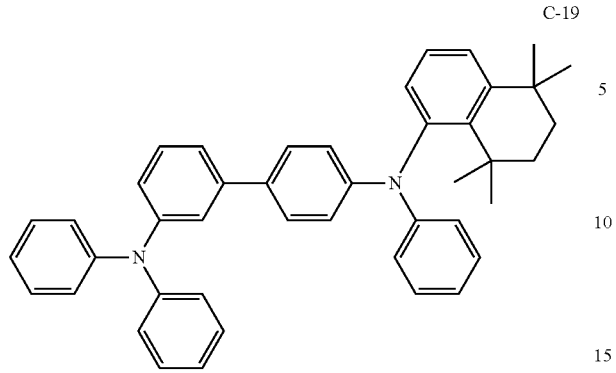
C-20
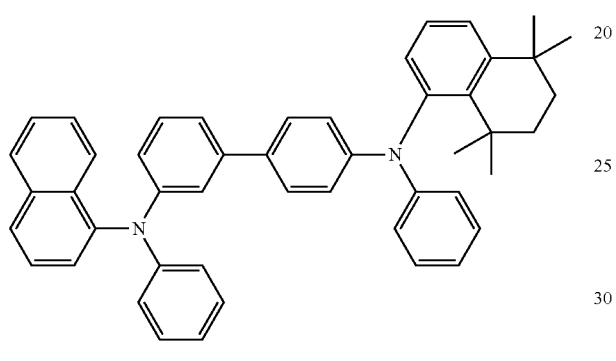
C-21
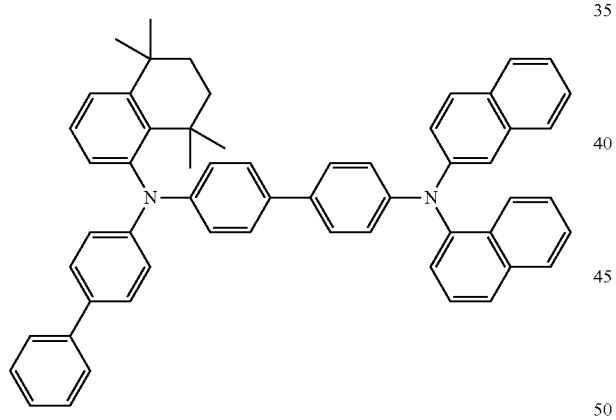
C-22
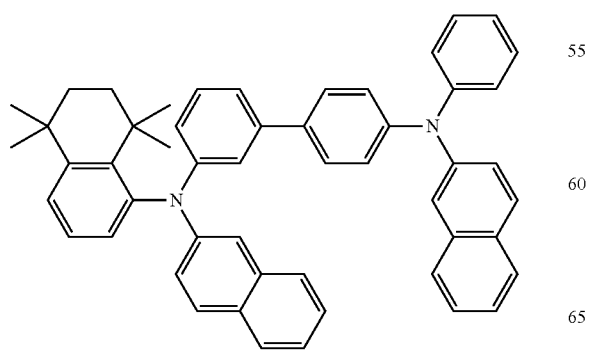
C-23
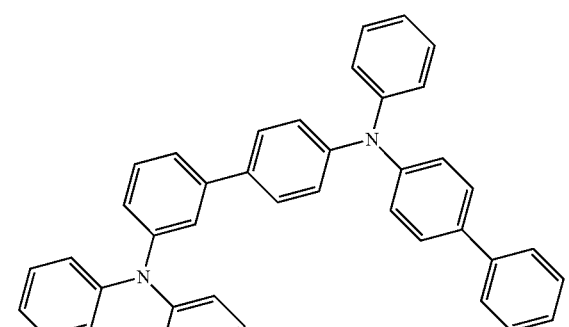
C-24
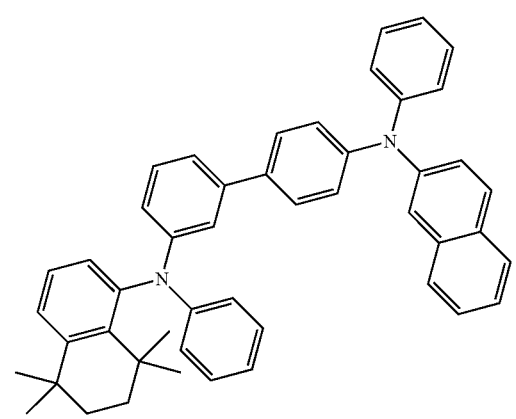

C-25 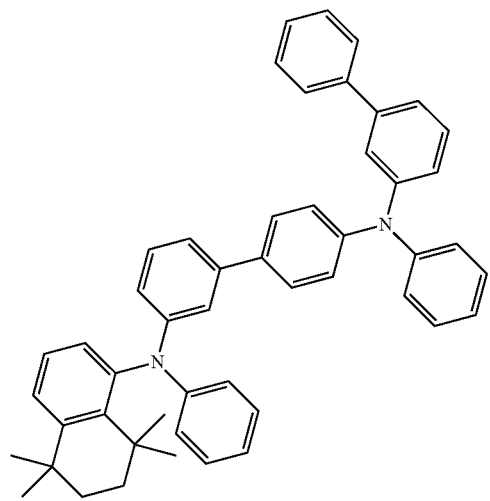
C-26 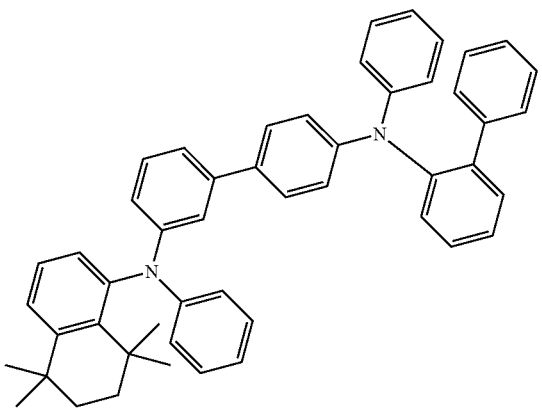
C-27 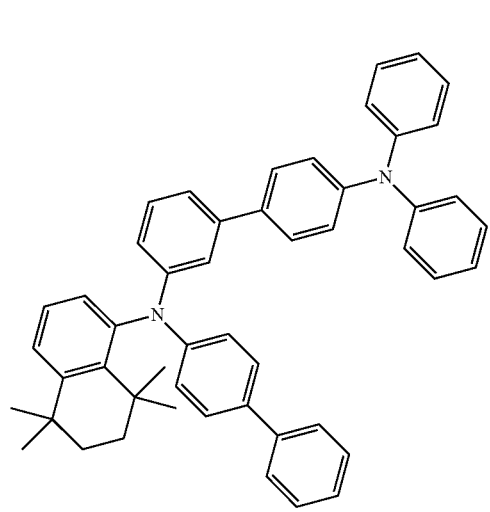
C-28 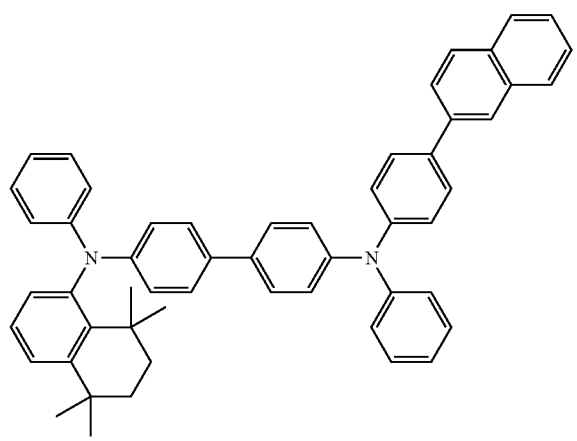
C-29 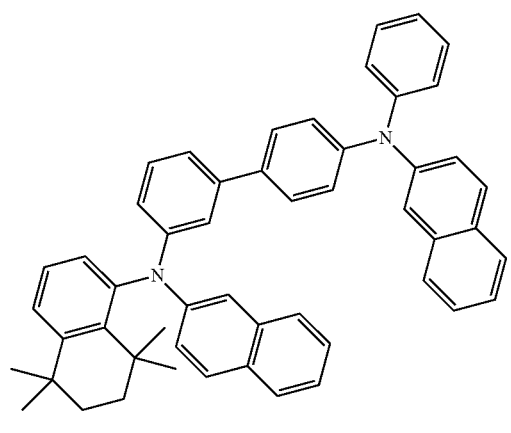
C-30 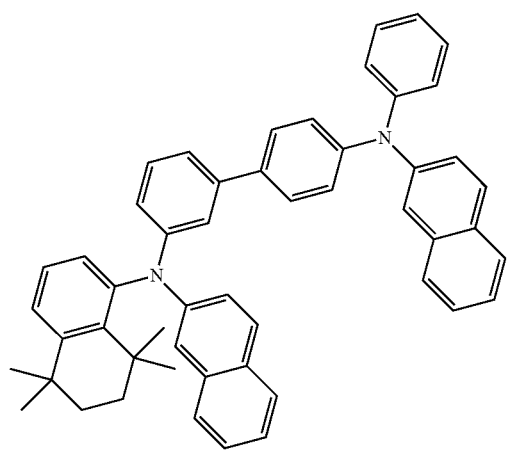

-continued
C-31
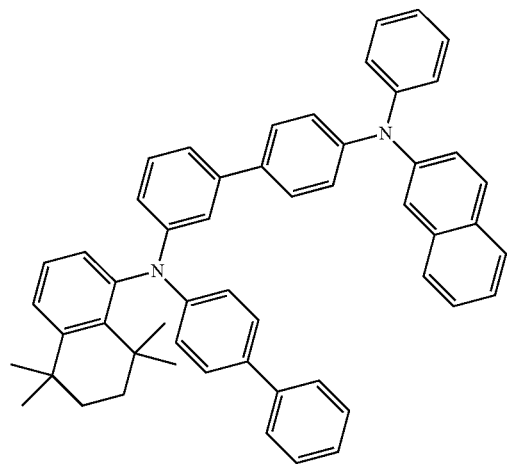
C-32
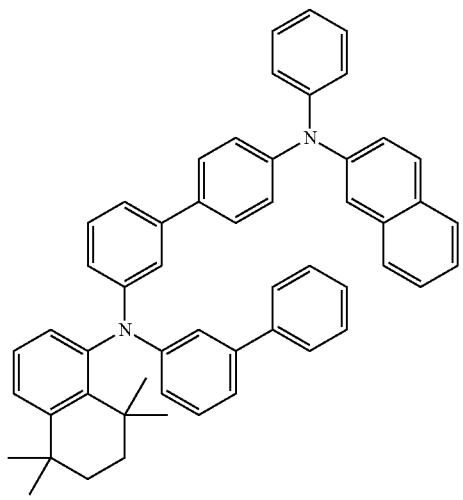
C-33
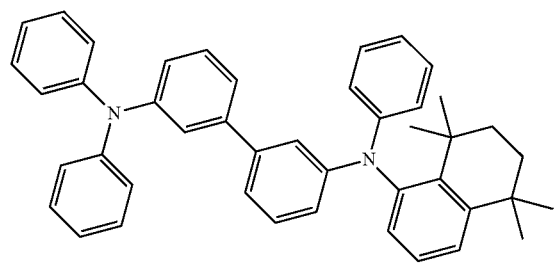
C-34
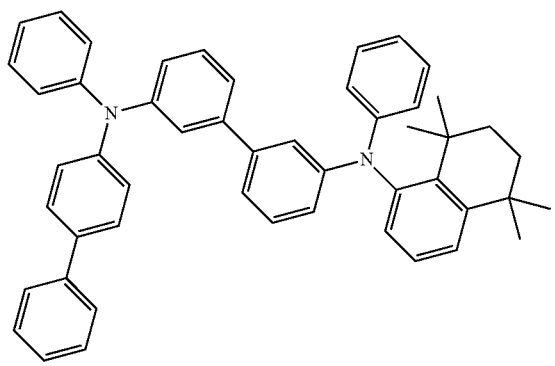
C-35
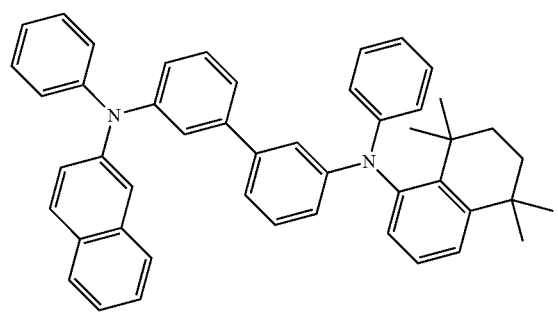
C-36
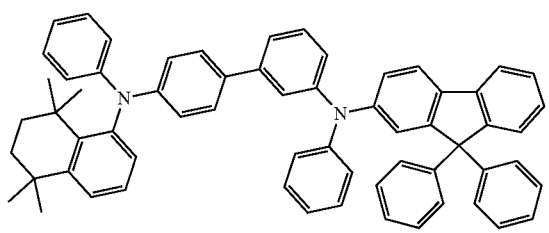

-continued
C-37
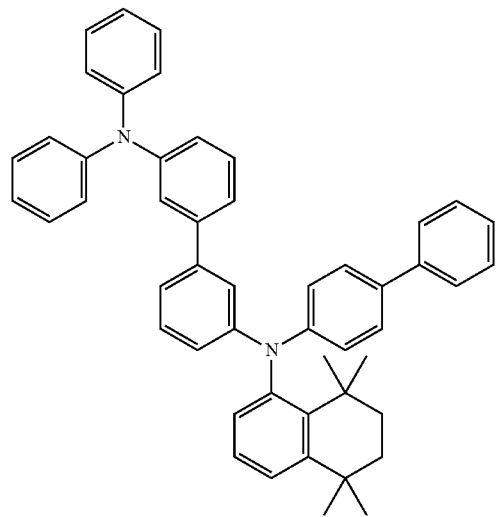
C-38
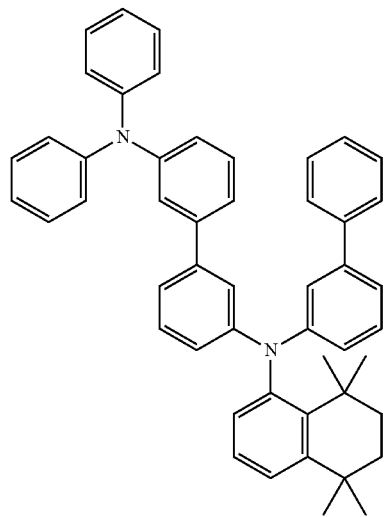
C-39
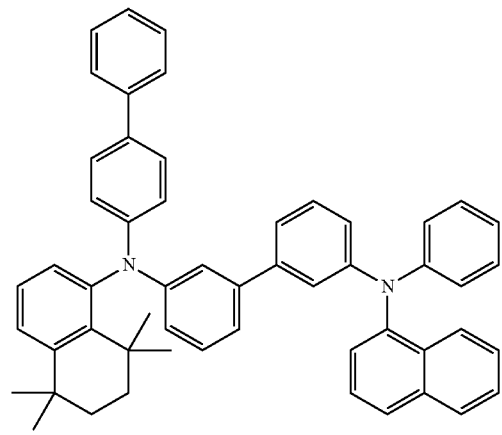
C-40
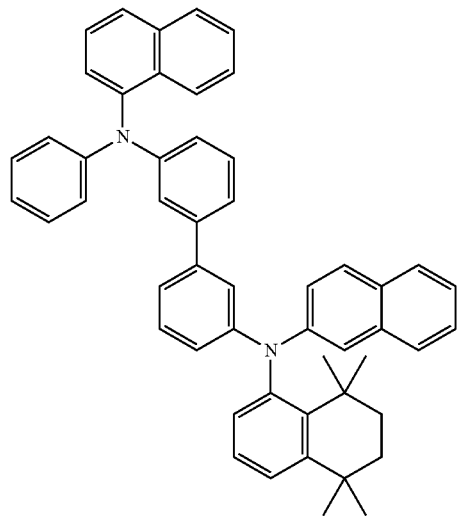
C-41
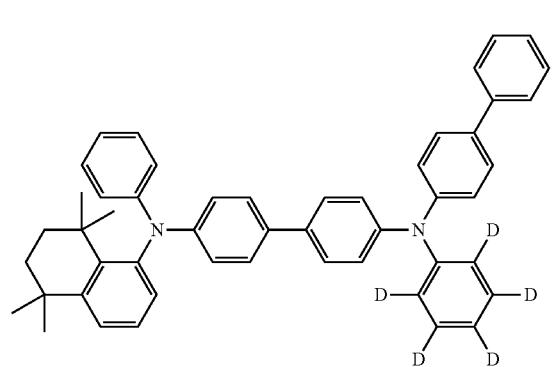
C-42
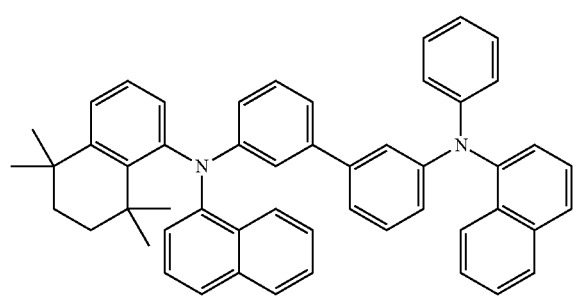

-continued
C-43
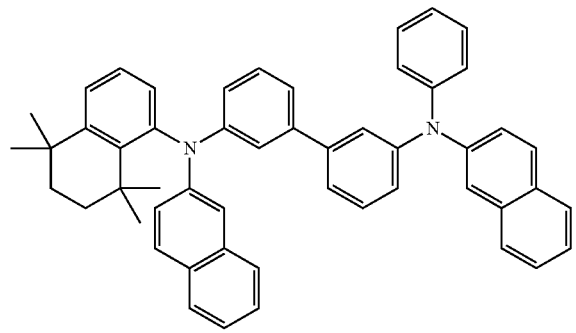
C-44
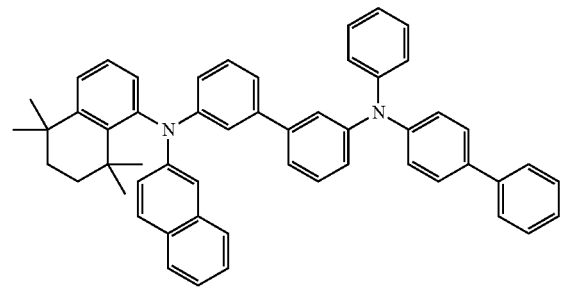
D-1
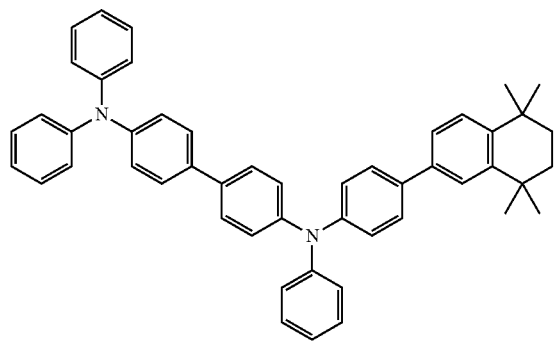
D-2
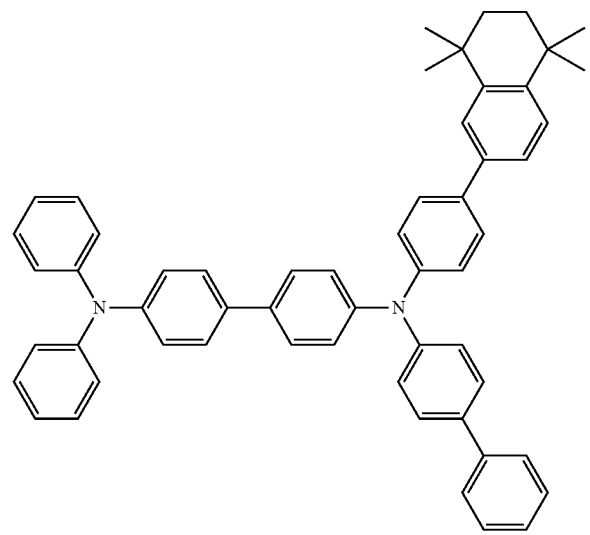
D-3
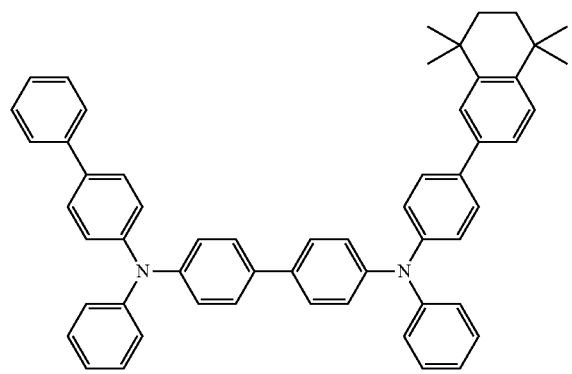
D-4
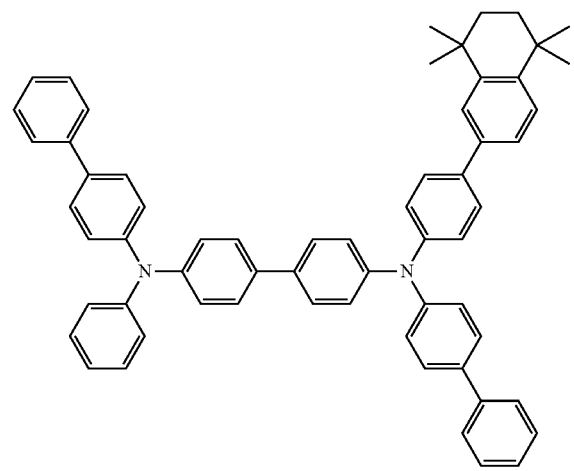

-continued
D-5
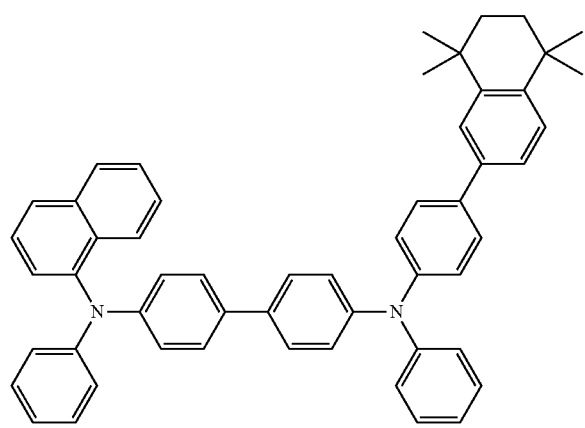
D-6
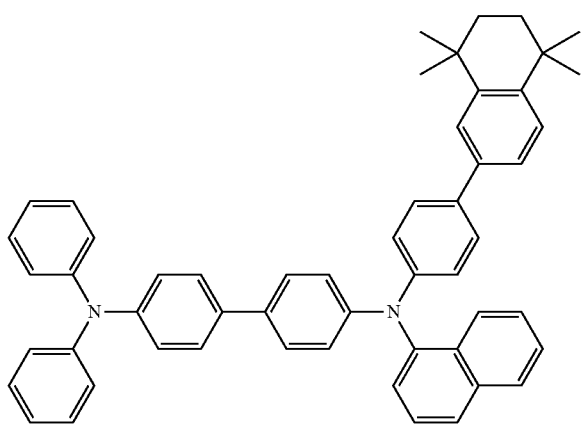
D-7
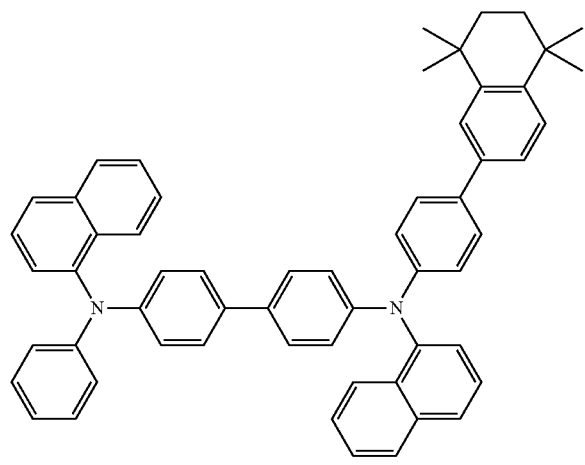
D-8
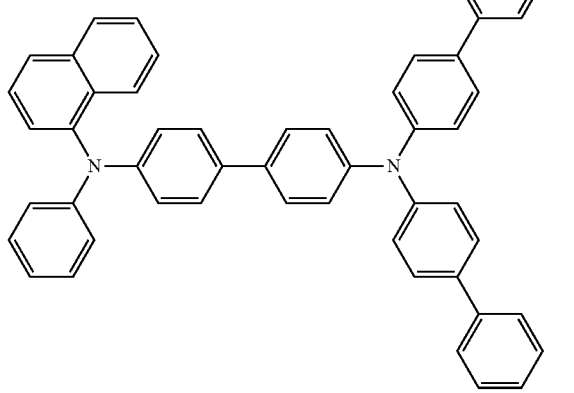
D-9
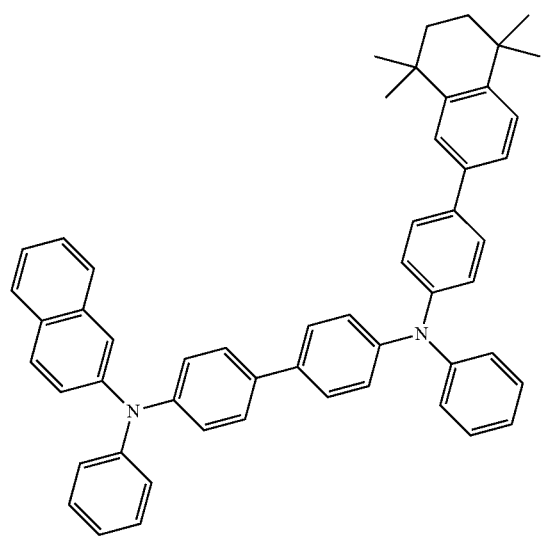
D-10
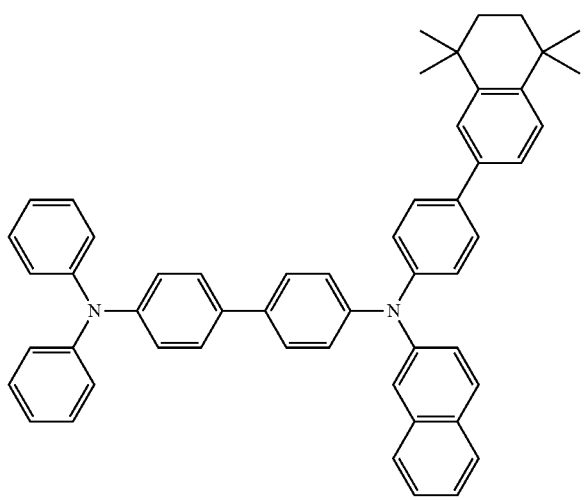

-continued
D-11
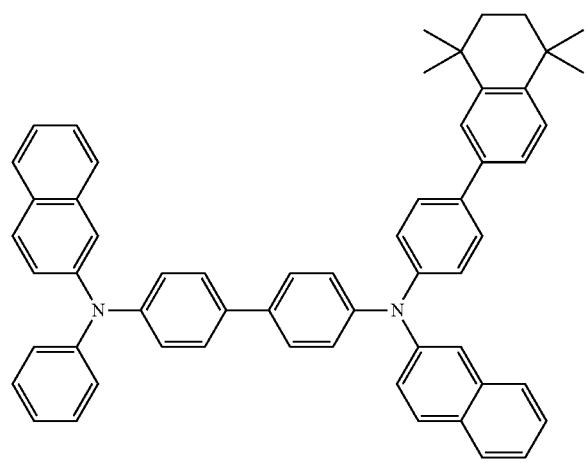
D-12
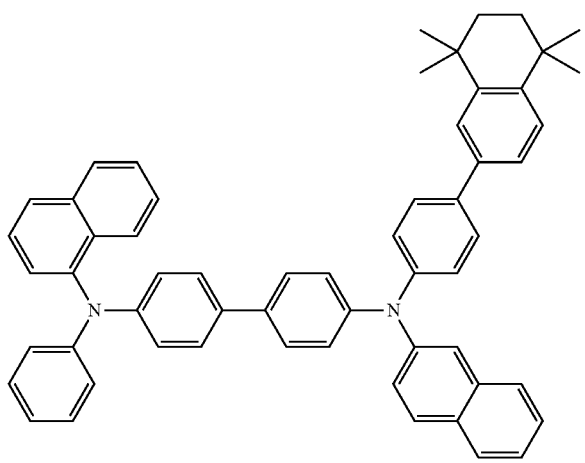
D-13
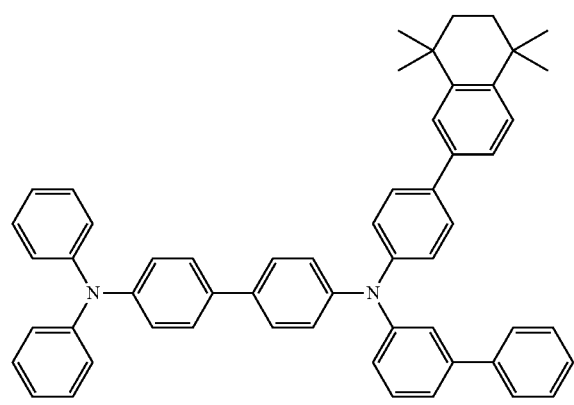
D-14
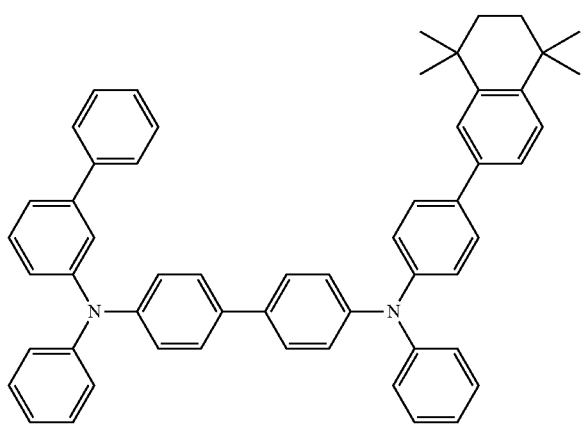
D-15
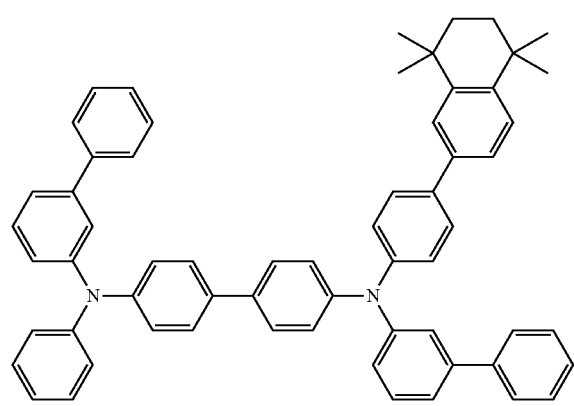
D-16
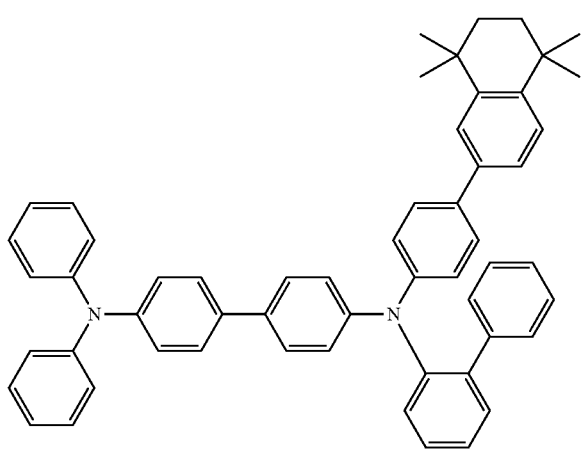

-continued
D-17
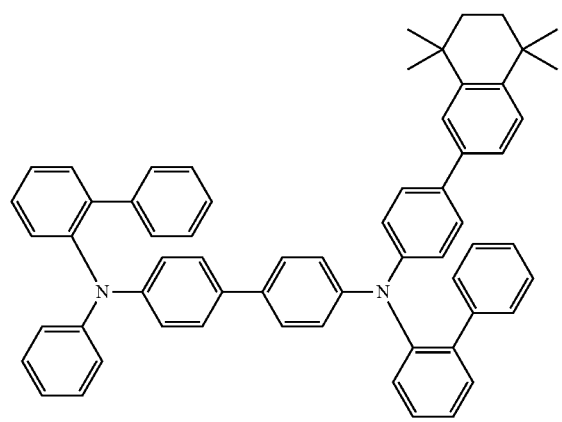
D-18
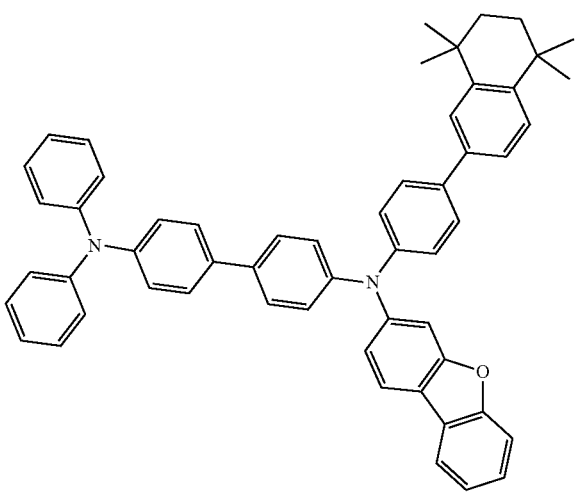
D-19
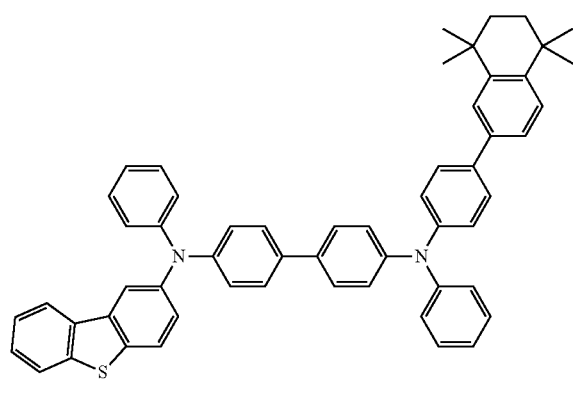
D-20
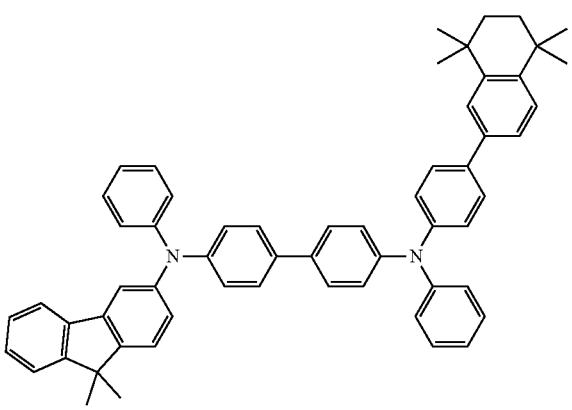
D-21
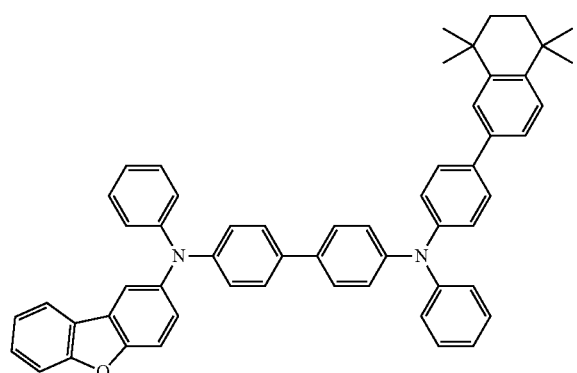
D-23
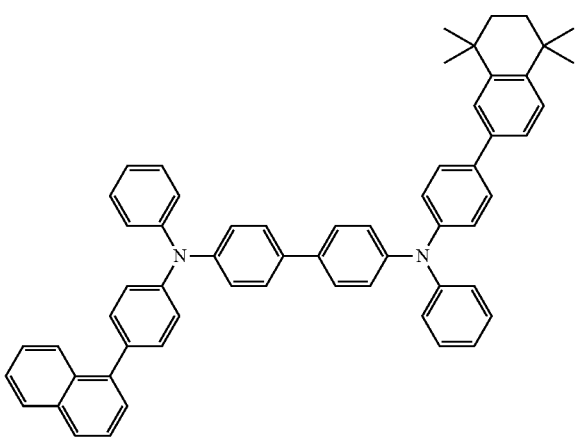

-continued
D-24
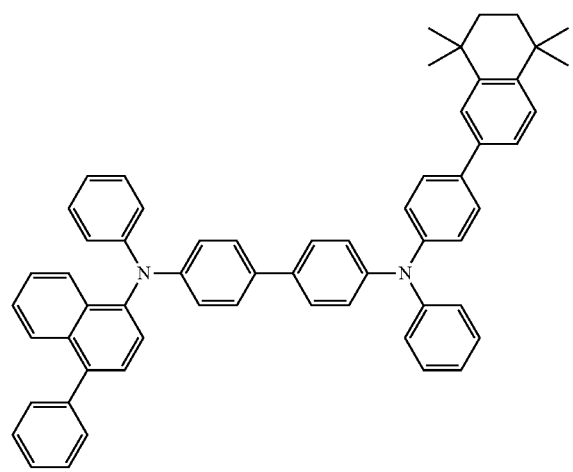
D-25
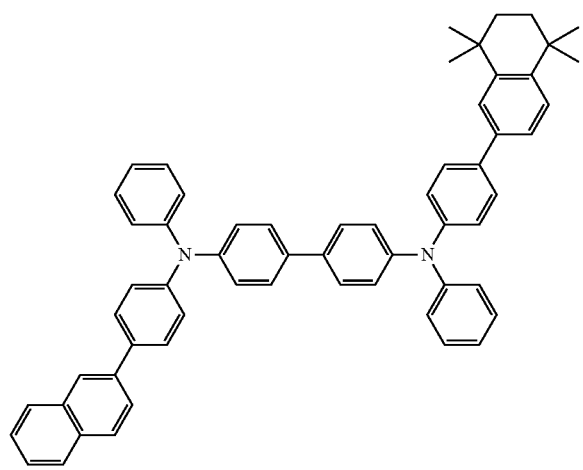
D-27
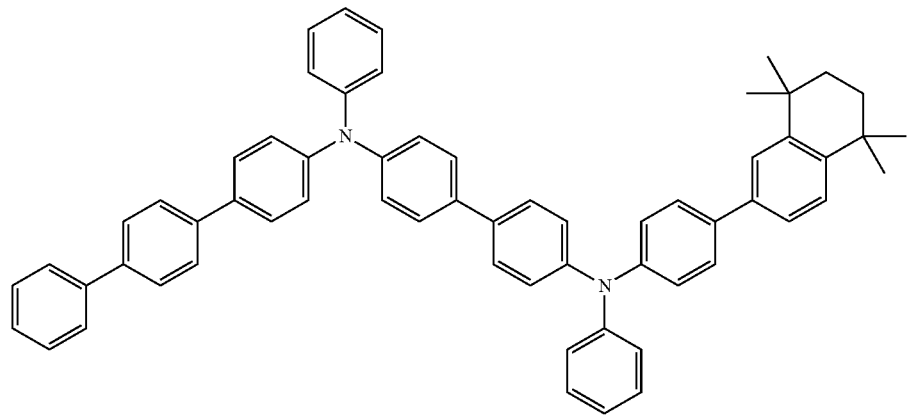
D-28
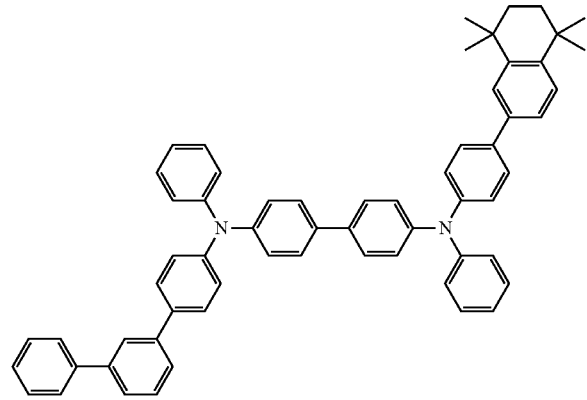

223 224
D-29
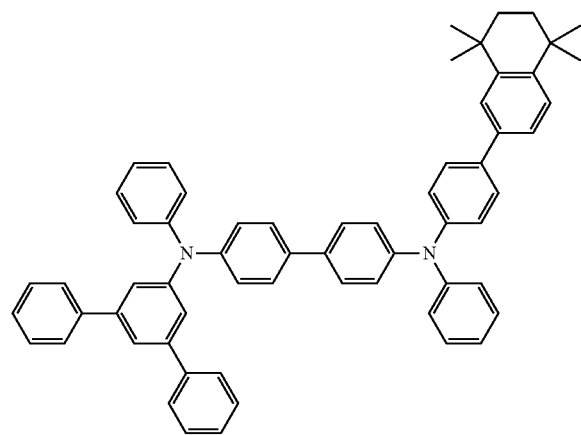
D-30
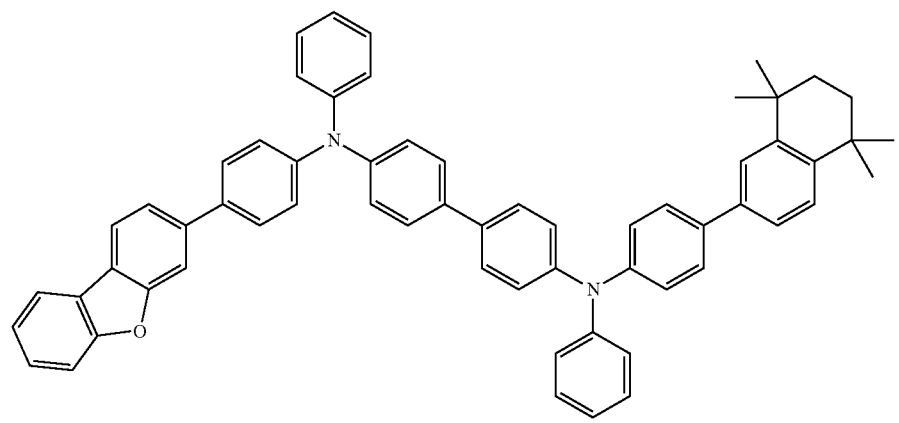
D-31
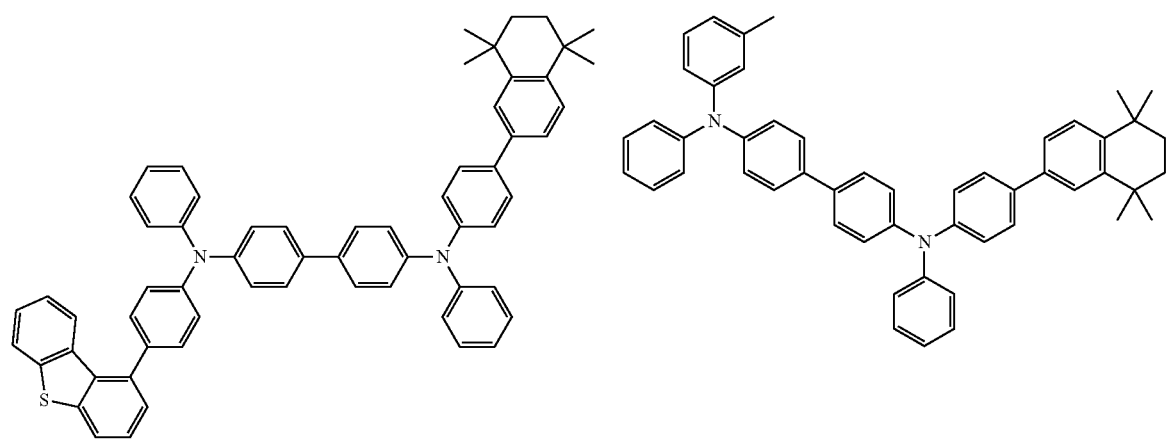
D-32

-continued
D-33
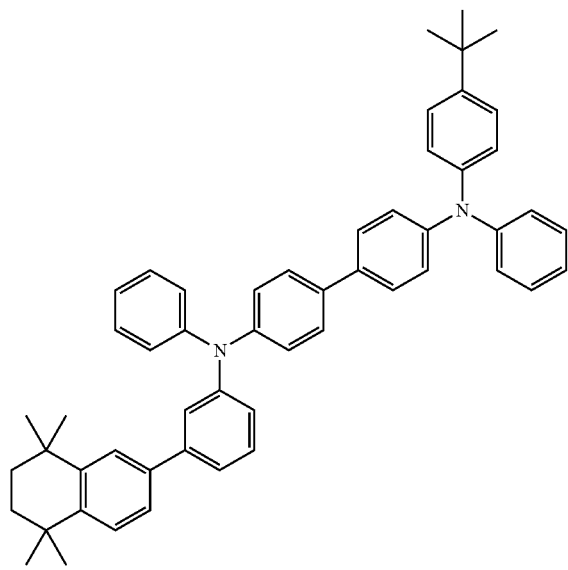
D-34
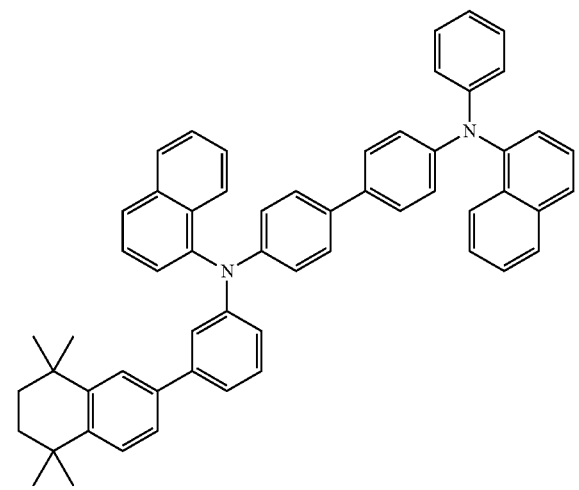
D-35
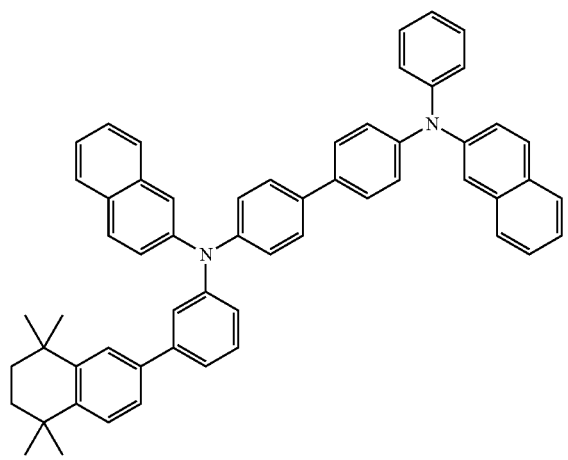
D-36
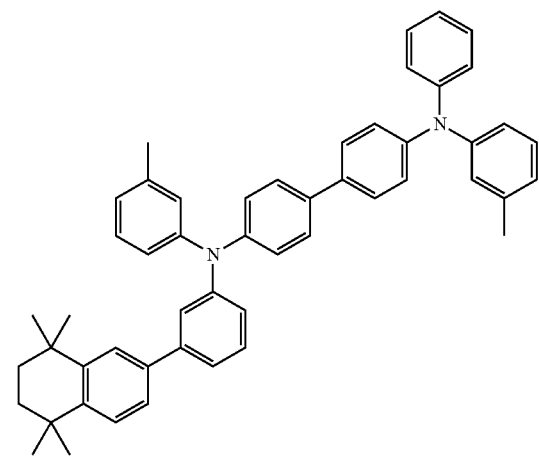
E-1
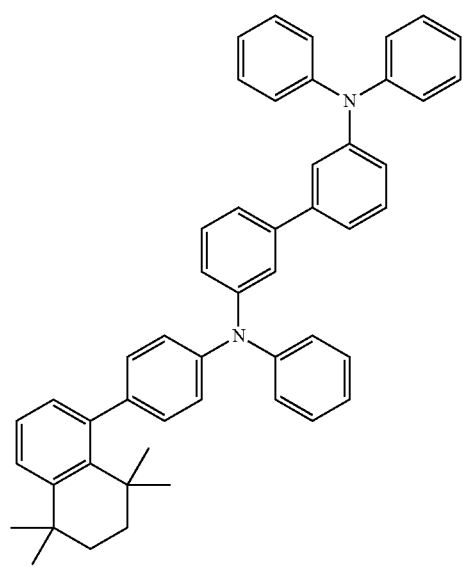
E-2
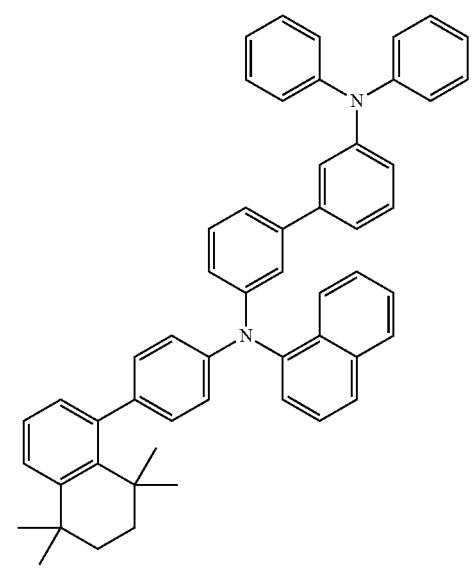

-continued
E-3
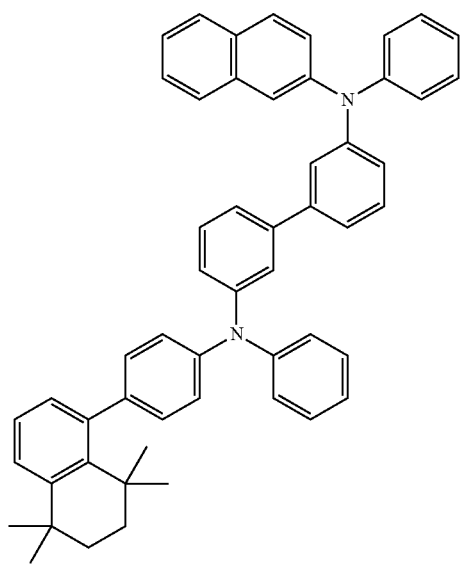
E-4
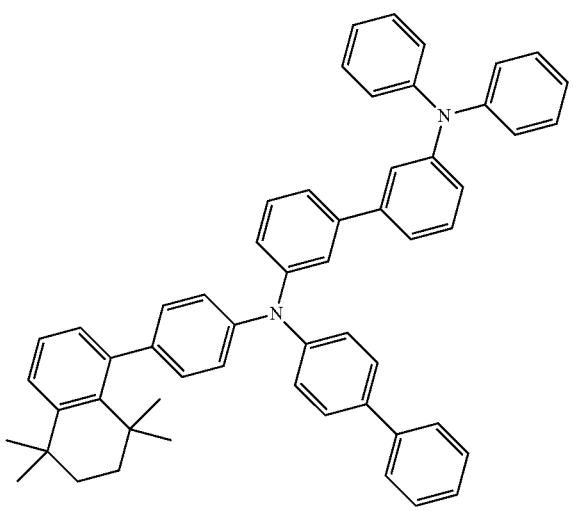
E-5
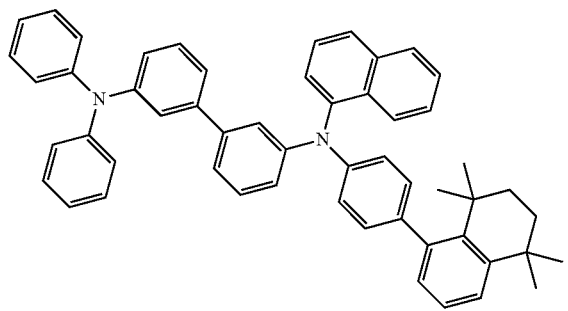
E-6
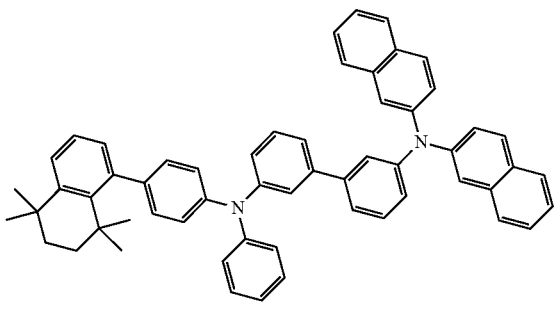
E-7
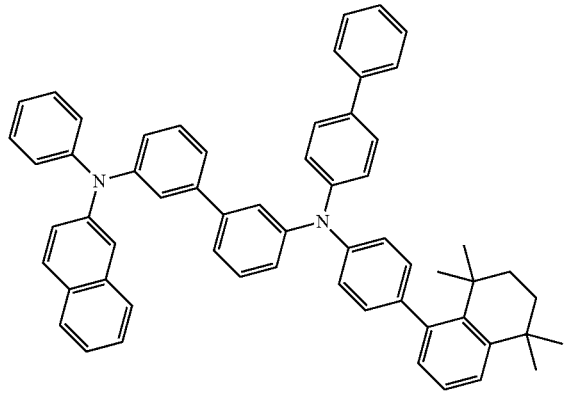
E-8
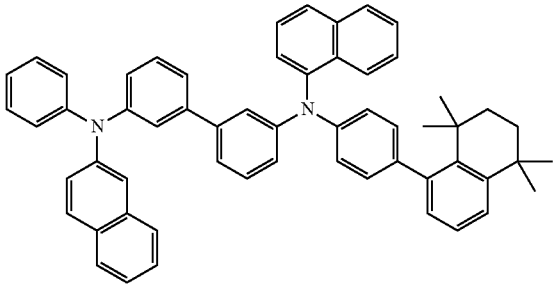

-continued
E-9
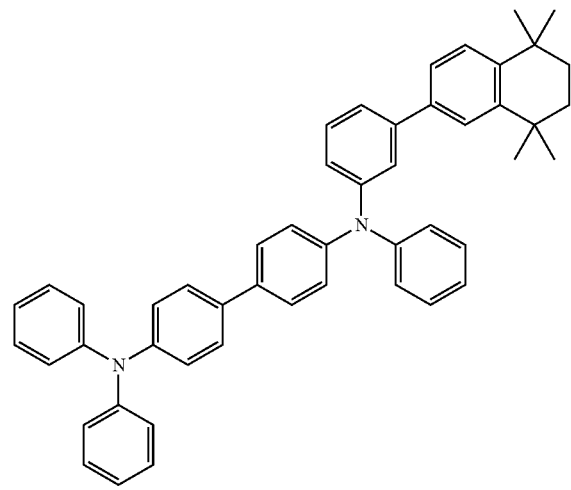
E-10
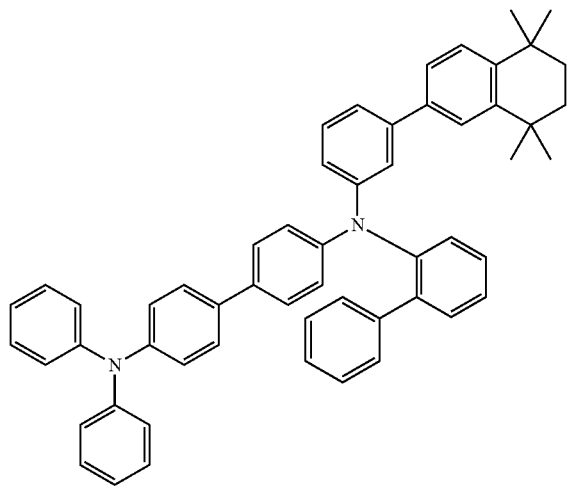
E-11
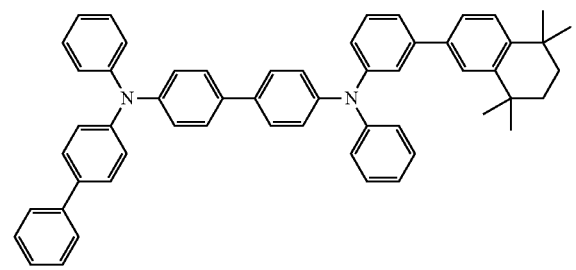
E-12
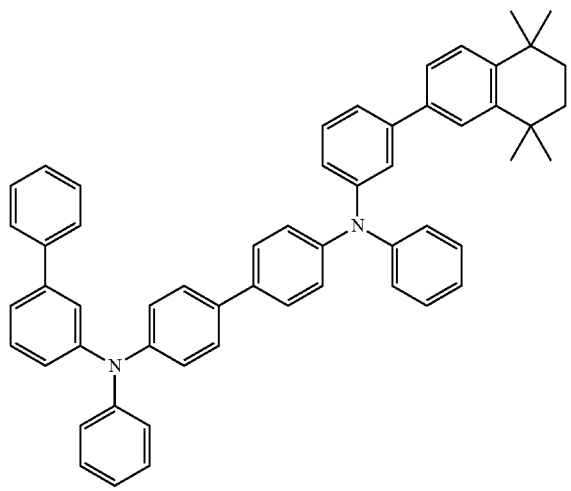
E-13
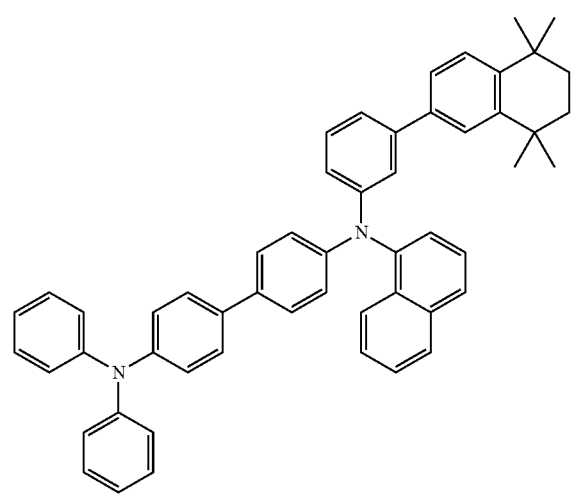
E-14
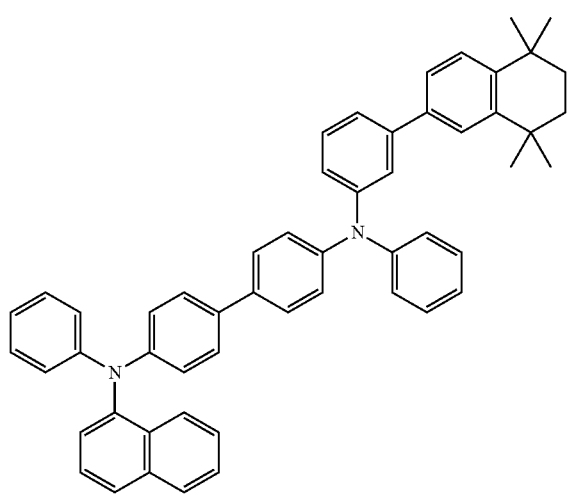

-continued
E-15
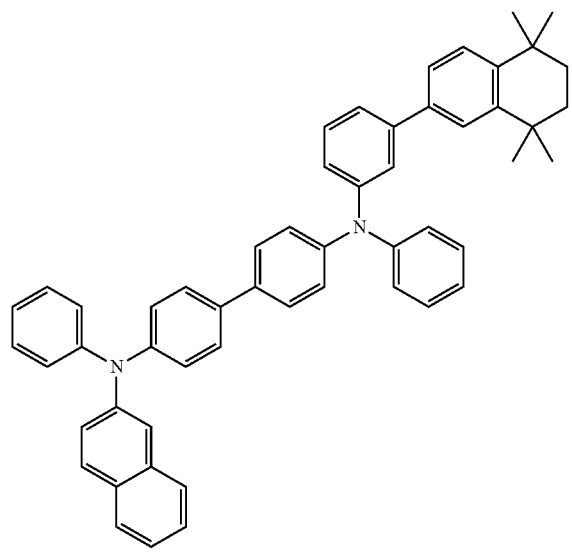
E-16
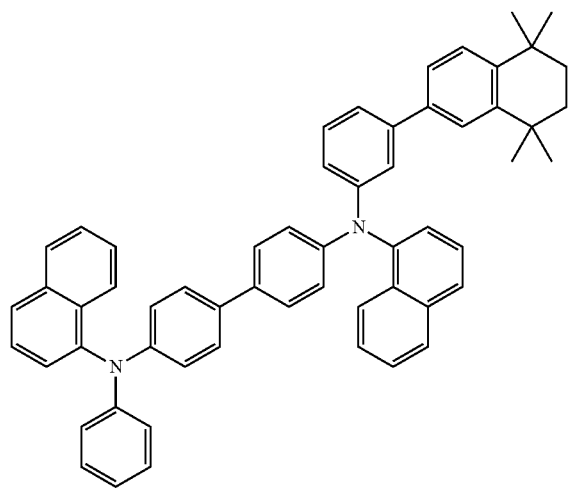
E-17
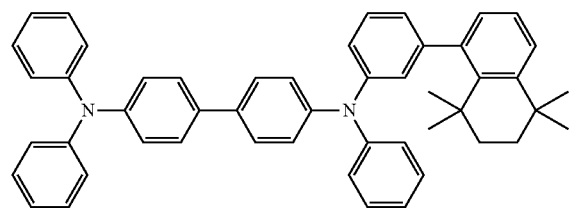
E-18
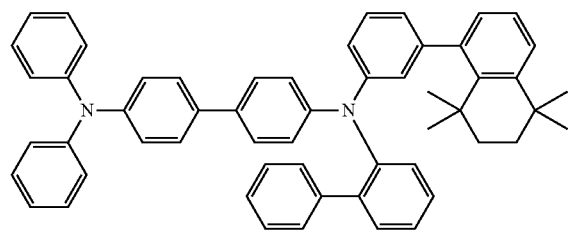
E-19
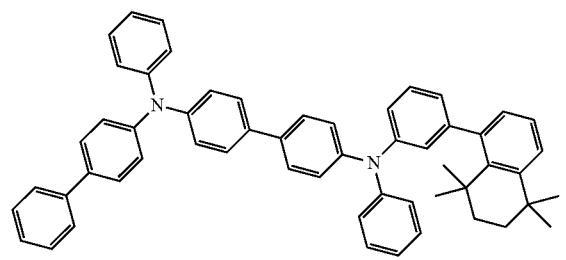
E-20
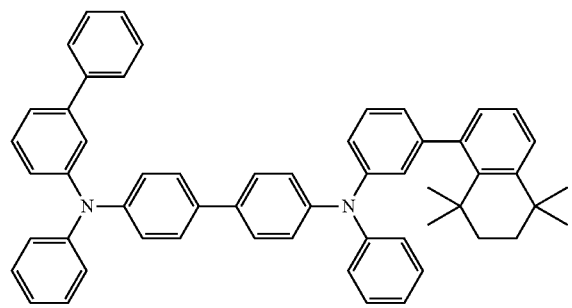

-continued
E-21
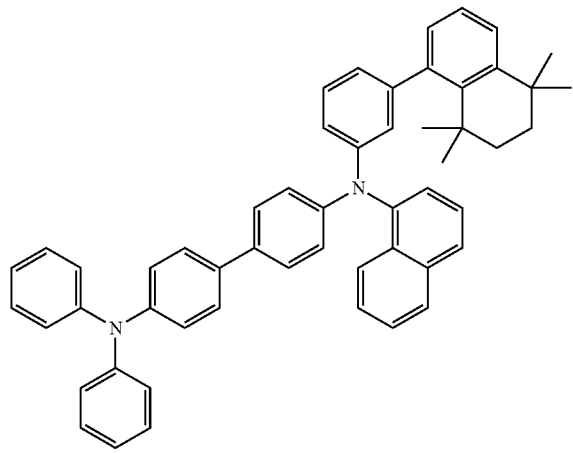
E-22
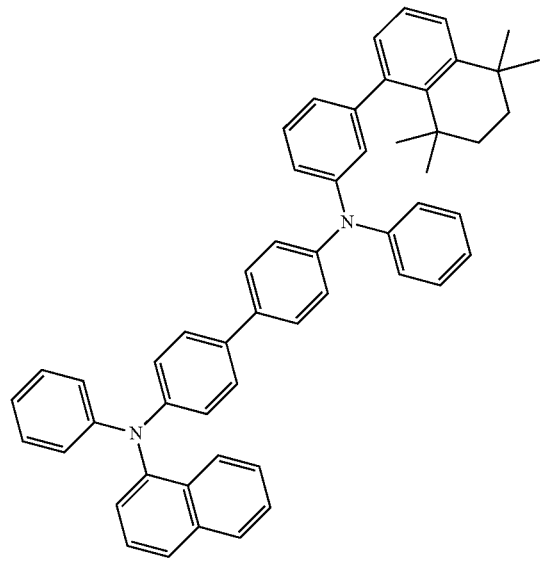
E-23
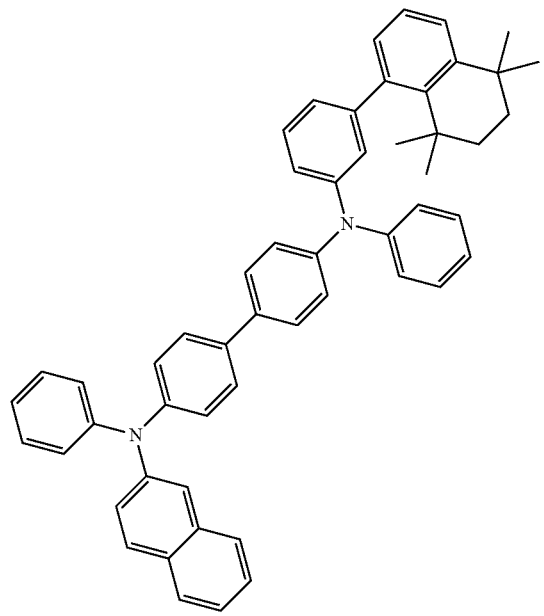
E-24
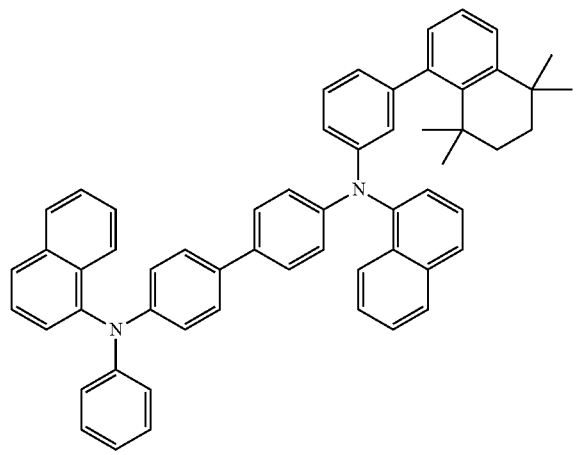
F-1
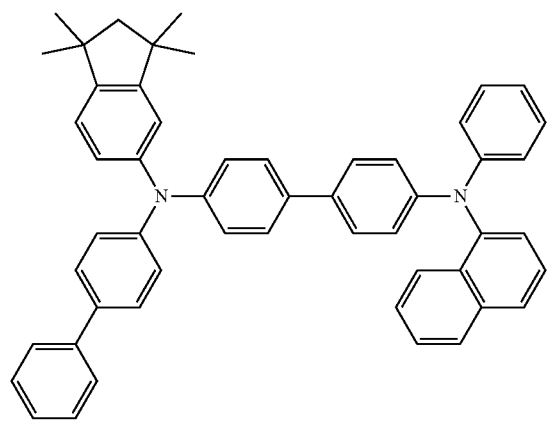
F-2
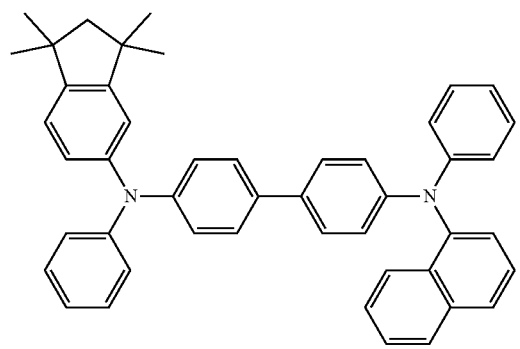

-continued
F-3
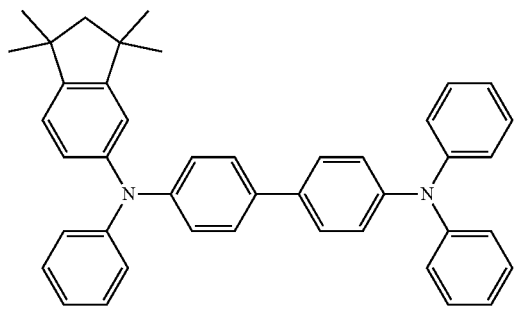
F-4
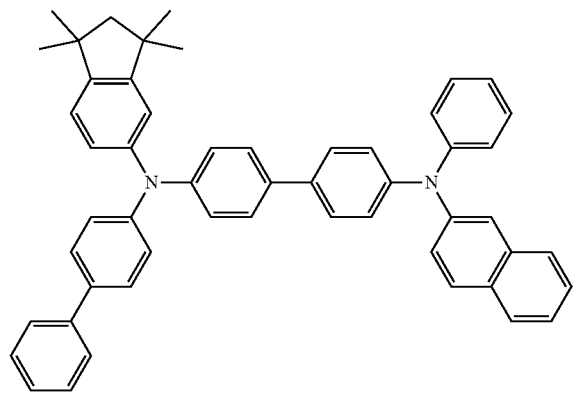
F-5
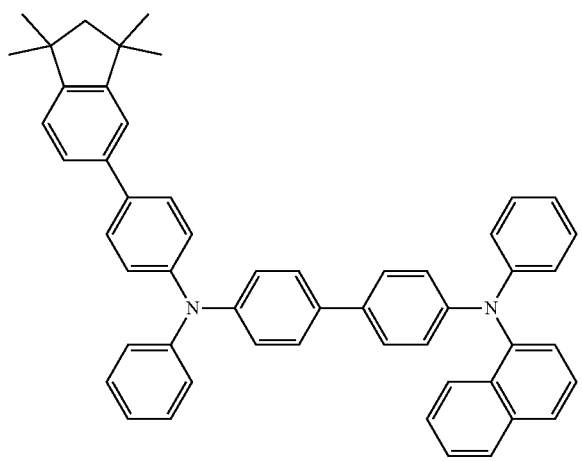
F-6
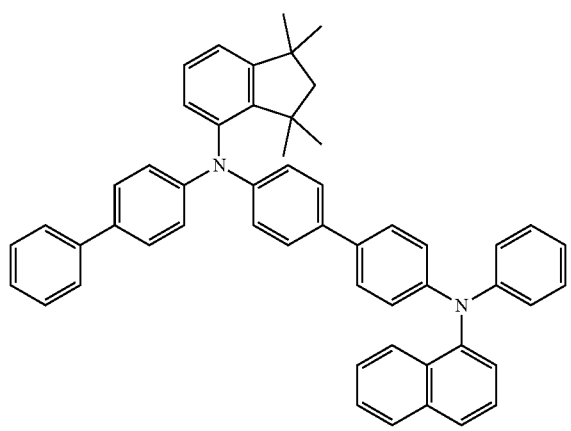
F-7
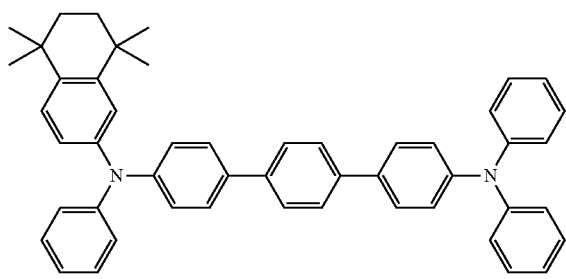
F-8
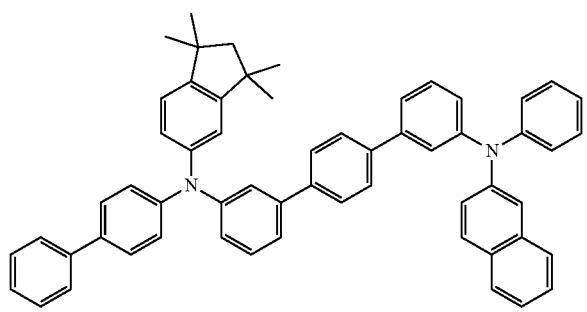

-continued
F-9
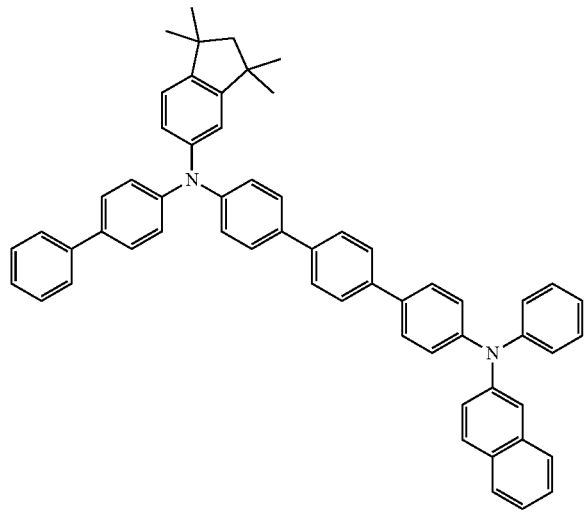
F-10
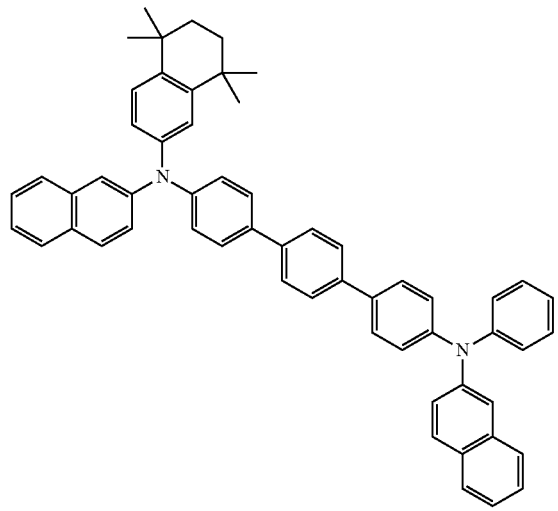
F-11
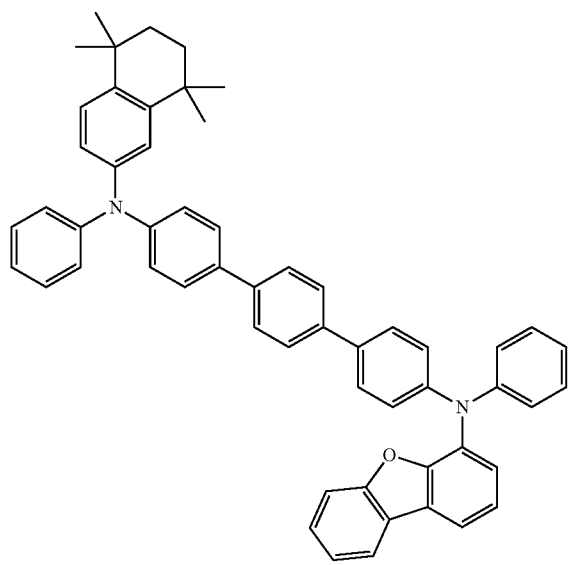
F-12
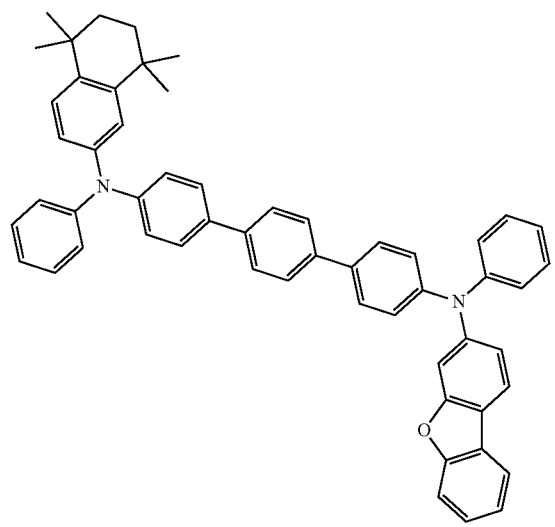
F-13
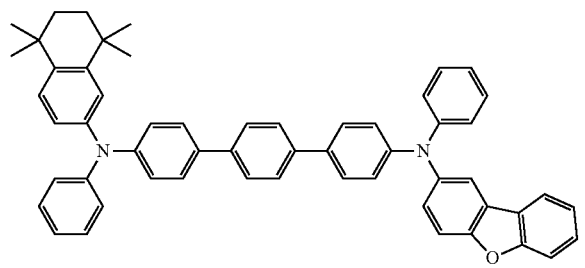
F-14
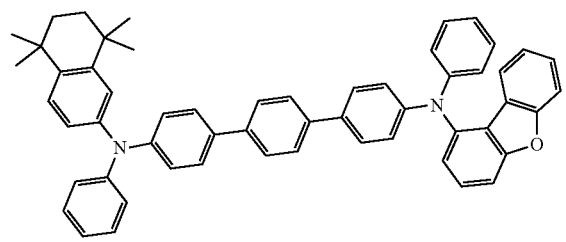

-continued
F-15
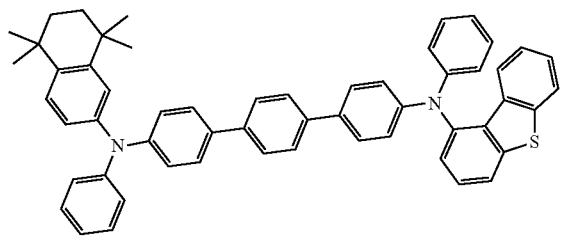
F-16
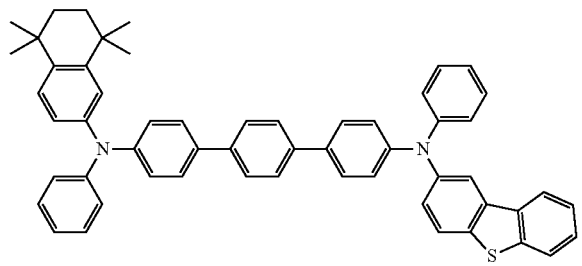
F-17
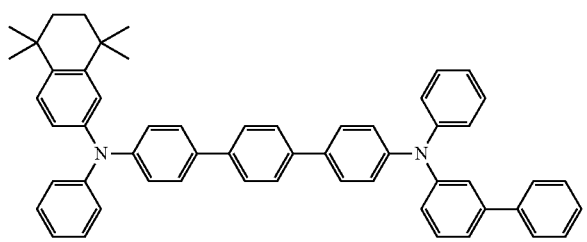
F-18
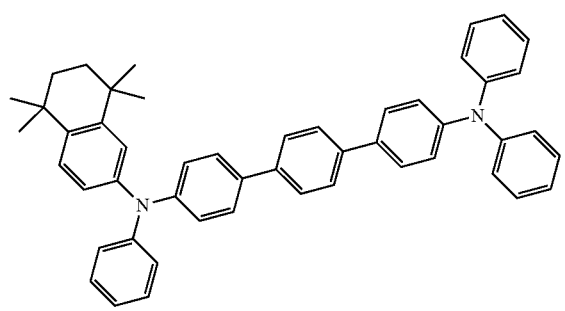
F-19
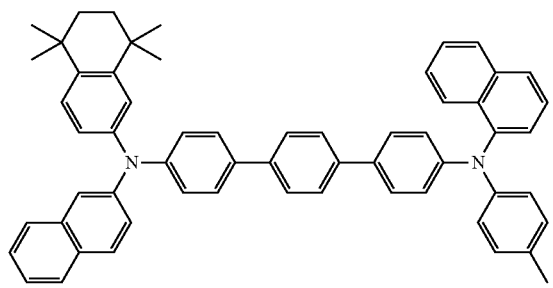
F-20
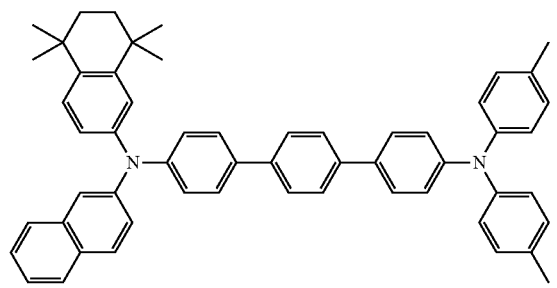
F-21
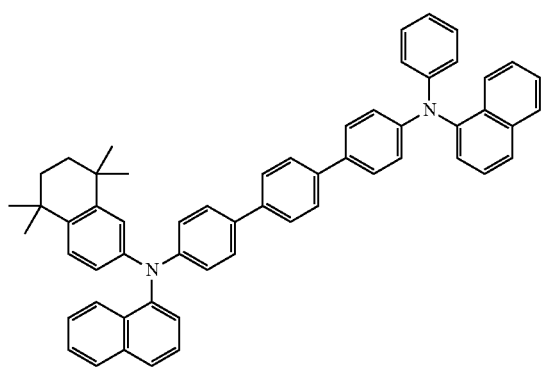
F-23
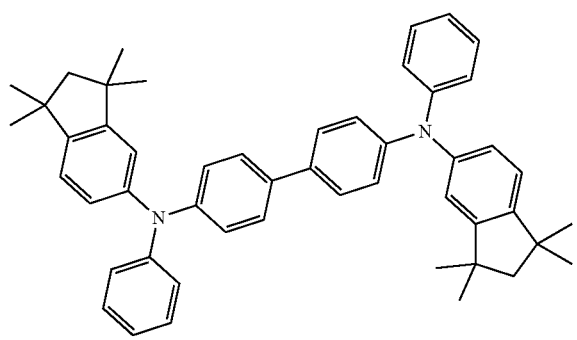

F-24

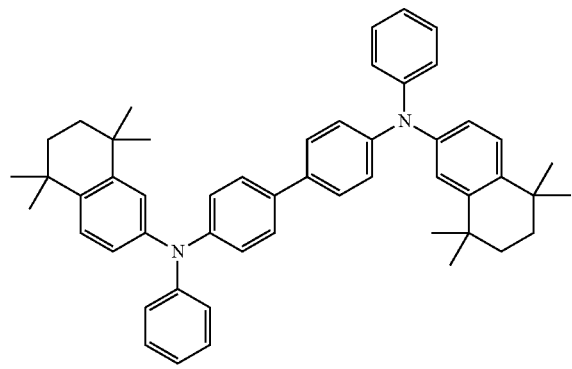

F-25

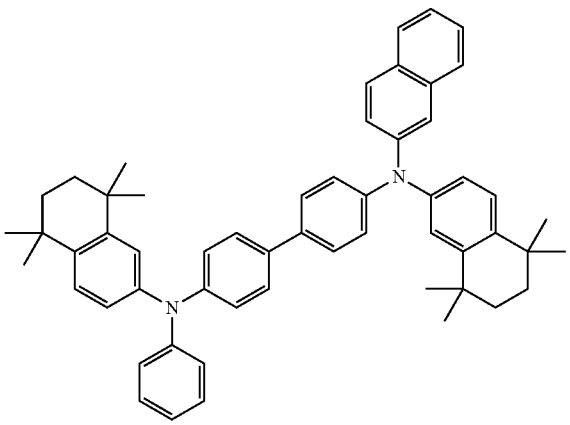

F-28

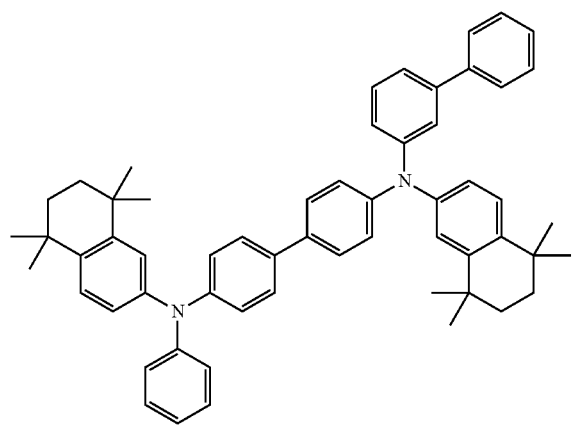

F-29

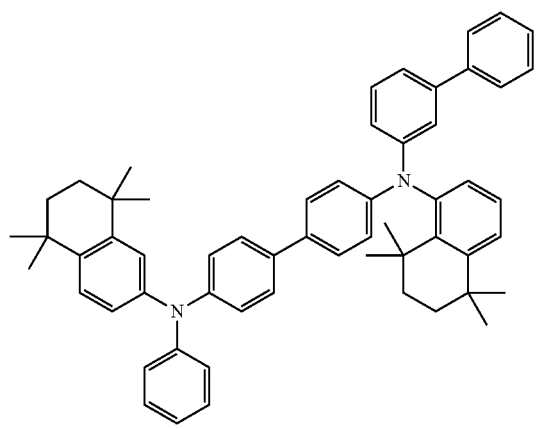

F-30

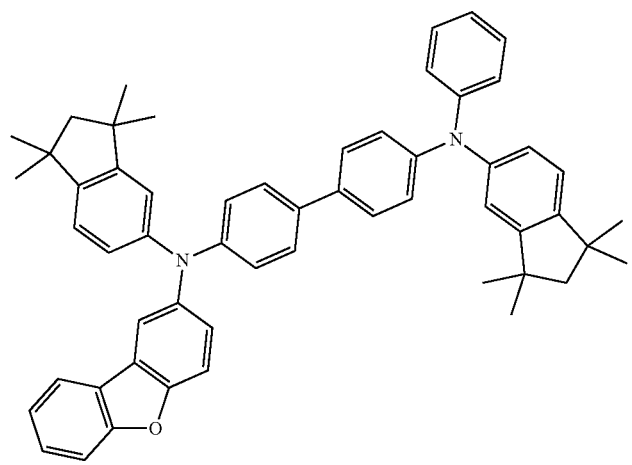

4. An electronic component, comprising an anode, a cathode, and a functional layer disposed between the anode and the cathode, wherein the functional layer comprises the organic compound according to claim 1.

5. The electronic component according to claim 4, wherein the functional layer comprises a hole transport layer comprising the organic compound.

6. The electronic component according to claim 4, wherein the electronic component is an organic electroluminescent device or a photoelectric conversion device.

7. The electronic component according to claim 6, wherein the organic electroluminescent device is a blue light organic electroluminescent device.

8. An electronic apparatus, comprising the electronic component according to claim 4.

* * * * *